United States Patent
Zhao et al.

(10) Patent No.: US 11,767,294 B2
(45) Date of Patent: *Sep. 26, 2023

(54) CONJUGATES OF CELL BINDING MOLECULES WITH CYTOTOXIC AGENTS

(71) Applicants: HANGZHOU DAC BIOTECH CO., LTD., Hangzhou (CN); R. Yongxin Zhao, Lexington, MA (US); Yue Zhang, Shenzhen (CN); Yourang Ma, Zhengzhou (CN)

(72) Inventors: R. Yongxin Zhao, Lexington, MA (US); Yue Zhang, Shenzhen (CN); Yourang Ma, Zhengzhou (CN)

(73) Assignee: HANGZHOU DAC BIOTECH CO., LTD., Hangzhou (CN)

( * ) Notice: Subject to any disclaimer, the term of this patent is extended or adjusted under 35 U.S.C. 154(b) by 1071 days.

This patent is subject to a terminal disclaimer.

(21) Appl. No.: 16/407,367

(22) Filed: May 9, 2019

(65) Prior Publication Data

US 2019/0330149 A1 Oct. 31, 2019

Related U.S. Application Data

(63) Continuation of application No. 14/253,881, filed on Apr. 16, 2014, now Pat. No. 10,399,941, which is a continuation of application No. PCT/IB2012/053554, filed on Jul. 12, 2012.

(51) Int. Cl.
| | |
|---|---|
| C07D 207/40 | (2006.01) |
| A61K 45/06 | (2006.01) |
| A61K 47/64 | (2017.01) |
| A61K 47/68 | (2017.01) |

(52) U.S. Cl.
CPC ............ C07D 207/40 (2013.01); A61K 45/06 (2013.01); A61K 47/64 (2017.08); A61K 47/6803 (2017.08); A61K 47/6811 (2017.08); A61K 47/6849 (2017.08); A61K 47/6851 (2017.08); A61K 47/6855 (2017.08); A61K 47/6863 (2017.08); A61K 47/6867 (2017.08); Y02A 50/30 (2018.01)

(58) Field of Classification Search
CPC ........ A61K 47/55; A61K 47/56; A61K 47/62; A61K 47/64; A61K 47/65; A61K 47/68; A61K 47/6801; A61K 47/6803
See application file for complete search history.

(56) References Cited

U.S. PATENT DOCUMENTS

| | | | |
|---|---|---|---|
| 10,399,941 B2 | 9/2019 | Zhao et al. | |
| 10,501,412 B2 | 12/2019 | Zhao et al. | |
| 2005/0238649 A1* | 10/2005 | Doronina | A61P 43/00 514/18.9 |
| 2006/0128754 A1 | 6/2006 | Hoefle et al. | |
| 2010/0048490 A1 | 2/2010 | Vlahov et al. | |
| 2011/0294998 A1 | 12/2011 | Davis et al. | |
| 2015/0250896 A1 | 9/2015 | Zhao | |
| 2015/0284416 A1 | 10/2015 | Zhao | |
| 2015/0314017 A1 | 11/2015 | Zhao | |
| 2017/0173168 A1 | 6/2017 | Zhao | |
| 2019/0127400 A1 | 5/2019 | Zhao et al. | |
| 2019/0367453 A1 | 12/2019 | Zhao et al. | |
| 2020/0172480 A1 | 6/2020 | Zhao et al. | |

FOREIGN PATENT DOCUMENTS

| | | | |
|---|---|---|---|
| CN | 101678124 A | 3/2010 | |
| CN | 105641707 A | 6/2016 | |
| CN | 109912683 A | 6/2019 | |
| EP | 3 411 074 A2 | 12/2018 | |
| JP | 2017-160205 A | 9/2017 | |
| JP | 2020-063254 A | 4/2020 | |
| JP | 2021-006531 A | 1/2021 | |
| TW | 202041237 A | 11/2020 | |
| WO | 2008112873 A2 | 9/2008 | |
| WO | WO-2009012958 A2 * | 1/2009 | ........... C07D 277/56 |
| WO | WO-2009134279 A1 * | 11/2009 | ............ A61K 38/07 |
| WO | 2011/017249 A1 | 2/2011 | |
| WO | 2011/069116 A1 | 6/2011 | |
| WO | 2012/171020 A1 | 12/2012 | |
| WO | 2013/085925 A1 | 6/2013 | |
| WO | 2015/151078 A2 | 10/2015 | |
| WO | 2015/151081 A2 | 10/2015 | |
| WO | 2016/059622 A2 | 4/2016 | |
| WO | 2018/086139 A1 | 5/2018 | |
| WO | 2018/185526 A1 | 10/2018 | |
| WO | 2019/127607 A1 | 7/2019 | |

(Continued)

OTHER PUBLICATIONS

Doronina et al (Bioconjugate Chemistry, 2008, vol. 19, pp. 1960-1963) (Year: 2008).*
Goldmacher and Kovtun et al. (Therapeutic Delivery 2011, vol. 2, pp. 397-416) (Year: 2011).*
Notice of Allowance dated Jul. 25, 2019, by the U.S. Patent and Trademark Office in related U.S. Appl. No. 14/430,230. (23 pages).
Office Action dated Dec. 17, 2018, by the Canadian Patent Office in corresponding Canadian Patent Application No. 2,878,733. (3 pages).
Communication under Rule 71(3) EPC dated Aug. 29, 2019, by the European Patent Office in corresponding European Patent Application No. 12 880 769.0. (5 pages).
Communication under Rule 94(3) EPC dated Sep. 6, 2019, by the European Patent Office in corresponding European Patent Application No. 17 151 529.9. (5 pages).

(Continued)

*Primary Examiner* — Karen A. Canella
(74) *Attorney, Agent, or Firm* — BUCHANAN INGERSOLL & ROONEY PC

(57) ABSTRACT

A conjugate of a potent cytotoxic agent with a cell-surface receptor binding molecule having a Formula (I), wherein T, L, m, n, $R^1$, $R^2$, $R^3$, $R^4$, $R^5$, $R^6$, $R^7$, $R^8$, $R^9$, $R^{10}$, $R^{11}$, $R^{12}$, and $R^{13}$ are defined herein, can be used for targeted treatment of cancer, autoimmune disease, and infectious disease.

20 Claims, 49 Drawing Sheets

(56) References Cited

FOREIGN PATENT DOCUMENTS

| WO | 2020/073345 A1 | 4/2020 |
|---|---|---|
| WO | 2020/257998 A1 | 12/2020 |
| WO | 2020/258893 A1 | 12/2020 |
| WO | 2021/000067 A1 | 1/2021 |

OTHER PUBLICATIONS

Office Action dated Nov. 6, 2019, by the Canadian Patent Office in corresponding Canadian Patent Application No. 2,977,032. (8 pages).
Decision to grant a European Patent pursuant to Article 97(1) EPC dated Jan. 8, 2020, by the European Patent Office in corresponding European Patent Application No. 12880769.0. (2 pages).
Communication pursuant to Article 94(3) EPC dated Jul. 8, 2020, by the European Patent Office in corresponding European Patent Application No. 17151529.9. (6 pages).
Extended European Search Report dated Jul. 5, 2021, by the European Patent Office in corresponding European Patent Application No. 21155131.2. (13 pages).
Communication pursuant to Article 94(3) EPC dated Aug. 12, 2021, by the European Patent Office in corresponding European Patent Application No. 17151529.9. (5 pages).
Leamon et al. "Folate Targeting Enables Durable and Specific Antitumor Responses from a Therapeutically Null Tubulysin B Analogue," Cancer Research, Dec. 1, 2008, vol. 68, No. 23, pp. 9839-9844.
International Preliminary Report on Patentability (Form PCT/IB/373) dated Jan. 13, 2015, by the International Bureau of WIPO in corresponding International Application No. PCT/IB2012/053554. (1 page).
International Search Report (Form PCT/ISA/210) dated Apr. 25, 2013, by the State Intellectual Property Office of the People's Republic of China in corresponding International Application No. PCT/IB2012/053554. (4 pages).
Written Opinion of the International Searching Authority (Form PCT/ISA/237), dated Apr. 25, 2013 by the State Intellectual Property Office of the People's Republic of China in corresponding International Application No. PCT/IB2012/053554. (6 pages).
Patent Examination Report No. 1 dated Sep. 17, 2015, by the Australian Government in corresponding Australian Patent Application No. 2012385228 (8 pages).
Notice of Grant for Patent dated Jan. 19, 2017, by the Australian Government in corresponding Australian Patent Application No. 2012385228 (1 page).
Notification of Reasons for Refusal dated Feb. 26, 2016, by the Japanese Patent Office in corresponding Japanese Patent Application No. 2015-521075 with an English translation of the Notification (8 pages).
Decision to Grant a Patent dated Feb. 10, 2017, by the Japanese Patent Office in corresponding Japanese Patent Application No. 2015-521075 with an English translation (5 pages).
Office Action dated Mar. 11, 2016, by the Canadian Patent Office in corresponding Canadian Patent Application No. 2,878,733 (7 pages).
Partial Supplementary European Search Report dated Oct. 14, 2015, by the European Patent Office in corresponding European Patent Application No. 12880769.0 (8 pages).
Extended European Search Report dated Feb. 9, 2016, by the European Patent Office in corresponding European Patent Application No. 12880769.0 (18 pages).
Balasubramanian, R. et al., Total Synthesis and Biological Evaluation of Tubulysin U, Tubulysin V, and Their Analogues, J. Med. Chem., 2009, 52 (2), pp. 238-240.
Office Action dated Apr. 28, 2017, by the Canadian Patent Office in corresponding Canadian Patent Application No. 2,878,733 (3 pages).
Extended European Search Report dated Jul. 4, 2017, by the European Patent Office in corresponding European Patent Application No. 17151529.9 (10 pages).
Office Action dated Jun. 20, 2018, by the Canadian Patent Office in corresponding Canadian Patent Application No. 2,977,032. (5 pages).

Communication pursuant to Article 94(3) EPC dated Jan. 17, 2018, by the European Patent Office in corresponding European Patent Application No. 12 880 769.0. (8 pages).
Office Action dated Mar. 1, 2017, by the Australian Patent Office in corresponding Australian Patent Application No. 2016228256. (4 pages).
Office Action dated Mar. 17, 2017, by the Australian Patent Office in corresponding Australian Patent Application No. 2016228256. (4 pages).
Notice of grant dated Aug. 3, 2017, by the Australian Patent Office in corresponding Australian Patent Application No. 2016228256. (1 page).
Office Action dated Feb. 5, 2018, by the Canadian Patent Office in corresponding Canadian Patent Application No. 2,878,733. (3 pages).
The extended European search report dated May 24, 2018, by the European Patent Office in corresponding European Patent Application No. 17206539.3. (10 pages).
Notification of Reasons for Refusal dated Mar. 1, 2016, by the Japanese Patent Office in corresponding Japanese Patent Application No. 2015-521075 and an English translation of the Office Action. (5 pages).
Robin et al., "Dibromomaleimide end functional polymers by RAFT polymerization without the need of protecting groups," (2012). (36 pages).
Ryan et al., "Tunable reagents for multi-functional bioconjugation: reversible or permanent chemical modification of proteins and peptides by control of maleimide hydrolysis," Chemical Communications, (2011), vol. 47, No. 19. (10 pages).
Schumacher et al., "In Situ Maleimide Bridging of Disulfides and a New Approach to Protein PEGylation," Bioconjugate Chemistry, (2011), vol. 22, pp. 132-136.
Office Action dated Feb. 11, 2019, by the U.S. Patent and Trademark Office in related U.S. Appl. No. 14/430,230. (22 pages).
Li et al., "Advances in the discovery of novel antimicrobials targeting the assembly of bacterial cell division protein FtsZ," European Journal of Medicinal Chemistry (2015), vol. 95, pp. 1-15.
Irani et al., "Molecular properties of human IgC subclasses and their implications for designing therapeutic monoclonal antibodies against infectious diseases," Molecular Immunology, (2015), vol. 67, pp. 171-182.
Pelegrin et al., "Antiviral Monoclonal Antibodies: Can They Be More Than Simple Neutralizing Agents?," Trends in Microbiology, (2015), vol. 23, No. 10, pp. 653-665.
Turner et al., "Antigens of selected Acanthamoeba species detected with monoclonal antibodies," Journal for Parasitology, (2005), vol. 35, pp. 981-990.
Douek et al., "HLA-DO is an intracellular class II molecule with distinctive thymic expression," International Immunology, (1997), vol. 9, No. 3, pp. 355-364.
Baeckstrom et al., "Expression of the Leukocyte-associated Sialoglycoprotein CD43 by a Colon Carcinoma Cell Line," The Journal of Biological Chemistry, (1995), vol. 270, No. 23, pp. 13688-13692.
Grossbard et al., "Serotherapy of B-Cell Neoplasms with Anti-B4-Blocked Ricin: A Phase I Trail of Daily Bolus Infusion," Blood, (1992), vol. 79, No. 3, pp. 576-585.
Pinto et al., "Schedule treatment design and quantitative in vitro evaluation of chemotherapeutic combinations for metastatic prostate cancer therapy," Chemotherapy and Pharmacology, (2011), vol. 67, pp. 275-284.
Office Action dated Aug. 10, 2018, by the U.S. Patent and Trademark Office in related U.S. Appl. No. 14/253,881 (16 pages).
Office Action dated Jan. 7, 2019, by the U.S. Patent and Trademark Office in related U.S. Appl. No. 14/253,881 (14 pages).
Notice of Allowance dated Apr. 3, 2019, by the U.S. Patent and Trademark Office in related U.S. Appl. No. 14/253,881 (8 pages).
Carter et al., "Antibody-Drug Conjugates for Cancer Therapy," The Cancer Journal, May/Jun. 2008, vol. 14, No. 3, pp. 154-169.
Office Action dated Mar. 3, 2022, by the U.S. Patent and Trademark Office in related U.S. Appl. No. 16/539,342. (19 pages).
Communication pursuant to Article 94(3) EPC dated Mar. 10, 2022, by the European Patent Office in corresponding European Patent Application No. 17206539.3. (7 pages).

(56) References Cited

OTHER PUBLICATIONS

Decision to Grant a Patent dated Feb. 22, 2022, by the Japanese Patent Office in corresponding Japanese Patent Application No. 2021-016477 and an English translation of the Decision. (6 pages).
Office Action dated Oct. 6, 2022, by the U.S. Patent and Trademark Office in related U.S. Appl. No. 16/782,456. (25 pages).
Decision to Grant a Patent dated Jan. 5, 2021, by the Japanese Patent Office in corresponding Japanese Patent Application No. 2019-095746, and an English translation of the Decision. (5 pages).
Decision to grant a European patent dated Nov. 24, 2022, by the European Patent Office in corresponding European Application No. 17151529.9. (2 pages).
Communication dated Aug. 17, 2022, by the European Patent Office in corresponding European Application No. 17151529.9. (6 pages).
Office Action dated Aug. 29, 2022, by the U.S. Patent and Trademark Office in related U.S. Appl. No. 16/539,342. (16 pages).
Liu et al., "On the Dynamics of TCR:CD3 Complex Cell Surface Expression and Downmodulation," Immunity, Nov. 2000, vol. 12, pp. 665-675.
Office Action issued by the U.S. Patent and Trademark Office in the U.S. Appl. No. 16/539,342, dated Mar. 22, 2023, by U.S. Patent and Trademark Office, Alexandria, VA. (14 pages).
Lopez-Bueno, et al., "Host-Selected Amino Acid Changes at the Sialic Acid Binding Pocket of the Parvovirus Capsid Modulate Cell Binding Affinity and Determine Virulence", Journal of Virology, 2006, vol. 80, No. 3, pp. 1563-1573.
Ramming, et al., "Homotypic T-cell/T-cell interaction induces T-cell activation, proliferation, and differentiation", Human Immunology, 2009, vol. 70, pp. 873-881.
Mansur, et al., "Suggestive Evidence for Genetic Linkage Between IgE Phenotypes and Chromosome 14q Markers", Am J Respir Crit Care Med, 1999, vol. 159, pp. 1796-1802.
Hsu, et al., "Tumor-Specific Idiotype Vaccines in the Treatment of Patients With B-Cell Lymphoma-Long-Term Results of a Clinical Trial", Blood, 1997, vol. 89, pp. 3129-3135.
Swisher, et al., "Genetic and Immunologic Therapies for Lung Cancer", Seminars in Oncology, 2002, vol. 29, No. 1, pp. 95-101.
Mohanty, et al., "Anti-tumor immunity induced by an anti-idiotype antibody mimicking human Her-2/neu", Breast Cancer Research, 2007, vol. 104, pp. 1-11.
Macworth-Young, et al., "Idiotypic markers of polyclonal B cell activation. Public idiotypes shared by monoclonal antibodies derived from patients with systemic lupus erythematosus or leprosy", Journal of Clinical Investigation, 1987, vol. 79, pp. 572-581.
May, et al., "Antibodies to Keyhole Limpet Hemocyanin Cross-React ,vith an Epitope on the Polysaccharide Capsule of Cryptococcus neoformans and Other Carbohydrates: Implications for Vaccine Development1", Journal of Immunology, 2003, vol. 171, pp. 4905-4912.
Musselli, et al., "Reevaluation of the Cellular Immune Response in Breast Cancer Patients Vaccinated With MUC1", International Journal of Cancer, 2002, vol. 97, pp. 660-667.
Kelley et al., "Antigen Binding Thermodynamics and Antiproliferative Effects of Chimeric and Humanized anti-p185HER2 Antibody Fab Fragments", Biochemistry, 1992, vol. 31, pp. 5434-5441.
Cheever, et al., "The Prioritization of Cancer Antigens: A National Cancer Institute Pilot Project for the Acceleration of Translational Research", Clinical Cancer Research, 2009, vol. 15, No. 17, pp. 5323-5337.
Gyles, L. C., "*Escherichia coli* cytotoxins and enterotoxinsCanadian", Journal of Microbiology, 1992, vol. 38, pp. 734-746.
Guichard, et al., "Anthrax toxins cooperatively inhibit endocytic recycling by the Rab11/ Sec15 exocyst", Nature, 2010, vol. 467, pp. 854-858.
Office Action dated Apr. 12, 2023, by the U.S. Patent and Trademark Office in U.S. Appl. No. 16/782,456, U.S. Patent and Trademark Office, Alexandria, VA. (27 pages).

\* cited by examiner

| # | Compound structures, MS, and IC$_{50}$ values |
|---|---|
| 106 | <br>MS 537.28 (M-H)$^-$, IC$_{50}$ > 500 nM |
| 283 | <br>MS 539.30 (M-H)$^-$; IC$_{50}$ > 500 nM |
| 232a | <br>MS: 1241.55 (M-H)$^-$, IC$_{50}$ = 27 nM, or 321 pM (in presence of 1 unit of acid phosphatase) |
| 232b | <br>MS: 1260.56 (M-H)$^-$; IC$_{50}$ = 47 nM, or 375 pM (in presence of 1 u of acid phosphatase) |
| 232c | <br>MS: 1241.54 (M-H)$^-$; IC$_{50}$ = 90 nM. |

| | |
|---|---|
| 232d | 
MS: 1260.55 (M-H)⁻; IC$_{50}$ = 107 nM |
| 232e | 
MS: 1347.64 (M+Na)⁺; IC$_{50}$ = 77 nM, or 121 pM (in presence of 1 u of glycosidase) |
| 232f | 
MS: 1366.65 (M+Na)⁺; IC$_{50}$ = 99 nM, or 115 pM (in presence of 1 u of glycosidase) |
| 232g | 
MS: 1283.60 (M-H)⁻; IC$_{50}$ = 37 nM, or 101 pM (in presence of 1 u of acid phosphatase) |
| 232h | 
MS: 1302.61 (M-H)⁻; IC$_{50}$ = 56 nM, or 116 pM (in presence of 1 u of acid phosphatase) |

| 232n |  |
|---|---|
| | MS: 1196.54 (M + Na)⁺; IC$_{50}$ = 1.6 nM |
| 232o |  |
| | MS: 1206.56 (M + Na)⁺; IC$_{50}$ = 127 pM |
| 232p |  |
| | MS: 1248.60 (M + Na)⁺; IC$_{50}$ = 191 pM |
| 232q |  |
| | MS: 1254.56 (M + Na)⁺; IC$_{50}$ = 387 pM |
| 232r |  |
| | MS: 1212.51 (M + Na)⁺; IC$_{50}$ = 219 pM |

| | |
|---|---|
| 233b | <br>MS: 1213.61 (M + Na)+; IC50 = 236 pM |
| 233c | <br>MS: 1185.57 (M + Na)+; IC50 = 337 pM |
| 233d | <br>MS: 1156.55 (M + Na)+; IC50 = 310 pM |
| 222a | <br>MS: 1200.61 (M + Na)+; IC50 = 412 pM |
| 308a | <br>MS: 988.46 (M + Na)+; IC50 = 167 pM |

| 206 |  MS: 1033.50 (M+Na)⁺, IC$_{50}$ = 307 pM |
| 211 |  MS: 977.47 (M+Na)⁺, IC$_{50}$ = 201 pM |
| 346 |  MS: 1032.42 (M-H)⁻, IC$_{50}$ = 1.0 nM, or 28 pM (in presence of an acid phosphatase) |
| 350 |  MS: 969.40 (M-H)⁻, IC$_{50}$ = 1.8 nM, or 110 pM (in presence of an acid phosphatase) |
| 354 |  MS: 1002.40 (M-H)⁻, IC$_{50}$ = 2.6 nM |

CONJUGATES OF CELL BINDING MOLECULES WITH CYTOTOXIC AGENTS

CROSS REFERENCE OF RELATED APPLICATIONS

This application is a continuation of U.S. patent application Ser. No. 14/253,881, filed on Apr. 16, 2014, entitled "CONJUGATES OF CELL BINDING MOLECULES WITH CYTOTOXIC AGENTS," which in turn is a continuation of PCT/IB2012/053554, filed on Jul. 12, 2012. The entire content of each of the prior applications is hereby incorporated by reference.

1. FIELD OF THE INVENTION

This invention relates to a conjugate of a potent cytotoxic agent with a cell-surface receptor binding molecule for targeted therapy. The invention also relates to use of the compositions comprising the cell-surface receptor binding molecule-antimitotic agent conjugates for treating cancer, autoimmune disease, and infectious disease.

2. BACKGROUND OF THE INVENTION

There are many articles appeared on the attempted specific targeting of pathogenic cells, in particular, cancer cells utilizing cytotoxic drug conjugated to cell-surface receptor binding agents, such as antibodies (Sela et al, in *Immunoconjugates* 189-216 (C. Vogel, ed. 1987); Ghose et al, in *Targeted Drugs* 1-22 (E. Goldberg, ed. 1983); Diener et al, in *Antibody mediated delivery systems* 1-23 (J. Rodwell, ed. 1988); Silverstein, *Nat. Immunol.* 2004, 5, 1211-7; Fanning et al, *Clin. Immunol Immunopathol.* 1996, 79, 1-14; Ricart A. D., et al., *Nature Clinical Practice Oncology* 2007, 4, 245-255; Singh R. et Rickson H. K., *Therapeutic Antibodies: Methods and Protocols,* 2009, 525, 445-467), folic acids (Sudimack, J. et al, Adv. Drug Delivery Rev. 2000, 41, 147-162; Reddy, et al. Mol. Pharm. 2009, 6, 1518-25); PMSA (prostate specific membrane antigen) binding ligands (Low, et al, WO 2009/026177 A1); albumin with peptides (Temming, et al Bioconjugate Chem. 2006, 17, 1385-1394); cobalamin and proteins (Gupta, et al, Crit. Rev. Therap. Drug Carrier Syst. 2008, 25, 347-79; Petrus, et al, Angew. Chem. Int. Ed. 2009, 48, 1022-8); carbohydrate (Darbre, et al, Curr. Top. Med. Chem. 2008, 8, 1286-93); bioactive polymers (Dhar, et al, Proc. Natl Acad. Sci. 2008, 105, 17356-61); dendrimers (Lee, et al, Nat. Biotechnol. 2005, 23, 1517-26; Almutairi, et al; Proc. Natl. Acad. Sci. 2009, 106, 685-90); nanoparticles with binding ligands (Liong, et al, ACS Nano, 2008, 19, 1309-12; Medarova, et al, Nat. Med. 2007, 13, 372-7; Javier, et al, Bioconjugate Chem. 2008, 19, 1309-12); liposomes (Medinai, et al, Curr. Phar. Des. 2004, 10, 2981-9); viral capsides (Flenniken, et al, Viruses Nanotechnol. 2009, 327, 71-93), etc.

Different families of cytotoxic agents like calicheamicin derivative (Giles, et al *Cancer* 2003, 98, 2095-104; Hamann, et al, *Bioconjug Chem* 2002, 13, 47-58), maytansin derivative (Widdison, et al, *J Med Chem* 2006, 49, 4392-2408; Ikeda, et al, *Clin Cancer Res* 2009, 15, 4028-37; Xie, et al, *Expert Opin Biol Ther* 2006, 6, 281-91), auristatins (Sutherland, et al, *J Biochem* 2006, 281, 10540-7; Doronina, et al, *Bioconjug Chem* 2006, 17, 114-24), taxane derivatives (Miller, et al, *J Med Chem* 2004, 47, 4802-51; WO 06061258), leptomycine derivatives (WO 07144709), CC-1065 and analogues (Suzawa, et al, *J Control Release* 002, 79, 229-42; Suzawa, et al, *Bioorg Med Chem,* 8, 2175-84; WO 2007102069), doxorubicin (Trail, et al, *Science* 1993, 261, 212-5; Saleh et al, *J Clin Oncol* 2000, 18, 2282-92), daunorubicin, vincristine, vinblastine, mitomycin C, or chlorambucil have been used for the conjugation with a cell-surface receptor binding agent, in particular with antibodies (Wu, et al, *Nat. Biotechnol.* 2005, 23, 1137-1146. Ricart, et al, *Nat. Clin. Pract. Oncol.* 2007, 4, 245-255).

The use of a cell-surface receptor binding agent, particularly a targeting antibody having an affinity for the pathogenic cells makes it possible to deliver the cytotoxic agent directly in the vicinity or directly in the pathogenic cell, thus increasing the efficiency of the cytotoxic agent while minimizing the side-effects commonly associated with the cytotoxic agents.

Several short peptidic compounds that found to have biological activity have been isolated from natural sources. One of them, Tubulysins (structures shown below), which were original isolated by Hofle and Reichenbach et al. (GBF Braunschweig) from a culture browth of the

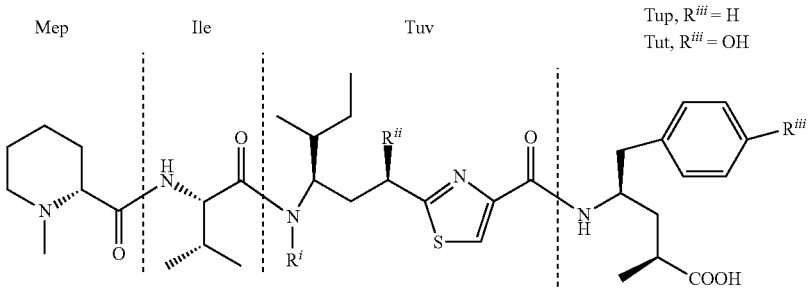

| Tubulysin | $R^i$ | $R^{ii}$ | $R^{iii}$ |
|---|---|---|---|
| A | $CH_2OCOCH_2CH(CH_3)_2$ | $OCOCH_3$ | OH |
| B | $CH_2OCOCH_2CH_2CH_3$ | $OCOCH_3$ | OH |
| C | $CH_2OCOCH_2CH_3$ | $OCOCH_3$ | OH |
| D | $CH_2OCOCH_2CH(CH_3)_2$ | $OCOCH_3$ | H |
| E | $CH_2OCOCH_2CH_2CH_3$ | $OCOCH_3$ | H |
| F | $CH_2OCOCH_2CH_3$ | $OCOCH_3$ | H |
| G | $CH_2OCOCH=CH_2$ | $OCOCH_3$ | OH |
| H | $CH_2OCOCH_3$ | $OCOCH_3$ | H |
| I | $CH_2OCOCH_3$ | $OCOCH_3$ | OH |
| U | H | $OCOCH_3$ | H |
| V | H | OH | H |
| Z | H | OH | OH |
| Pretubulysin | $CH_3$ | H | H |

(The structures of existing tubulysin compounds)

myxobacterial strains of Archangium gephyra (F. Sasse et al. J. Antibiot. 2000, 53, 879-885; WO9813375), are members of group of antimitotic peptides that inhibit tubulin polymerization in dividing cells, and thus inducing apoptosis. With the exceptional potency exceeding that of vinblastine, taxol and epothilones (Wipf, et al, Org. Lett. 2004, 6, 4057-60; Peltier, et al, J. Am. Chem. Soc. 2006, 128, 16018-9; Wipf, et al, Org. Lett., 2007, 9, 1605-1607; Wang, et al, Chem. Biol. Drug Des. 2007, 70, 75-86; Pando, et al, Org. Lett. 2009, 11, 5567-9), these antimitotic peptides are exciting leads for targeted therapies. Structurally, the tetrapeptide tubulysins comprise of N-methylpipecolinic acid (Mep) at the N-terminus, isoleucine (Ile) as the second residue, the unique thiazole-containing tubuvaline (Tuv) as the third residue, and two possible γ-amino acids at the C-terminus (tubutyrosine (Tut) or tubuphenylalanine (Tup)). Despite several tubulysins have recently been synthesized, significant general toxicities (>15% animal body weight loss) of the existing tubulysins at doses required for achieving a therapeutic effect compromise their efficacy (US Patent appl. 2010/0048490). We have been interested in the art of a conjugate of a cell surface binding ligand, particularly using an antibody to conjugate with tubulysin derivatives for having significantly lower general toxicity, yet useful therapeutic efficiency. However, the tubulysins are hardly soluble in a buffer solution, resulting in significant amount of antibody aggregation when conjugated with the tubulysins. A simpler analog, such as using phenyl alanine (Phe) and tyrosine (Tyr) to replace Tup and Tut components respectively for the antibody conjugation leads to the hydrolysis of Phe and Tyr in the animal blood circulation and generates the much less potent Mep-Ile-Tuv moiety (over 200 fold less potency than tubulysin A and D). Here this patent discloses conjugates of a cell surface binding ligand with water soluble and stable, as well as in lower systematical toxicity, tubulysin derivatives and using these conjugates for treating cancer and immune disorders.

3. SUMMARY OF THE INVENTION

In one illustrative embodiment of the invention provides a conjugate of formula (I):

Wherein $R^5$, $R^6$, $R^8$ and $R^{10}$ are independently H, $C_1$~$C_4$ of alkyl or heteroalkyl.

Wherein $R^7$ is independently selected from H, $R^{14}$, or —$R^{14}C(=O)X^1R^{15}$ or —$R^{14}X^1R^{15}$, wherein $R^{14}$ and $R^{15}$ are independently selected from $C_1$~$C_8$ of alkyl, or heteroalkyl; $C_2$~$C_8$ of alkenyl, alkynyl; heterocyclic, carbocyclic, cycloalkyl; $C_3$~$C_8$ of aryl, heterocycloalkyl, heteroaralkyl, heteroalkylcycloalkyl, alkylcarbonyl; $X^1$ is selected from O, S, S—S, NH, or $NR^{14}$.

Wherein $R^9$ is independently H, —O—, —$OR^{14}$—, —OC(=O)$R^{14}$—, —OC(=O)$NHR^{14}$—, —OC(=O)$R^{14}SSR^{15}$—, OP(=O)($OR^{14}$)—, or $OR^{14}$OP(=O)($OR^{15}$), wherein $R^{14}$, $R^{15}$ are independently $C_1$~$C_8$ of alkyl, heteroalkyl; $C_2$~$C_8$ of alkenyl, alkynyl, heterocyclic, carbocyclic; $C_3$~$C_8$ of aryl, cycloalkyl, alkylcycloalkyl, heterocycloalkyl, heteroalkylcycloalkyl, heteroaralkyl, alkylcarbonyl.

Wherein $R^{11}$ is independently H, $R^{14}$, —$R^{14}C(=O)R^{16}$, —$R^{14}X^2R^{16}$, —$R^{14}C(=O)X^2$, wherein $X^2$ is —O—, —S—, —NH—, —N($R^{14}$)—, —O—$R^{14}$—, —S—$R^{14}$—, —S(=O)—$R^{14}$—, or —$NHR^{14}$—; $R^{14}$ is $C_1$~$C_8$ of alkyl, heteroalkyl; $C_2$~$C_8$ of alkenyl, alkynyl, heterocyclic, carbocyclic; $C_3$~$C_8$ of aryl, cycloalkyl, alkylcycloalkyl, heterocycloalkyl, heteroalkylcycloalkyl, heteroaralkyl, alkylcarbonyl; $R^{16}$ is H, OH, $R^{14}$ or one to four amino acid units;

Wherein $R^{12}$ is independently $R^{14}$, —O—, —S—, —N—, =N—, =NNH—, —NH($R^{14}$)—, —$OR^{14}$—, —C(O)O—C(O)$OR^{16}$—, C(O)NH—, C(O)$NHR^{14}$, —$SR^{14}$—, —S(=O)$R^{14}$—, —P(=O)($OR^{16}$)—, —OP(=O)($OR^{16}$)—, —$CH_2$OP(=O)($OR^{16}$)—, —$SO_2R^{16}$—. $R^{14}$ is independently $C_1$~$C_8$ of alkyl, heteroalkyl; $C_2$~$C_8$ of alkenyl, alkynyl, hetero-cyclic, carbocyclic; $C_3$~$C_8$ of aryl, cycloalkyl, alkylcycloalkyl, heterocycloalkyl, heteroaralkyl, heteroalkylcycloalkyl, alkylcarbonyl. $R^{16}$ is H, OH, $R^{14}$ or one to four amino acid units;

Wherein $R^{13}$ is $C_1$~$C_{10}$ of alkyl, heteroalkyl, alkyl acid, alkyl amide, alkyl amine, or Ar; Ar refers to a aromatic or hetero aromatic group, composed of one or several rings, comprising four to ten carbon, preferentially four to six

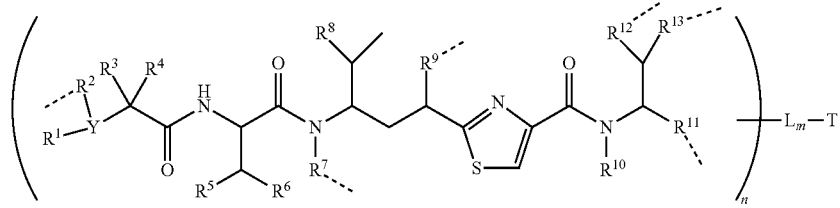

(I)

and pharmaceutical acceptable salts and solvates thereof

Wherein T is a targeting or binding ligand; L is a releasable linker; - - - - - is a linkage bond that L connects to a molecule inside the round bracket independently; n is 1~20 and m is 1~10.

Inside the round bracket (parentheses) is a potent antimitotic agent/drug wherein $R^1$, $R^2$, $R^3$, and $R^4$ are independently $C_1$~$C_8$ of alkyl, heteroalkyl; $C_2$~$C_8$ of heterocyclic, carbocyclic, alkylcycloalkyl, heterocycloalkyl, $C_3$~$C_8$ of aryl, Ar-alkyl, heteroalkylcycloalkyl, alkylcarbonyl; or two R's, such as $R^1R^2$, $R^2R^3$, $R^3R^4$, $R^5R^6$ and $R^{12}R^{13}$ can be 3~7 members of a carbocyclic, cycloalkyl, or heterocyclic, heterocycloalkyl ring system; Y is N or CH; In addition, $R^1$, $R^3$, and $R^4$ can be H; and $R^2$ can be absent.

carbon atoms. The term of hetero aromatic group refers one or several carbon on aromatic group, preferentially one, two or three carbon atoms are replaced by O, N, Si, Se, P or S, preferentially O, S, N. The term aryl or Ar also refers to a aromatic group, wherein one or several H atoms are replaced independently by $R^{17}$, F, Cl, Br, I, $OR^{16}$, $SR^{16}$, $NR^{16}R^{17}$, N=$NR^{16}$, N=$R^{16}$, $NR^{16}R^{17}$, $NO_2$, $SOR^{16}R^{17}$, $SO_2R^{16}$, $SO_3R^{16}$, $OSO_3R^{16}$, $PR^{16}R^{17}$, $POR^{16}R^{17}$, $PO_2R^{16}R^{17}$, OP(O)($OR^{17}$)$_2$, $OCH_2$OP(O)($OR^{17}$)$_2$, PO($OR^{16}$)($OR^{17}$), OC(O)OP(O)($OR^{17}$)$_2$, OP(O)($OR^{17}$)OP(O)($OR^{17}$)$_2$, OC(O)$R^{17}$ or OC(O)$NHR^{17}$, wherein $R^{16}$, $R^{17}$ are independently H, $C_1$~$C_8$ of alkyl, heteroalkyl; $C_2$~$C_8$ of alkenyl, alkynyl, heterocyclic, carbocyclic; $C_3$~$C_8$ of aryl, cycloalkyl, alkylcycloalkyl, heterocycloalkyl, heteroalkylcycloalkyl, heteroaralkyl, alkylcarbonyl or $C_4$~$C_{12}$ glycosides, or pharmaceutical salts.

In addition, $R^{12}$ can be H when $R^{10}$ is not H, or when $R^{13}$ is:

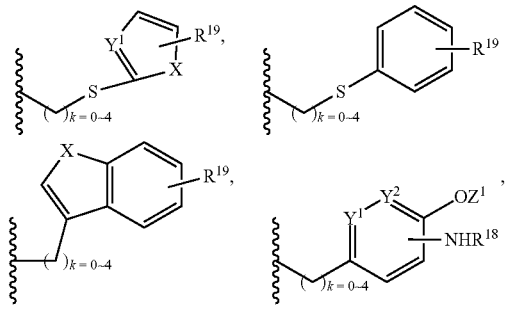

wherein $Z^1$ is H, $CH_2OP(O)(OR^{18})_2$, $PO(OR^{18})_2$, $C(O)OP(O)(OR^{18})_2$, $C(O)R^{18}$, $C(O)NHR^{18}$, $SO_2(OR^{18})$, $C_4$~$C_{12}$ glycosides or $C_1$~$C_8$ of alkyl, carboxyalkyl, heterocyclic; $R^{18}$ is H, $C_1$~$C_8$ of alkyl, carboxyalkyl, heteroalkyl; $C_2$~$C_8$ of alkenyl, alkynyl, heterocyclic; $C_3$~$C_8$ of aryl, alkylcarbonyl; $R^{19}$ is H, OH, $NH_2$, $OSO_2(OR^{18})$, $XCH_2OP(O)(OR^{18})_2$, $XPO(OR^{18})_2$, $XC(O)R^{18}$, $XC(O)NHR^{18}$, $C_1$~$C_8$ of alkyl, carboxyalkyl, carboxylic acid derivative; $C_2$~$C_8$ of alkenyl, alkynyl, heterocyclic; $C_3$~$C_8$ of aryl, alkylcarbonyl; or pharmaceutical salts; X is O, S, NH; $Y^1$ and $Y^2$ are N or CH respectively.

Or $R^{12}$ can be H when $R^{11}$ is:

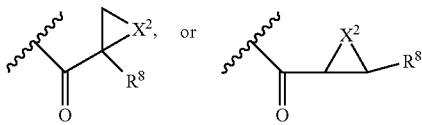

$X^2$ is O, S, N—$R^8$; $R^8$ is H, $C_1$~$C_6$ of alkyl or heteroalkyl.

In another embodiment, the linker L of the potent antimitotic agent-binding molecule conjugates has the formula: -Ww-(Aa)r-Vv-; wherein: -W- is a Stretcher unit; w is 0 or 1; each -Aa- is independently an Amino Acid unit; r is independently an integer ranging from 0 to 12; -V- is a Spacer unit; and v is 0, 1 or 2. The Stretcher unit W may independently contain a self-immolative spacer, peptidyl units, a hydrazone bond, disulfide or thioether bonds.

In another embodiment, the cell-surface binding molecule T may be of any kind presently known, or which become known cell binding ligands, such as peptides and non-peptides. Generally the binding molecule T is an antibody; a single chain antibody; an antibody fragment that binds to the target cell; a monoclonal antibody; a single chain monoclonal antibody; or a monoclonal antibody fragment that binds the target cell; a chimeric antibody; a chimeric antibody fragment that binds to the target cell; a domain antibody; a domain antibody fragment that binds to the target cell; adnectins that mimic antibodies; DARPins; a lymphokine; a hormone; a vitamin; a growth factor; a colony stimulating factor; or a nutrient-transport molecule (a transferrin); a binding peptide, or protein, or antibody, or small molecule attached on albumin, polymers, dendrimers, liposomes, nanoparticles, vesicles, (viral) capsids. Preferably the binding molecule T is a monoclonal antibody.

In yet another aspect, a compound of formula I~VII or a pharmaceutically acceptable salt or solvate thereof is used for treating cancer, an autoimmune disease or an infectious disease in a human or an animal.

4. A BRIEF DESCRIPTION OF THE DRAWINGS

Conditions: a. $CuSO_4$, $H_2SO_4$, Acetone, 95%; b: DIBAL-H, THF/Tol, −78° C., 95%; c: $NH_2OH$, $NaHCO_3$, $CH_3OH/H_2O$; d: isobutyraldehyde, $MgSO_4$, $CH_2Cl_2$, 85% (2 steps); e: (2R)—N-(acryloyl)bornane-10,2-sultams (74), 40° C., 48 h, $CH_2Cl_2$ 83%; f: LiOH, THF/$H_2O$, 86%; g: $HClO_4$, $CH_3CN/H_2O$, 98%; h: $BOC_2O$, $Na_2CO_3$, THF/$H_2O$, 95%; i: L-(S)-Tr-cysteine methyl ester, EDC, $CH_2Cl_2$, 85%; j: $Ph_3P$=O, $Tf_2O$, $CH_2Cl_2$; k: $MnO_2$, $CH_2Cl_2$, 76% (2 steps); l: $Mo(CO)_6$, $CH_3CN/H_2O$, 87%; m: $Ac_2O$, Pyr., 95%; n: NaH, THF, $CH_3I$, 85%; o): $HOSnMe_3$, $ClCH_2CH_2Cl$, 80° C.; 95%.

Figure 1:
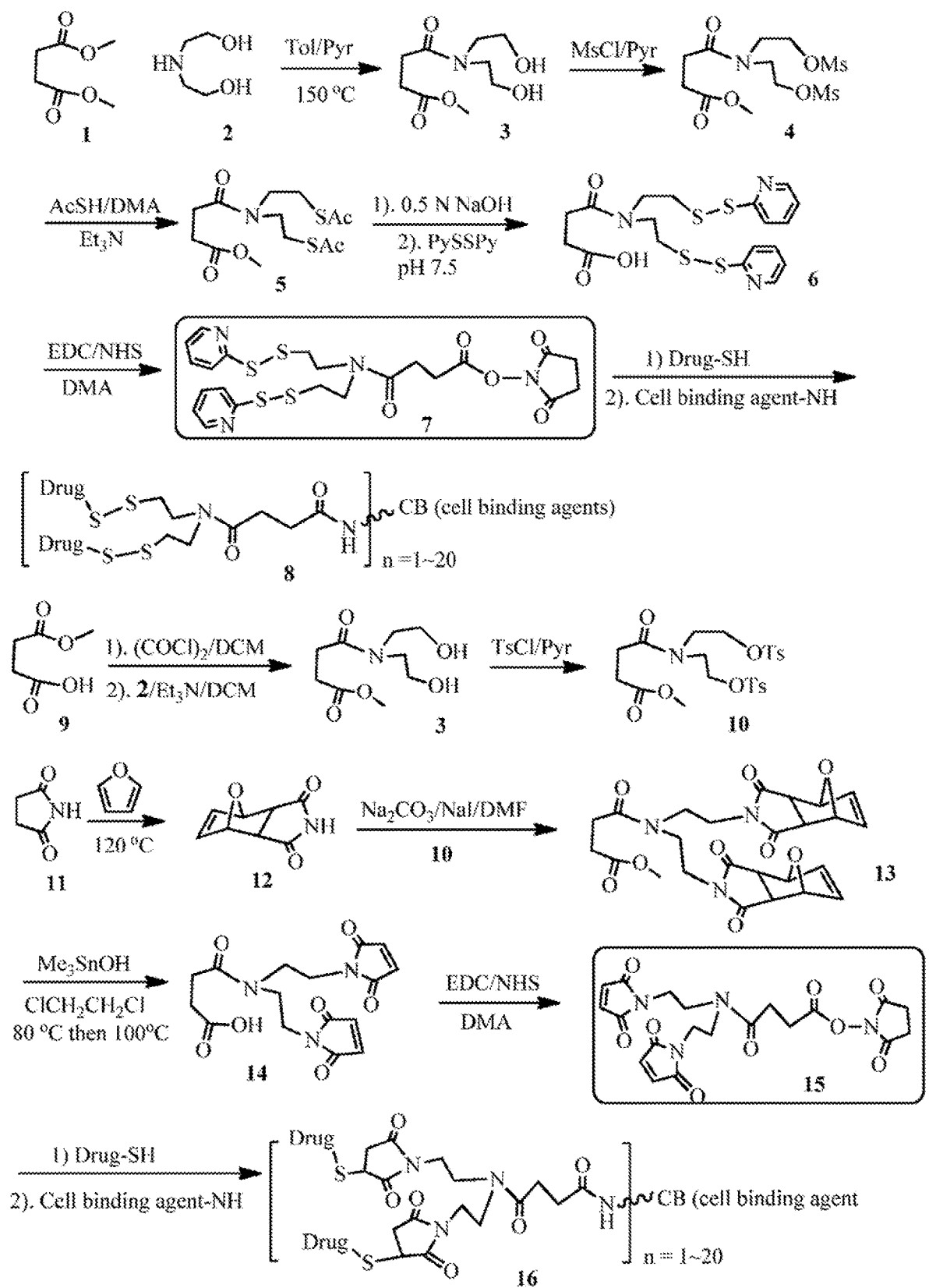
FIG. 1 shows the synthesis of branched linkers for conjugation of drugs to cell binding agents.
Figure 2:
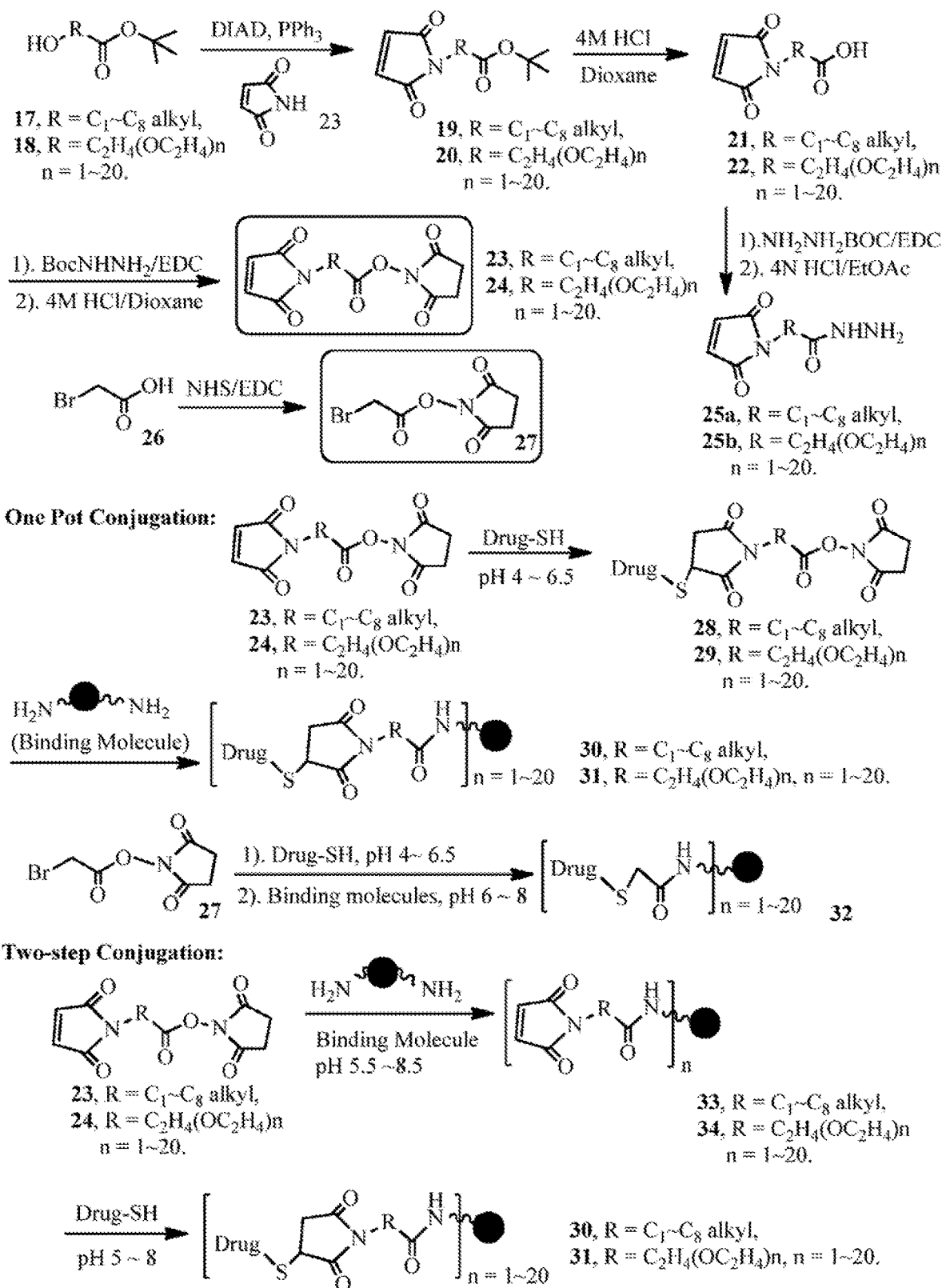
FIG. 2 shows the synthesis of maleimido linkers and their use for the drug-binding molecule conjugation.
Figure 3:
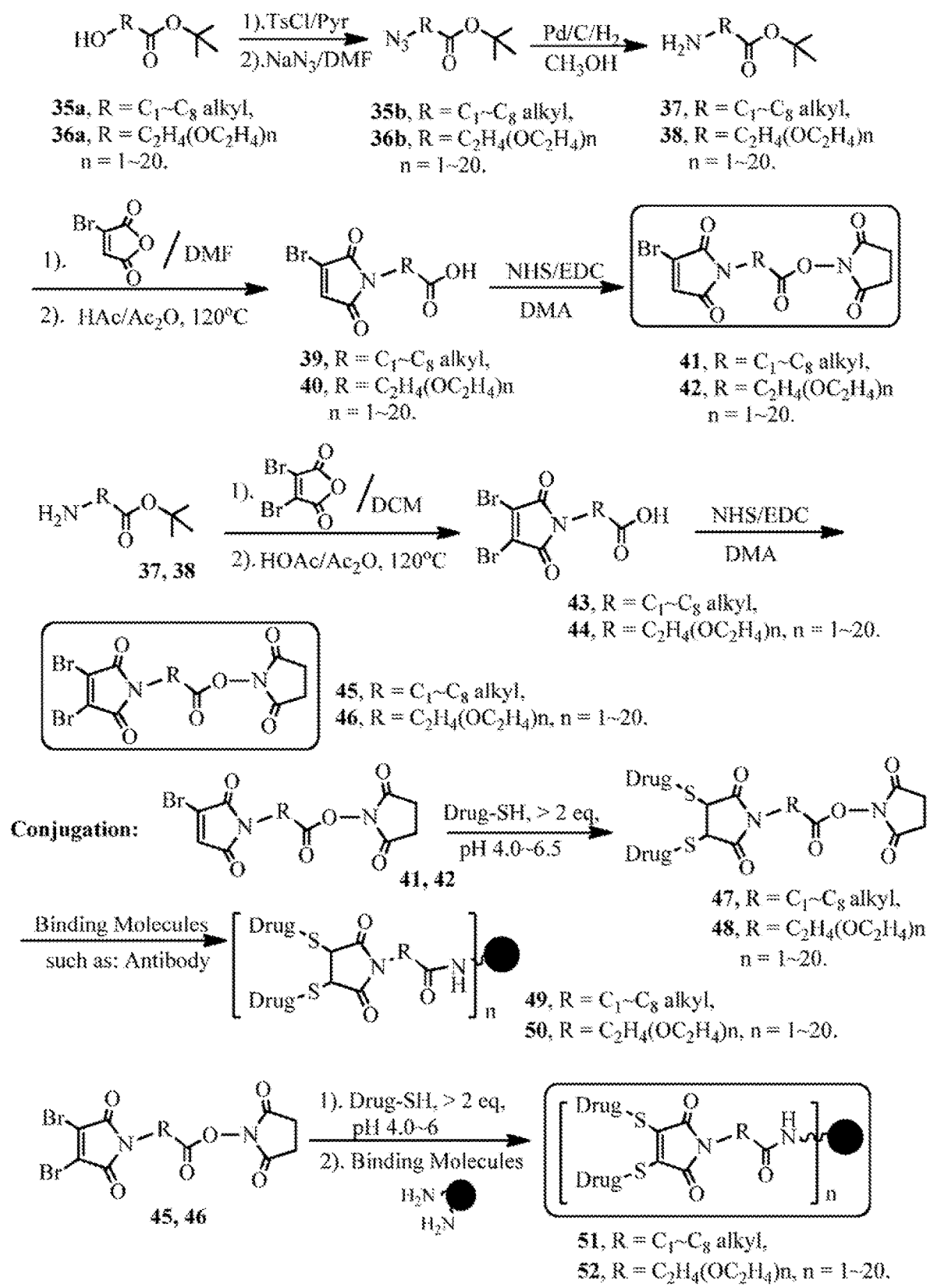
FIG. 3 shows the synthesis of bromomaleimido and dibromomaleimido linkers and their uses for the drug-binding molecule conjugation.
Figure 4:
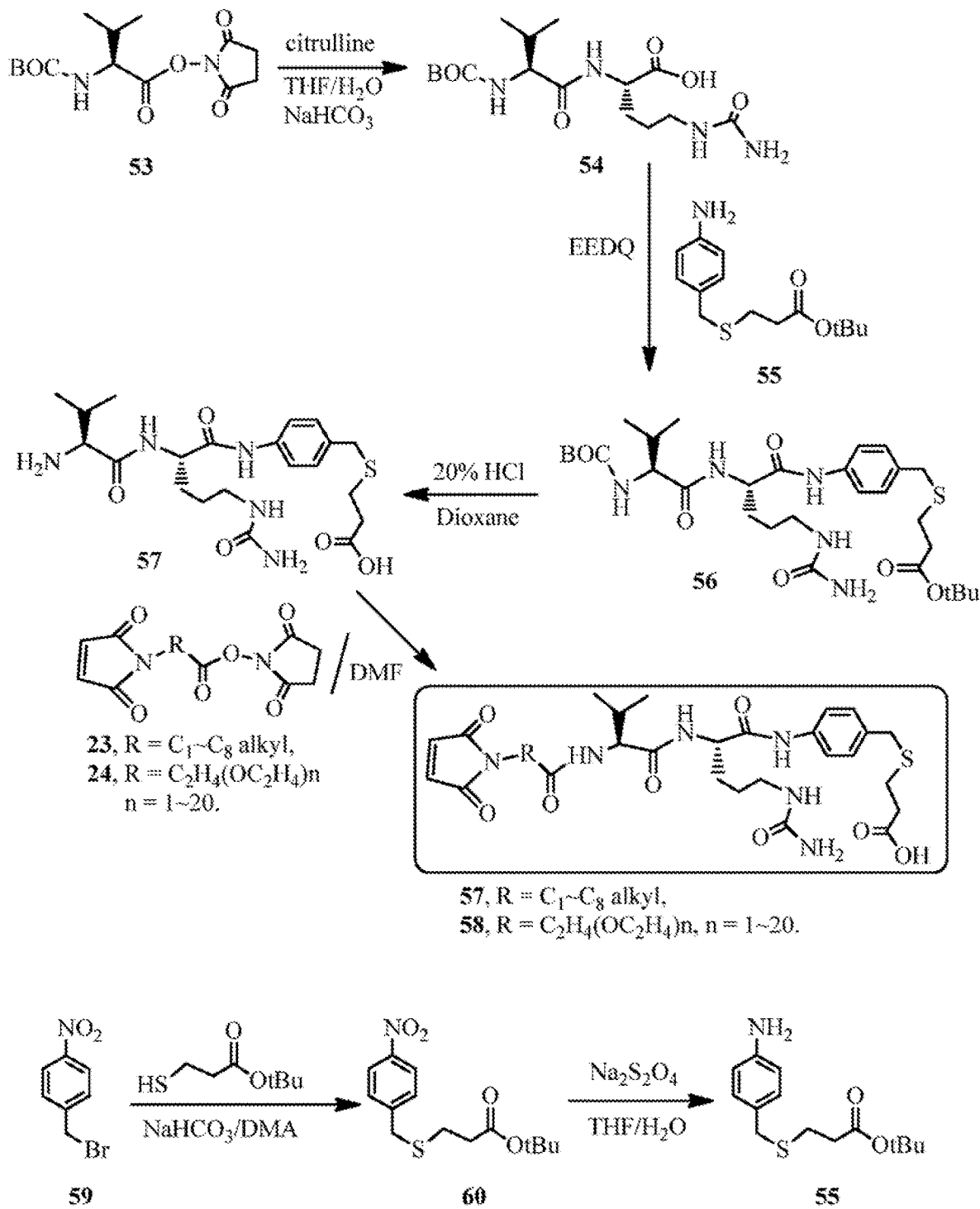
FIG. 4 shows the synthesis of amino acid (Val-Cit) linkers for the conjugation antimitotic agents with a cell surface binding ligand.
Figure 5:
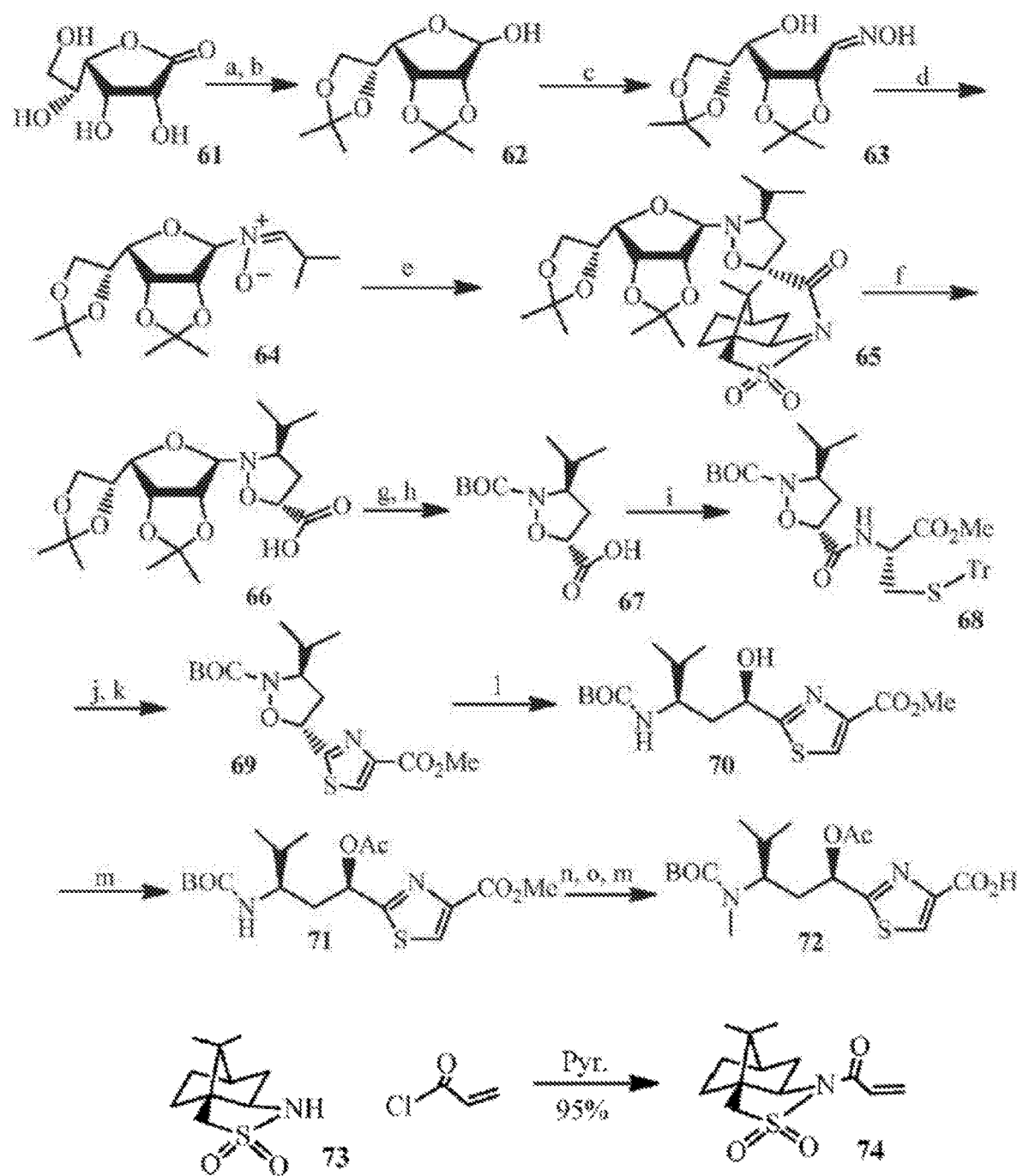
FIG. 5 shows the synthesis of Tuv component of the antimitotic agents.
Figure 6:
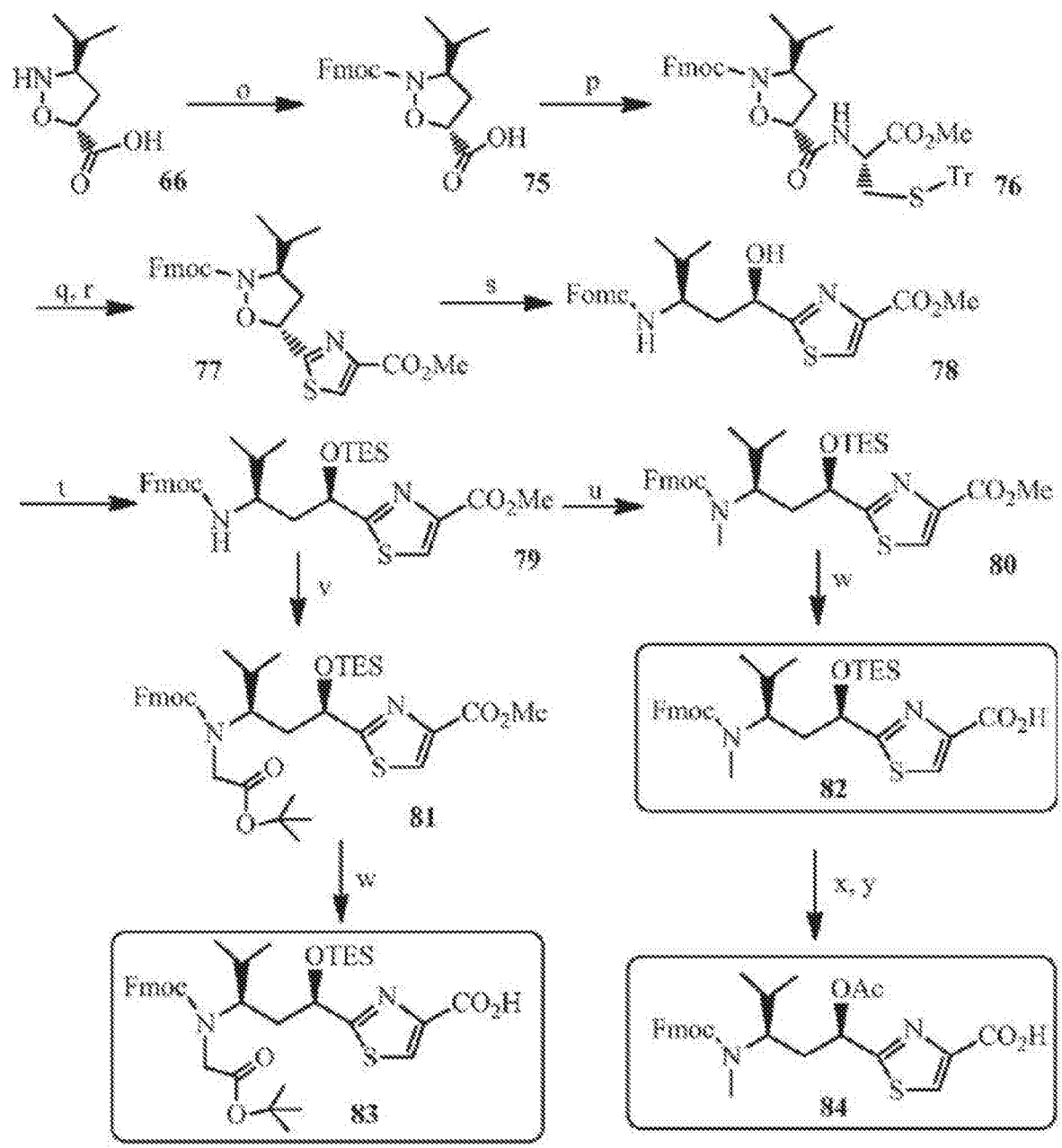

FIG. 6 shows the synthesis of Tuv components of the antimitotic agents.

Conditions: o): Fmoc-Cl, $NaHCO_3$, THF/$H_2O$, 95%; p): L-(S)-Tr-cysteine methyl ester, EDC, $CH_2Cl_2$, 87%; q): $Ph_3P$=O, $Tf_2O$, $CH_2Cl_2$; r): $MnO_2$, $CH_2Cl_2$, 76% (2 steps); s): $Mo(CO)_6$, $CH_3CN/H_2O$, 87%; t): TES-Cl, Pyr., 95%; u): NaH, THF, $CH_3I$, 90%; v): NaH, THF, $BrCH_2COOtBu$, 0° C., 87%; w): $HOSnMe_3$, $ClCH_2CH_2Cl$, 80° C., ~90%; x): $Bu_4NF$, THF; y): $Ac_2O$, Pyr. 81%.

Figure 7:
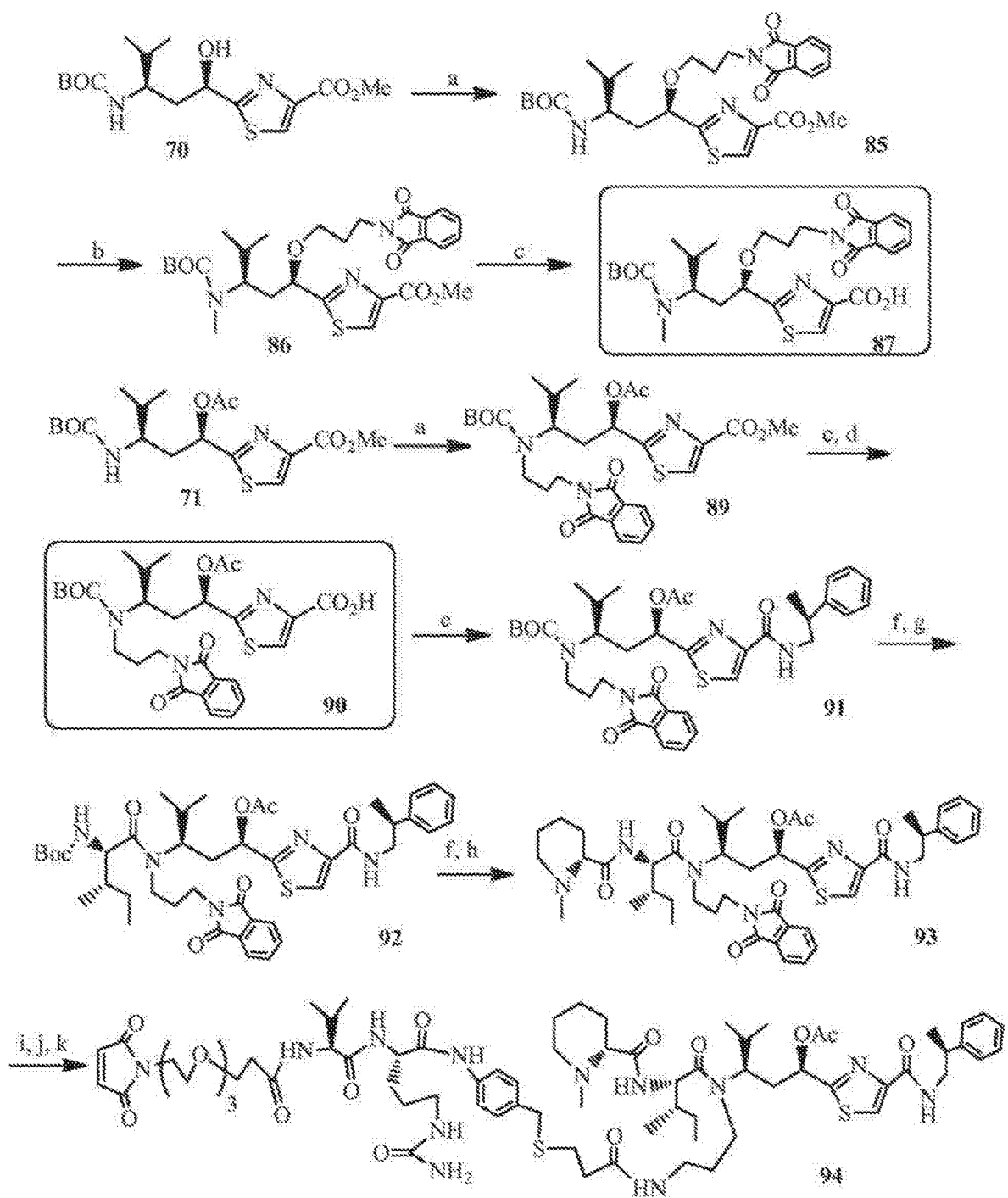

FIG. 7 shows the synthesis of Boc-Tuv moieties and a conjugatable antimitotic agent.

Conditions: a): NaH, THF, N-(4-Bromobutyl)phthalimide, NaI, ~83%; b); NaH, DMF, $CH_3I$, 90%; c): $HOSnMe_3$, $ClCH_2CH_2Cl$, 80° C., ~85%; d): $Ac_2O$, Pyr.; e): (R)-(+)-b-Methylphenethylamine, EDC, DMA, 85%; f): 4M HCl, dioxane; g); Boc-Ile-OH, PyBroP, DMAP, DMA, 78%; h): D-Mep, PyBroP/$CH_2Cl_2$, 81%; i): $NH_2NH_2$, DMA; j); 58 (n=3), EDC, DMA, k): $Ac_2O$, Pyr. 56%.

Figure 8:
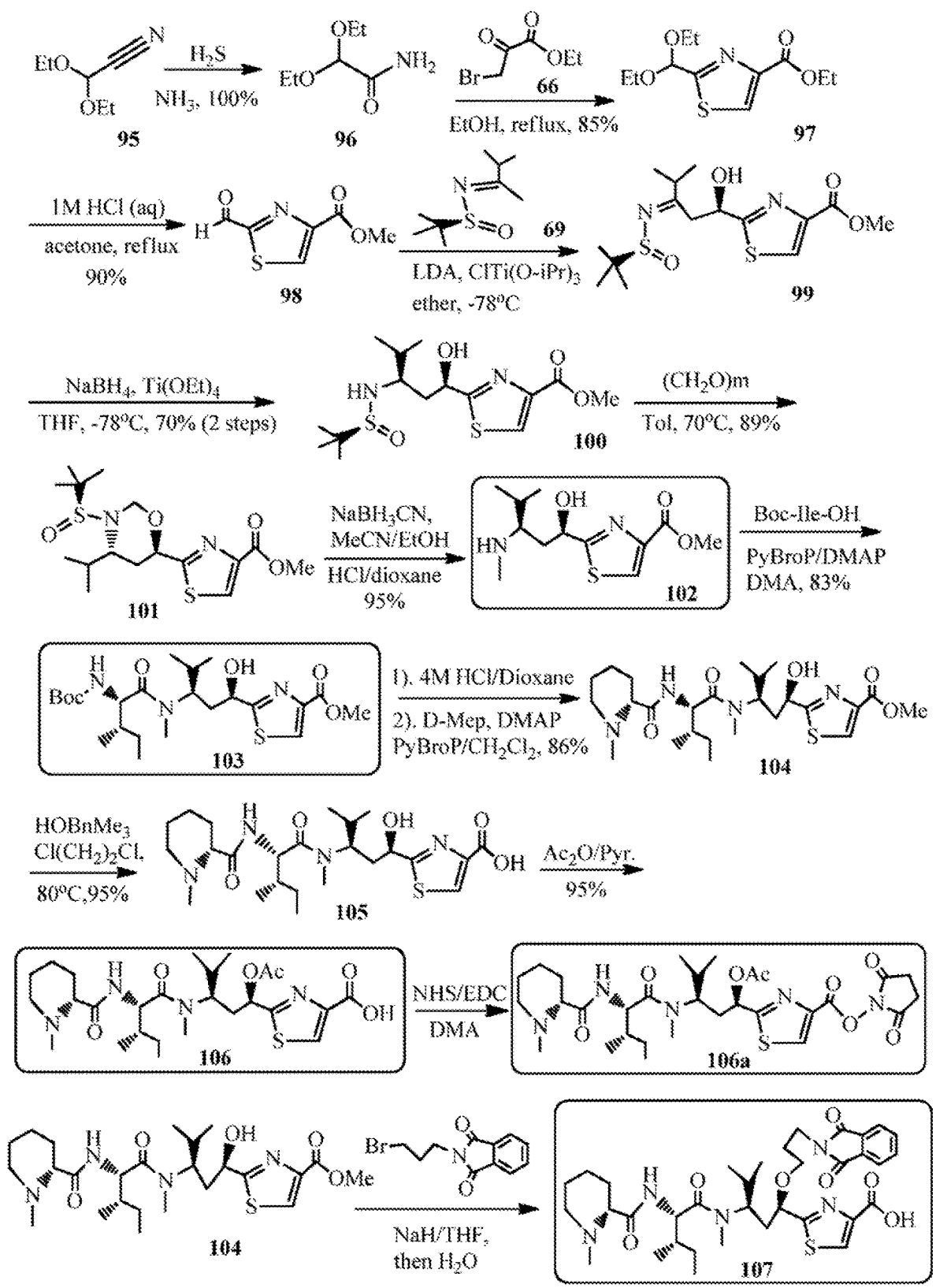

FIG. 8 shows the synthesis of Tuv, Ile-Tuv and Mep-Ile-Tuv moieties of the antimitotic agents.

Figure 9:
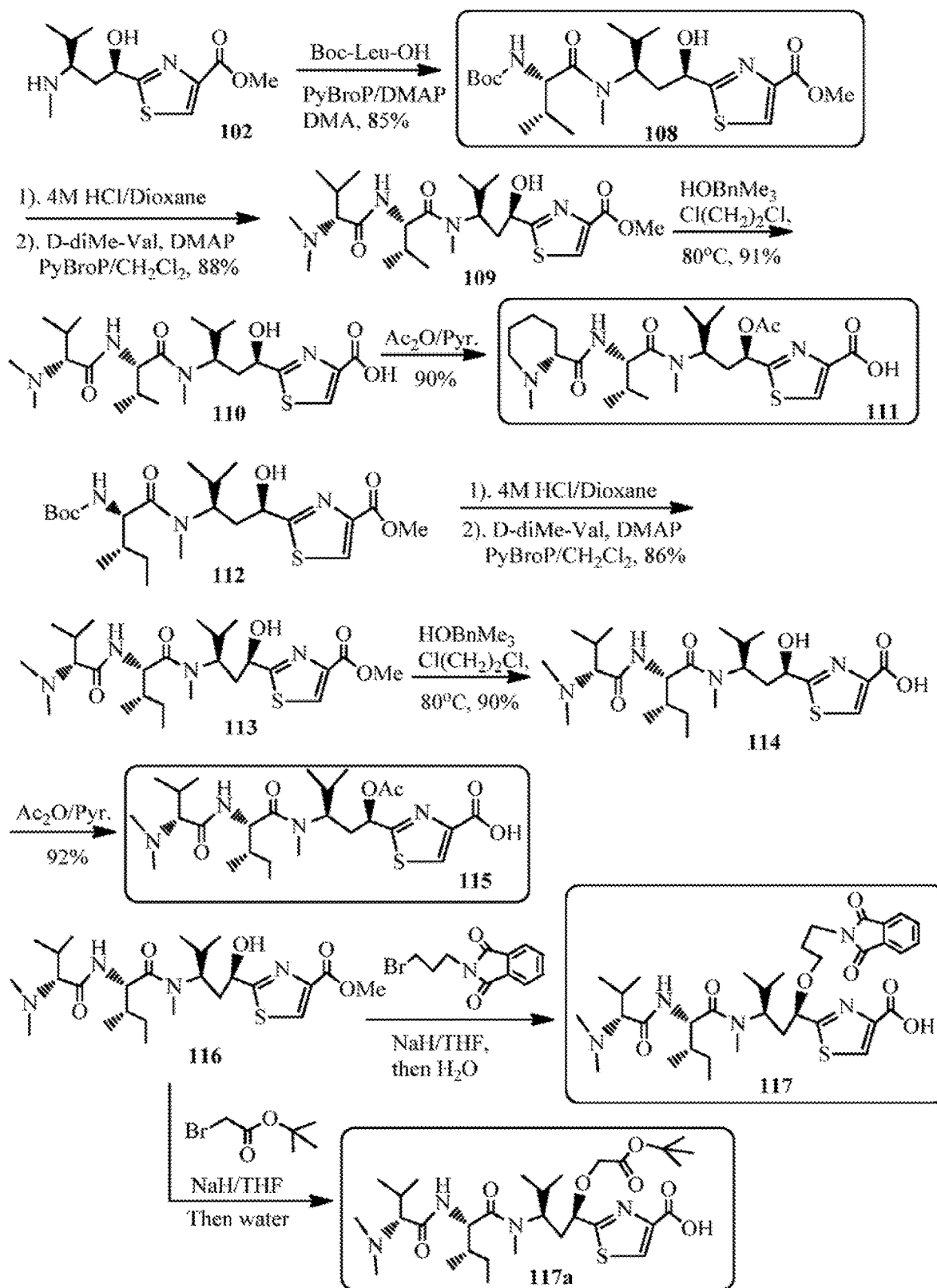

FIG. 9 shows the synthesis of Ile-Tuv, Mep-Leu-Tuv, Val-Ile-Tuv and Val-Ile-Tuv (O-alkyl) moieties of the antimitotic agents.

Figure 10:
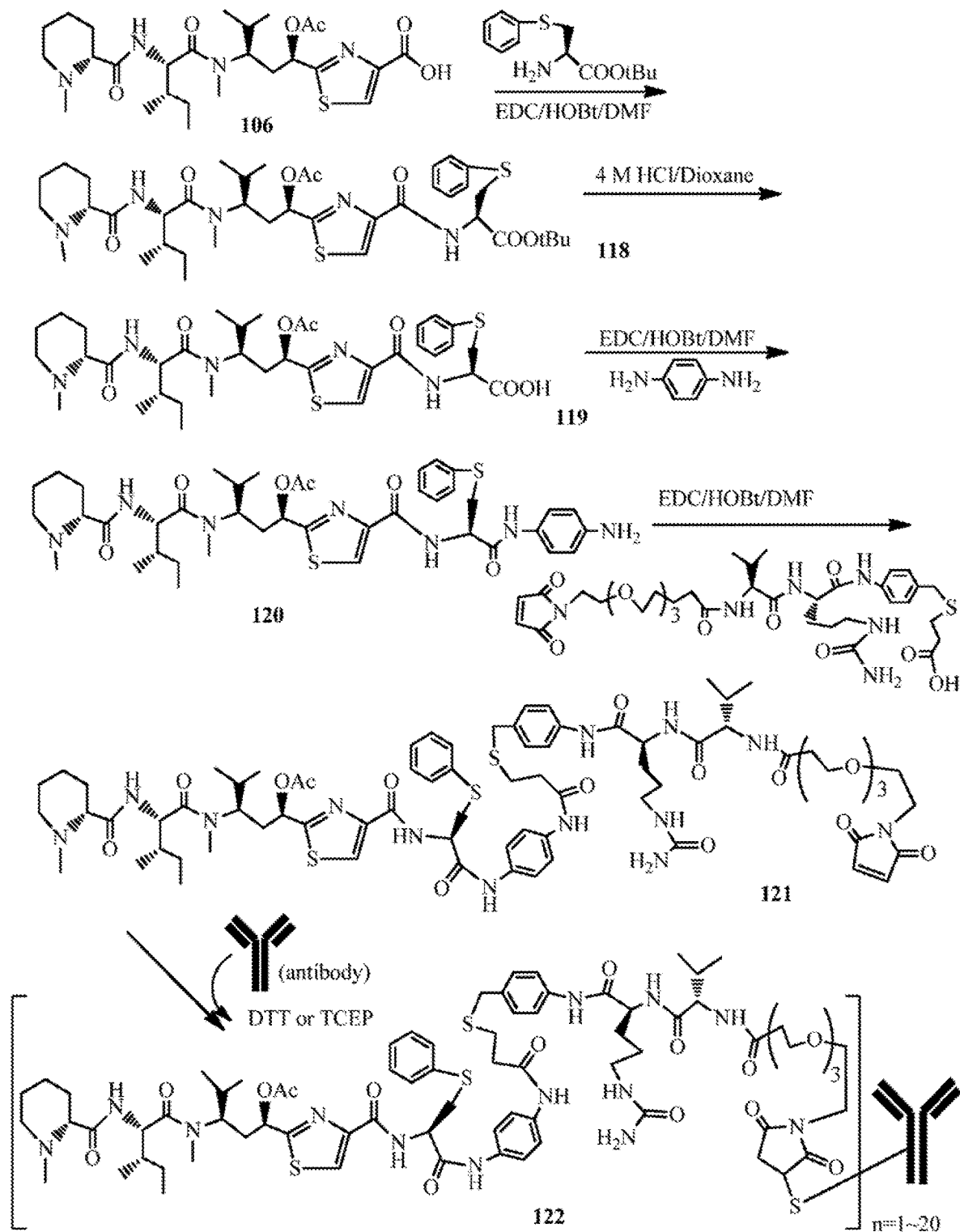

FIG. 10 shows the synthesis of a conjugatable antimitotic agent and its conjugation to an antibody.

Figure 11:
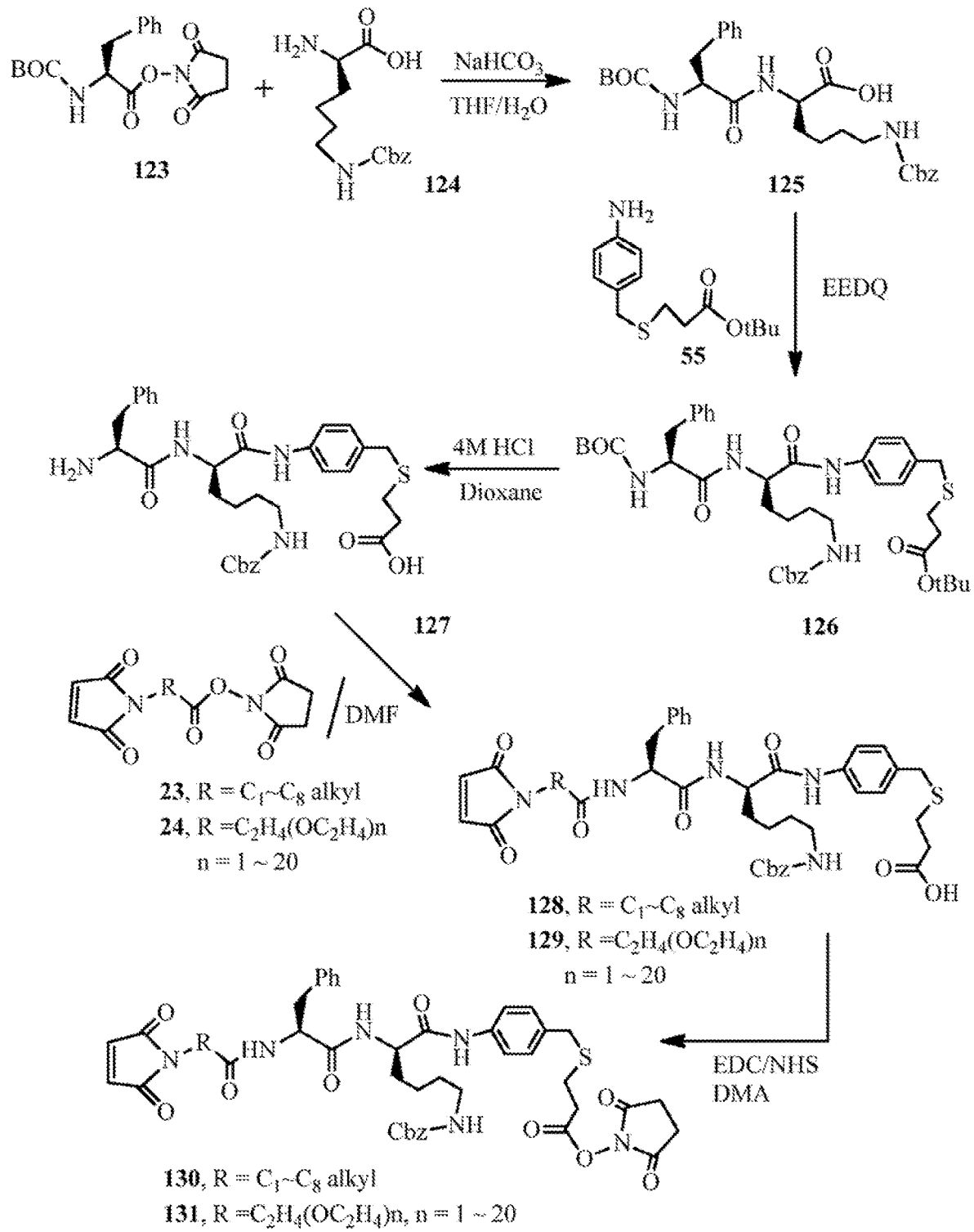

FIG. 11 shows the synthesis of amino acid (Phe-(D)Lys) linkers for conjugation of the antimitotic agents.

Figure 12:
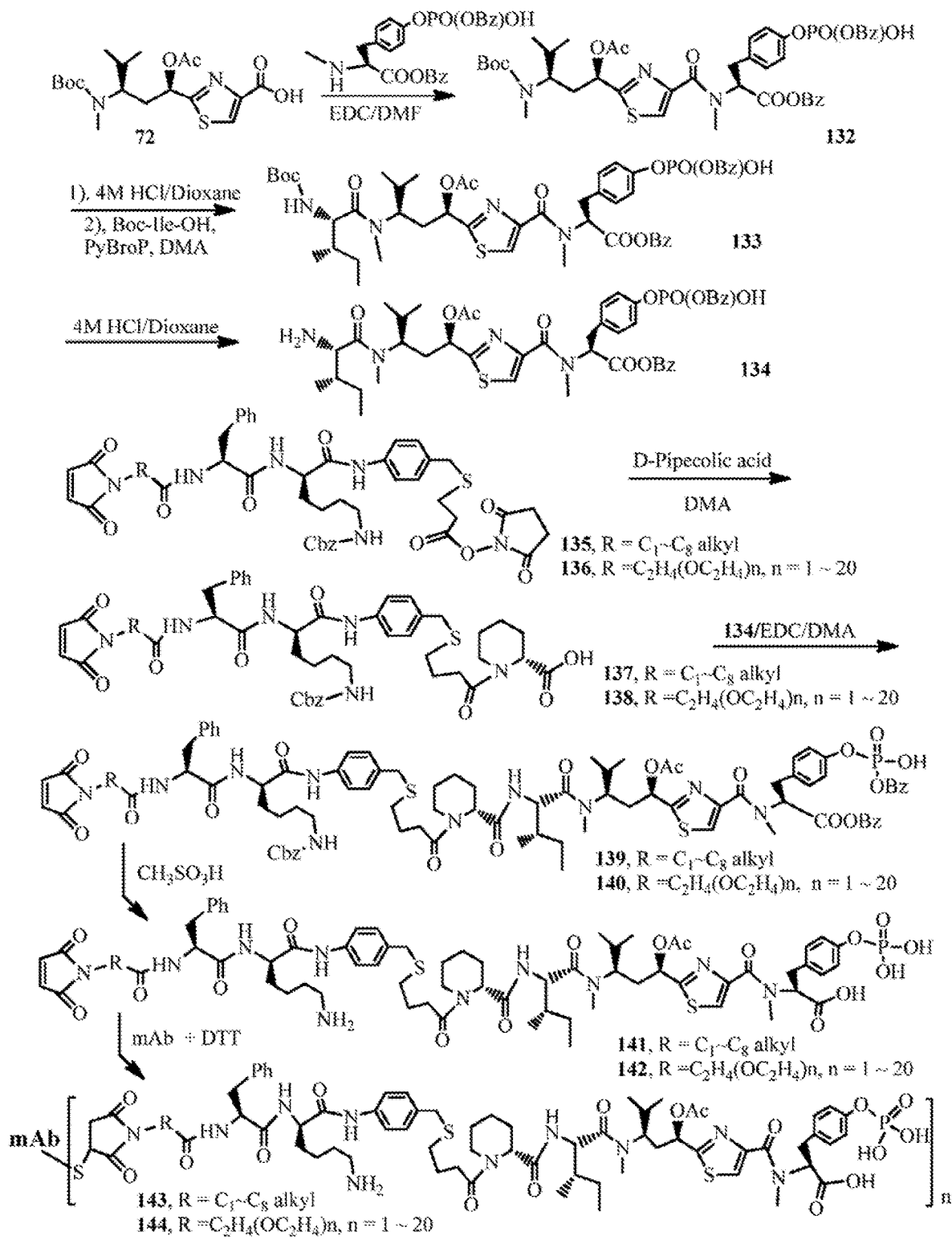

FIG. 12 shows the synthesis of antibody-antimitotic agent conjugates.

Figure 13:
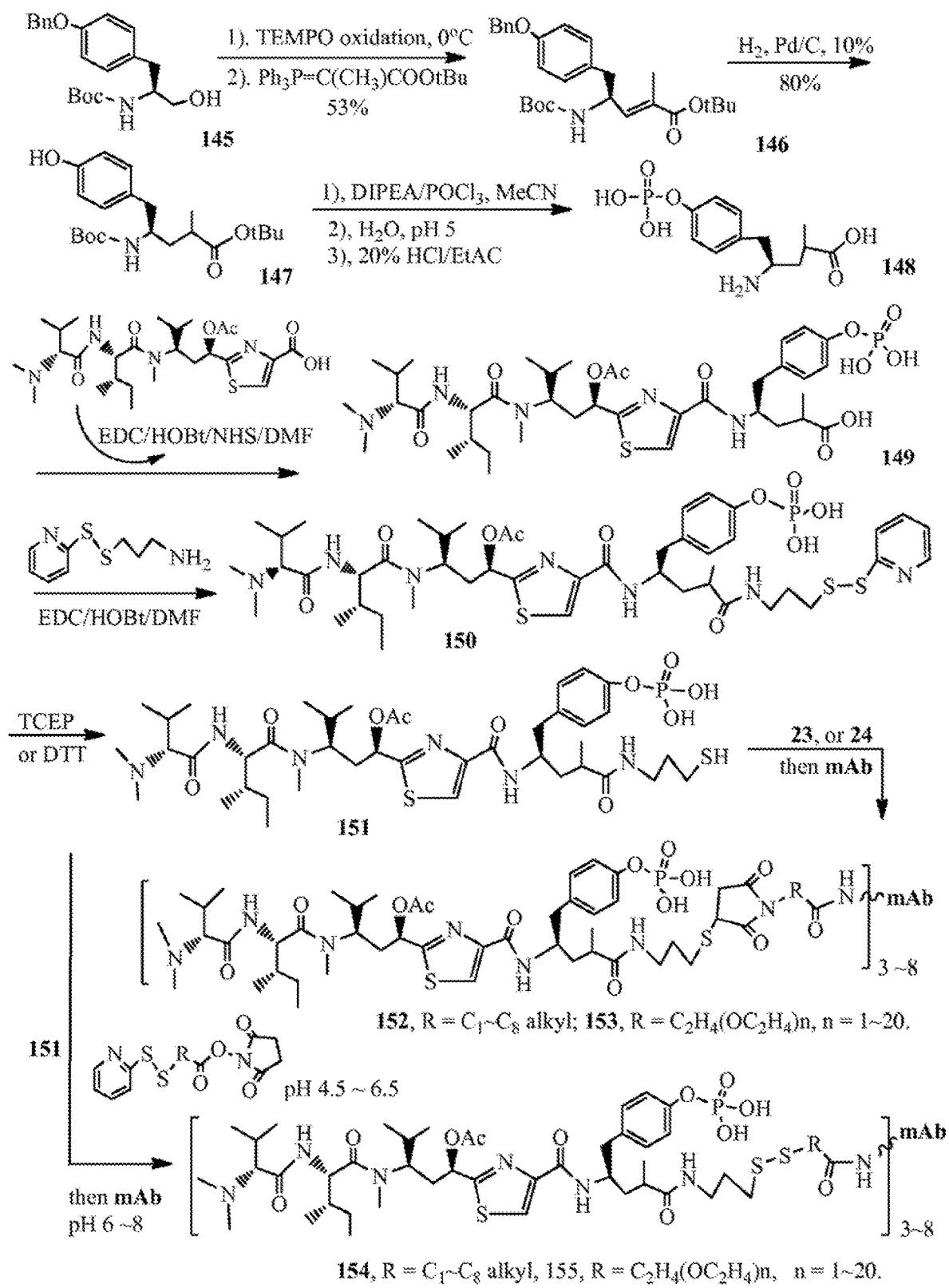

FIG. 13 shows the synthesis of antibody-antimitotic agent conjugates.

Figure 14:
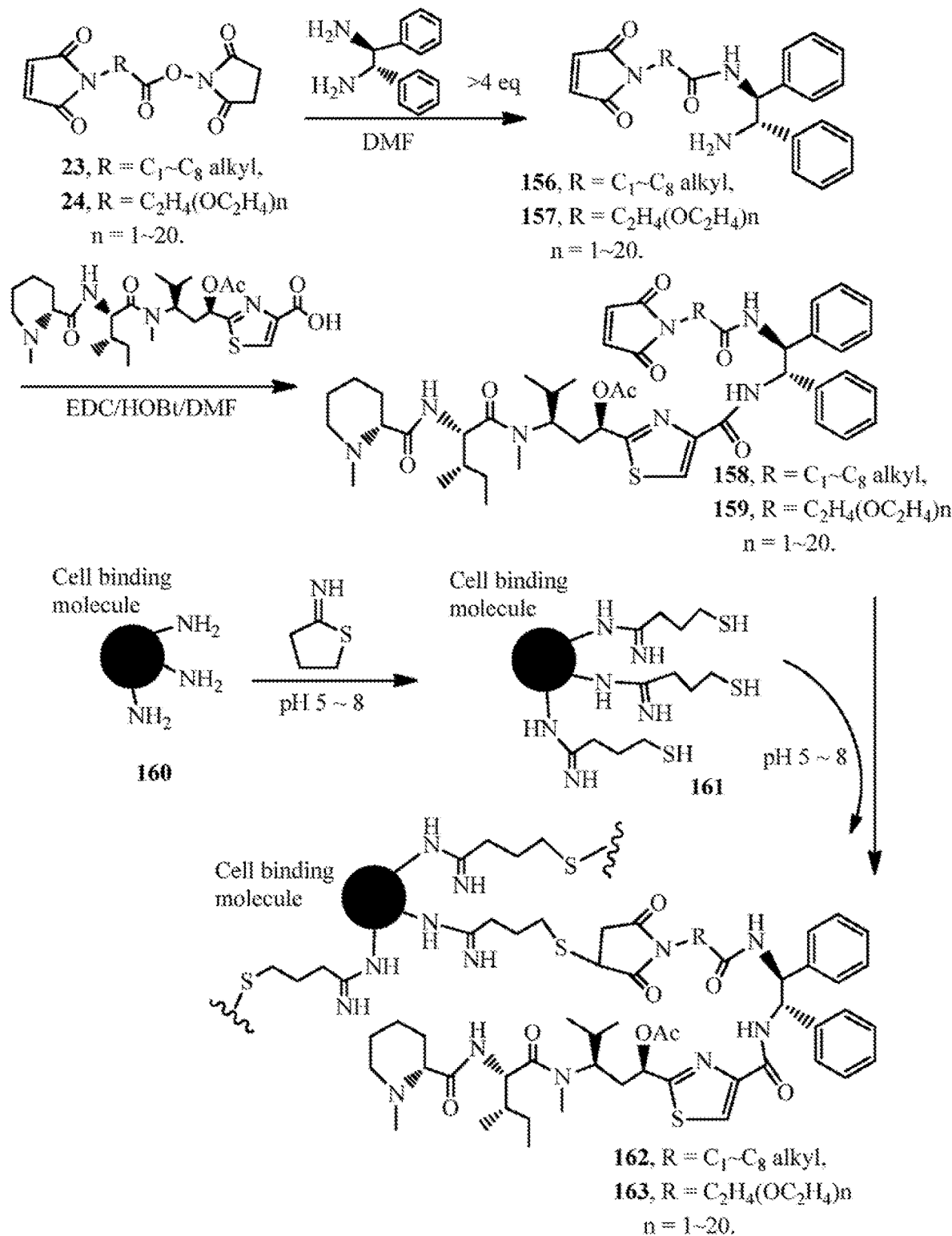

FIG. 14 shows the synthesis of the binding molecule-antimitotic agent conjugates.

Figure 15:
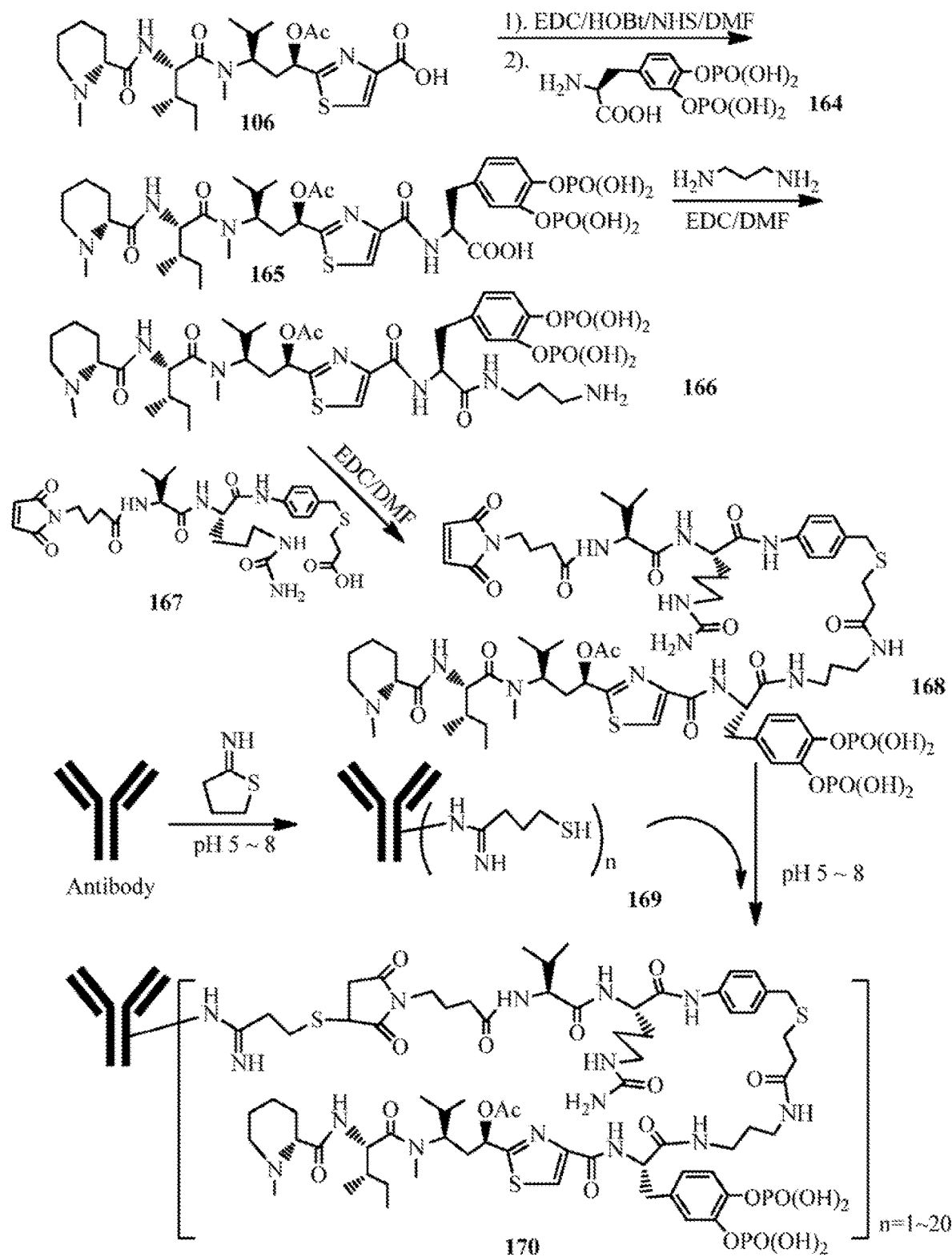

FIG. 15 shows the synthesis of a binding molecule-antimitotic agent conjugate.

Figure 16:
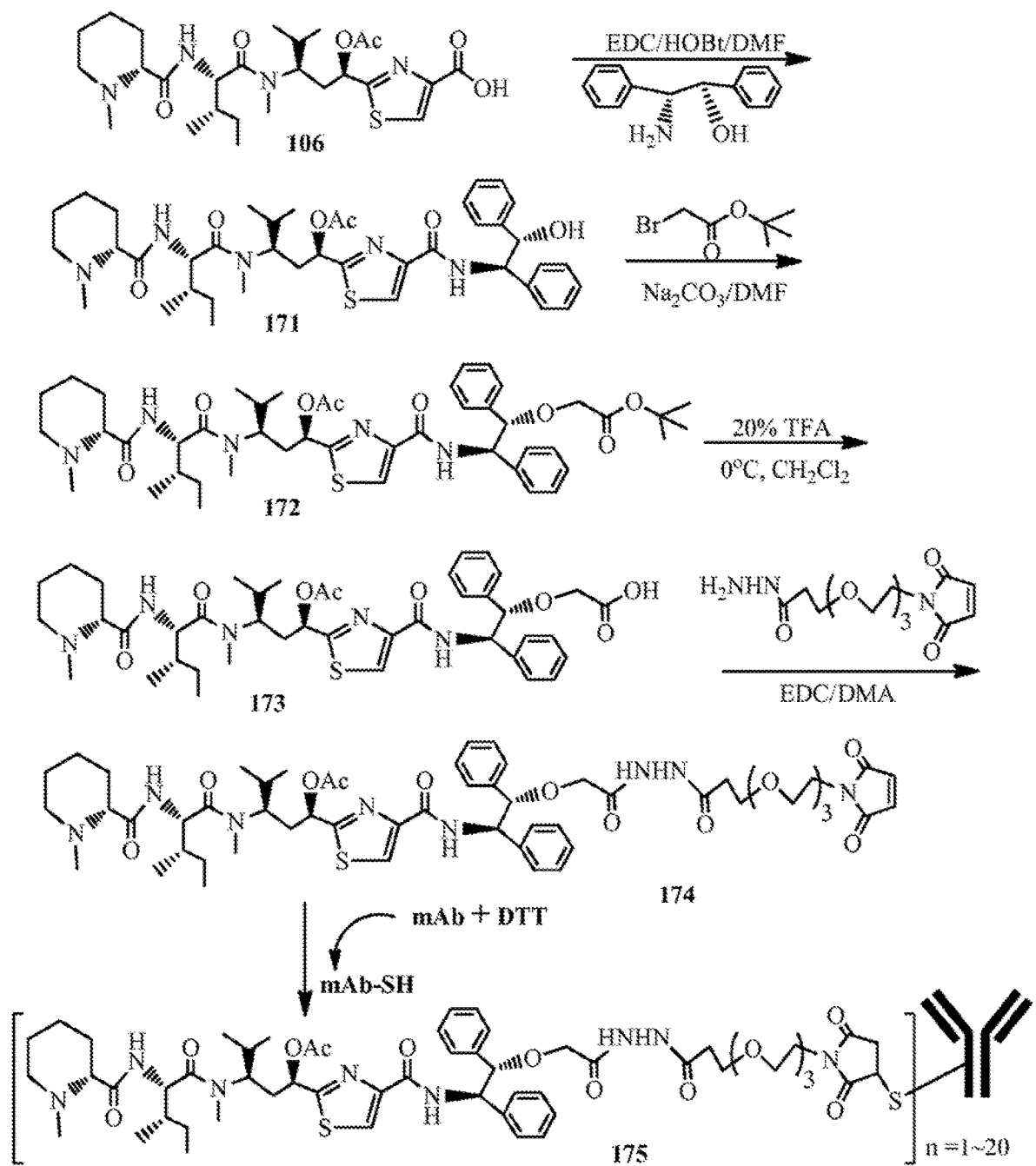

FIG. 16 shows the synthesis of an antibody-antimitotic agent conjugate.

Figure 17:
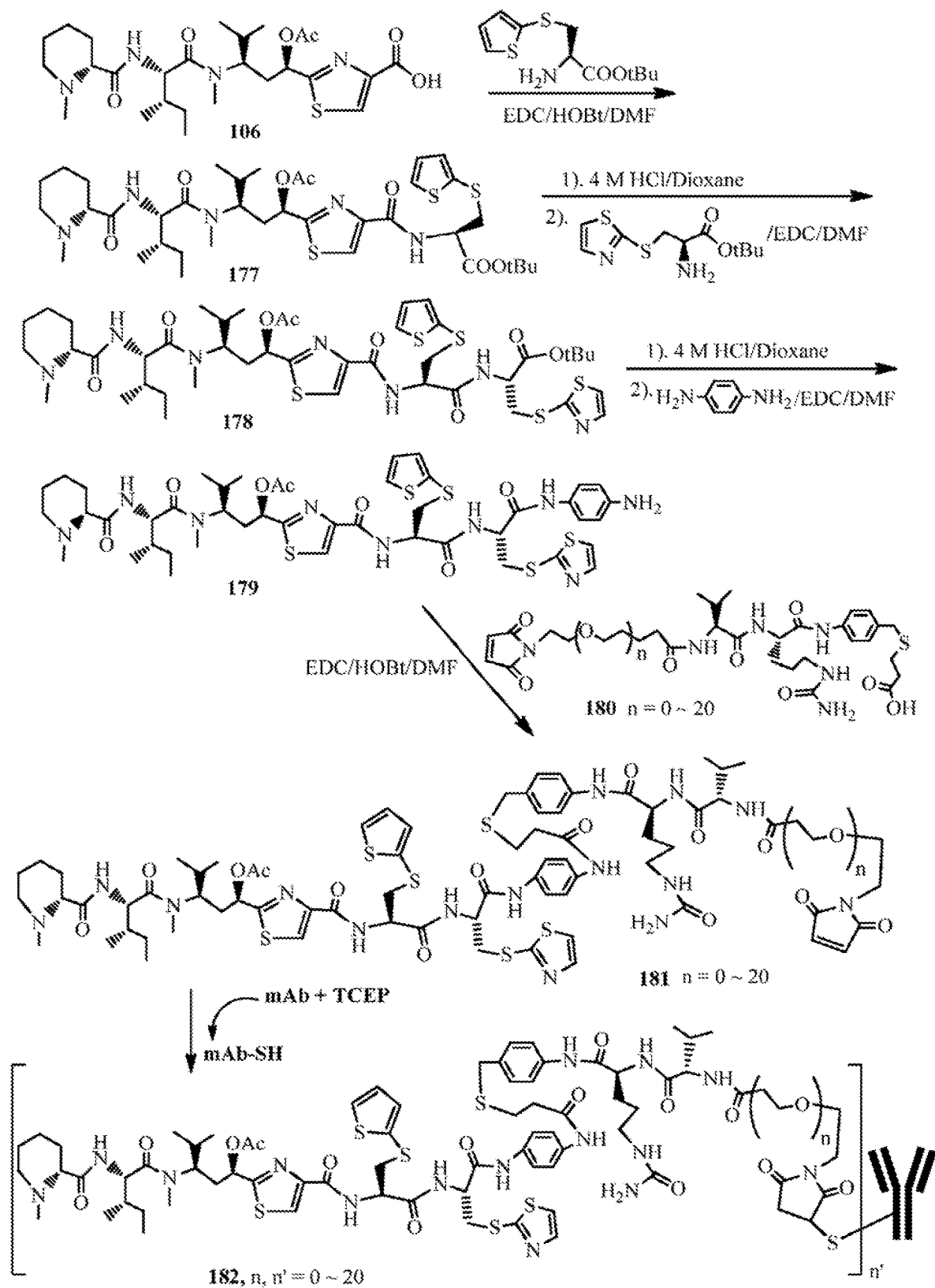

FIG. 17 shows the synthesis of an antibody-antimitotic agent conjugate.

Figure 18:
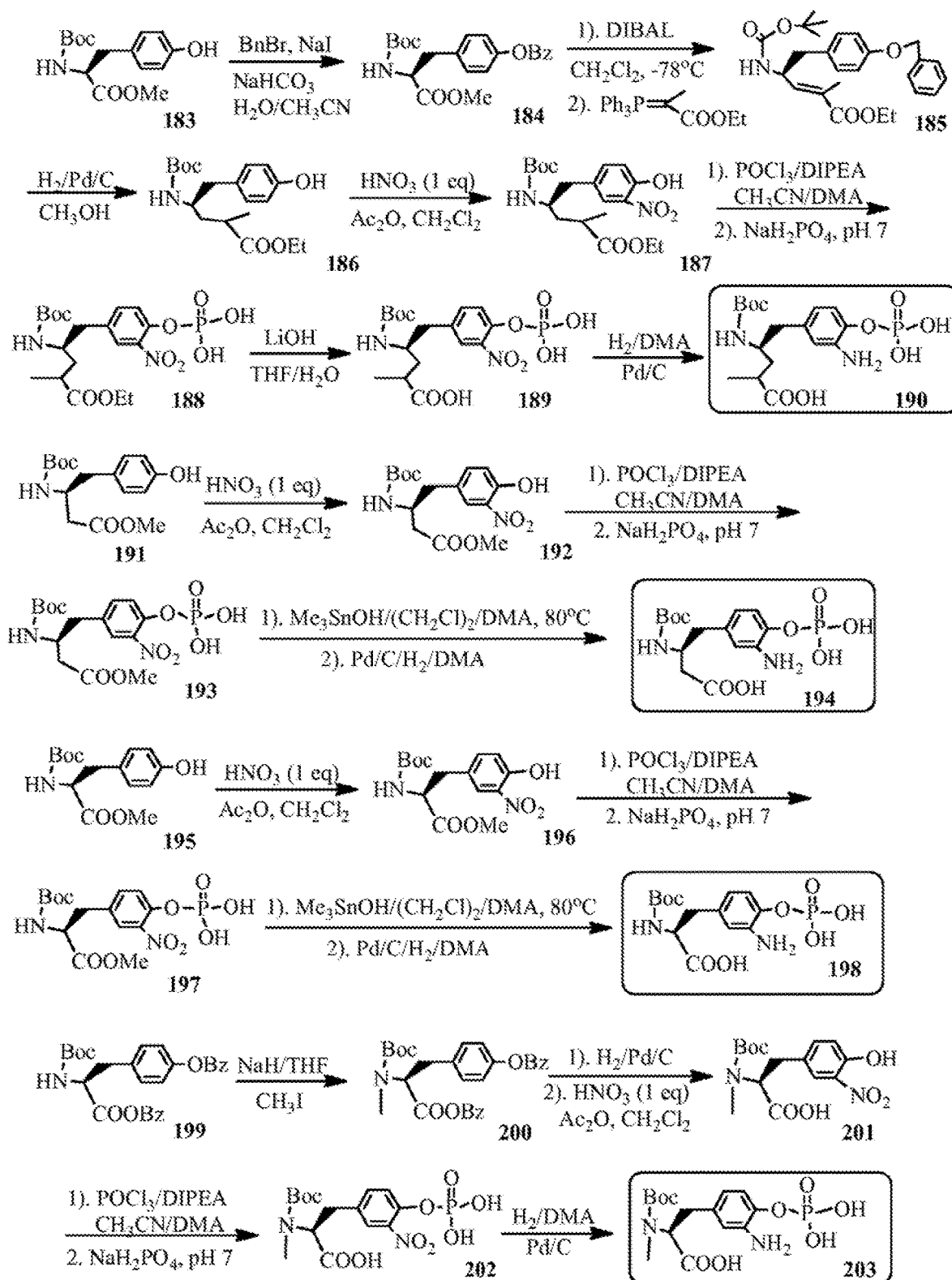

FIG. 18 shows the synthesis of hydrophilic Tut analogs for the synthesis of the hydrophilic (phosphate prodrug of) antimitotic agents.

Figure 19:
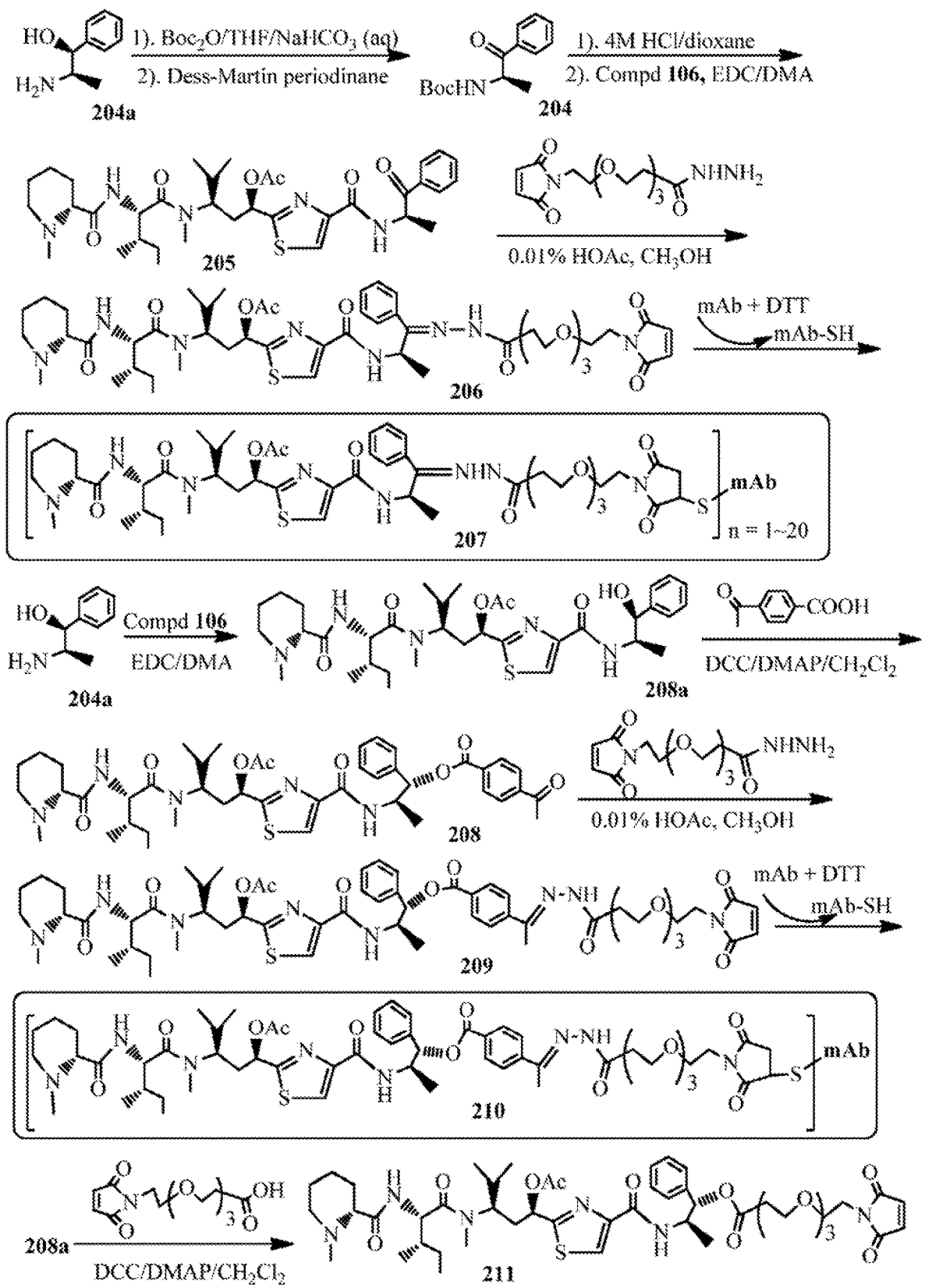

FIG. 19 shows the synthesis of the conjugates of the antimitotic agents with an antibody.

Figure 20:
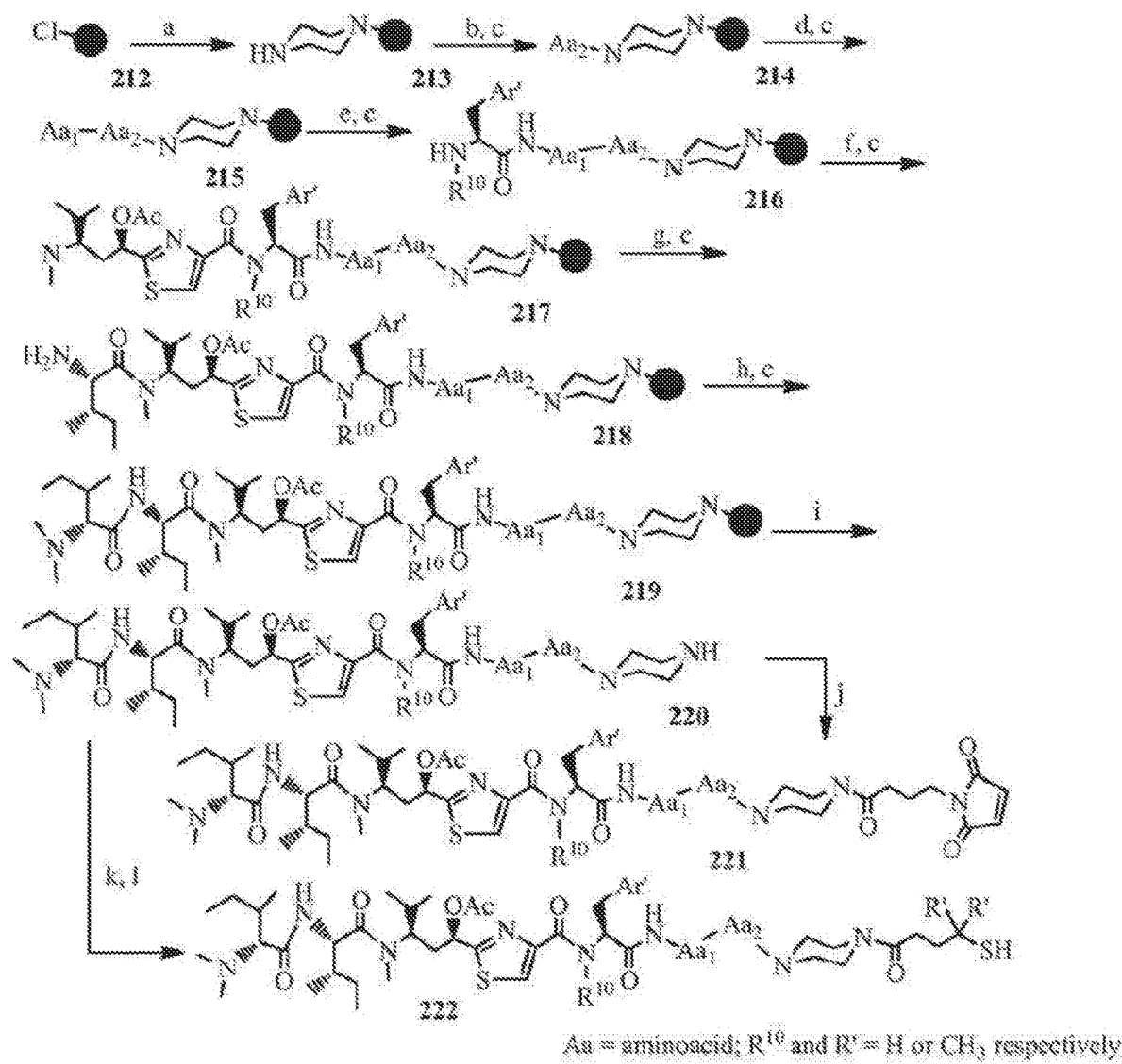

FIG. 20 shows the Boc solid-phase synthesis of the conjugatable antimitotic agents.

Conditions: a): Piperazine (5~20 eq), CH$_2$Cl$_2$, 4 h; b): Boc-Aa$_2$-OH (2~5 eq), PyBroP (2~5 eq), DIPEA (3~10 eq), DMF, 4 h; c): 4M HCl/Dioxane, 0.5 h; then washed with DIPEA (2~3 eq), DMF; d): Boc-Aal-OH (2~5 eq), TBTU (2~5 eq), DIPEA (3~10 eq), DMF, 4 h; e): BocNMe-Phe-OH, or Boc-Trp-OH, or BocNMe-Tyr(PO(OBz)OH)—OH (2~5 eq), or BocNMe-(Pyr)Ala-OH, or Boc(Thienyl)Ser-OH, or Boc-(Thiazolyl)-Ala-OH, PyBroP (2~5 eq), DIPEA (3~10 eq), DMF, 4 h; f): Boc-N(Me)-Tuv-OH (1.5~3 eq), PyBroP (2~5 eq), DIPEA (3~10 eq), DMF, 2 h; g): Boc-Ile-OH (2~5 eq), PyBroP (2~5 eq), DIPEA (3~10 eq), DMF, 3 h; h): NMe$_2$-Ile-OH, TBTU (2~5 eq), DIPEA (3~10 eq), DMF, 2 h; i): TFA, anisole; j): 4-maleimido butyric acid NHS ester (1.5~2 eq), DIPEA (3~10 eq), DMF, 2 h; k): 4-(methyldisulfanyl)butanoic acid NHS ester (1.5~2 eq), or 4,4-dimethyl 4-(methyldisulfanyl)-butanoic acid NHS ester (1.5~2 eq), DIPEA (3~10 eq), DMF, 2 h; l): TCEP (3~10 eq), Dioxane/buffer pH 7.0, then solid supported guanidine.

Figure 21:
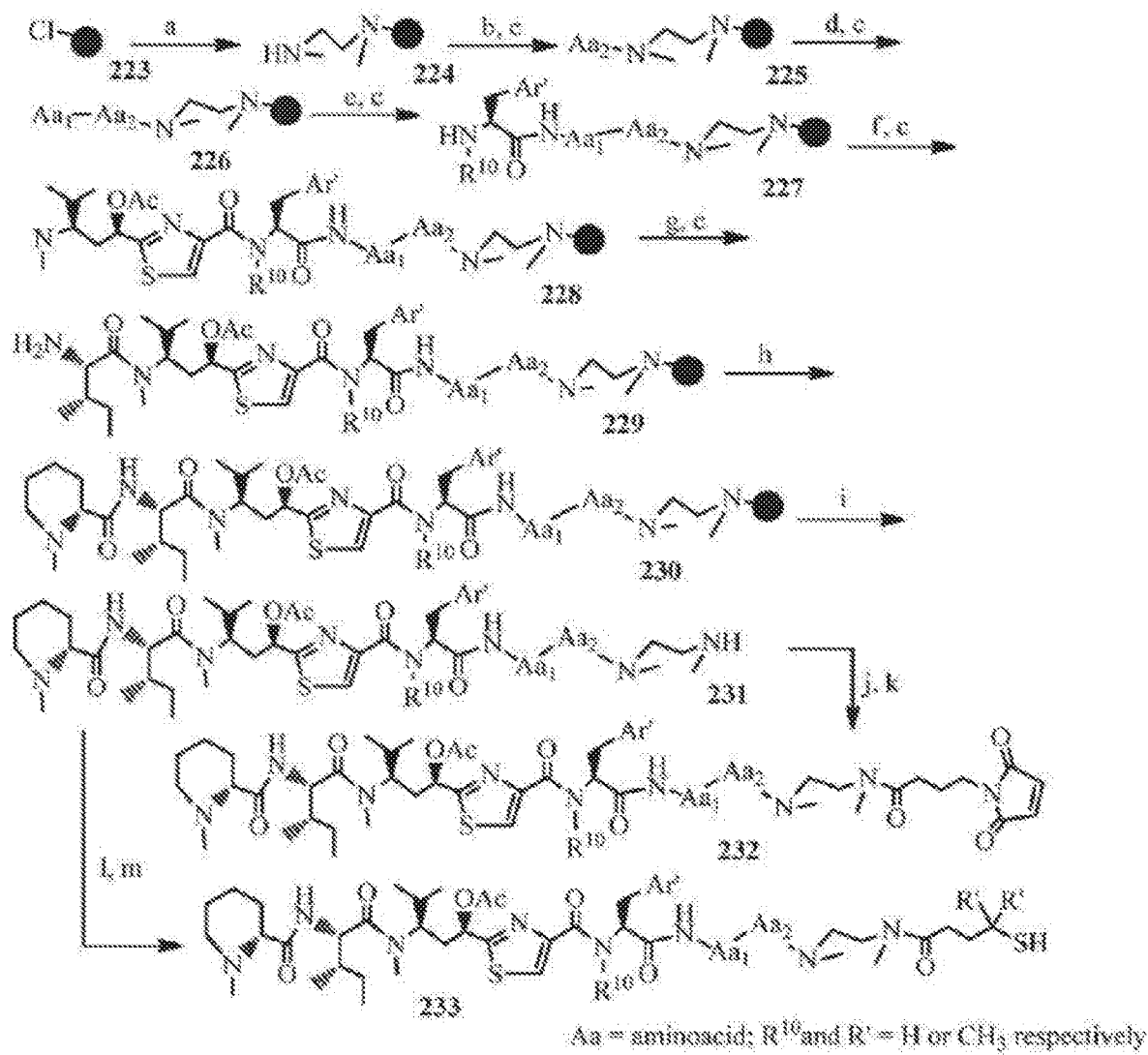

FIG. 21 shows the Fmoc solid-phase synthesis of the conjugatable antimitotic agents.

Conditions: a): (MeNCH$_2$)$_2$ (5~20 eq), DCM, 4 h; b): Fmoc-Aa2-OH (2~5 eq), PyBroP (2~5 eq), DIPEA (3~10 eq), DMF, 4 h; c): 20% piperidine, DMF, 2 h; d): Fmoc-Aal-OH (2~5 eq), TBTU (2~5 eq), DIPEA (3~10 eq), DMF, 4 h; e): (2~5 eq) FmocNMe-Tyr(SO$_3$H)—OH, or Fmoc-TrpOH—OH, or FmocNMe-Tyr(PO(OBz)-OH)—OH or FmocNMe2-Tyr(Glucose)-OH, or Boc-(quinolyl)Ala-OH, or Fmoc-(thieny)Ser-OH, PyBroP (2~5 eq), DIPEA (3~10 eq), DMF, 4 h; f): Fmoc-N(Me)-Tuv-OH (1.5~3 eq), PyBroP (2~5 eq), DIPEA (3~10 eq), DMF, 4 h; g): Fmoc-Ile-OH (2~5 eq), PyBroP (2~5 eq), DIPEA (3~10 eq), DMF, 4 h; h): Mep-OH (2~4 eq), or NMe$_2$Leu-OH, TBTU (2~5 eq), DIPEA (3~10 eq), DMF, 2 h; i): TFA, DCM, anisole; j): 4-maleimidobutyric acid NHS ester (1.5~2 eq), DIPEA (3~10 eq), DMF, 4 h; k): 20% TFA, DCM; l): 4-(methyldisulfanyl)butanoic acid NHS ester (1.5~2 eq), or 4,4-dimethyl 4-(methyldisulfanyl)-butanoic acid NHS ester (1.5~2 eq), DIPEA (3~10 eq), DMF, 4 h; m): TCEP (8 eq), Dioxane, buffer pH 7.0, then solid supported guanidine.

Figure 22:
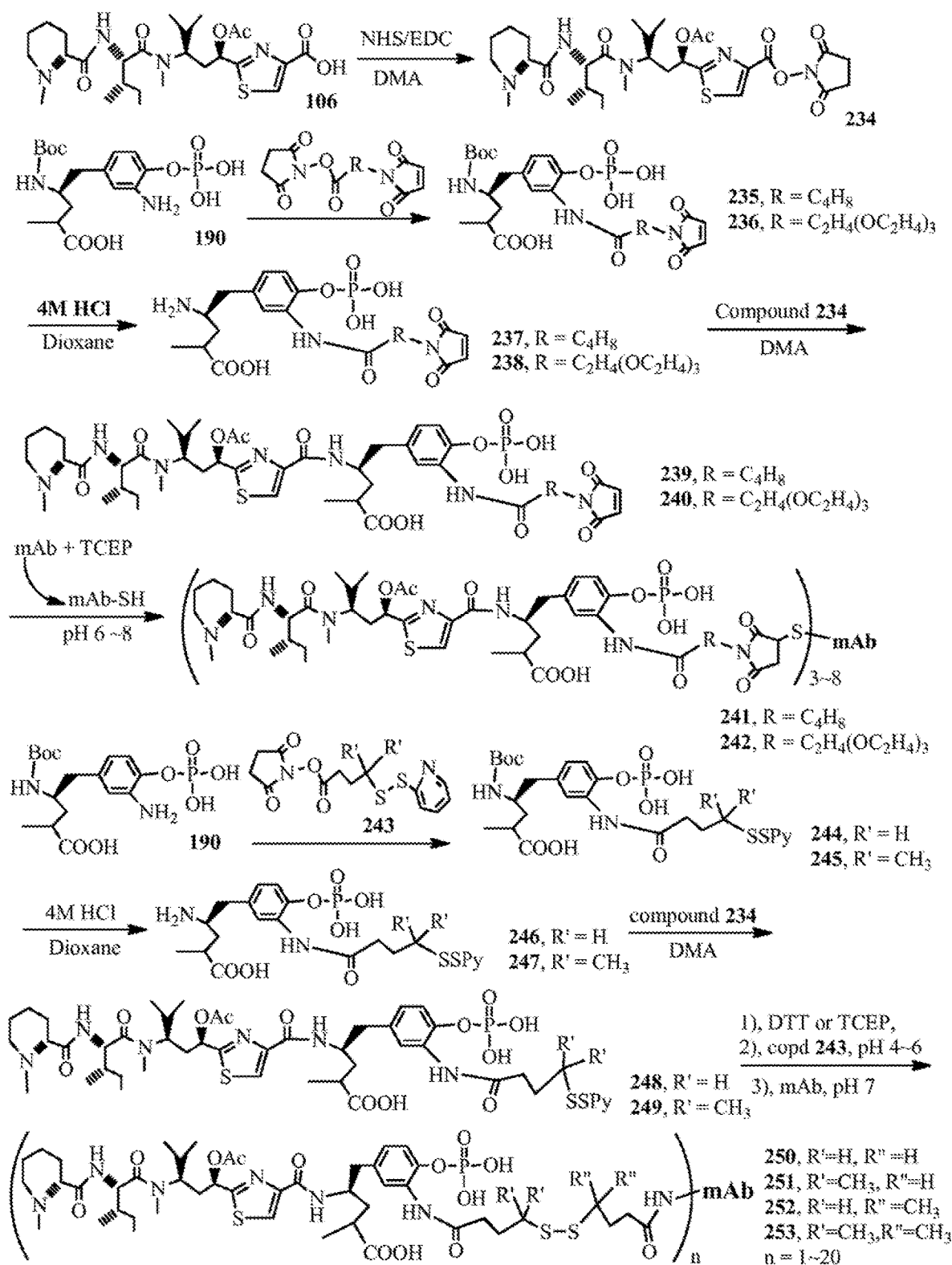

FIG. 22 shows the synthesis of the hydrophilic antimitotic drugs and their conjugates with an antibody.

Figure 23:
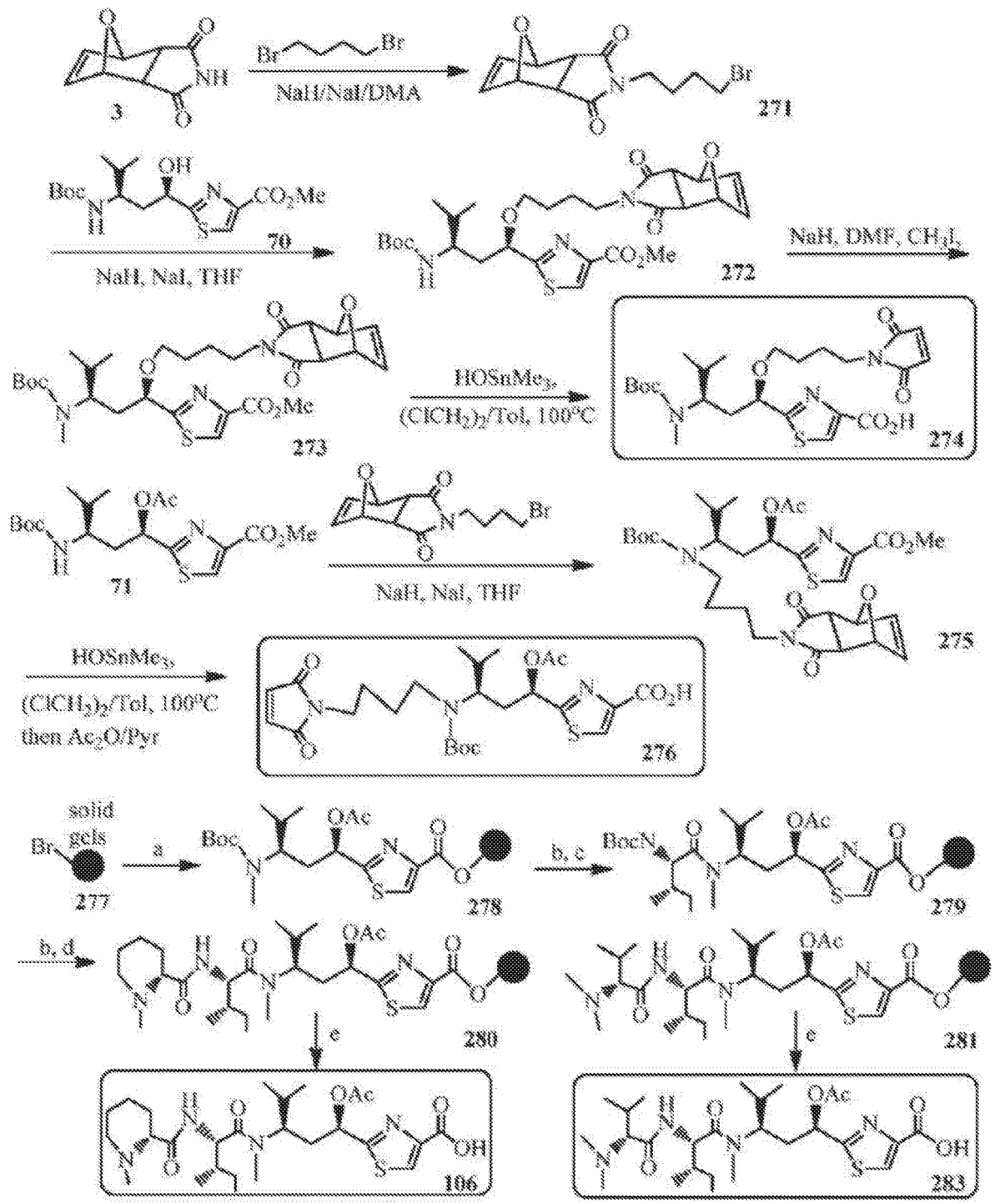

FIG. 23 shows the synthesis of Tuv derivatives and the solid phase synthesis of components of Mep-Ile-Tuv and NMe$_2$-Val-Ile-Tuv.

Conditions: a): compound 72, DIPEA, CsI, DMF, 2 h; b): 20% TFA/DCM, 0.5 h, then washed with DIPEA, MeOH, DCM; c): Boc-Ile-OH (3~5 eq), PyBroP (3~5 eq), DIPEA (3~10 eq), DMF, 6 h; d): Mep-OH (2~4 eq), or NMe$_2$Leu-OH, TBTU (2~5 eq), DIPEA (3~10 eq), DMF, 6 h; e): 95% TFA/anisole/DCM.

Figure 24:
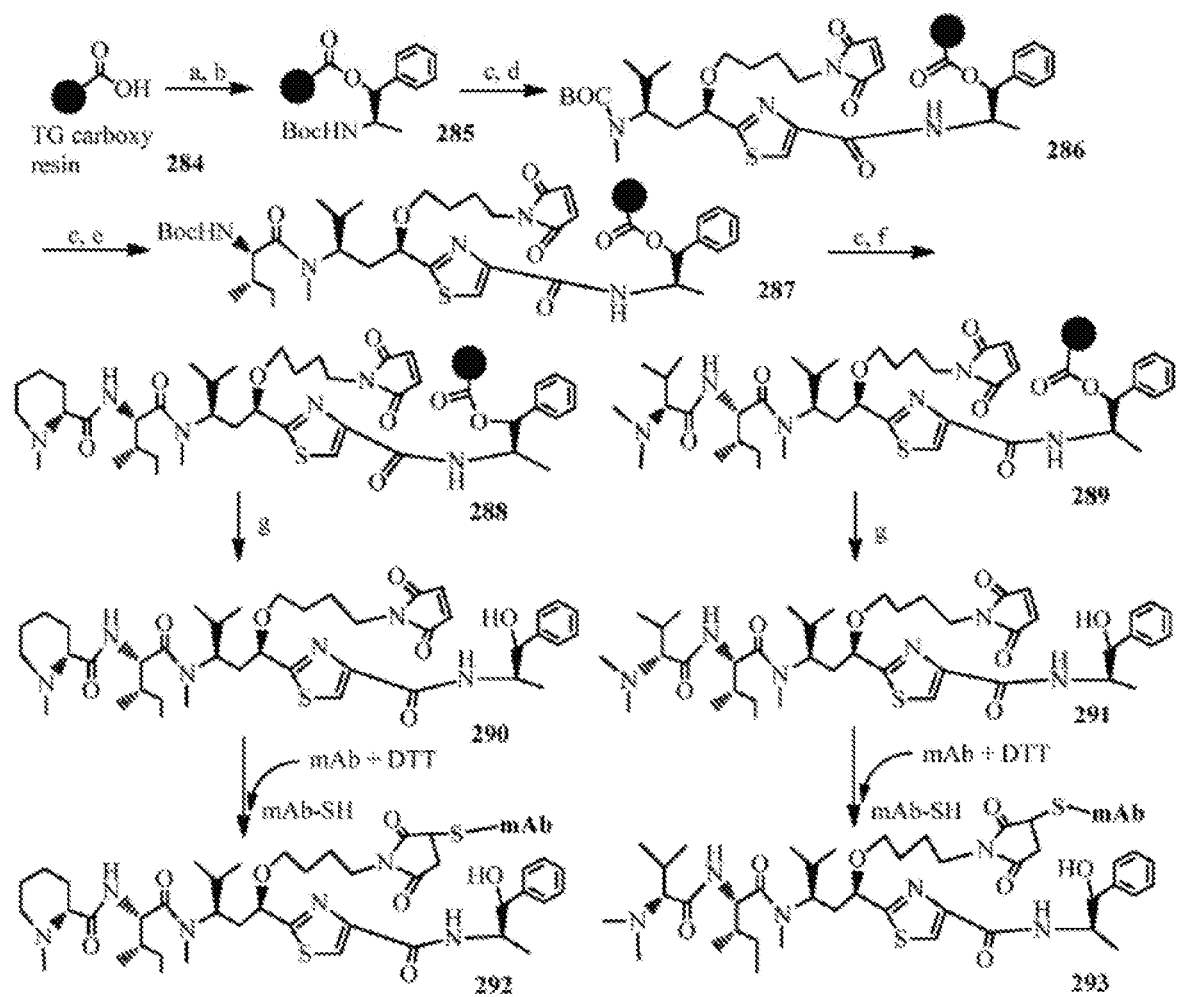

FIG. 24 shows the synthesis of the antimitotic agents and their conjugation with an antibody.

Conditions: a): (COCl)$_2$ 6 eq, DMF (cat), DCM, 1 h; b): D-(+)-Boc-norephedrine 4 eq, DIPEA, DCM, 4 h; c): 20% TFA/DCM, 0.5 h, then washed with DIPEA, MeOH, DCM; d): compound 274 (1.2 eq), DMF, 6 h; e): Boc-Ile-OH (3~5 eq), PyBroP (3~5 eq), DIPEA (3~10 eq), DMF, 4 h; f): Mep-OH (2~4 eq), or NMe$_2$-Leu-OH, TBTU (2~5 eq), DIPEA (3~10 eq), DMF, 2 h; g): HOSnM$_3$, ClCH$_2$CH$_2$Cl, 80° C., 8 h.

Figure 25:
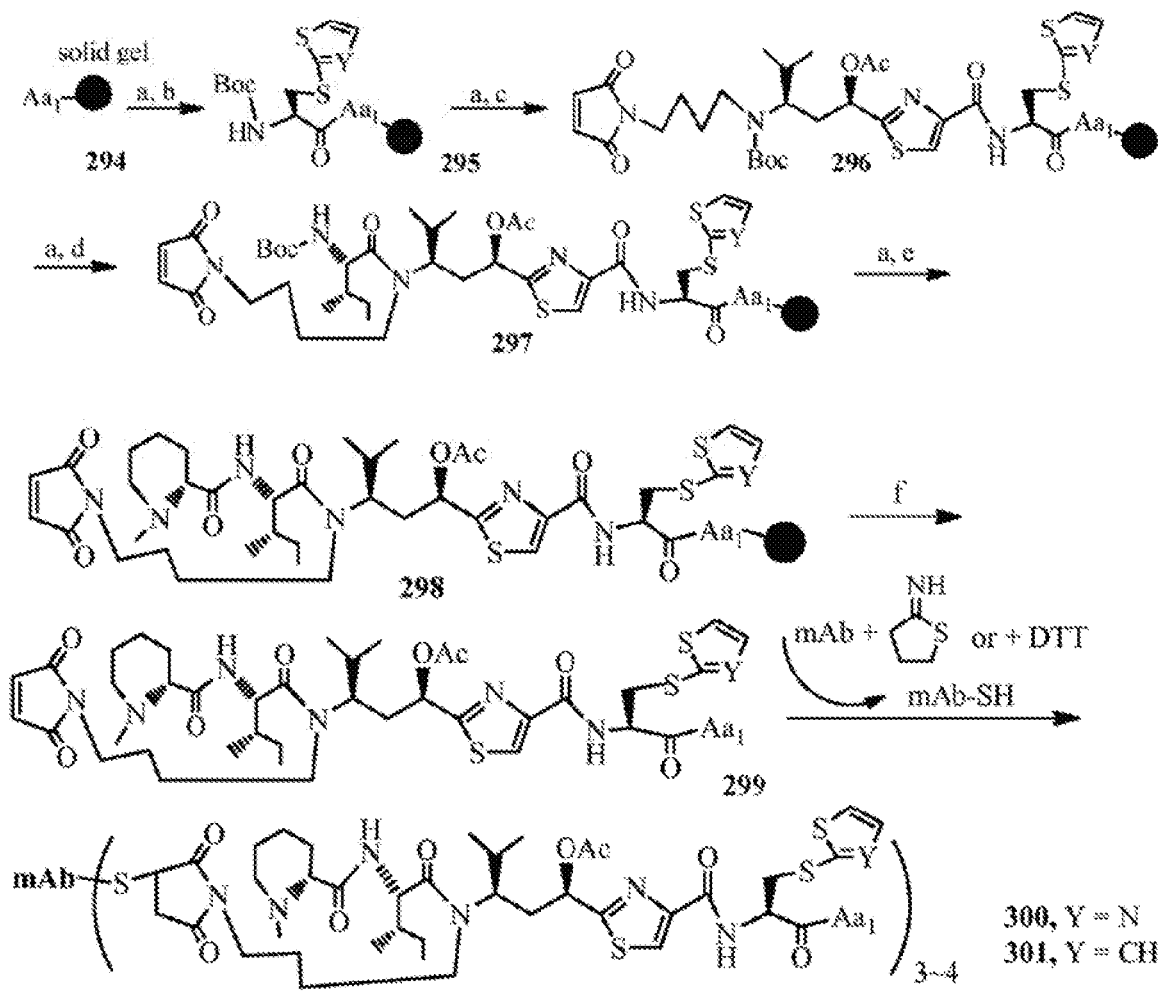

FIG. 25 shows the solid phase synthesis of antimitotic agents and their conjugates with an antibody.

Conditions: a): 20% TFA/DCM, 0.5 h, then washed with DIPEA, MeOH, DCM; b): Boc-tiazolyl-Ala-OH (2 eq), PyBroP (4 eq), DIPEA (4 eq), DMF, 6 h; c): compound 276, TBTU (4 eq), DIPEA (4 eq), DMF, 6 h; d): Boc-Ile-OH (4 eq), PyBroP (4 eq), DIPEA (4 eq), DMF, 6 h; e): Mep-OH (2~4 eq), or NMe2-Leu-OH, TBTU (2~5 eq), DIPEA (3~10 eq), DMF, 2 h; f): TFA/DCM/anisole/p-thiolcresole (95:4:0.5:0.5).

Figure 26A:
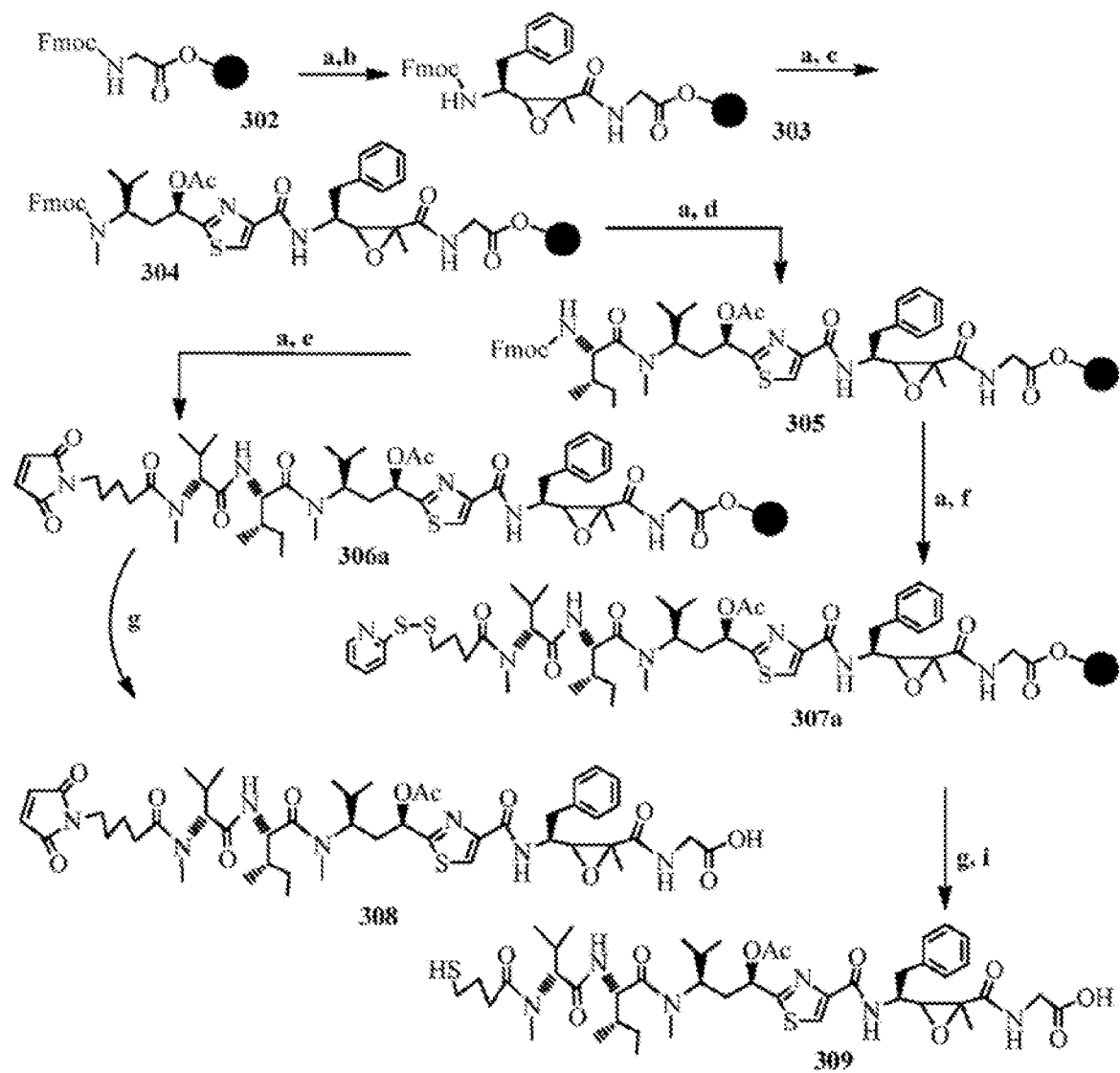
Figure 26B:
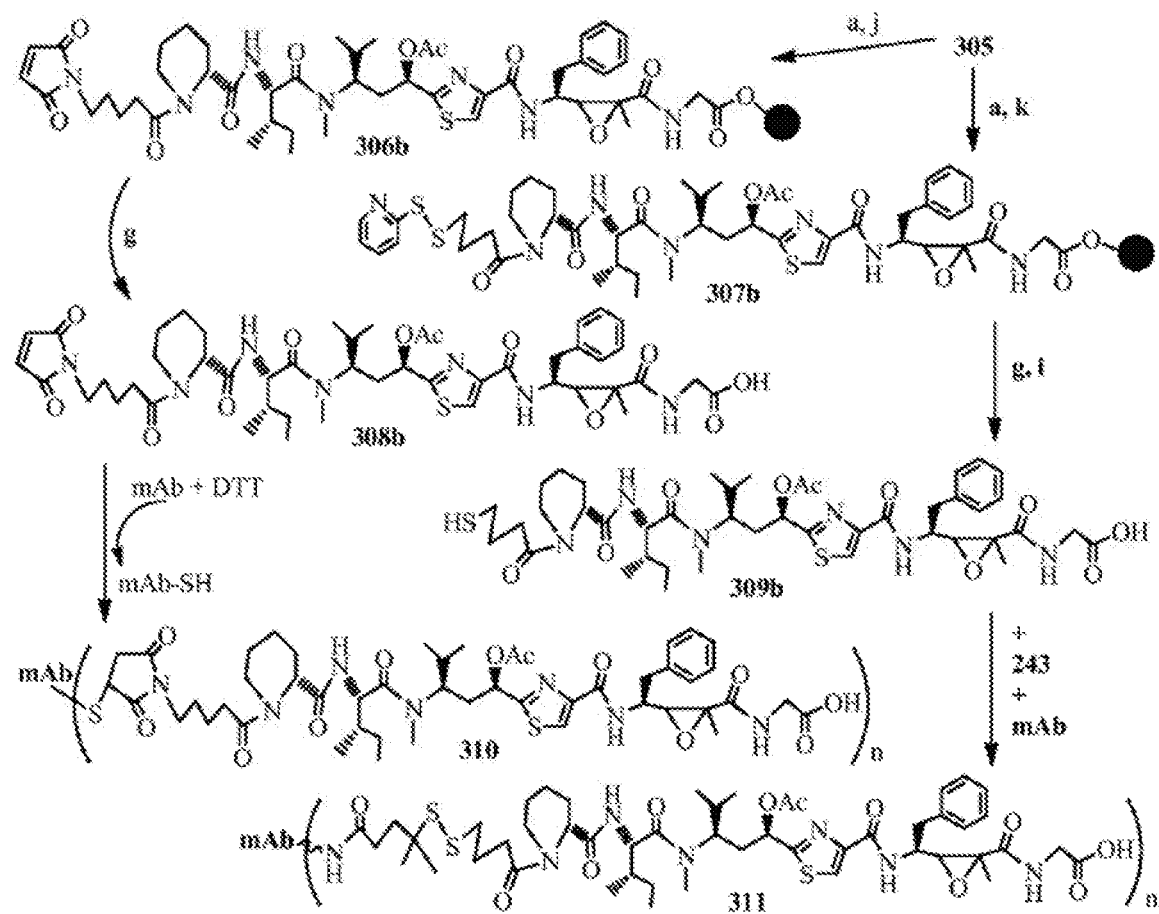

FIGS. 26A-26B shows the solid-phase synthesis of antimitotic drugs and their conjugates with an antibody.

Conditions: a: DMF/Piperidine (4:1); b: 331/DMF/PyBroP (2~5 eq); c: Fmoc-Tuv-OH (1.2 eq), TBTU (5 eq), DMF; d: Fmoc-Ile-OH (4 eq), PyBroP (4 eq), DIPEA (4 eq), DMF; e: N,N (methyl, Maleimido-pentanoic)-Val-OH (2 eq), TBTU, DMF; f: N,N-(methyl, 2'-pyridinyl-disulfanylbutyric)-Val-OH, TBTU (4 eq), DMF; g: 5% TFA/DCM/l % TIS; i: DTT/pH 7.0 PBS buffer/DMF, then HPLC; j: N, N (methyl, Maleimido-pentanoic)-Mep-OH (2 eq), TBTU, DMF; k: N,N-(methyl, 2'-pyridinyl-disulfanylbutyric)-Mep-OH, TBTU (4 eq), DMF.

Figure 27:
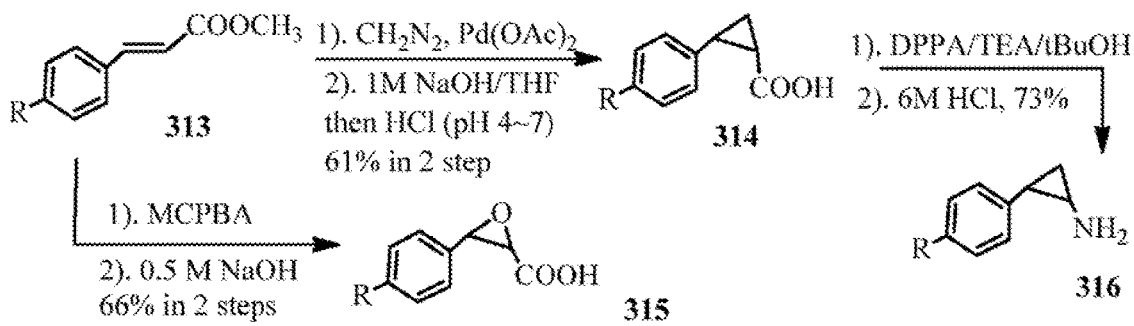

FIG. 27 shows the synthesis of trans-2-arylcyclopropylamines, trans-2-arylcyclopropyl-carboxyl acids and trans-2-arylethylepoxidyl carboxyl acids.

Figure 28:
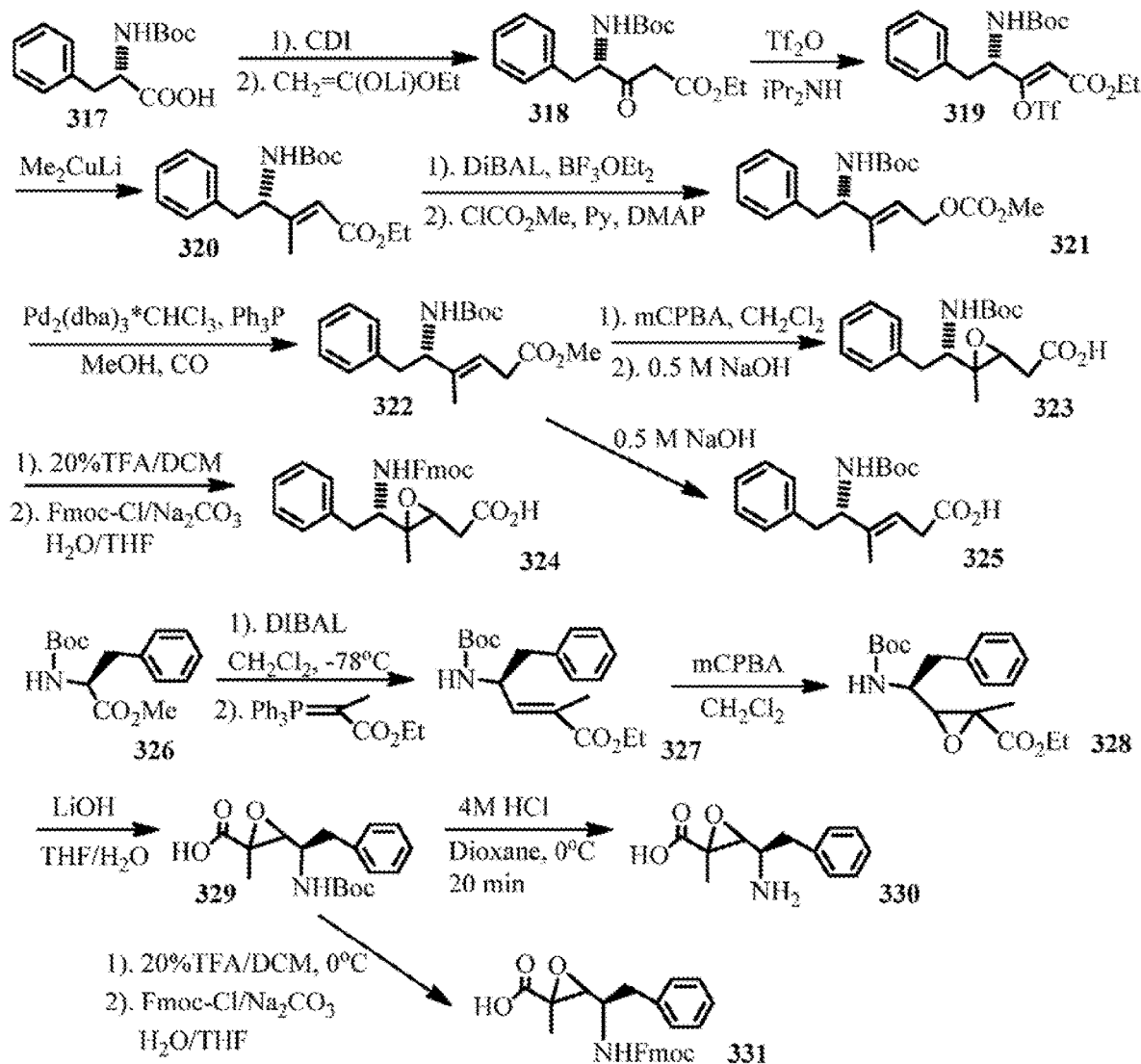

FIG. 28 shows the synthesis of alkene amino acids and alkyl epoxidyl amino acids.

Figure 29:
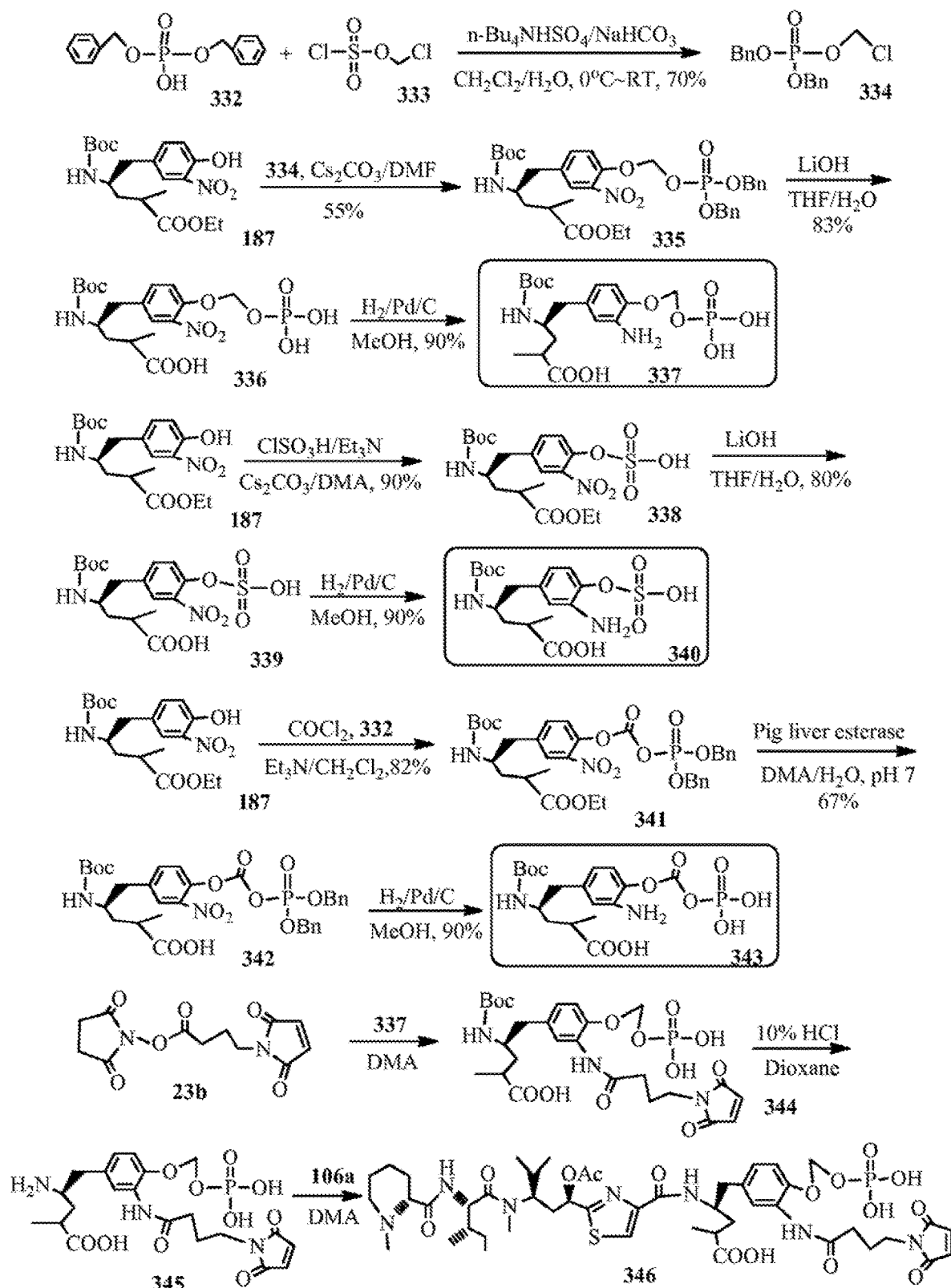

FIG. 29 shows the synthesis of hydrophilic Tut analogs for the synthesis of the hydrophilic prodrugs of antimitotic agents.

Figure 30:
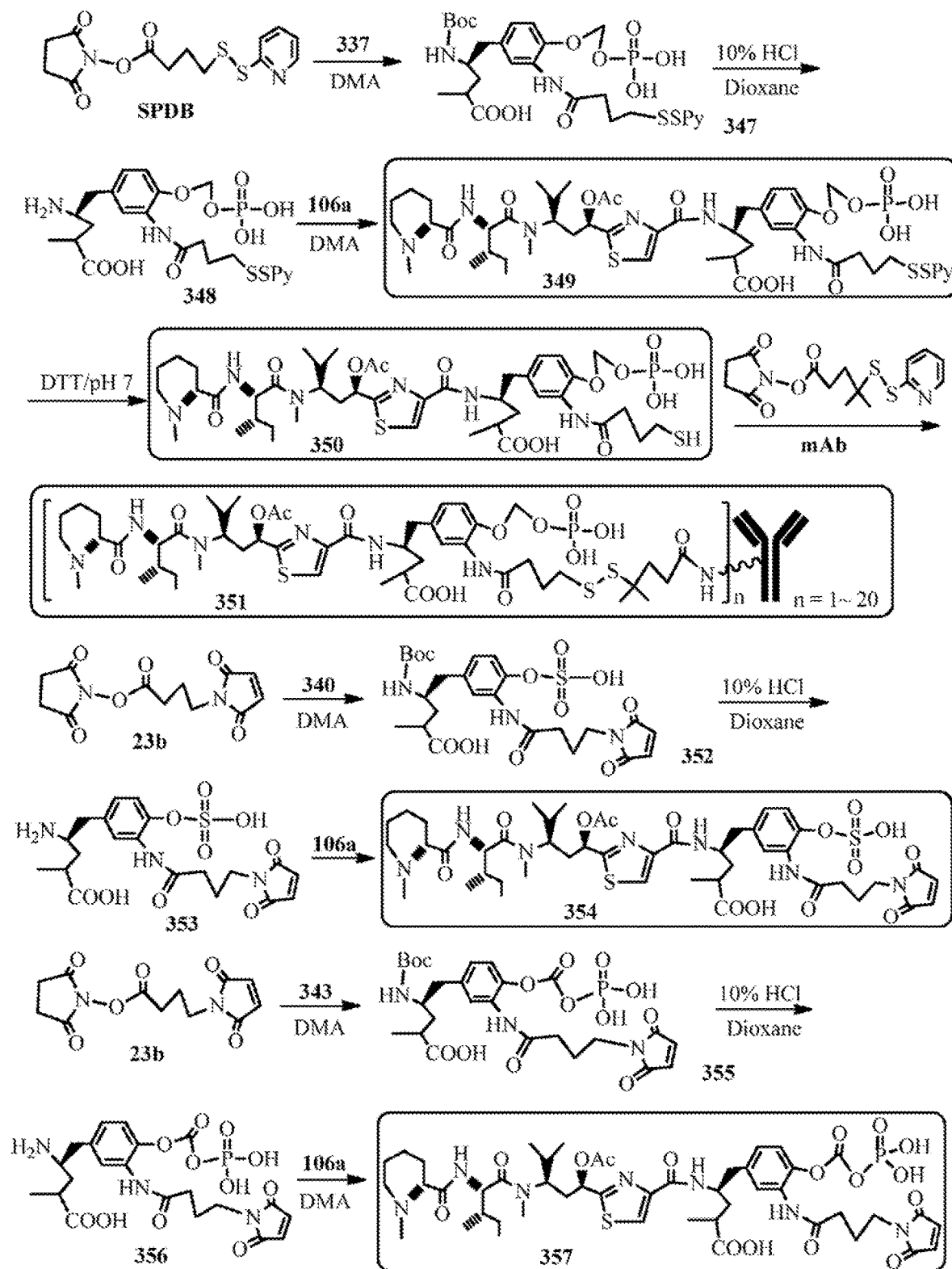

FIG. 30 shows the synthesis of the hydrophilic prodrugs of antimitotic agents for the conjugation with a cell binding agent.

Figure 31:
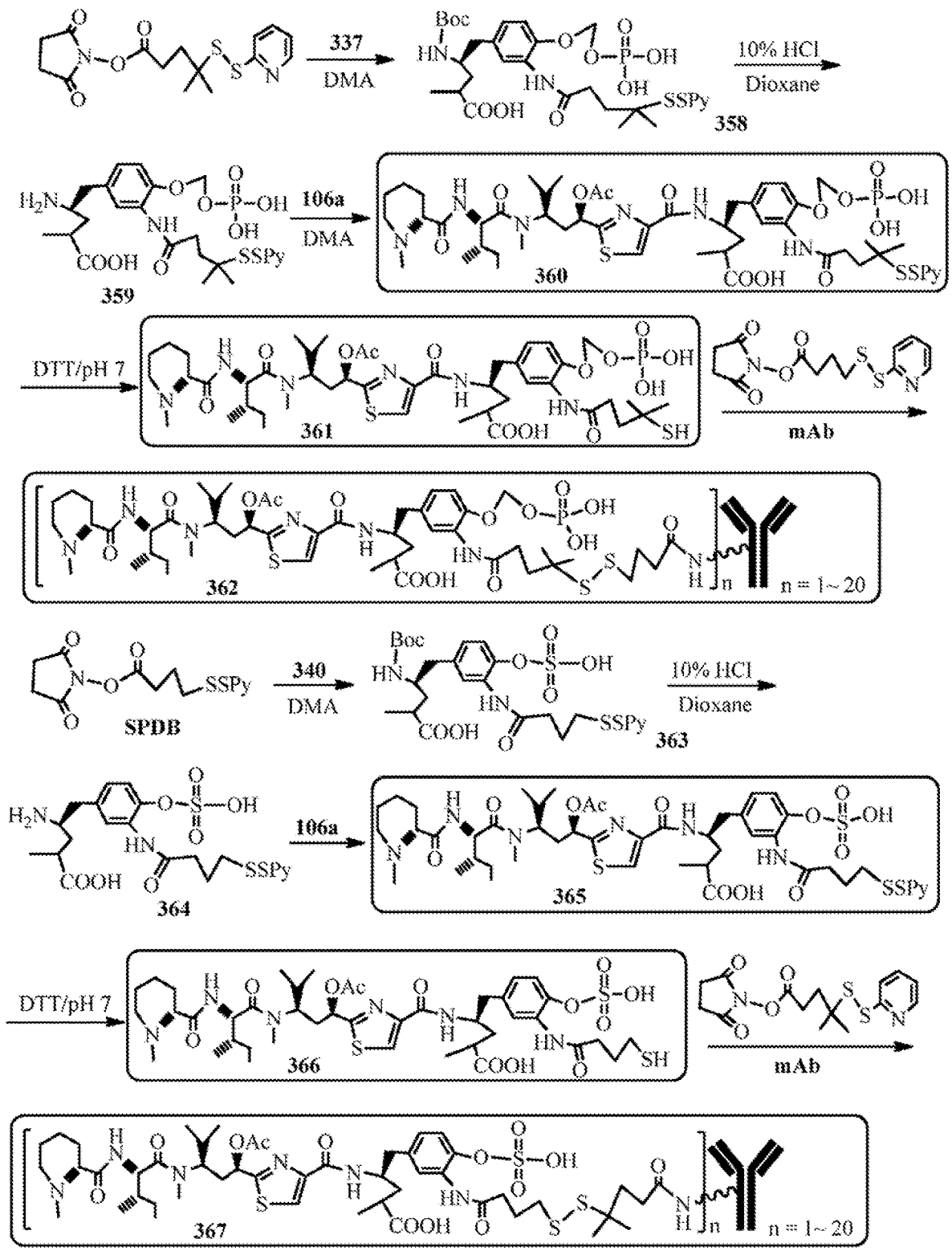

FIG. 31 shows the synthesis of the hydrophilic prodrugs of antimitotic agents for the conjugation with an antibody.

Figure 32:
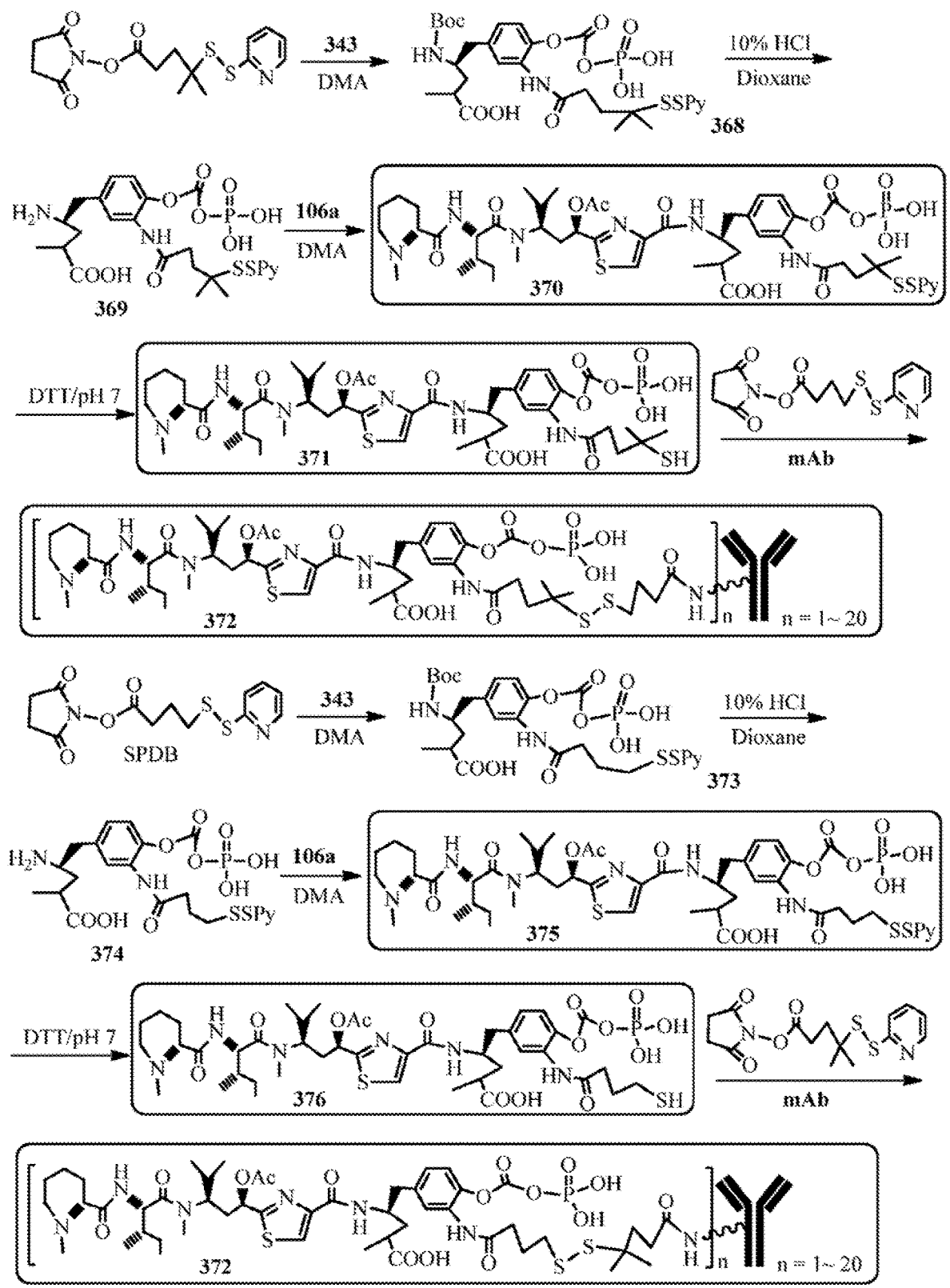

FIG. 32 shows the synthesis of the hydrophilic prodrugs of antimitotic agents for the conjugation with an antibody.

Figure 33:
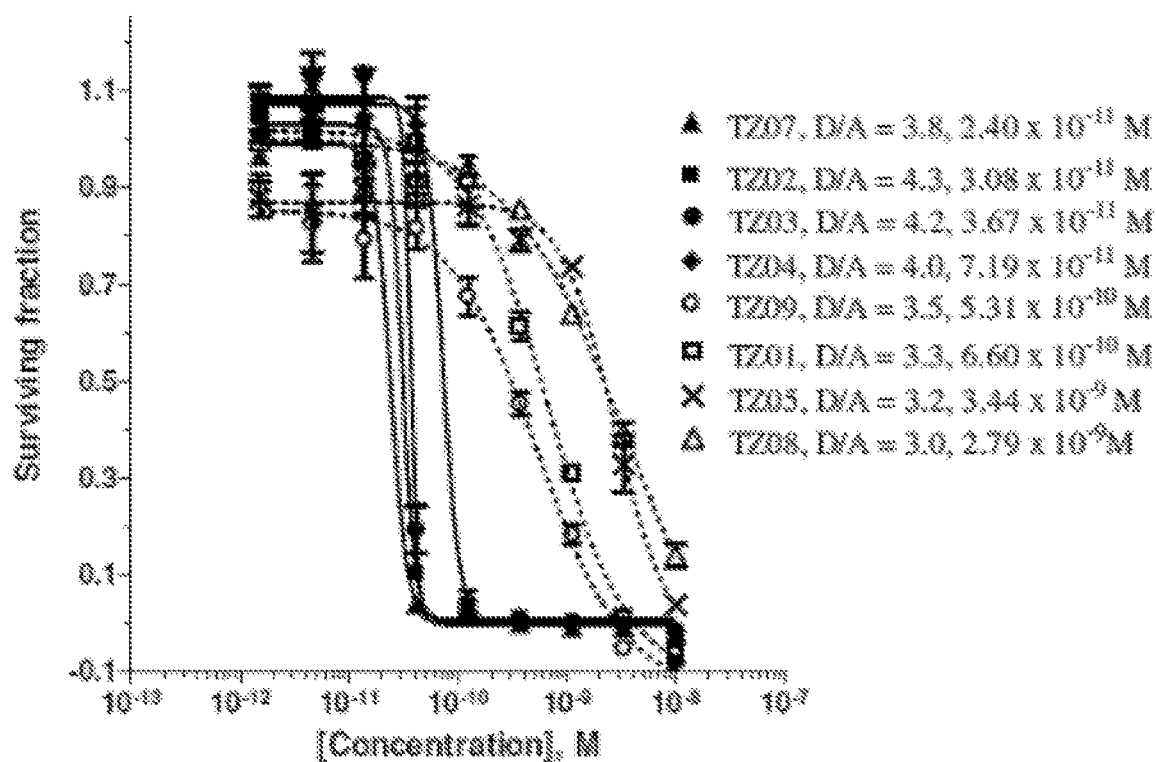

FIG. 33 shows the in vitro cytotoxic effects of antiCD22 antibody-antimitotic agent (TZ01~TZ09) conjugates with drug/antibody ratio (DI A) 3.0~4.3 on Ramos (Burkitt lymphoma cell line). The cells were incubated with the conjugates for 5 days and the IC$_{50}$ values are indicated on the figure.

Figure 34:
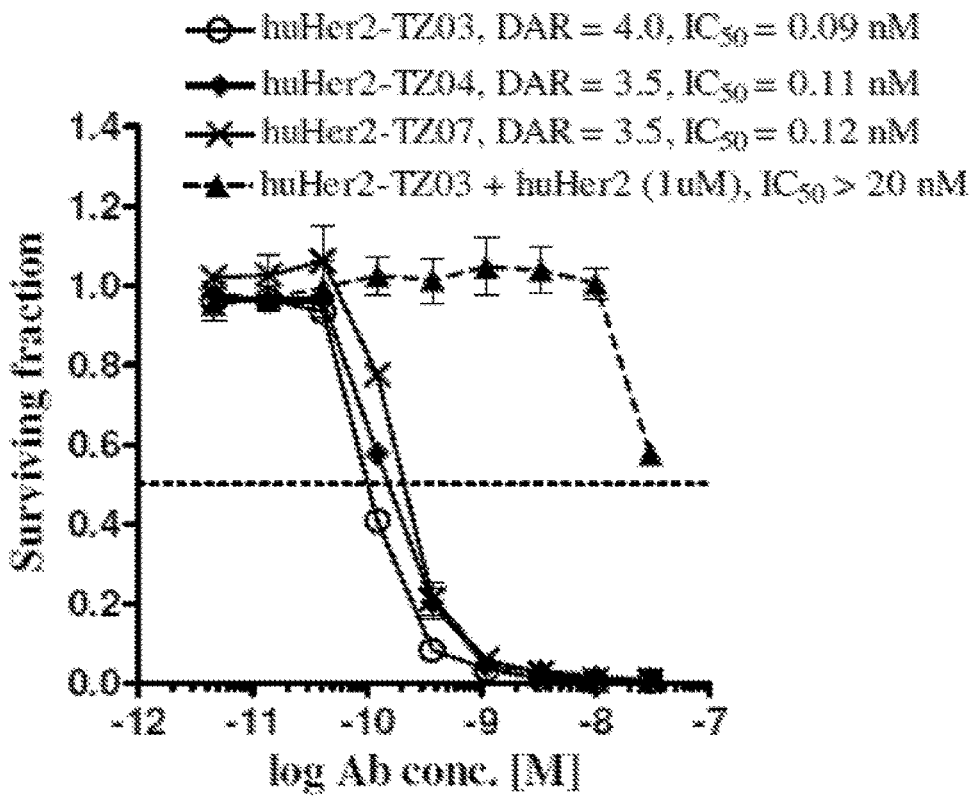

FIG. 34 shows the cytotoxic effects of Trastuzumab-antimitotic agent (TZ03, TZ04, and TZ07) conjugates with drug/antibody ratio (DAR) 3.5~4.0 on KPL-4 (breast cancer cell line). It also shows that Trastuzumab-TZ03 conjugate induces a specifically potent antiproliferative effect—with IC$_{50}$=90 pM in the absence of unconjugated Trastuzumab and IC$_{50}$>20 nM in the presence of 1 micromole concentration of Trastuzumab (to saturate the antigen binding) respectively. The specificity window is >222 (IC$_{50}$=20 nM/IC$_{50}$=0.09 nM).

Figure 35:
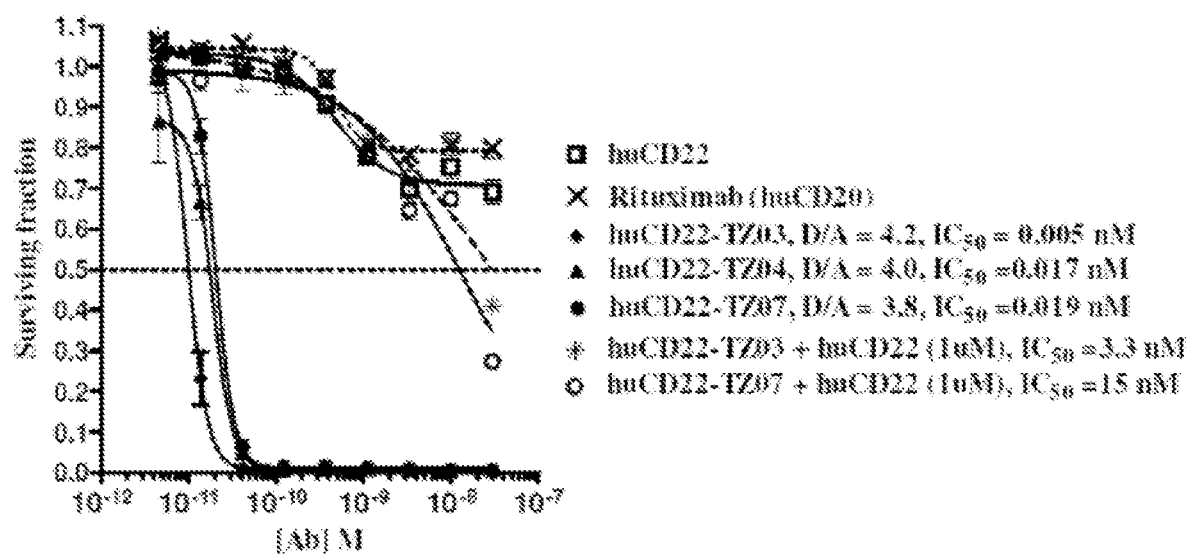
Figure 36A:
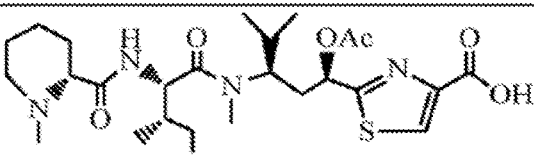
Figure 36A:
Figure 36A:
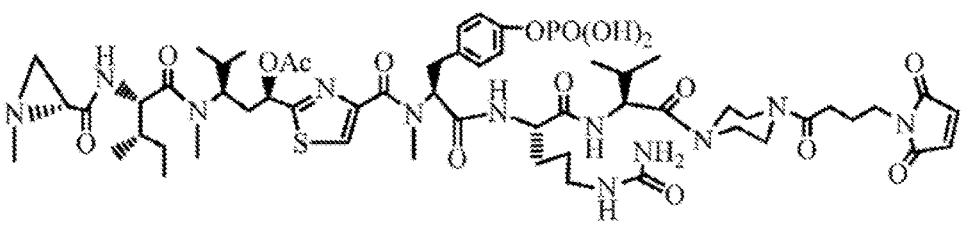
Figure 36A:
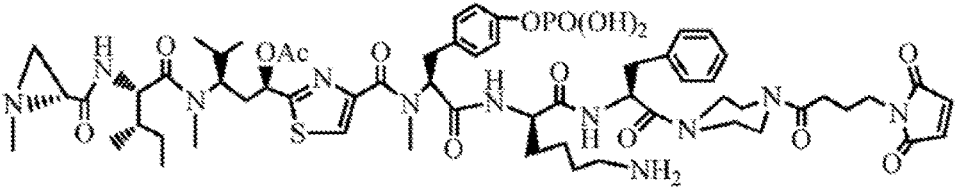
Figure 36A:
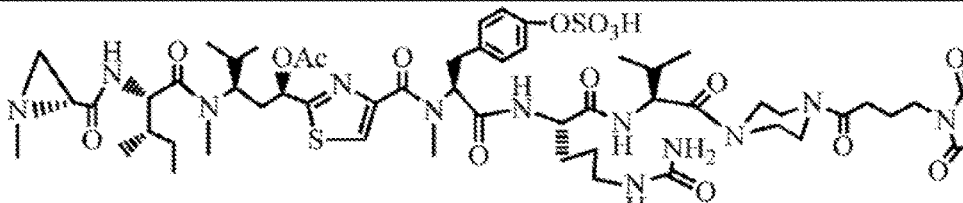
Figure 36B:
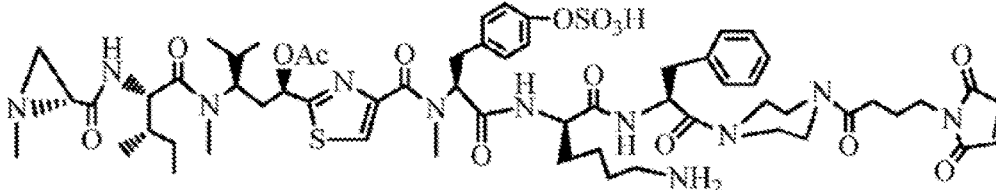
Figure 36B:
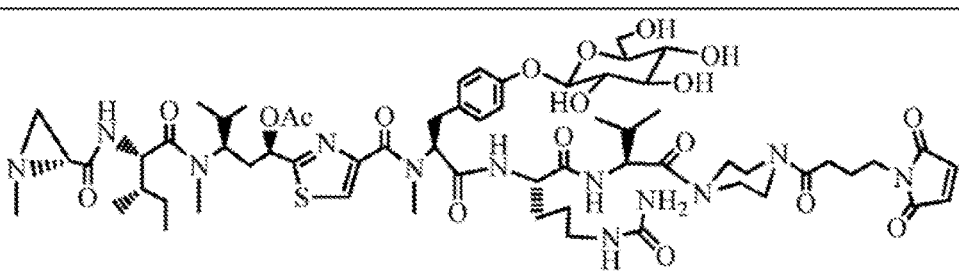
Figure 36B:
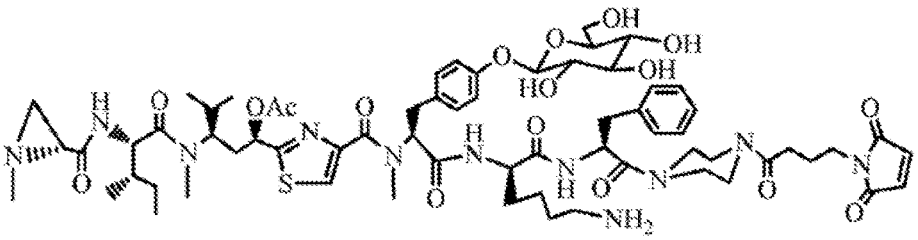
Figure 36B:
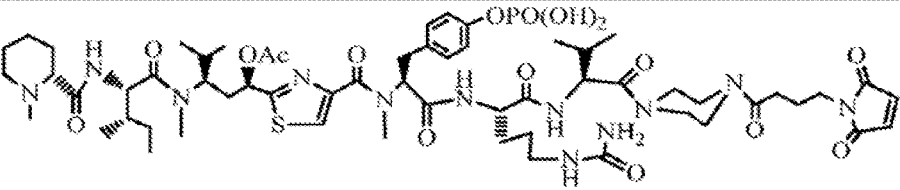
Figure 36B:
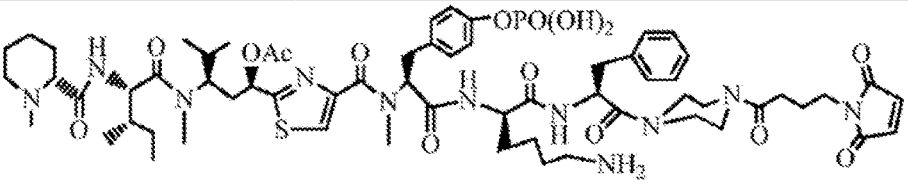
Figure 36C:
Figure 36D:
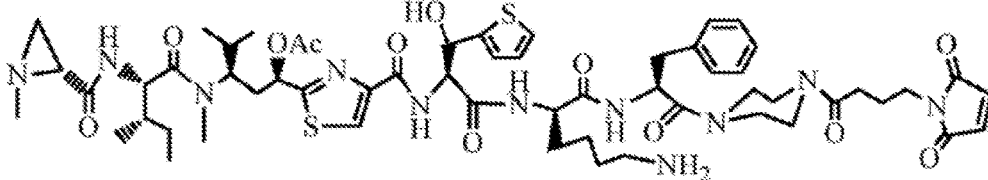
Figure 36D:
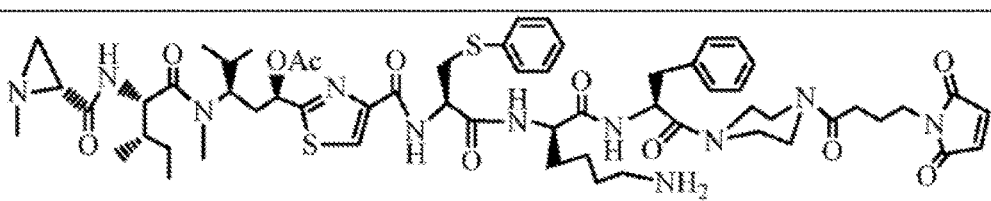
Figure 36D:
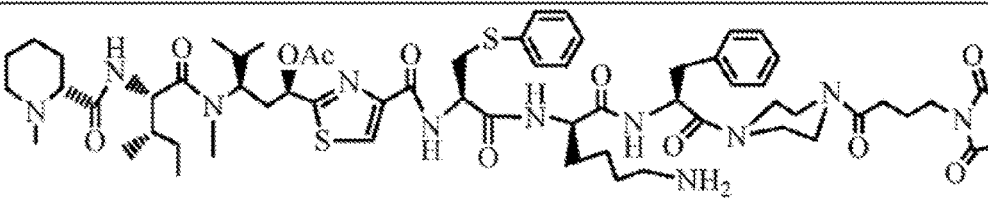
Figure 36D:
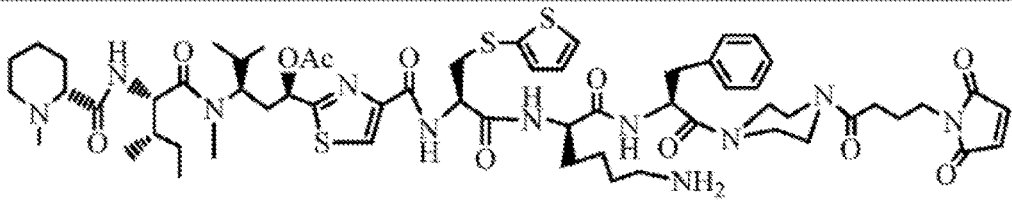
Figure 36D:
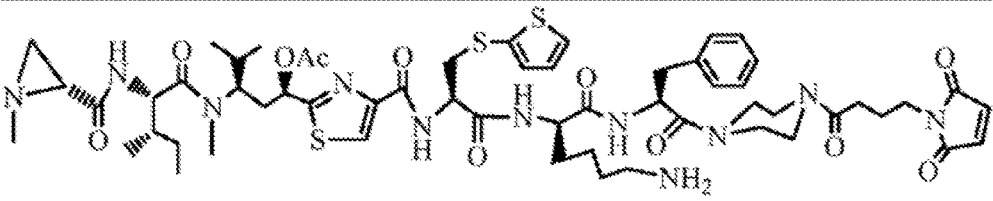
Figure 36E:
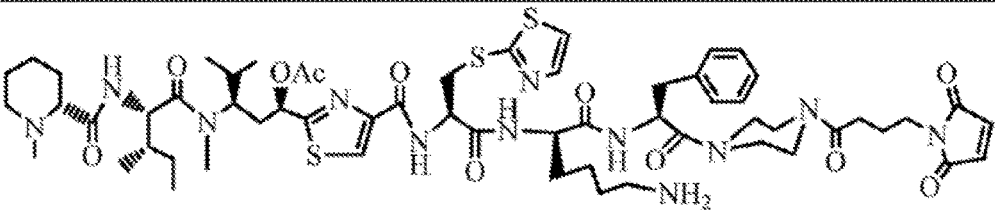
Figure 36F:
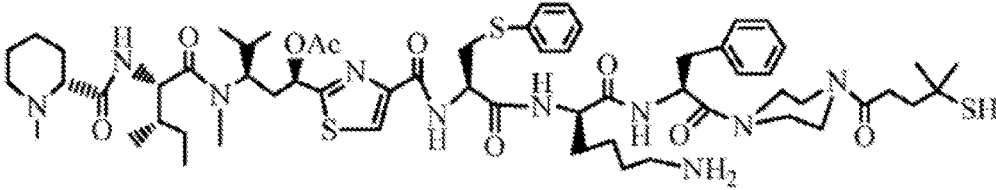
Figure 36F:
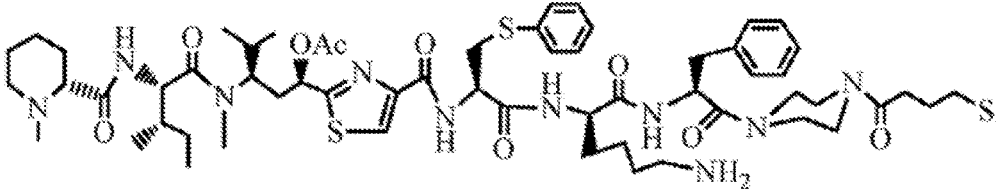
Figure 36F:
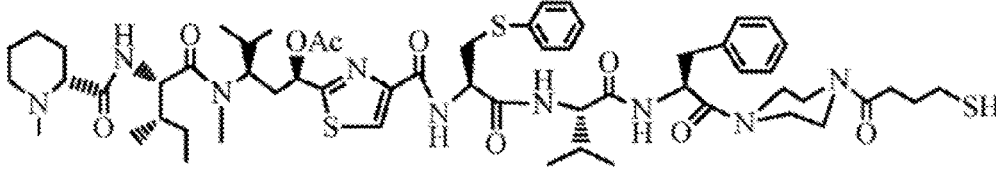
Figure 36F:
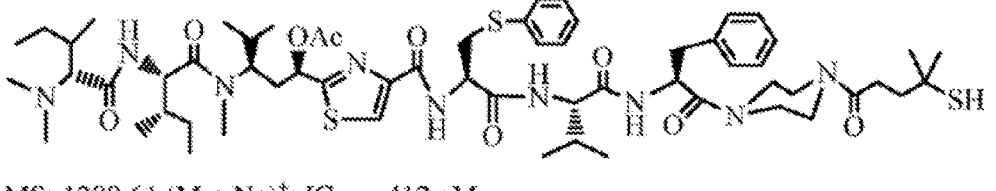
Figure 36F:
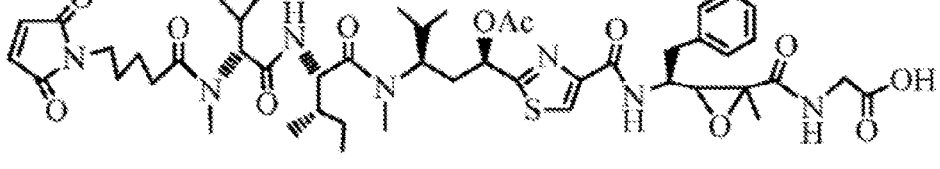
Figure 36G:
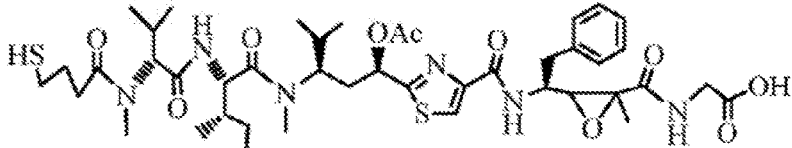
Figure 36H:
Figure 36I:
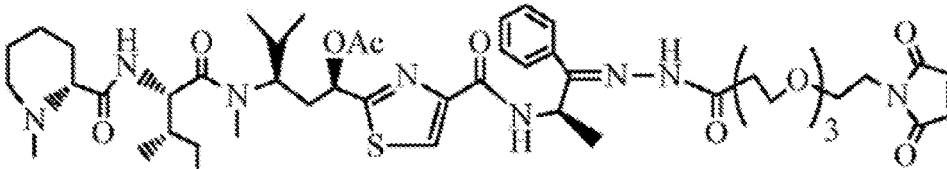
Figure 36I:
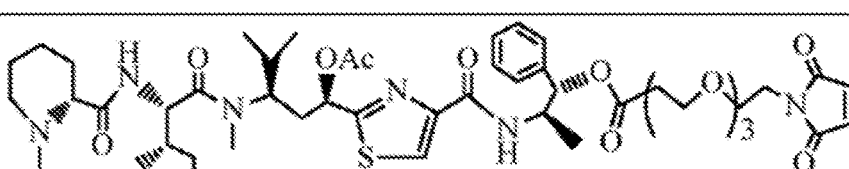
Figure 36I:
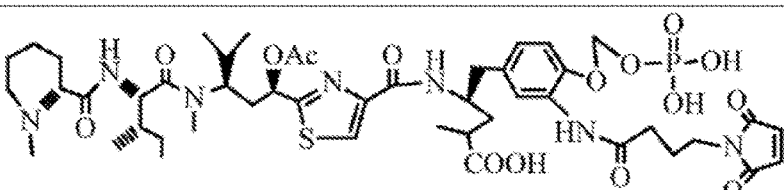
Figure 36I:
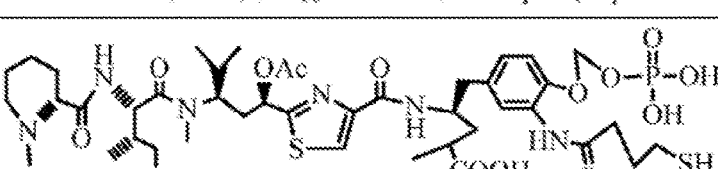
Figure 36I:
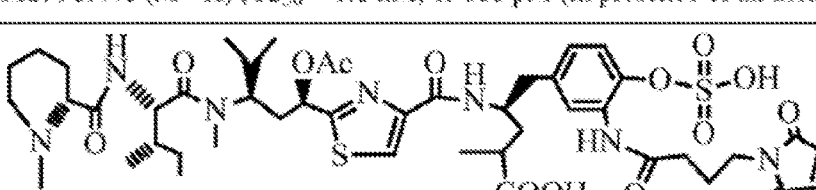
Figure 36J:
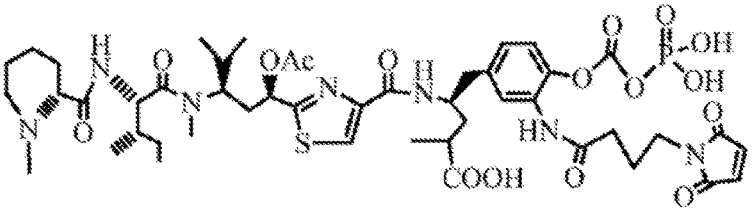
Figure 37A:
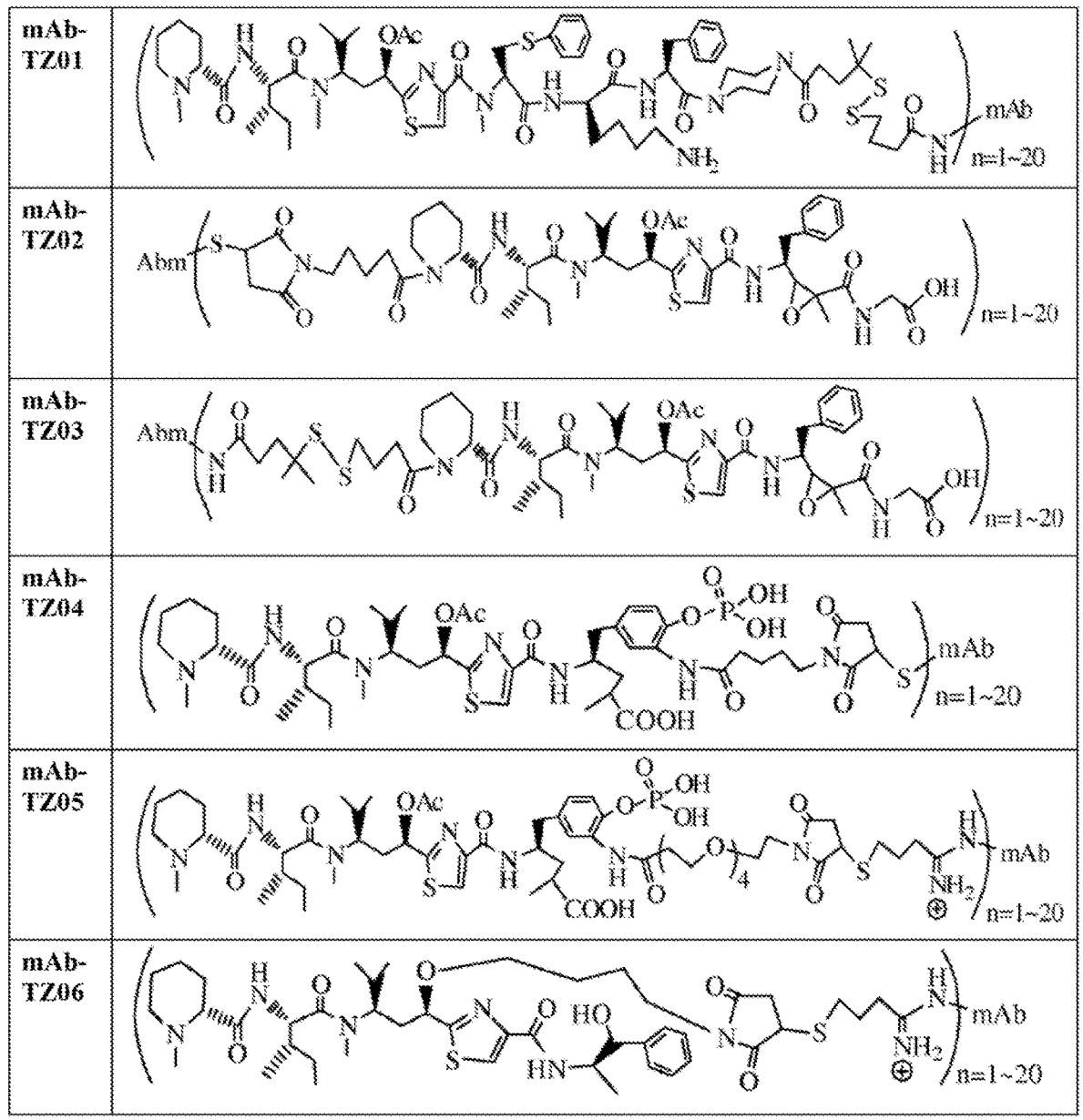
Figure 37B:
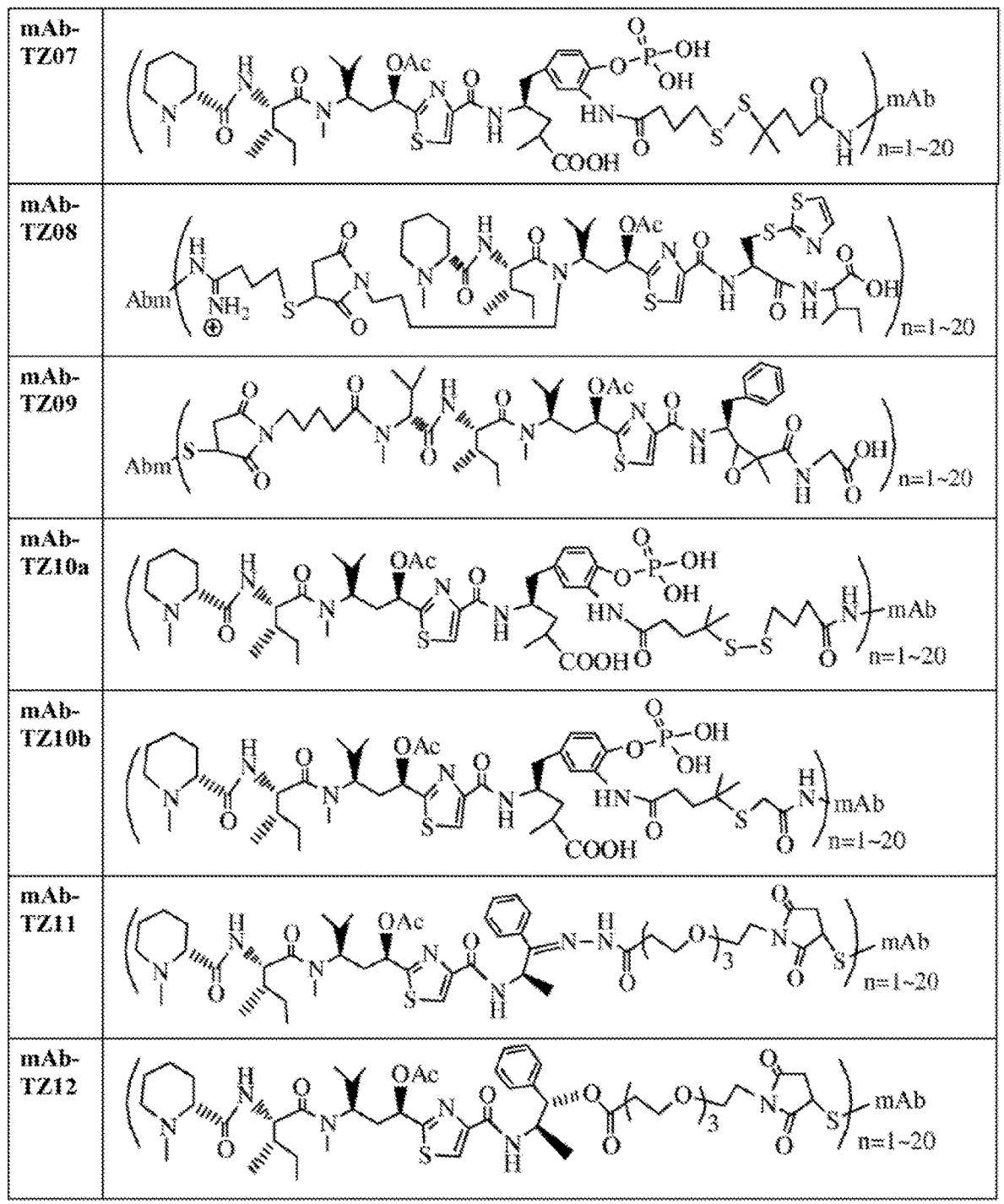
Figure 37C:
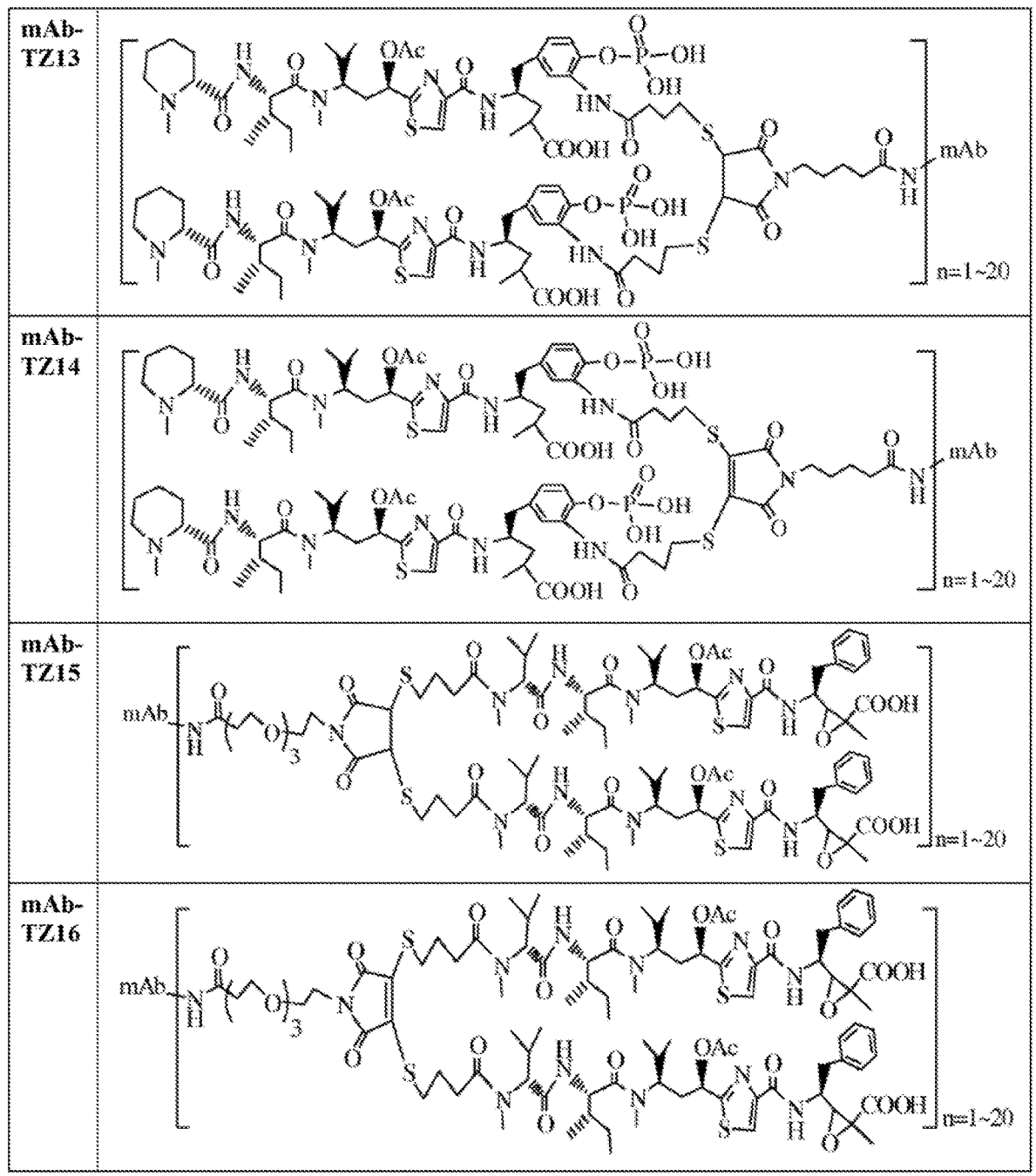
Figure 37D:
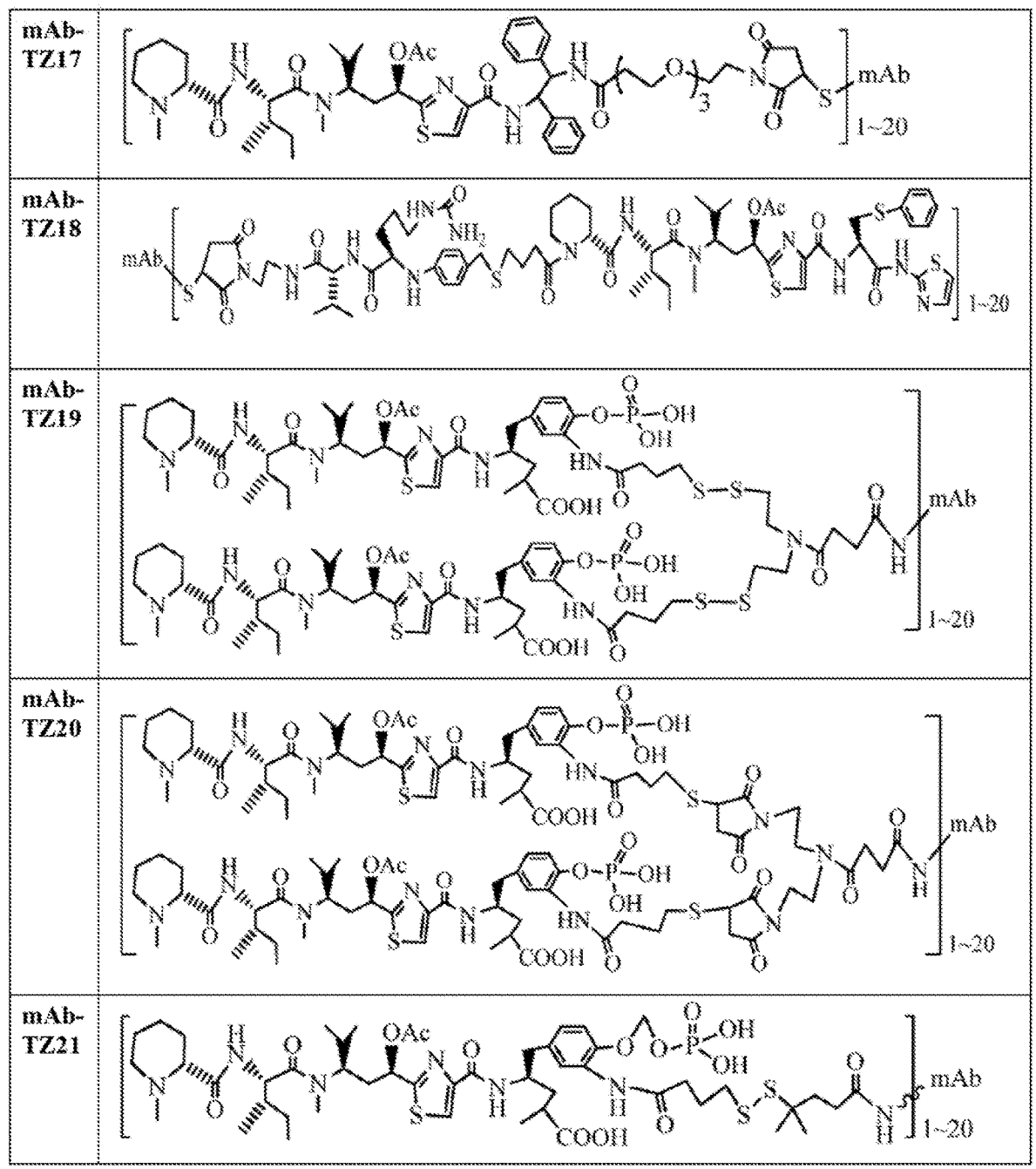
Figure 37E:
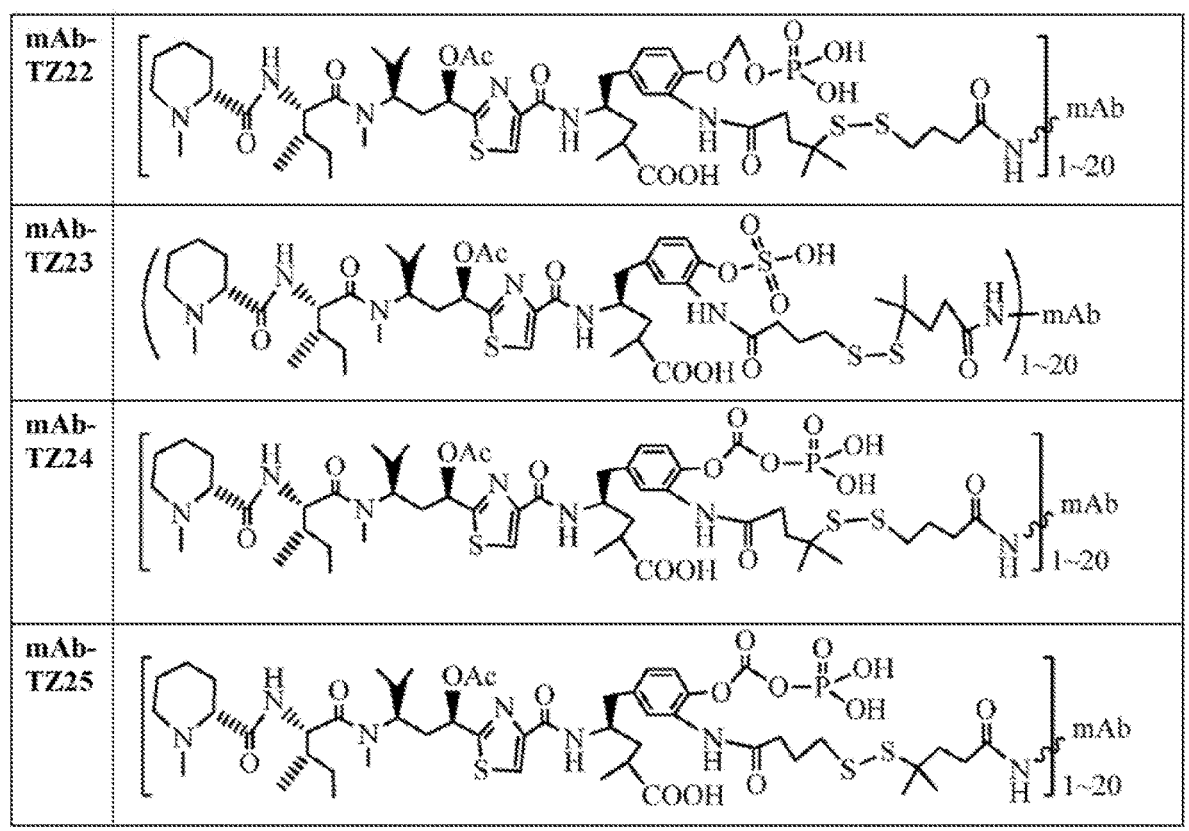

FIG. 35 shows the cytotoxic effects of antiCD22 antibody-antimitotic agent (TZ03, TZ04, and TZ07) conjugates with drug/antibody ratio (D/A) 3.8~4.2 and of unconjugated CD22 antibody as well as of CD20 antibody (Rituximab) on BJAB (Burkitt lymphoma cell line). It shows that the conjugate induces much more potent antiproliferative effect—with $IC_{50}$=5~19 pM than the unconjugated antibodies with $IC_{50}$>20 nM. The specificity windows when used 1 micromole concentration of unconjugated CD22 antibody to saturate the antigen binding are >660 ($IC_{50}$=3.3 nM/$IC_{50}$=0.005 nM) for huCD22-TZ03 conjugate and >790 ($IC_{50}$=15 nM/$IC_{50}$=0.019 nM) for huCD-TZ07 conjugate.

FIGS. 36A-36J display the structure of the antimitotic drugs made through solid phase synthesis and their molecular ion of mass spectra and in vitro cytotoxicity of these drugs against Ramos cell (ATCC, a human Burkitt's lymphoma cell).

FIGS. 37A-37E display the structures of some experimental antibody-antimitotic agent conjugates.

5. DETAILED DESCRIPTION OF THE INVENTION

5.1 Definitions

"Alkyl" means an aliphatic hydrocarbon group which may be straight or branched having 1 to 8 carbon atoms in the chain or cyclic. "Branched" means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl, cyclopentyl, cyclohexyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylehexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A $C_1$~$C_8$ alkyl group can be unsubstituted or substituted with one or more groups including, but not limited to, —$C_1$~$C_8$ alkyl, —O—($C_1$~$C_8$ alkyl), —O—($C_1$~$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen (F, Cl, Br, or I), —N$_3$, —NH$_2$, —NH(R'), —N(R')$_2$ and —CN; where each R' is independently selected from —$C_1$~$C_8$ alkyl and aryl.

A "$C_3$~$C_8$ carbocyle" means a 3-, 4-, 5-, 6-, 7- or 8-membered saturated or unsaturated non-aromatic carbocyclic ring. Representative $C_3$~$C_8$ include, but are not limited to, -cyclopropyl, -cyclobutyl, -cyclopentyl, -cyclopentadienyl, -cyclohexyl, -cyclohexenyl, -1,3-cyclohexadienyl, 1,4-cyclohexadienyl, -cycloheptyl, -1,3-cycloheptadienyl, -1,3,5-cycloheptatrienyl, -cycloheptatrienyl, -cyclooctyl, and -cyclooctadienyl. A $C_3$~$C_8$ carbocycle group can be unsubstituted or substituted with one or more groups including, but not limited to, —$C_1$~$C_8$ alkyl, —O—($C_1$~$C_8$ alkyl), -aryl, —C(O)R', —OC(O)R', C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; where each R' is independently selected from —$C_1$~$C_8$ alkyl and aryl.

A "$C_3$~$C_8$ carbocyclo" refers to a $C_3$~$C_8$ carbocycle group defined above wherein one of hydrogen atoms on the carbocyle is replaced with a bond.

"Alkenyl" means an aliphatic hydrocarbon group containing a carbon-carbon double bond and which may be straight or branched having 2 to 8 carbon atoms in the chain. Exemplary alkenyl groups include ethenyl, propenyl, n-butenyl, i-butenyl, 3-methylbut-2-enyl, n-pentenyl, hexylenyl, heptenyl, octenyl.

"Alkynyl" means an aliphatic hydrocarbon group containing a carbon-carbon triple bond and which may be straight or branched having 2 to 8 carbon atoms in the chain. Exemplary alkynyl groups include ethynyl, propynyl, n-butynyl, 2-butynyl, 3-methylbutynyl, pentynyl, n-pentynyl, hexylynyl, heptynyl, and octynyl.

"Heteroalkyl" is $C_2$~$C_8$ alkyl in which one to four carbon atoms are independently replaced with a heteroatom from the group consisting of O, S and N.

"Aryl" or Ar refers to an aromatic or hetero aromatic group, composed of one or several rings, comprising three to fourteen carbon atoms, preferentially six to ten carbon atoms. The term of hetero aromatic group refers one or several carbon on aromatic group, preferentially one, two, three or four carbon atoms are replaced by O, N, Si, Se, P or S, preferentially by O, S, and N. The term aryl or Ar also refers to a aromatic group, wherein one or several H atoms are replaced independently by $R^{13}$, F, Cl, Br, I, $OR^{13}$, or $SR^{13}$, $NR^{13}R^{14}$, N=$NR^{13}$, N=$R^{13}$, $NR^{13}R^{14}$, $NO_2$, $SOR^{13}R^{14}$, $SO_2R^{13}$, $SO_3R^{13}$, $OSO_3R^{13}$, $PR^{13}R^{14}$, $POR^{13}R^{14}$, $PO_2R^{13}R^{14}$, $OPO_3R^{13}R^{14}$, or $PO_3R^{13}R^{14}$ wherein $R^{13}$, $R^{14}$ are independently H, alkyl, alkenyl, alkynyl, heteroalkyl, aryl, arylalkyl, carbonyl, or pharmaceutical salts.

"Halogen atom" refers to fluorine, chlorine, bromine or iodine atom; preferably fluorine and chlorine atom.

"Heterocycle" refers to an aromatic or non-aromatic $C_2$~$C_8$ heterocycle in which one to four of the ring carbon atoms are independently replaced with a heteroatom from the group of O, N, S Se, and P. Preferable heteroatoms are oxygen, nitrogen and sulfur. Suitable heterocycles are also disclosed in *The Handbook of Chemistry and Physics,* 78th Edition, CRC Press, Inc., 1997-1998, p. 2-25 to 2-26, the disclosure of which is hereby incorporated by reference. Preferred non aromatic heterocyclic include, but are not limited to, epoxy, aziridinyl, thiiranyl, pyrrolidinyl, pyrazolidinyl, imidazolidinyl, oxiranyl, tetrahydrofuranyl, dioxolanyl, tetrahydro-pyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydro-pyranyl, tetrahydropyranyl, dihydropyranyl, tetrahydro-pyridyl, dihydropyridyl, tetrahydropyrinidinyl, dihydrothiopyranyl, azepanyl, as well as the fused systems resulting from the condensation with a phenyl group.

The term "heteroaryl" or aromatic heterocycles refers to a 5 to 14, preferably 5 to 10 membered aromatic hetero, mono-, bi- or multicyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group.

"Alkyl", "cycloalkyl", "alkenyl", "alkynyl", "aryl", "heteroaryl", "heterocycle" and the like refer also to the corresponding "alkylene", "cycloalkylene", "alkenylene", "alkynylene", "arylene", "heteroarylene", "heterocyclene" and the likes which are formed by the removal of two hydrogen atoms.

"Pharmaceutically" or "pharmaceutically acceptable" refer to molecular entities and compositions that do not produce an adverse, allergic or other untoward reaction when administered to an animal, or a human, as appropriate.

"Pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions as suitable therapeutic combinations.

As used herein, "pharmaceutical salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucuronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutical salts of the present invention can be synthesized from the parent compound which contains a basic or acidic moiety by conventional chemical methods. Generally, such salts can be prepared by reaction of the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, PA, 1985, p. 1418, the disclosure of which is hereby incorporated by reference.

5.2 Drug-Linker-Binding Ligand Conjugates

As stated above, this invention provides a cell surface binding molecule-antimitotic agent conjugate of formula (I):

carbocyclic, cycloalkyl, or heterocyclic, heterocycloalkyl ring system; Y is N or CH; In addition, $R^1$, $R^3$, and $R^4$ can be H; and $R^2$ can be absent.

Wherein $R^5$, $R^6$, $R^8$ and $R^{10}$ are independently H, $C_1 \sim C_4$ of alkyl or heteroalkyl.

Wherein $R^7$ is independently selected from H, $R^{14}$, or $-R^{14}C(=O)X^1R^{15}$ or $-R^{14}X^1R^{15}$, wherein $R^{14}$ and $R^{15}$ are independently selected from $C_1 \sim C_8$ of alkyl, or heteroalkyl; $C_2 \sim C_8$ of alkenyl, alkynyl; heterocyclic, carbocyclic, cycloalkyl; $C_3 \sim C_8$ of aryl, heterocycloalkyl, heteroaralkyl, heteroalkylcycloalkyl, alkylcarbonyl; $X^1$ is selected from O, S, S—S, NH, or $NR^{14}$.

Wherein $R^9$ is independently H, —O—, $-OR^{14}$—, —OC(=O)$R^{14}$—, —OC(=O)NHR$^{14}$—, —OC(=O)$R^{14}$SSR$^{15}$—, OP(=O)(OR$^{14}$)—, or OR$^{14}$OP(=O)(OR$^{15}$), wherein $R^{14}$, $R^{15}$ are independently $C_1 \sim C_8$ of alkyl, heteroalkyl; $C_2 \sim C_8$ of alkenyl, alkynyl, heterocyclic, carbocyclic; $C_3 \sim C_8$ of aryl, cycloalkyl, alkylcycloalkyl, heterocycloalkyl, heteroalkylcycloalkyl, heteroaralkyl, alkylcarbonyl.

Wherein $R^1$ is independently H, $R^{14}$, $-R^{14}C(=O)R^{16}$, $-R^{14}X^2R^{16}$, $-R^{14}C(=O)X^2$, wherein $X^2$ is —O—, —S—, —NH—, $-N(R^{14})$—, —O—$R^{14}$—, —S—$R^{14}$—, —S(=O)—$R^{14}$—, or —NHR$^{14}$—; $R^{14}$ is $C_1 \sim C_8$ of alkyl, heteroalkyl; $C_2 \sim C_8$ of alkenyl, alkynyl, heterocyclic, carbocyclic; $C_3 \sim C_8$ of aryl, cycloalkyl, alkylcycloalkyl, heterocycloalkyl, heteroalkylcycloalkyl, heteroaralkyl, alkylcarbonyl; $R^{16}$ is H, OH, $R^{14}$ or one to four amino acid units;

Wherein $R^{12}$ is independently $R^{14}$, —O—, —S—, —N—, =N—, =NNH—, $-NH(R^{14})$—, $-OR^{14}$—, —C(O)O—C(O)OR$^{16}$—, C(O)NH—, C(O)NHR$^{14}$, —SR$^{14}$—, —S(=O)R$^{14}$—, —P(=O)(OR$^{16}$)—, —OP(=O)(OR$^{16}$)—, $CH_2OP(=O)(OR^{16})$—, —C(O)OP(=O)(OR$^{16}$)—, —SO$_2$R$^{16}$—. $R^{14}$ is independently $C_1 \sim C_8$ of alkyl, heteroalkyl; $C_2 \sim C_8$ of alkenyl, alkynyl, hetero-cyclic, carbocyclic; $C_3 \sim C_8$ of aryl, cycloalkyl, alkylcycloalkyl, heterocycloalkyl, heteroaralkyl, heteroalkylcycloalkyl, alkylcarbonyl. $R^{16}$ is H, OH, $R^{14}$ or one to four amino acid units;

Wherein $R^{13}$ is $C_1 \sim C_{10}$ of alkyl, heteroalkyl, alkyl acid, alkyl amide, alkyl amine, or Ar; Ar refers to a aromatic or hetero aromatic group, composed of one or several rings,

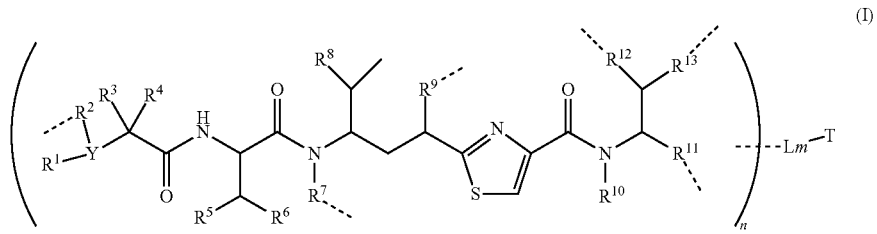

(I)

and pharmaceutical acceptable salts and solvates thereof

Wherein T is a targeting or binding ligand; L is a releasable linker; - - - - - is a linkage bond that L connects to a molecule inside the bracket independently; n is 1~20 and m is 1~10.

Inside the round bracket is a potent antimitotic agent/drug wherein $R^1$, $R^2$, $R^3$, and $R^4$ are independently $C_1 \sim C_8$ of alkyl, heteroalkyl; $C_2 \sim C_8$ of heterocyclic, carbocyclic, alkylcycloalkyl, heterocycloalkyl, $C_3 \sim C_8$ of aryl, Ar-alkyl, heteroalkylcycloalkyl, alkylcarbonyl; or two R's, such as $R^1R^2$, $R^2R^3$, $R^3R^4$, $R^5R^6$ and $R^{12}R^{13}$ can be 3~7 members of a comprising four to ten carbon, preferentially four to six carbon atoms. The term of hetero aromatic group refers one or several carbon on aromatic group, preferentially one, two or three carbon atoms are replaced by O, N, Si, Se, P or S, preferentially O, S, N. The term aryl or Ar also refers to a aromatic group, wherein one or several H atoms are replaced independently by $R^{17}$, F, Cl, Br, I, OR$^{16}$, SR$^{16}$, NR$^{16}$R$^{17}$, N=NR$^{16}$, N=R$^{16}$, NR$^{16}$R$^{17}$, NO$_2$, SOR$^{16}$R$^{17}$, SO$_2$R$^{16}$, SO$_3$R$^{16}$, OSO$_3$R$^{16}$, PR$^{16}$R$^{17}$, POR$^{16}$R$^{17}$, PO$_2$R$^{16}$R$^{17}$, OP(O)(OR)$_2$, OCH$_2$OP(O)(OR$^{17}$)$_2$, OC(O)OP(O)(OR$^{17}$)$_2$, PO(OR$^{16}$)(OR$^{17}$), OP(O)(OR$^{16}$)OP(O)(OR$^{17}$)$_2$, OC(O)R$^{17}$ or OC(O)NHR$^{17}$, wherein $R^{16}$, $R^{17}$ are independently H, $C_1$~$C_8$ of alkyl, heteroalkyl; $C_2$~$C_8$ of alkenyl, alkynyl, heterocyclic, carbocyclic; $C_3$~$C_8$ of aryl, cycloalkyl, alkylcycloalkyl, heterocycloalkyl, heteroalkylcycloalkyl, heteroaralkyl, alkylcarbonyl or $C_4$~$C_{12}$ glycosides, or pharmaceutical salts.

In addition, $R^{12}$ can be H when $R^{10}$ is not H, or when $R^{13}$ is:

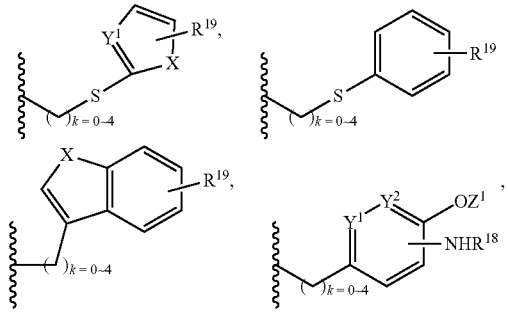

wherein $Z^1$ is H, $CH_2OP(O)(OR^8)_2$, $C(O)OP(O)(OR^{18})_2$, $PO(OR^{18})_2$, $C(O)R^{18}$, $C(O)NHR^{18}$, $SO_2(OR^{18})$, $C_4$~$C_{12}$ glycosides or $C_1$~$C_8$ of alkyl, carboxyalkyl, heterocyclic; $R^{18}$ is H, $C_1$~$C_8$ of alkyl, carboxyalkyl, heteroalkyl; $C_2$~$C_8$ of alkenyl, alkynyl, heterocyclic; $C_3$~$C_8$ of aryl, alkylcarbonyl; $R^{19}$ is H, OH, $NH_2$, $OSO_2(OR^8)$, $XCH_2OP(O)(OR^{18})_2$, $XPO(OR^{18})_2$, $XC(O)R^{18}$, $XC(O)NHR^{18}$, $C_1$~$C_8$ of alkyl, carboxyalkyl, carboxylic acid derivative; $C_2$~$C_8$ of alkenyl, alkynyl, heterocyclic; $C_3$~$C_8$ of aryl, alkylcarbonyl; or pharmaceutical salts; X is O, S, NH; $Y^1$ and $Y^2$ are N or CH respectively.

Or $R^{12}$ can be H when $R^{11}$ is:

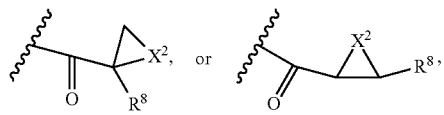

wherein $X^2$ is O, S, N—$R^8$; $R^8$ is H, $C_1$~$C_6$ of alkyl or heteroalkyl

In another embodiment, conjugates of antimitotic agents have the formula (II)

eroalkylcycloalkyl, alkylcarbonyl; or two R's, such as $R^1R^2$, $R^2R^3$, $R^3R^4$, $R^5R^6$ and $R^{12}R^{13}$ can be 3~7 members of a carbocyclic, cycloalkyl, or heterocyclic, heterocycloalkyl ring system; Y is N or CH; In addition, $R^1$, $R^3$, and $R^4$ can be H; and $R^2$ can be absent.

Wherein $R^5$, $R^6$, $R^8$ and $R^{10}$ are independently H, $C_1$~$C_4$ of alkyl or heteroalkyl.

Wherein $R^7$ is independently selected from H, $R^{14}$, or —$R^{14}C(=O)XR^{15}$ or —$R^{14}X^1R^{15}$, wherein $R^{14}$ and $R^{15}$ are independently selected from $C_1$~$C_8$ of alkyl, or heteroalkyl; $C_2$~$C_8$ of alkenyl, alkynyl; heterocyclic, carbocyclic, cycloalkyl; $C_3$~$C_8$ of aryl, heterocycloalkyl, heteroaralkyl, heteroalkylcycloalkyl, alkylcarbonyl; $X^1$ is selected from O, S, S—S, NH, or $NR^{14}$.

Wherein $R^9$ is independently H, —O—, —$OR^{14}$, —$OC(=O)R^{14}$, —$OC(=O)NHR^{14}$, —$OC(=O)R^{14}SSR^{15}$, $OP(=O)(OR^{14})$, or $OR^{14}OP(=O)(OR^{15})$, wherein $R^{14}$, $R^{15}$ are independently $C_1$~$C_8$ of alkyl, heteroalkyl; $C_2$~$C_8$ of alkenyl, alkynyl, heterocyclic, carbocyclic; $C_3$~$C_8$ of aryl, cycloalkyl, alkylcycloalkyl, heterocycloalkyl, heteroalkylcycloalkyl, heteroaralkyl, alkylcarbonyl.

Wherein $R^{11}$ is independently H, $R^{14}$, —$R^{14}C(=O)R^{16}$, —$R^{14}X^2R^{16}$, —$R^4C(=O)X^2$, wherein $X^2$ is —O—, —S—, —NH—, —$N(R^{14})$—, —O—$R^{14}$—, —S—$R^{14}$—, —S(=O)—$R^{14}$—, or —$NHR^{14}$—; $R^{14}$ is $C_1$~$C_8$ of alkyl, heteroalkyl; $C_2$~$C_8$ of alkenyl, alkynyl, heterocyclic, carbocyclic; $C_3$~$C_8$ of aryl, cycloalkyl, alkylcycloalkyl, heterocycloalkyl, heteroalkylcycloalkyl, heteroaralkyl, alkylcarbonyl; $R^{16}$ is H, OH, $R^{14}$ or one to four amino acid units;

Wherein $R^{12}$ is independently $R^{14}$, —OH, —SH, —$NH_2$, =NH, =$NNH_2$, —$NH(R^{14})$, —$OR^{14}$, $COR^{16}$, $COOR^{14}$, $C(O)NH_2$, $C(O)NHR^{14}$, —$SR^{14}$, —$S(=O)R^{14}$, —$P(=O)(OR^{16})_2$, —$OP(=O)(OR^{16})_2$, —$CH_2OP(=O)(OR^{16})_2$, —$SO_2R^{16}$. $R^{14}$ is independently $C_1$~$C_8$ of alkyl, heteroalkyl; $C_2$~$C_8$ of alkenyl, alkynyl, hetero-cyclic, carbocyclic; $C_3$~$C_8$ of aryl, cycloalkyl, alkylcycloalkyl, heterocycloalkyl, heteroaralkyl, heteroalkylcycloalkyl, alkylcarbonyl. $R^{16}$ is H, OH, $R^{14}$ or one to four amino acid units;

Wherein $R^{13}$ is $C_1$~$C_{10}$ of alkyl, heteroalkyl, alkyl acid, alkyl amide, alkyl amine, or Ar; Ar refers to a aromatic or hetero aromatic group, composed of one or several rings, comprising four to ten carbon, preferentially four to six carbon atoms. The term of hetero aromatic group refers one or several carbon on aromatic group, preferentially one, two or three carbon atoms are replaced by O, N, Si, Se, P or S,

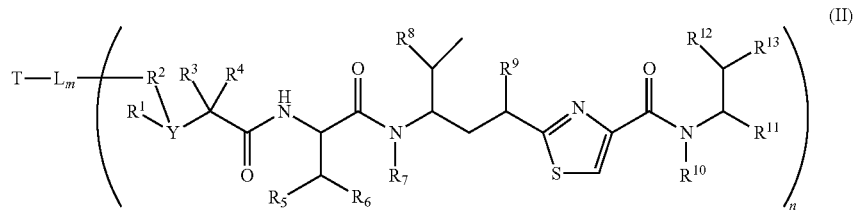

and pharmaceutical acceptable salts and solvates thereof

Wherein T is a targeting or binding ligand; L is a releasable linker; - - - - - is a linkage bond that L connects to a molecule inside the bracket independently; n is 1~20 and m is 1~10.

Inside the round bracket is a potent antimitotic agent/drug wherein $R^1$, $R^2$, $R^3$, and $R^4$ are independently $C_1$~$C_8$ of alkyl, heteroalkyl; $C_2$~$C_8$ of heterocyclic, carbocyclic, alkylcycloalkyl, heterocycloalkyl, $C_3$~$C_8$ of aryl, Ar-alkyl, hetpreferentially O, S, N. The term aryl or Ar also refers to a aromatic group, wherein one or several H atoms are replaced independently by $R^{17}$, F, Cl, Br, I, $OR^{16}$, $SR^{16}$, $NR^{16}R^{17}$, N=$NR^{16}$, N=$R^{16}$, $NR^{16}R^{17}$, $NO_2$, $SOR^{16}R^{17}$, $SO_2R^{16}$, $SO_3R^{16}$, $OSO_3R^{16}$, $PR^{16}R^{17}$, $POR^{16}R^{17}$, $PO_2R^{16}R^{17}$, $OP(O)(OR)_2$, $OCH_2OP(O)(OR^7)_2$, $OC(O)OP(O)(OR^7)_2$, $PO(OR^{16})(OR^{17})$, $OPO(OR^{16})OPO(OR^{16})(OR^{17})$, OC(O)$R^{17}$ or OC(O)NH$R^{17}$, wherein $R^{16}$, $R^{17}$ are independently H, $C_1$~$C_8$ of alkyl, heteroalkyl; $C_2$~$C_8$ of alkenyl, alkynyl, heterocyclic, carbocyclic; $C_3$~$C_8$ of aryl, cycloalkyl, alkylcycloalkyl, heterocycloalkyl, heteroalkylcycloalkyl, heteroaralkyl, alkylcarbonyl or $C_4$~$C_{12}$ glycosides, or pharmaceutical salts.

In addition, $R^{12}$ can be H when $R^{10}$ is not H, or when $R^{13}$ is:

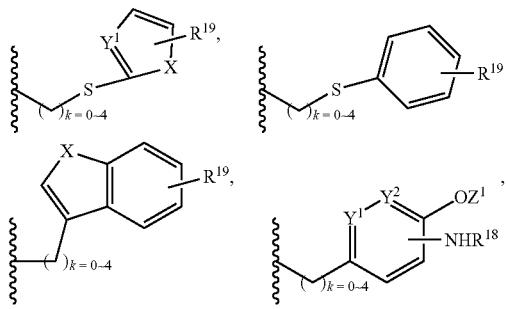

wherein $Z^1$ is H, $CH_2OP(O)(OR^{18})_2$, $C(O)OP(O)(OR^{18})_2$, $PO(OR^{18})_2$, $C(O)R^{18}$, $C(O)NHR^{18}$, $SO_2(OR^{18})$, $C_4$~$C_{12}$ glycosides or $C_1$~$C_8$ of alkyl, carboxyalkyl, heterocyclic; $R^{18}$ is H, $C_1$~$C_8$ of alkyl, carboxyalkyl, heteroalkyl; $C_2$~$C_8$ of alkenyl, alkynyl, heterocyclic; $C_3$~$C_8$ of aryl, alkylcarbonyl; $R^{19}$ is H, OH, $NH_2$, $OSO_2(OR^{18})$, $XCH_2OP(O)(OR^{18})_2$, $XC(O)OP(O)(OR^{18})_2$, $XPO(OR^{18})_2$, $XC(O)R^{18}$, $XC(O)NHR^{18}$, $C_1$~$C_8$ of alkyl, carboxyalkyl, carboxylic acid derivative; $C_2$~$C_8$ of alkenyl, alkynyl, heterocyclic; $C_3$~$C_8$ of aryl, alkylcarbonyl; or pharmaceutical salts; X is O, S, NH; $Y^1$ and $Y^2$ are N or CH respectively.

Or $R^{12}$ can be H when $R^{11}$ is:

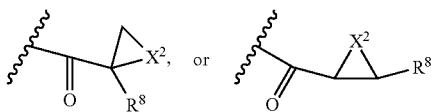

$X^2$ is O, S, N—$R^8$; $R^8$ is H, $C_1$~$C_6$ of alkyl or heteroalkyl

Illustrative classes of compounds of formula II have the structures:

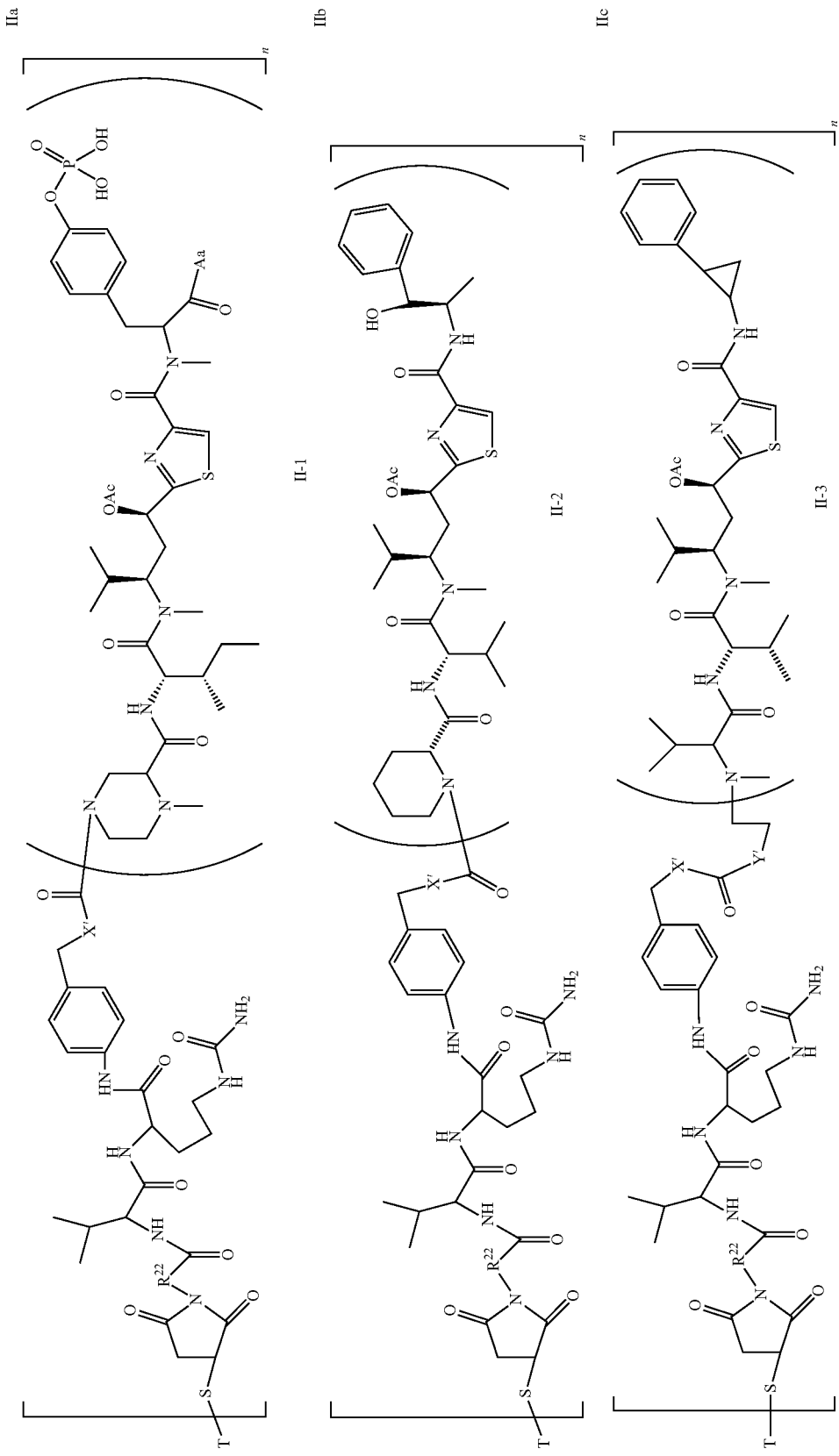

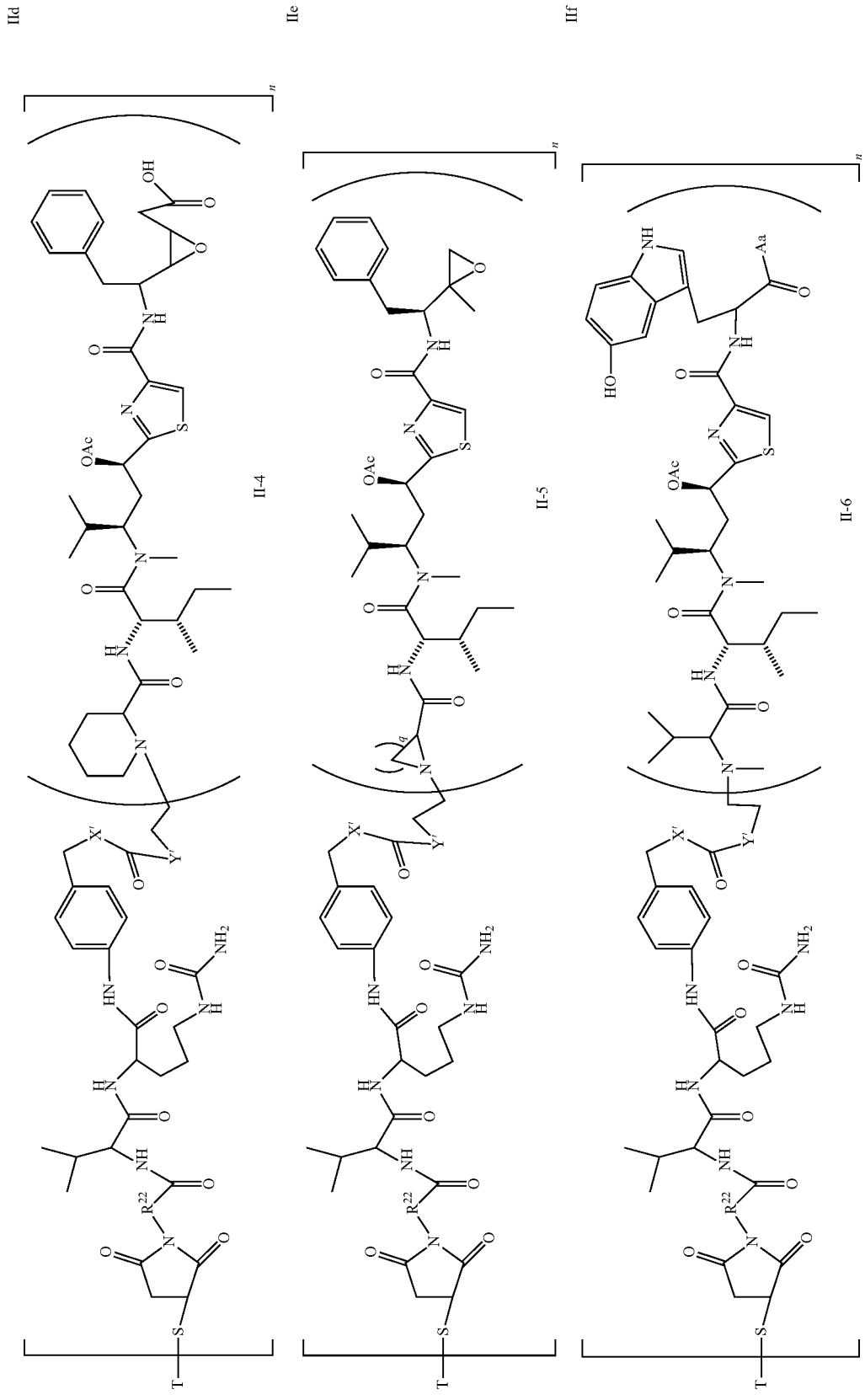

-continued
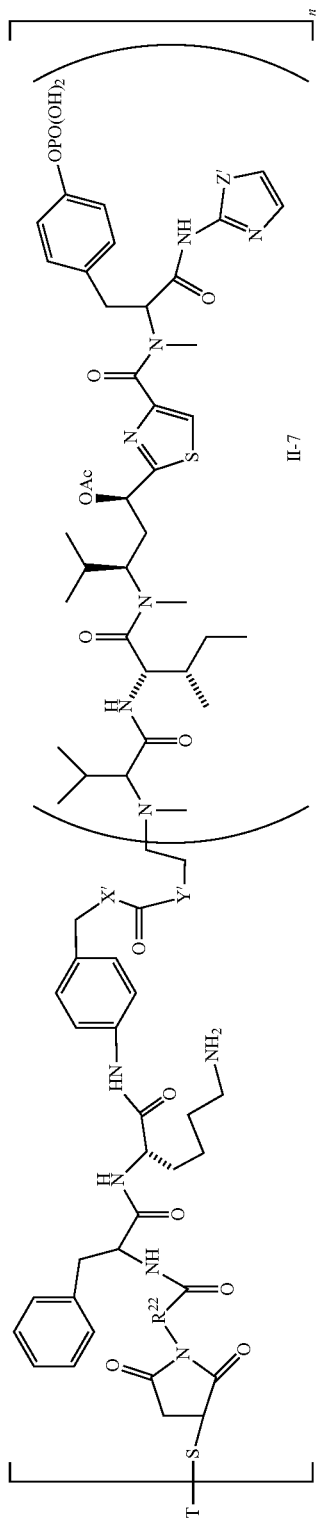
IIg
II-7
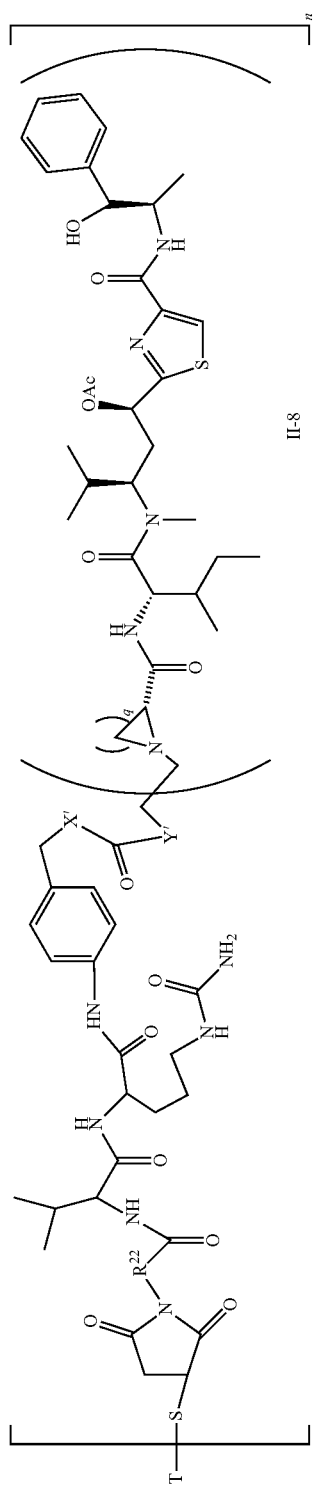
IIh
II-8
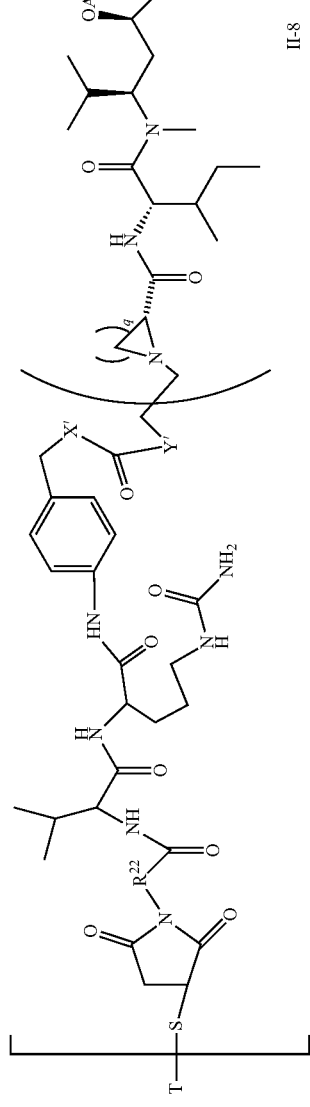
IIi
II-8
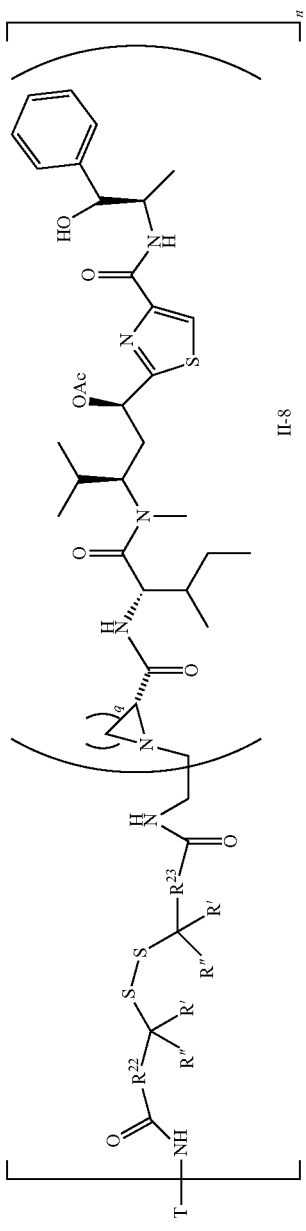

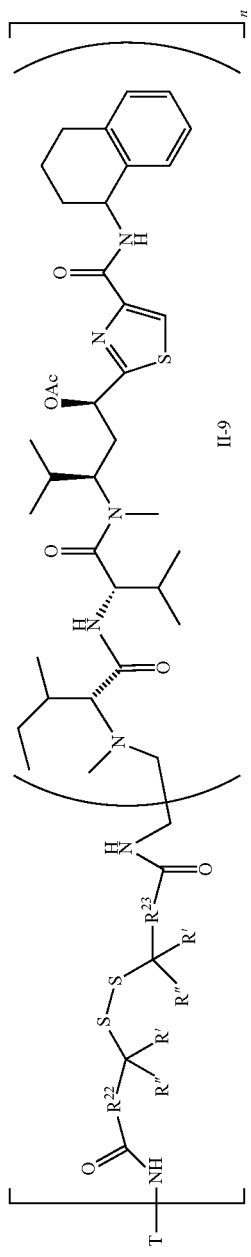
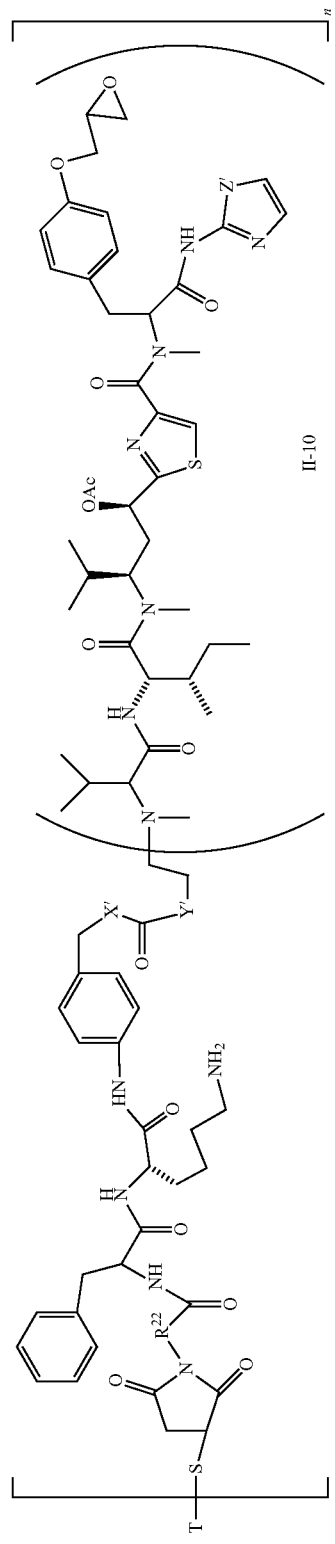
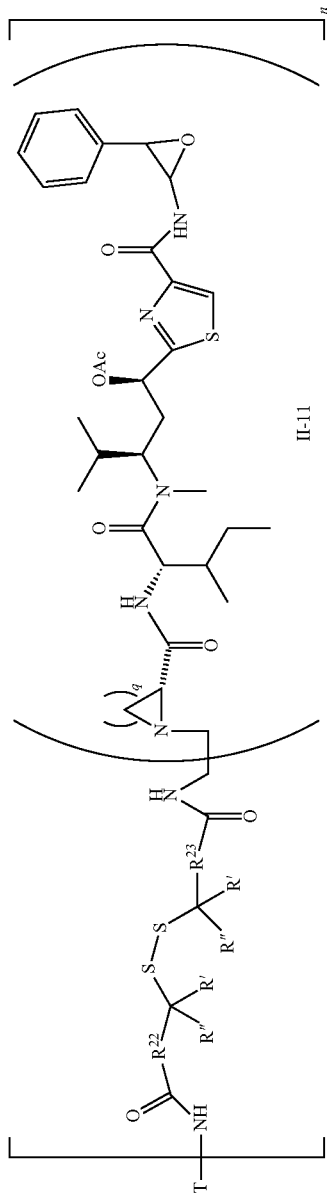

-continued
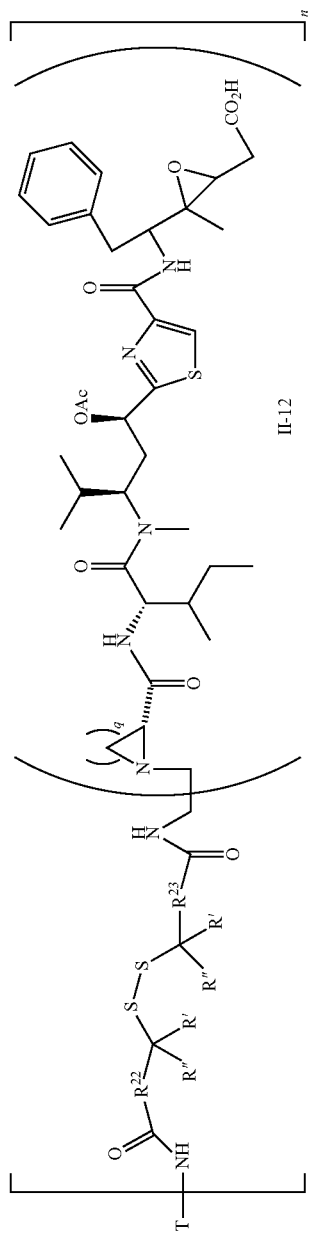
II-12
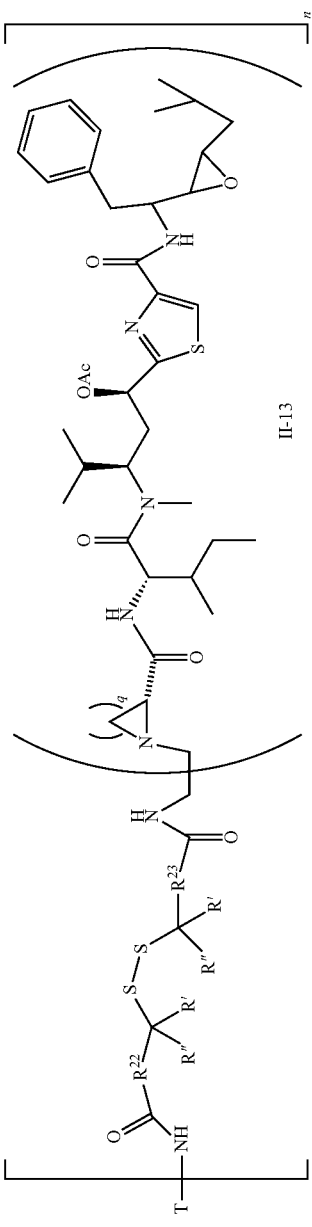
II-13
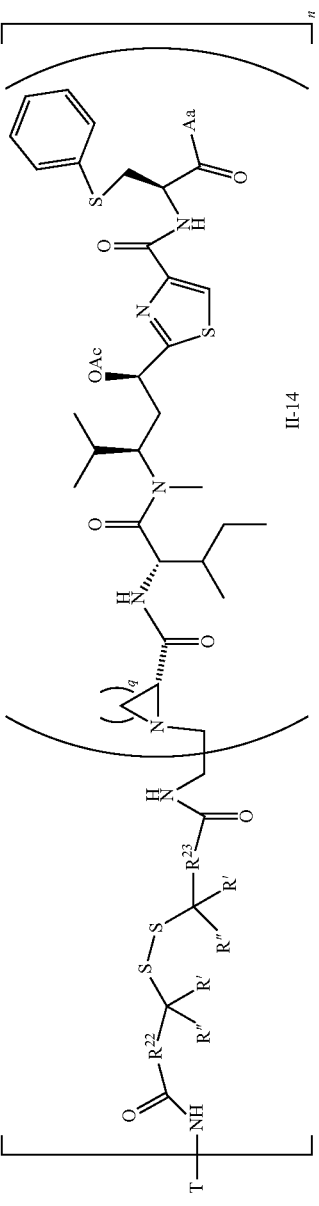
II-14

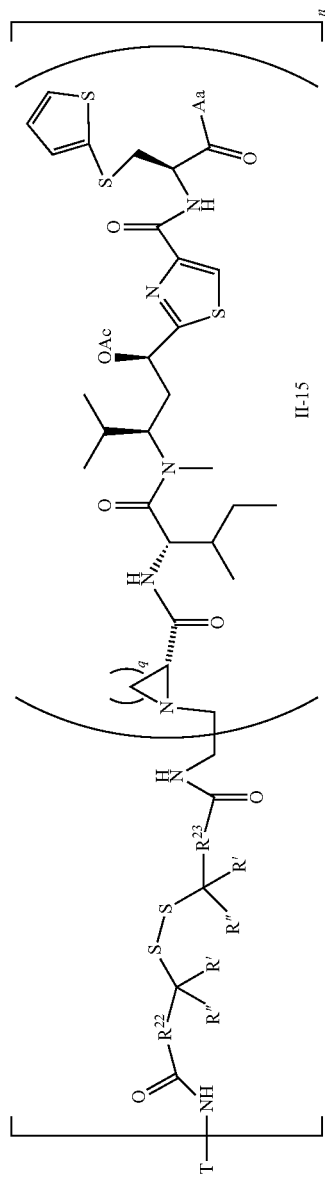
II-15
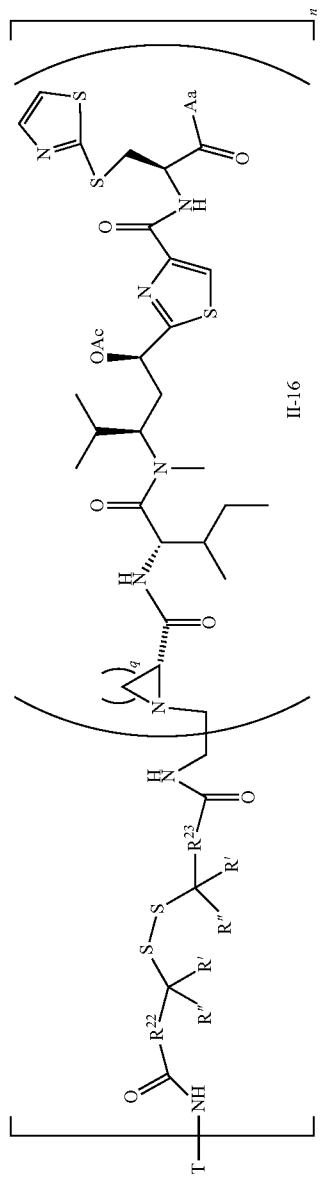
II-16
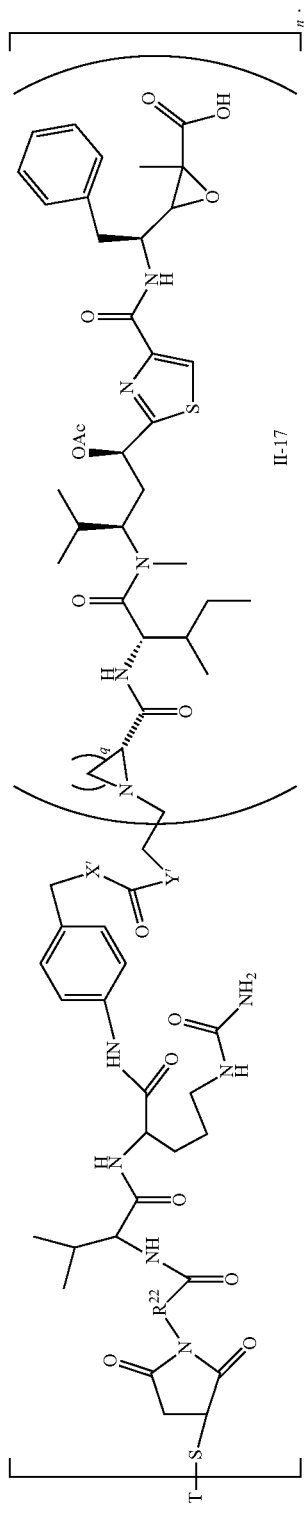
II-17 wherein Aa is a natural or an unnatural amino acid; n is 1~20; q=1~5; X', Y' and Z' are independently CH, O, S, NH, or $NR^{22}$; $R^{22}$ and $R^{23}$ are independently $C_1$~$C_8$ of alkyl; $C_2$~$C_8$ of alkenyl, alkynyl, heteroalkyl; $C_3$~$C_8$ of aryl, heterocyclic, carbocyclic, cycloalkyl, alkylcycloalkyl, heterocycloalkyl, Ar-alkyl, heteroalkylcycloalkyl, heteroaralkyl, or —$(OCH_2CH_2)_n$—; R' and R'' are independently H or $CH_3$. Inside the round brackets are the antimitotic drugs and the inside square brackets are the antimitotic drug with linkers.

In another embodiment, a conjugate of a cell binding molecule-antimitotic agent has the formula (III):

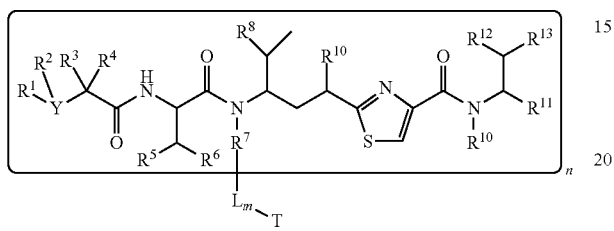

(III)

wherein T, L, m, Y, $R^1$, $R^2$, $R^3$, $R^4$, $R^5$, $R^6$, $R_8$, $R^9$, $R^{10}$, $R^{11}$, $R^{12}$, $R^{13}$ and n are defined the same as in formula (II).

Wherein $R^7$ is independently selected from $R^{14}$, or —$R^{14}C(=O)X^1R^{15}$— or —$R^{14}XR^{15}$—. $R^{14}$ and $R^{15}$ are independently selected from $C_1$~$C_8$ of alkyl, or heteroalkyl; $C_2$~$C_8$ of alkenyl, alkynyl; heterocyclic, carbocyclic, cycloalkyl; $C_3$~$C_8$ of aryl, heterocycloalkyl, heteroaralkyl, heteroalkylcycloalkyl, alkylcarbonyl; $X^1$ is selected from O, S, S—S, NH, or $NR^{14}$.

Illustrative examples of compounds of formula (III) have the structures:

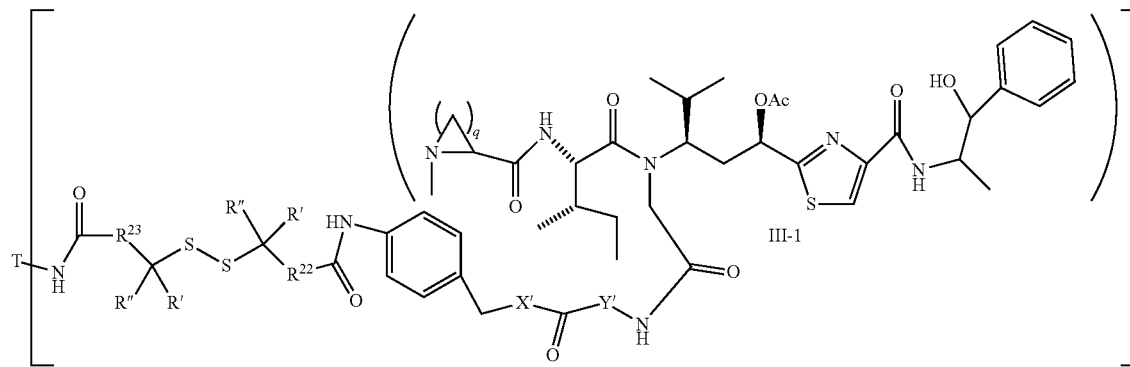

IIIa

III-1

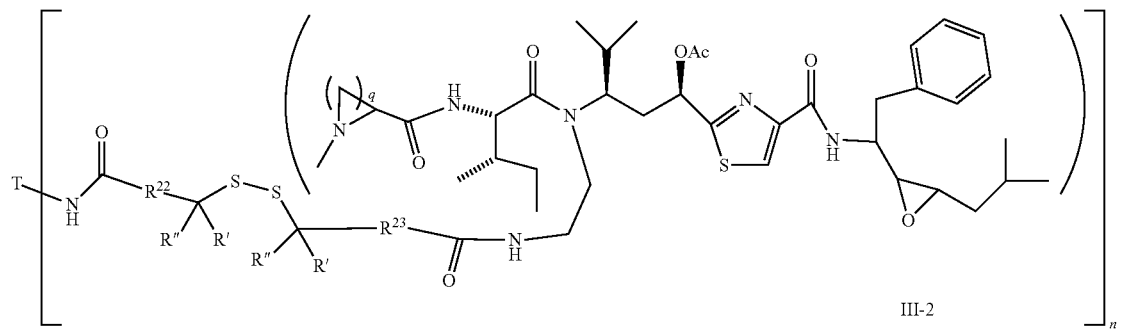

IIIb

III-2

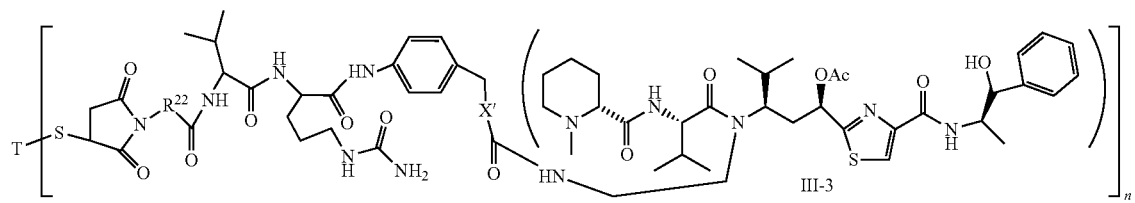
IIIc
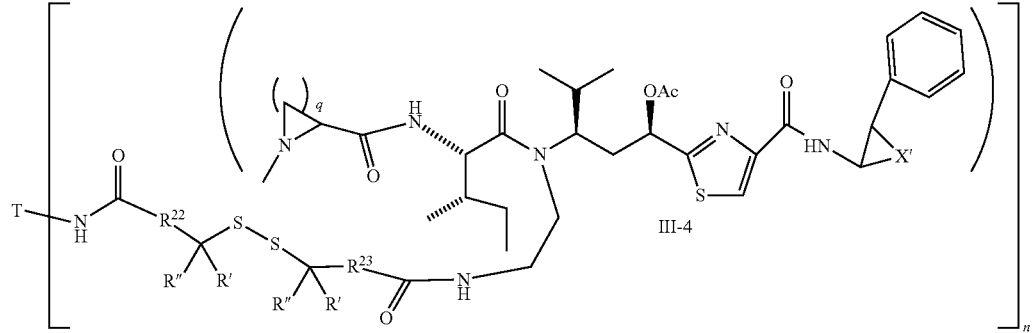
IIId
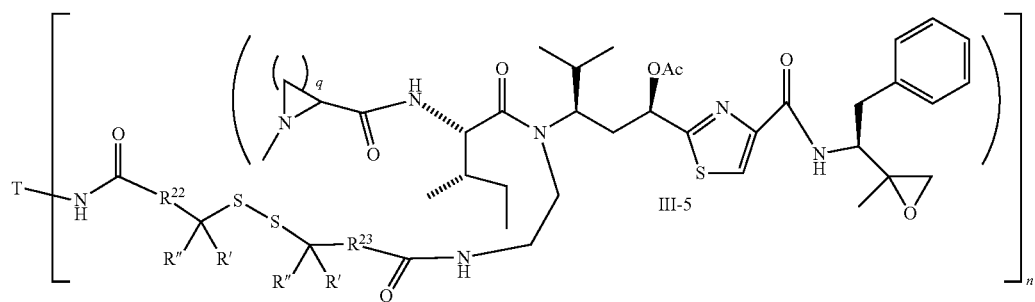
IIIe
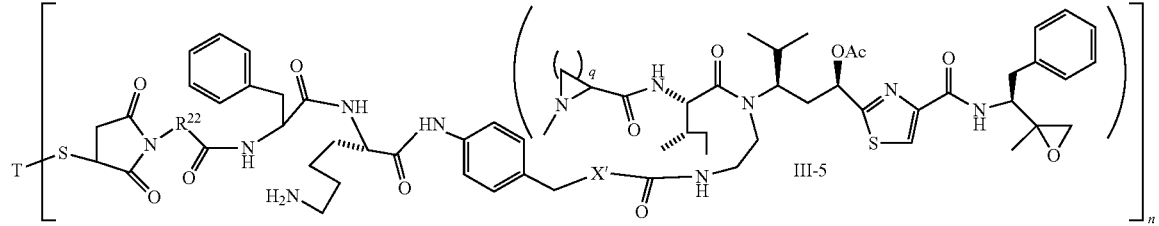
IIIf
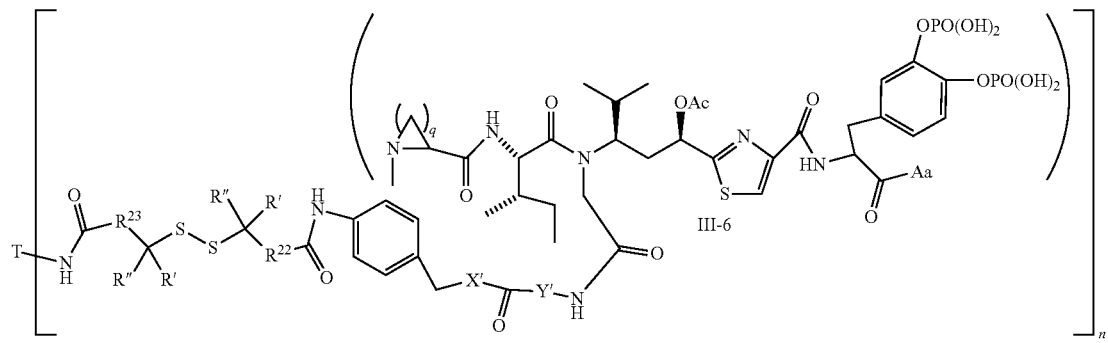
IIIg

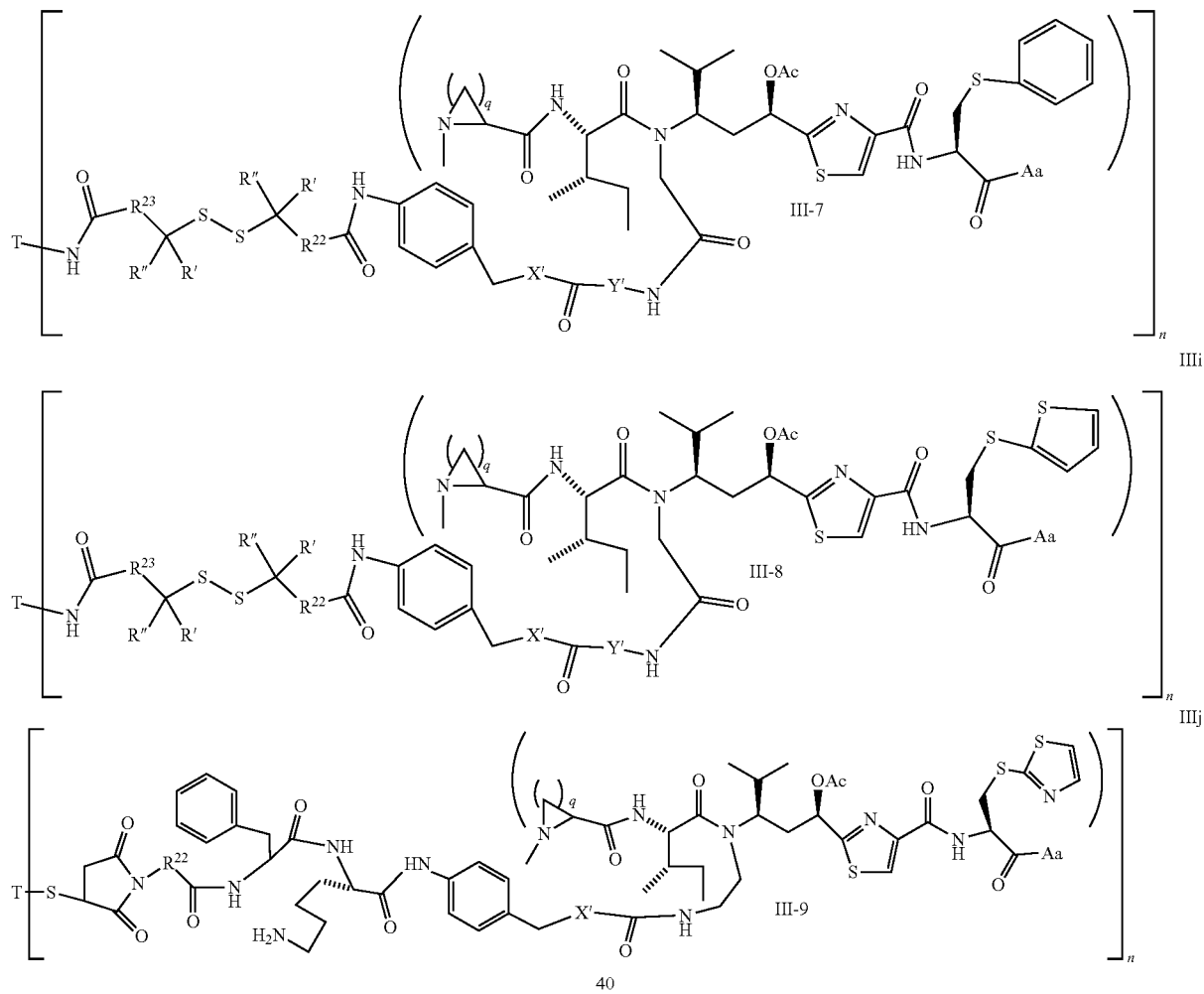

wherein Ar, n, q, X', Y', Z', $R^{22}$, $R^{23}$, R' and R" are defined the same as for formula IIa~IIr.

In another embodiment, a binding molecule-antimitotic agent conjugate has the formula (IV)

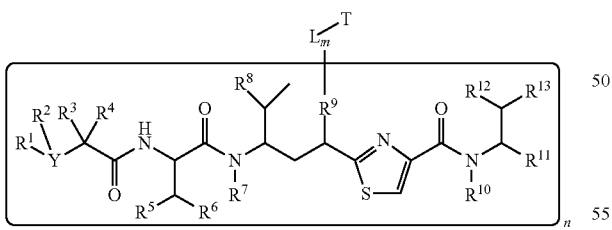

(IV)

wherein T, L, m, Y, $R^1$, $R^2$, $R^3$, $R^4$, $R^5$, $R^6$, $R^7$, $R^8$, R, $R^{12}$, $R^{13}$ and n are defined the same as in formula (II).

Wherein $R^9$ is independently, —O—, —$OR^{14}$—, —OC(=O)$R^{14}$—, —OC(=O)NH$R^{14}$—, —OC(=O)$R^{14}SSR^{15}$—, —OP(=O)(O$R^{14}$)O—, wherein $R^{14}$, $R^{15}$ are independently $C_1$~$C_8$ of alkyl, heteroalkyl; $C_3$~$C_8$ of aryl, heteroaryl, heterocyclic, carbocyclic, cycloalkyl, alkylcycloalkyl, heterocycloalkyl, heteroalkylcycloalkyl, heteroaralkyl, alkylcarbonyl or pharmaceutical salts. In addition, $R^9$ can be absent.

Illustrative examples of compounds of formula (IV) have the structures:
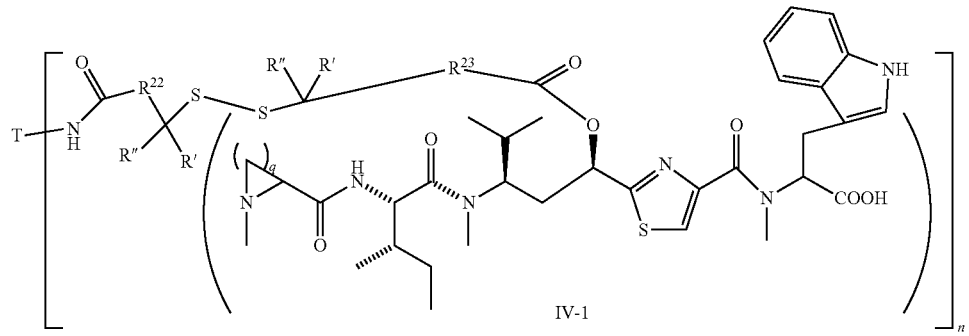
IVa
IV-1
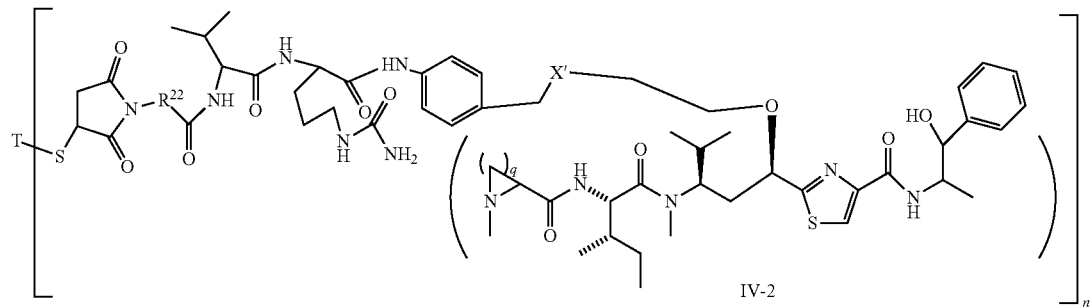
IVb
IV-2
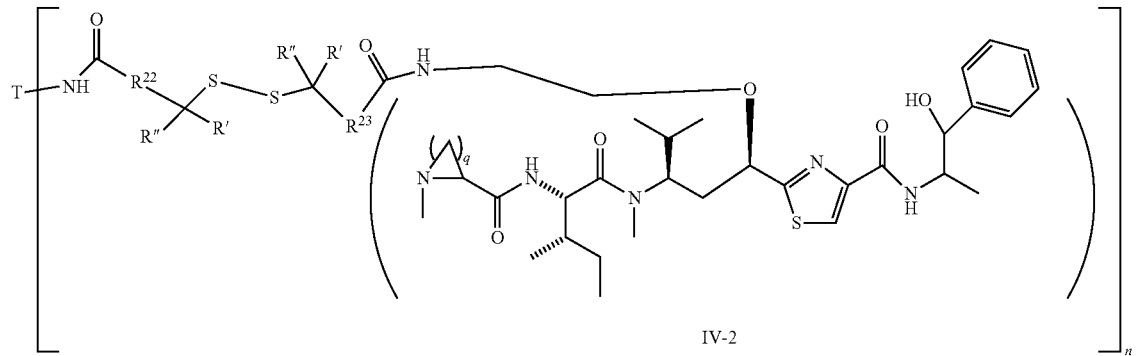
IVc
IV-2
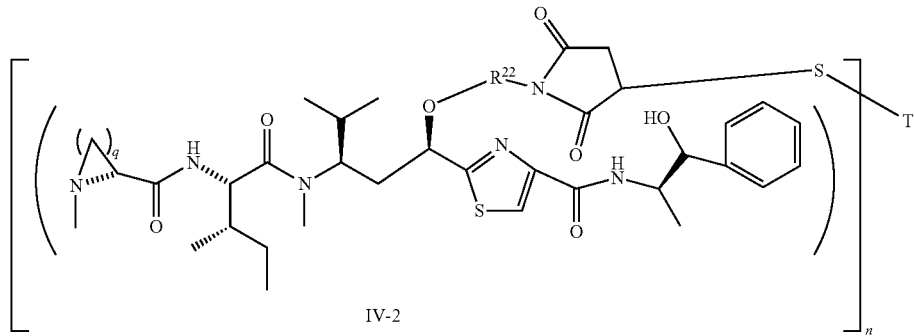
IVd
IV-2

-continued

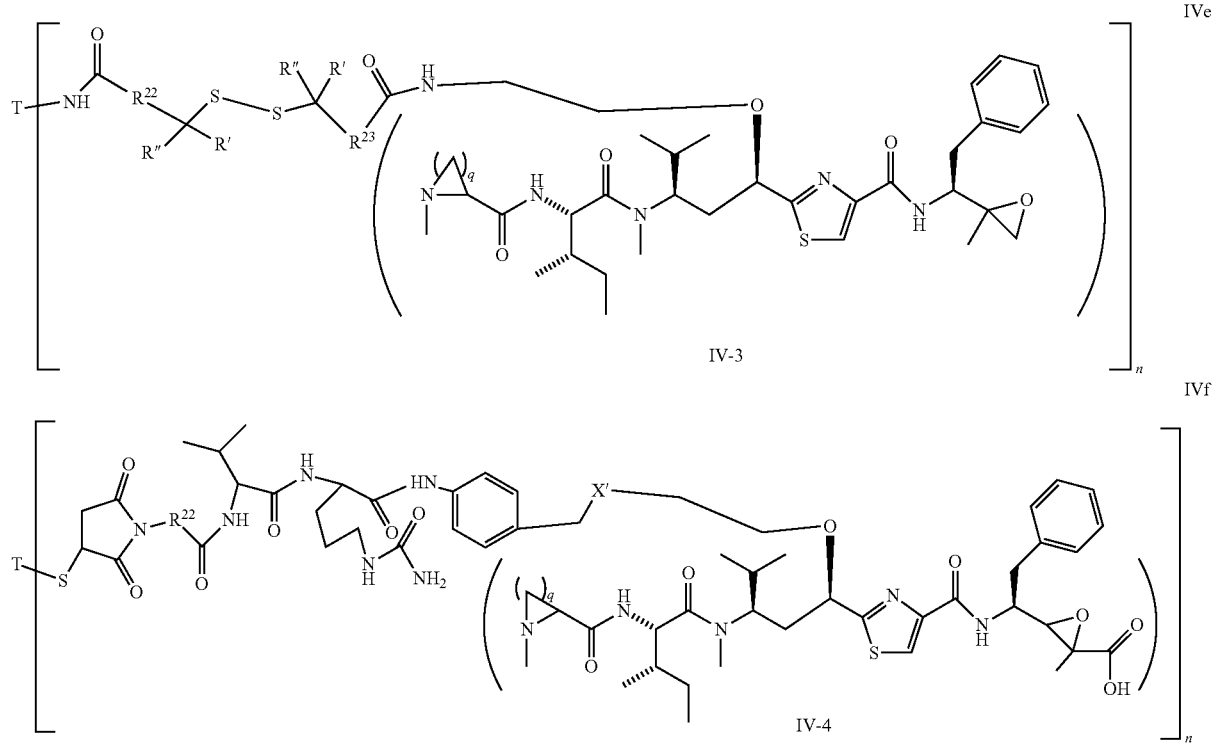

wherein Ar, Aa, n, q, X', Y', $R^{22}$, $R^{23}$, R' and R" are defined the same as for formula IIa~IIr.

In another embodiment, a binding molecule-antimitotic agent conjugate has the formula (V)

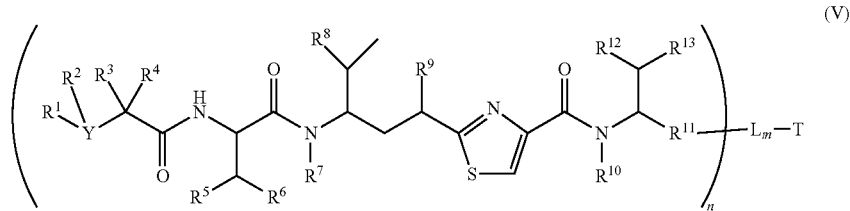

wherein T, L, m, Y, $R^1$, $R^2$, $R^3$, $R^3$, $R^4$, $R^5$, $R^6$, $R^7$, $R^8$, $R^9$, $R^{10}$, $R^{12}$, $R^{13}$ and n are defined the same as in formula (II).

Wherein $R^{11}$ is independently —$R^{14}$—, —$R^{14}$C(=O)$R^{17}$—, —$R^{14}X^2R^{17}$—, —$R^{14}$C(=O)$X^2$—, wherein $R^{17}$ is independently H, OH, $C_1$~$C_8$ of alkyl; $C_2$~$C_8$ of alkenyl, alkynyl, heteroalkyl; $C_3$~$C_8$ of aryl, arylene, heterocyclic, carbocyclic, heterocycloalkyl; or an amino acid, or two amino acid units; $X^2$ is —O—, —S—, —NH—, —N($R^{14}$)—, —O—$R^{14}$—, —S—$R^{14}$—, —S(=O)—$R^{14}$—, or —NH$R^{14}$—; $R^{14}$ is $C_1$~$C_8$ of alkyl, heteroalkyl; $C_2$~$C_8$ of alkenyl, alkynyl; $C_3$~$C_8$ of aryl, heterocyclic, carbocyclic, cycloalkyl, alkylcycloalkyl, heterocycloalkyl, heteroalkylcycloalkyl, heteroaralkyl, alkylcarbonyl.

Illustrative examples of compounds of formula (V) have the structures:

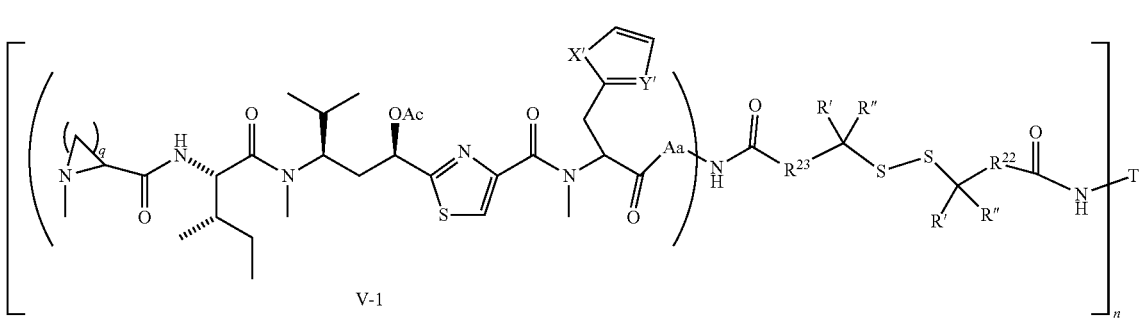

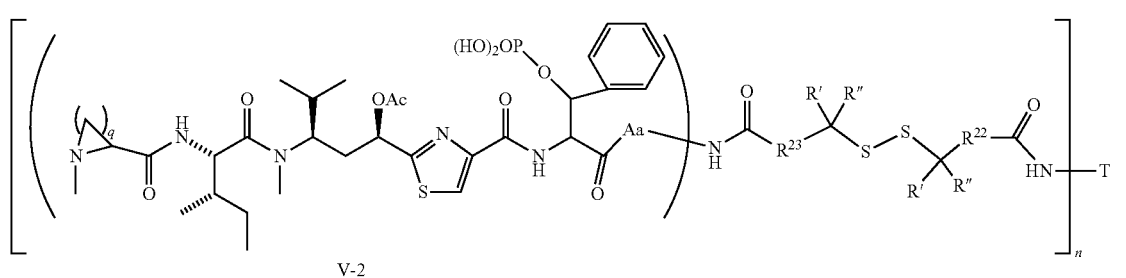
V-2
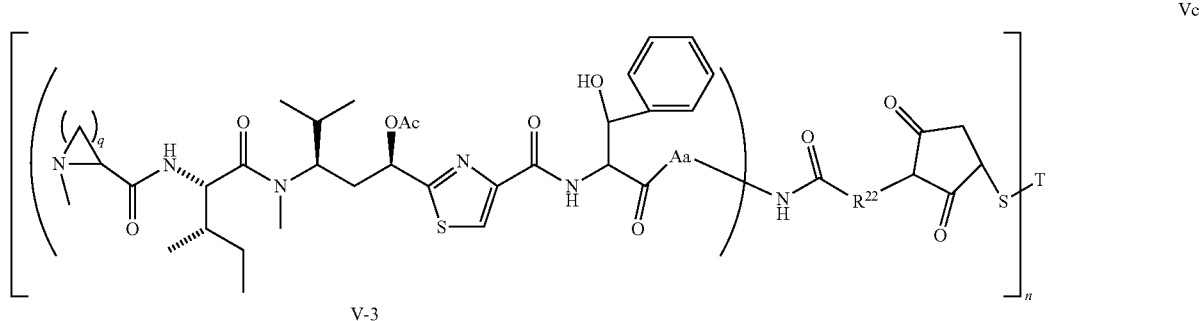
V-3
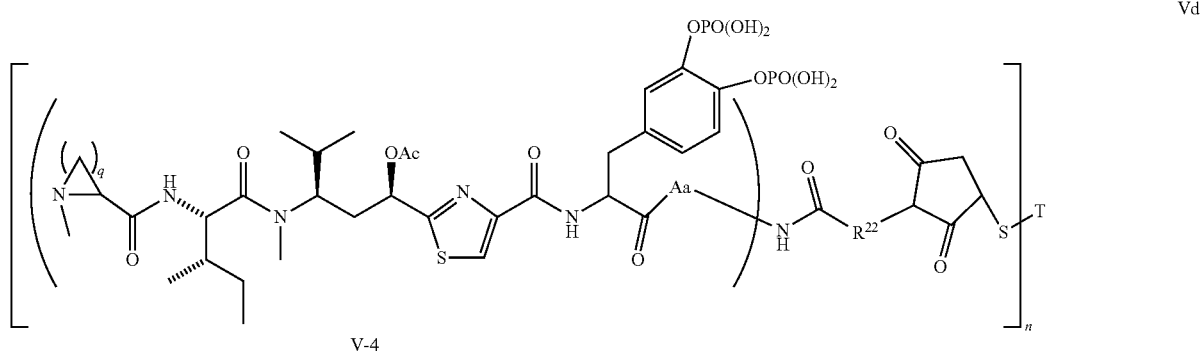
V-4
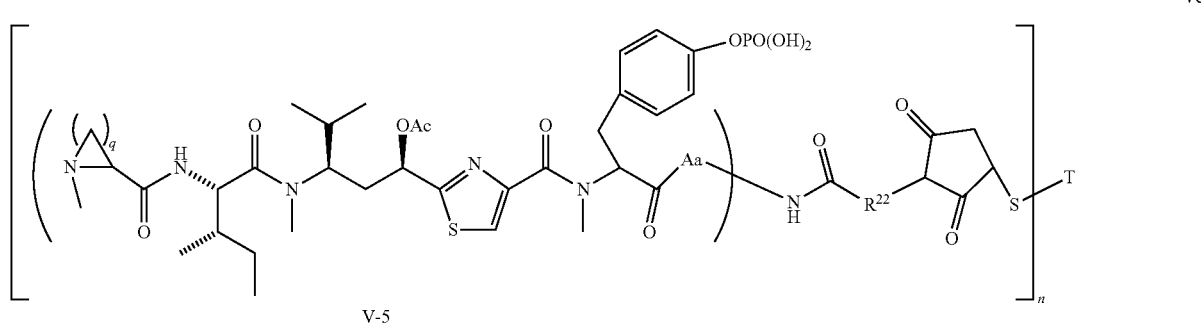
V-5
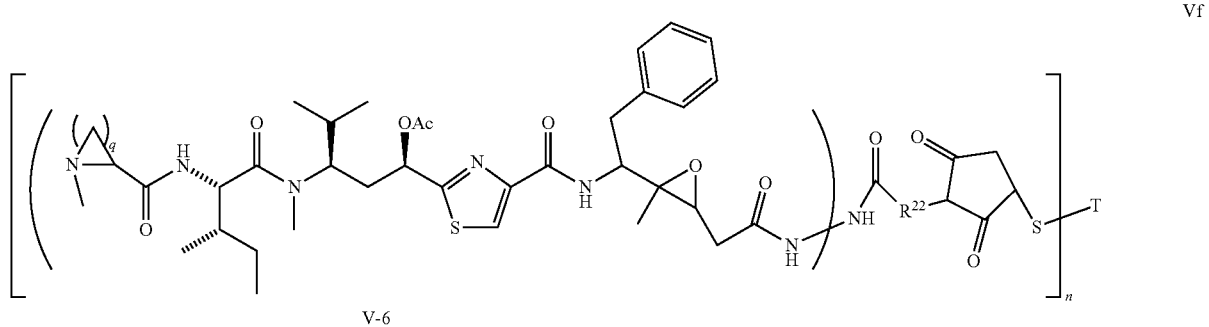
V-6

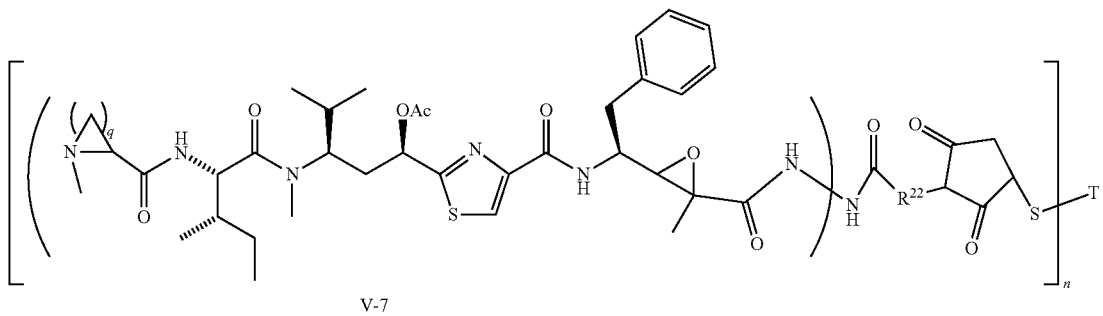

Vg

V-7

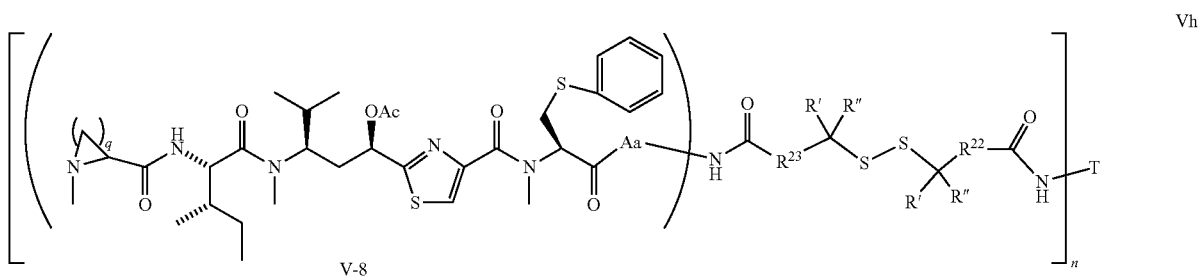

Vh

V-8

Wherein Ar, Aa, n, q, X', $R^{22}$, $R^{23}$, R', and R" are defined the same as for formula IIa~IIr.

In another embodiment, a conjugates of a cell binding-antimitotic agent have the formula (VI)

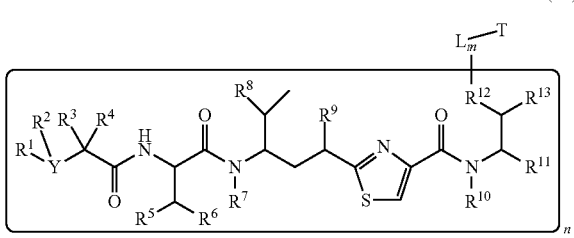

(VI)

wherein T, L, m, $R^1$, $R^2$, $R^3$, $R^4$, $R^5$, $R^6$, $R^7$, $R^8$, $R^9$, $R^{11}$, $R^{13}$ and n are defined the same as formula (II).

Wherein $R^{12}$ is independently $R^{14}$, —O—, —S—, —Ni—, =N—, =NNH—, —N($R^4$)—, —$OR^4$—, C(O)O—, C(O)NH—, C(O)NR—, —$SR^{14}$—, —S(=O)$R^{14}$—, —$NHR^{14}$—, —$CH_2OP$(=O)($OR^{15}$)—, —P(=O)($OR^{15}$)—, —OP(=O)($OR^{15}$)O—, —$SO_2R^{14}$. $R^{14}$, $R^{15}$ are independently $C_1$~$C_2$ of alkyl, heteroalkyl; $C_2$~$C_8$ of alkenyl, alkynyl; $C_3$~$C_8$ of aryl, heterocyclic, carbocyclic, cycloalkyl, alkylcycloalkyl, heterocycloalkyl, heteroaralkyl, heteroalkylcycloalkyl, alkylcarbonyl.

Illustrative examples of compounds of formula VI have the following structures:

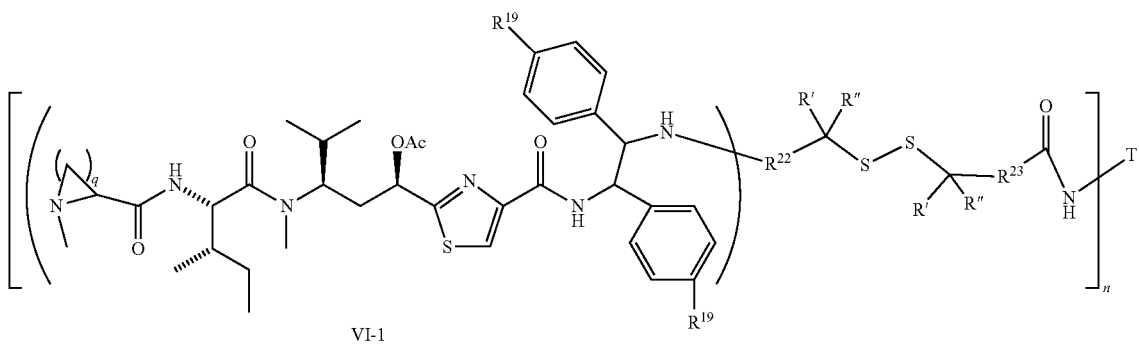

VIa

VI-1

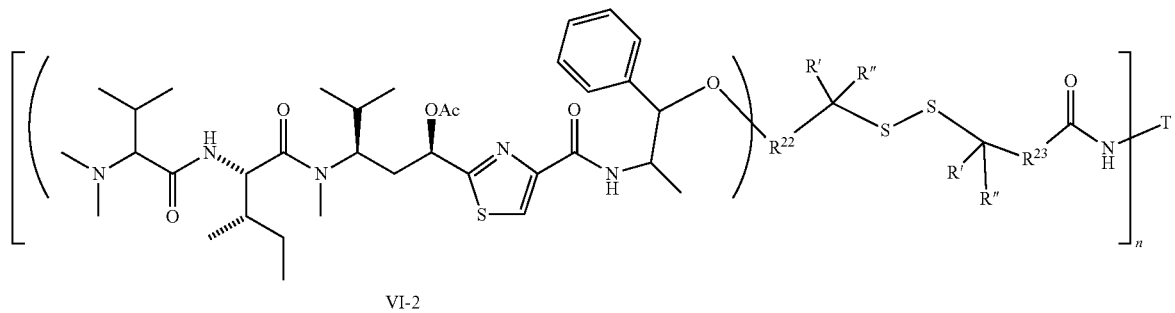
VI-2
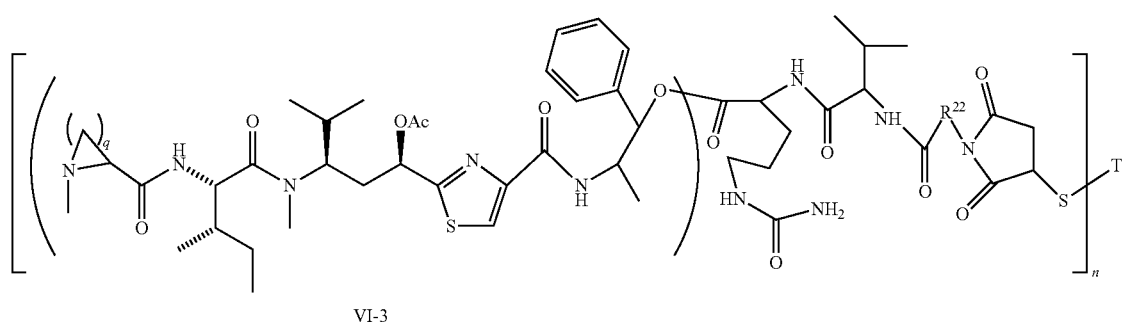
VI-3
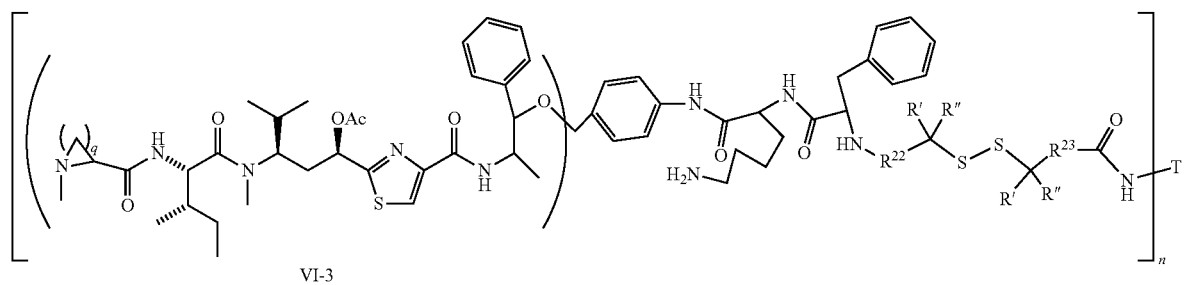
VI-3
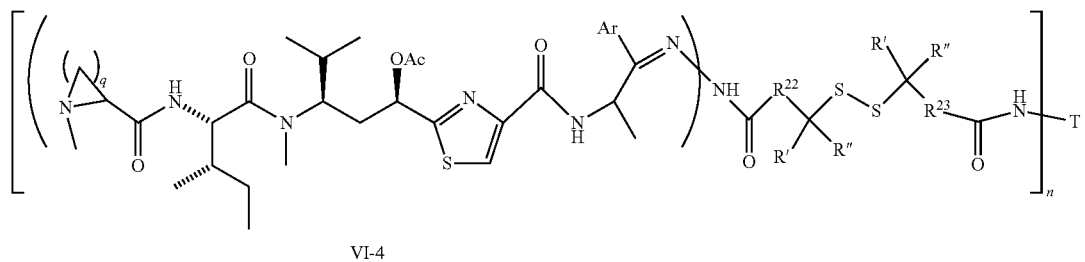
VI-4

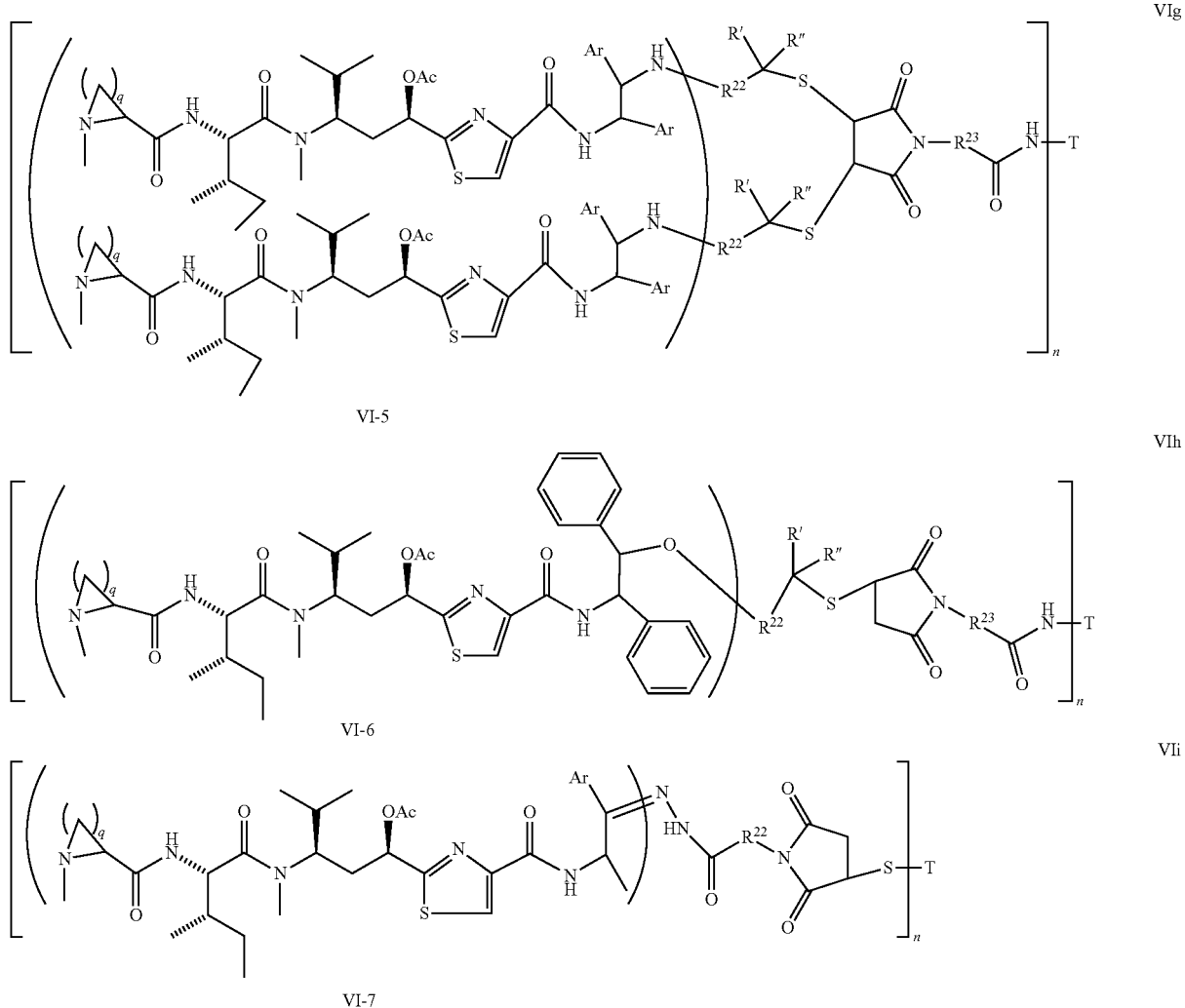

VI-5

VI-6

VI-7

Wherein Ar, Aa, n, q, X', $R^{22}$, $R^{23}$, R' and R" are defined the same as for formula IIa~IIr.

In another embodiment, the conjugates of the cell-surface binding molecule-antimitotic agents have the formula (VII)

or three carbon atoms are replaced by O, N, Si, Se, P or S, preferentially O, S, N. The term aryl or Ar also refers to a aromatic group, wherein one or several H atoms are replaced independently by $R^{18}$, F, Cl, Br, I, $OR^{16}$, $SR^{16}$, $R^{16}R^{18}$,

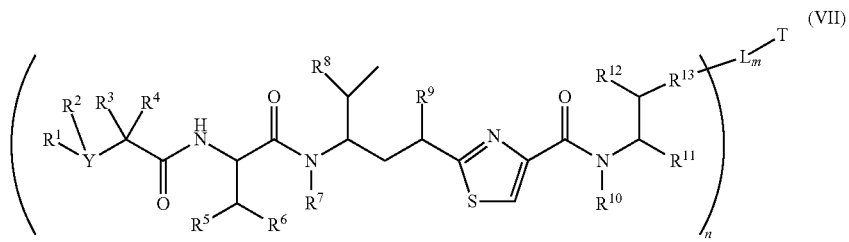

Wherein T, L, m, $R_1$, $R_2$, $R_3$, $R_4$, $R_5$, $R_6$, $R_7$, $R_8$, $R_9$, $R_{11}$, $R_{12}$ and n are defined the same as in formula (II).

Wherein $R^{13}$ is $C_1$~$C_{10}$ of alkyl, heteroalkyl, alkyl acid, alkyl amide, alkyl amine, or Ar; Ar refers to a aromatic or hetero aromatic group, composed of one or several rings, comprising four to ten carbon, preferentially four to six carbon atoms. The term of hetero aromatic group refers one or several carbon on aromatic group, preferentially one, two $N=NR^{16}$, $N=R^{16}$, $R^{16}R^{18}$, $NO_2$, $SOR^{16}R^{18}$, $SO_2R^{16}$, $SO_2R^{16}$, $SO_3R^{16}$, $OSO_3R^{16}$, $PR^{16}R^{18}$, $POR^{16}R^{18}$, $PO_2R^{16}R^{18}$, $OPO_3R^{16}R^{18}$, $OPO_2R^{16}OPO_3R^{18}$ or $PO_3R^{16}R^{18}$ wherein $R^{16}$, $R^{18}$ are independently H, $C_1$~$C_8$ of alkyl; $C_2$~$C_8$ of alkenyl, alkynyl, heteroalkyl; $C_3$~$C_8$ of aryl, heterocyclic, carbocyclic, cycloalkyl, alkylcycloalkyl, heterocycloalkyl, heteroaralkyl, heteroalkylcycloalkyl, alkylcarbonyl; or $C_4$~$C_{12}$ glycosides; or pharmaceutical salts.

In addition, $R^{12}$ can be H when $R^{10}$ is not H, or when $R^{13}$ is:

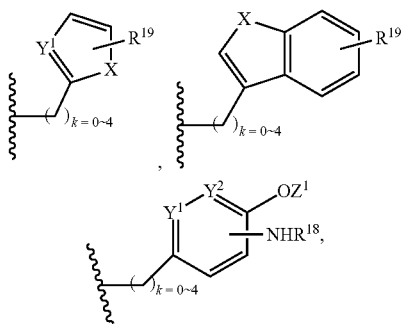

wherein $Z^1$ is H, $CH_2OP(O)(OR^{18})_2$, $C(O)OP(O)(OR^{18})_2$, $PO(OR^{18})_2$, $PO(OR^8)OPO(OR^{18})_2$, $C(O)R^8$, $C(O)NHR^{18}$, $SO_2(OR^8)$, $C_4\sim C_{12}$ glycosides, or $C_1\sim C_8$ of alkyl, carboxyalkyl, heterocyclic; $R^{18}$ is H, $C_1\sim C_8$ of alkyl, carboxyalkyl, heteroalkyl; $C_2\sim C_8$ of alkenyl, alkynyl, heterocyclic; $C_3\sim C_8$ of aryl, alkylcarbonyl; $R^{19}$ is H, OH, $NH_2$, $OSO_2(OR^{18})$, $XCH_2OP(O)(OR^{18})_2$, $XC(O)OP(O)(OR^{18})_2$, $XPO(OR^{18})_2$, $XC(O)R^{18}$, $XC(O)NHR^{18}$, $C_1\sim C_8$ of alkyl, carboxyalkyl, carboxylic acid derivative; $C_2\sim C_8$ of alkenyl, alkynyl, heterocyclic; $C_3\sim C_8$ of aryl, alkylcarbonyl; or pharmaceutical salts; X is O, S, NH; $Y^1$ and $Y^2$ are N or CH respectively.

Or $R^{12}$ can be H when $R^{11}$ is:

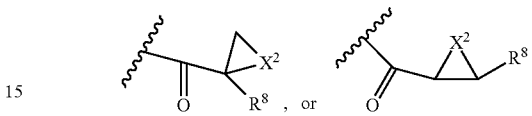

$X^2$ is O, S, N—$R^8$; $R^8$ is H, $C_1\sim C_4$ of alkyl or heteroalkyl.

Illustrative examples of compounds of formula VII have the following structures:

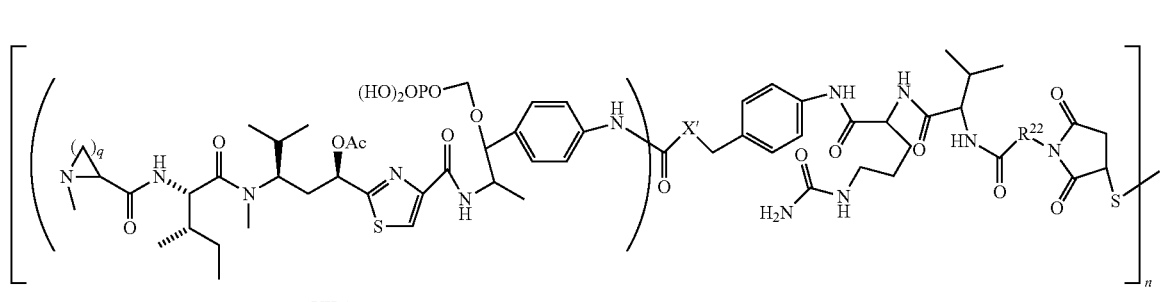

VIIa

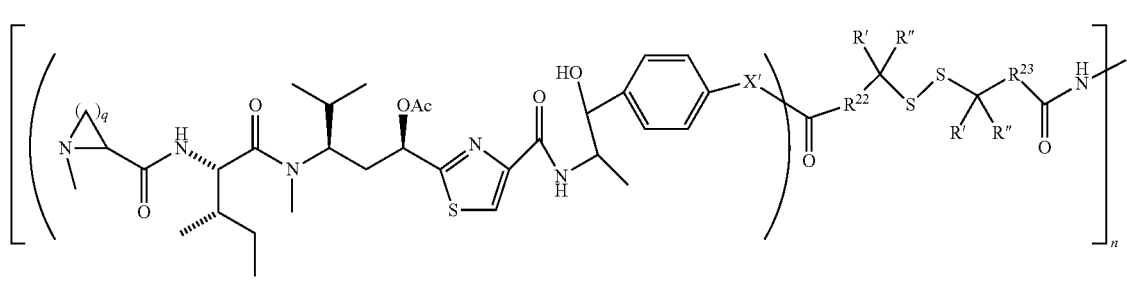

VIIb

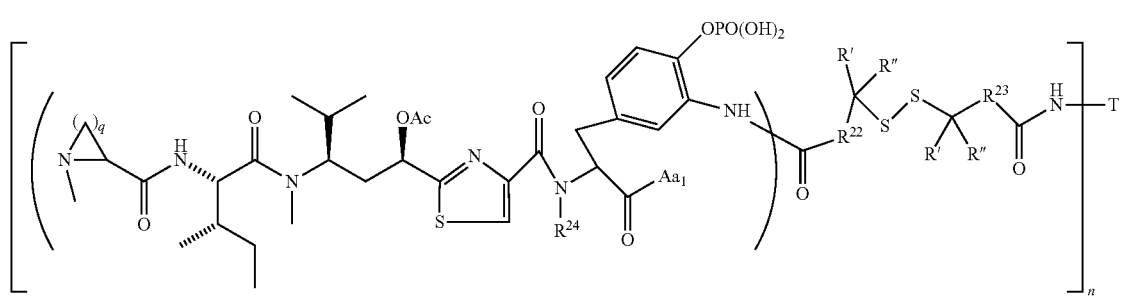

VIIc

-continued
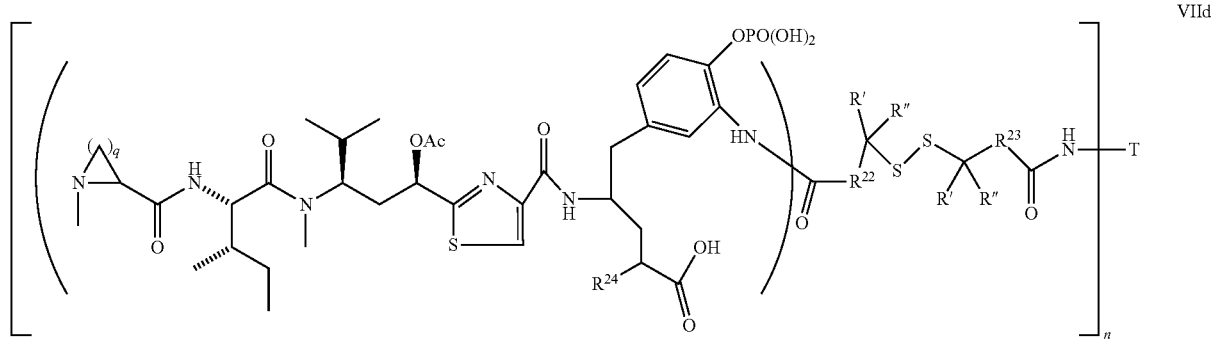
VIId
VII-4
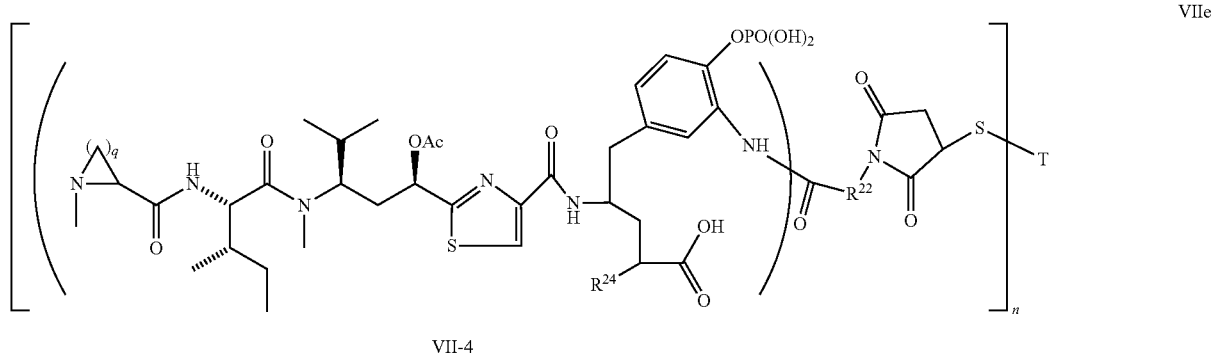
VIIe
VII-4
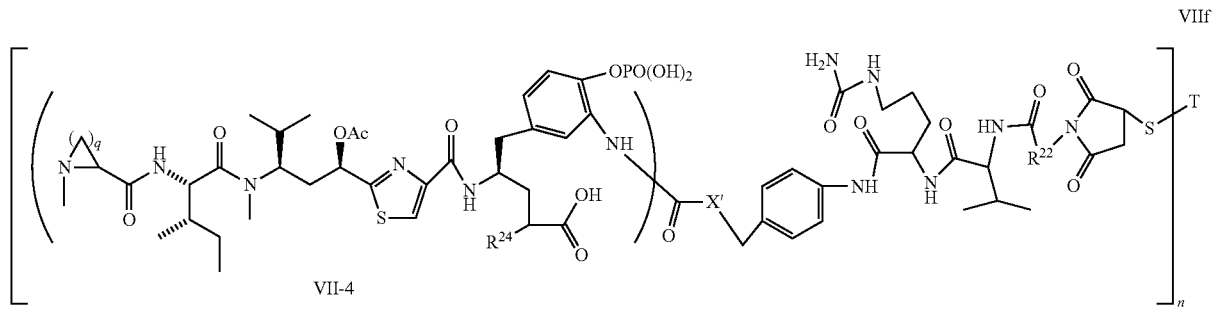
VIIf
VII-4
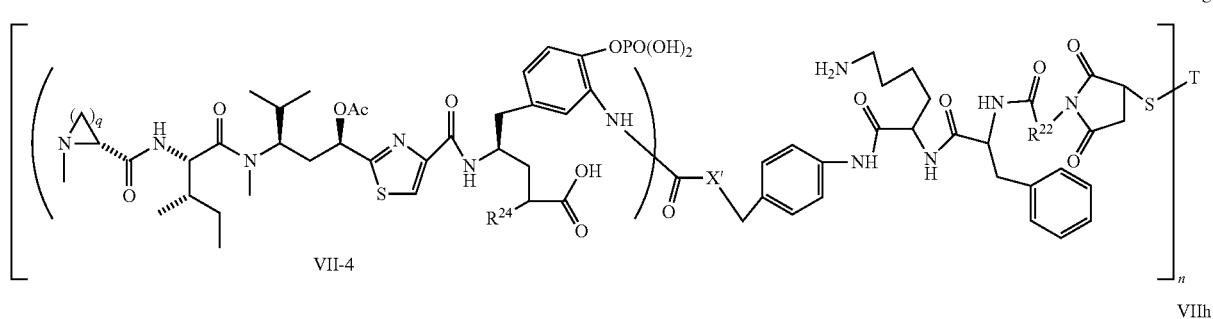
VIIg
VII-4
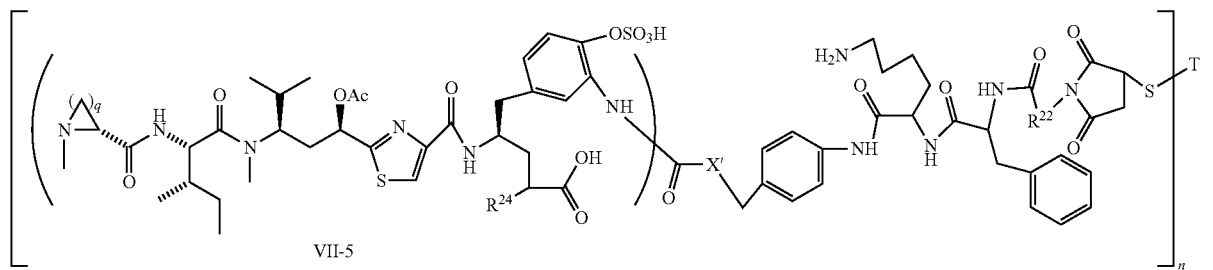
VIIh
VII-5

-continued
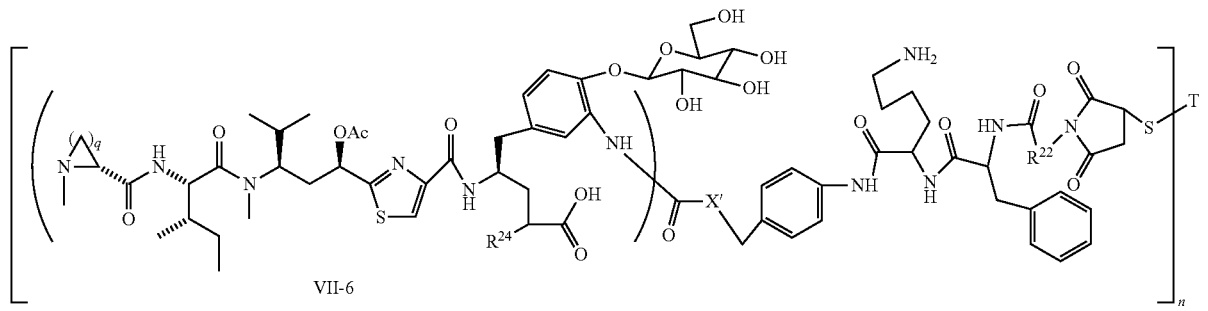
VIIi
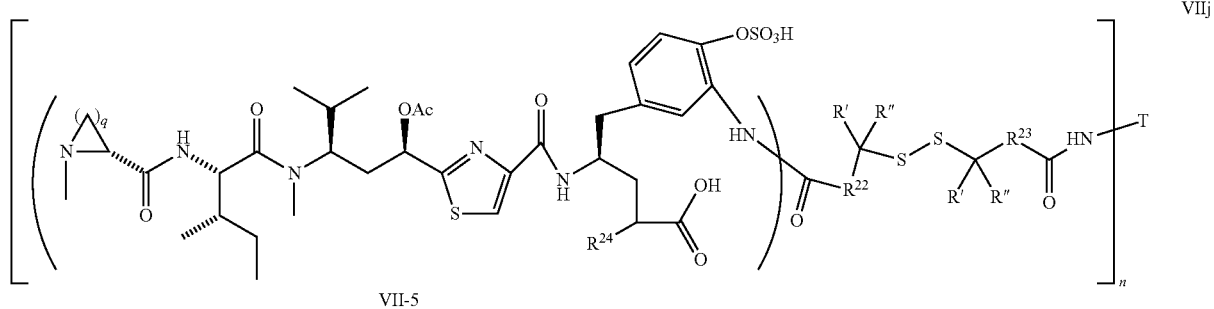
VIIj
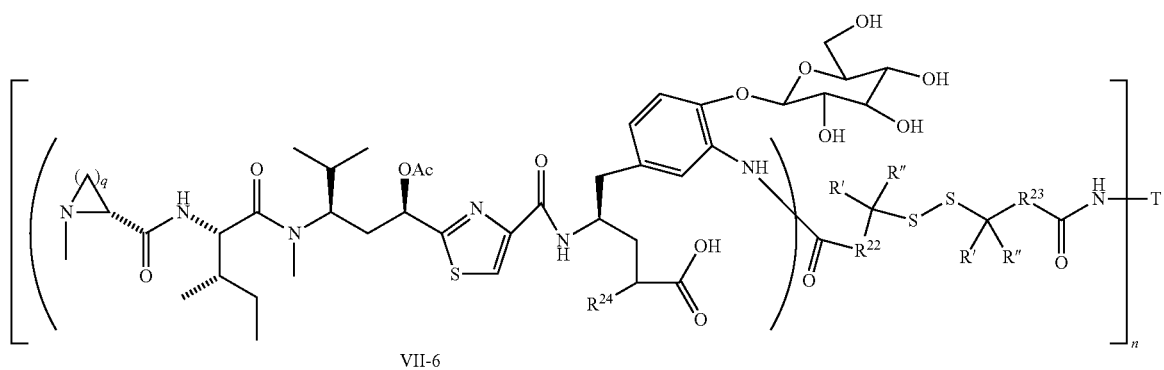
VIIk
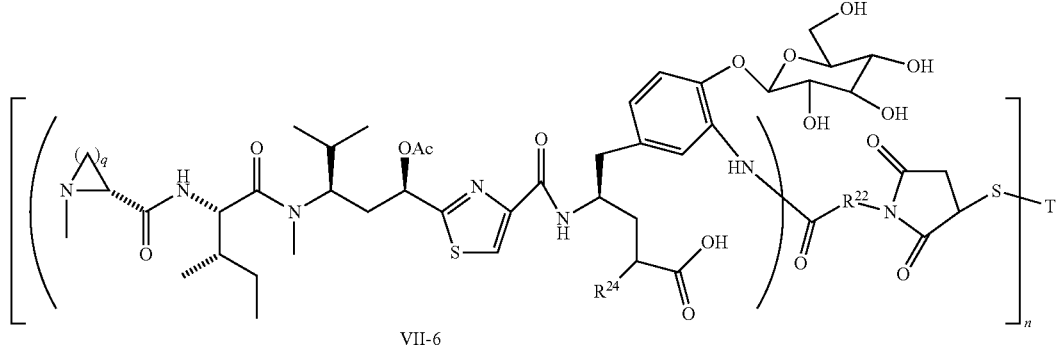
VIII

-continued
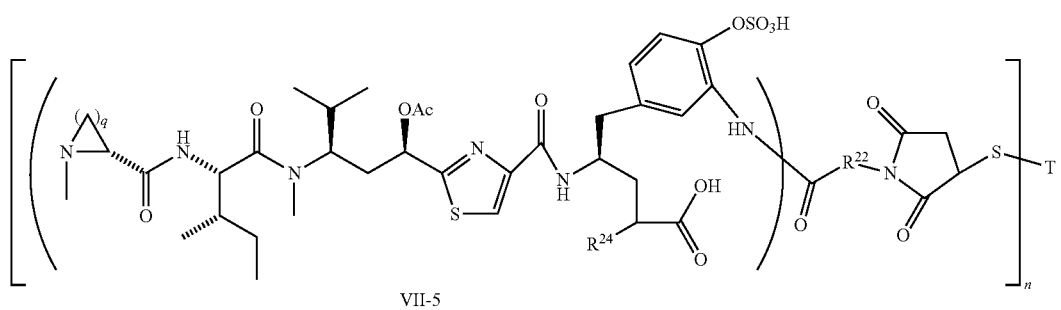
VII-5
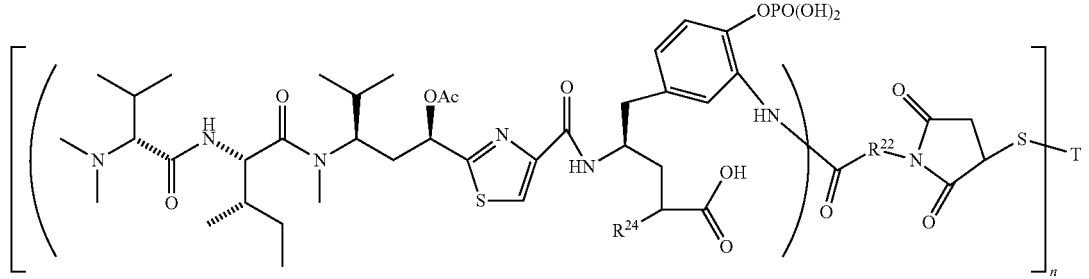
VII-7
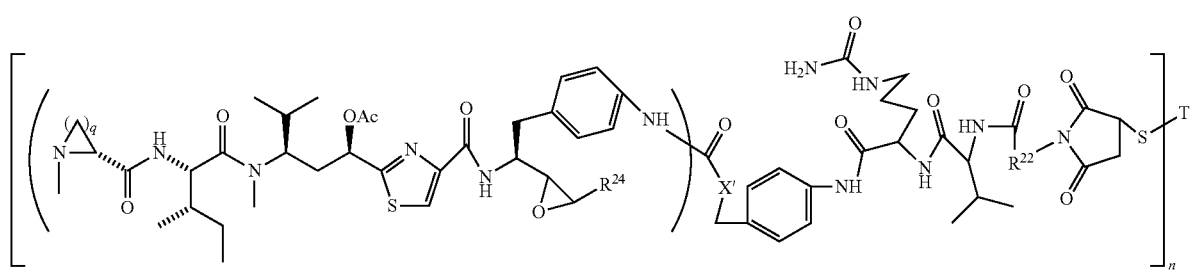
VII-8
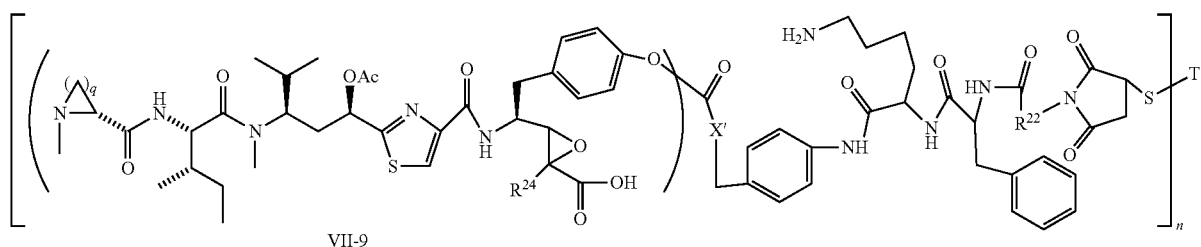
VII-9
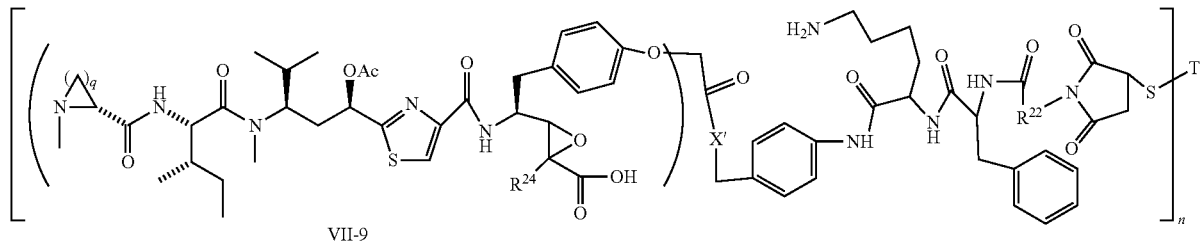
VII-9

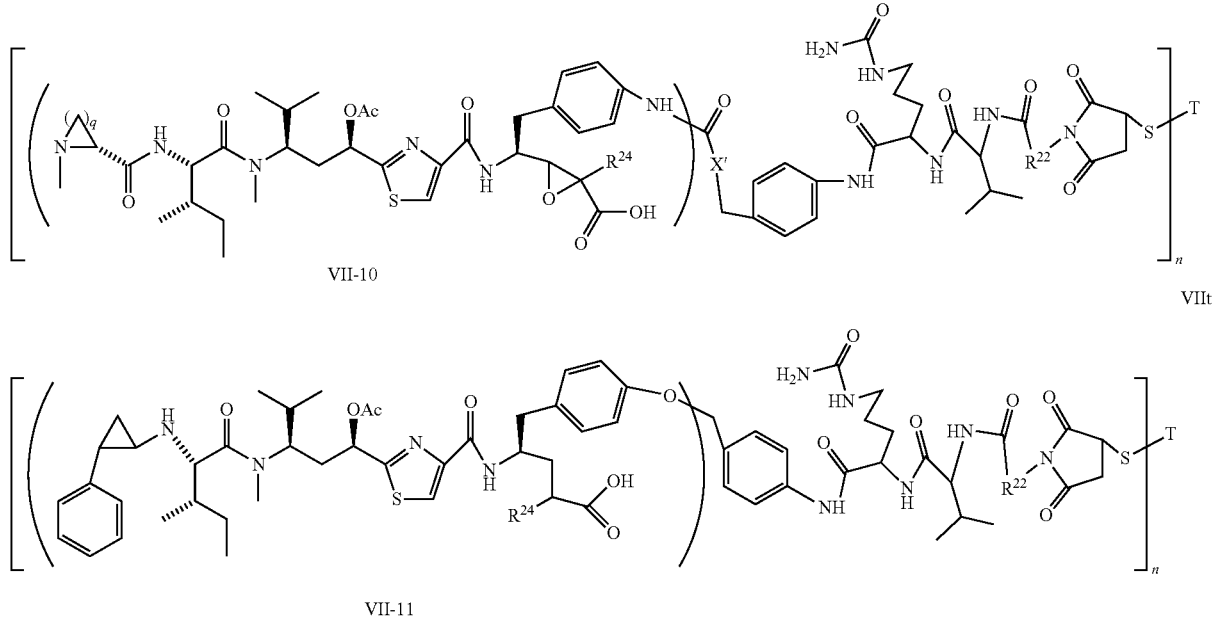

VII-10

VII-11

Wherein Ar, Aa, n, q, X', $R^{22}$, $R^{23}$, R' and R'' are defined the same as for formula IIa–IIr; $R^{24}$ is H or $CH_3$.

In another embodiment, the synthetic routes to produce the antimitotic agents and their conjugation to a cell-surface receptor binding molecules of the present invention are exampled, but not limited to, shown in FIGS. 1-32.

In another embodiment, the releasable linker (L) used for the conjugation of the present invention is a chain of atoms selected from C, N, O, S, Si, and P that covalently connects the cell-surface binding ligand (T) to the potent antimitotic agents. The linker may have a wide variety of lengths, such as in the range from about 2 to about 100 atoms, The atoms used in forming the linker may be combined in all chemically relevant ways, such as forming alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, acyloxylamines, hydroxamic acids, and many others. In addition, it is to be understood that the atoms forming the releasable linker (L) may be either saturated or unsaturated, or may be radicals, or may be cyclized upon each other to form divalent cyclic structures, including cyclo alkanes, cyclic ethers, cyclic amines, arylenes, heteroarylenes, and the like in the linker.

The term releasable linker refers to a linker that includes at least one bond that can be broken under physiological conditions, such as a pH-labile, acid-labile, base-labile, oxidatively labile, metabolically labile, biochemically labile, or enzyme-labile bond. It is appreciated that such physiological conditions resulting in bond breaking do not necessarily include a biological or metabolic process, and instead may include a standard chemical reaction, such as a hydrolysis or substitution reaction, for example, an endosome having a lower pH than cytosolic pH, and/or disulfide bond exchange reaction with a intracellular thiol, such as a millimolar range of abundant of glutathione inside the malignant cells.

The releasable linker L of conjugates may have the formula: -Ww-(Aa)r-Vv- wherein: -W- is a Stretcher unit; w is 0 or 1; each -Aa- is independently an Amino Acid unit; r is independently an integer ranging from 0 to 12; -V- is a Spacer unit; and v is 0, 1 or 2.

The Stretcher unit (-W-), when present, links a targeted binding molecular unit (T) to an amino acid unit (-Aa-), or links V when an Aa is not present. The Stretcher unit W may independently contain a self-immolative spacer, peptidyl units, a hydrazone bond, disulfide or thioether bonds. In this regard a binding molecular (T) has a functional group that can form a bond with a functional group of a Stretcher. Useful functional groups that can be present on a binding molecular, either naturally or via chemical manipulation include, but are not limited to, sulfhydryl (—SH), amino, hydroxyl, carbonyl, the anomeric hydroxyl group of a carbohydrate, and carboxyl. Preferred functional groups are sulfhydryl, carboxy and amino. Sulfhydryl groups can be generated by reduction of an intramolecular disulfide bond of a binding ligand, such as of an antibody. Alternatively, sulfhydryl groups can be generated by reaction of an amino group of a lysine moiety of a binding molecular using 2-iminothiolane (Traut's reagent) or thiolactone or another sulfhydryl generating reagent, such as modifies T with a disulfide bond linker, or a thiol ester following by reduction or hydrolysis respectively.

Illustrative examples of W linked to T have the structures:

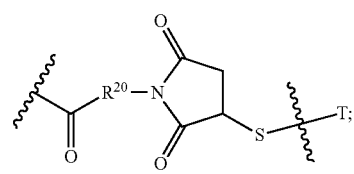

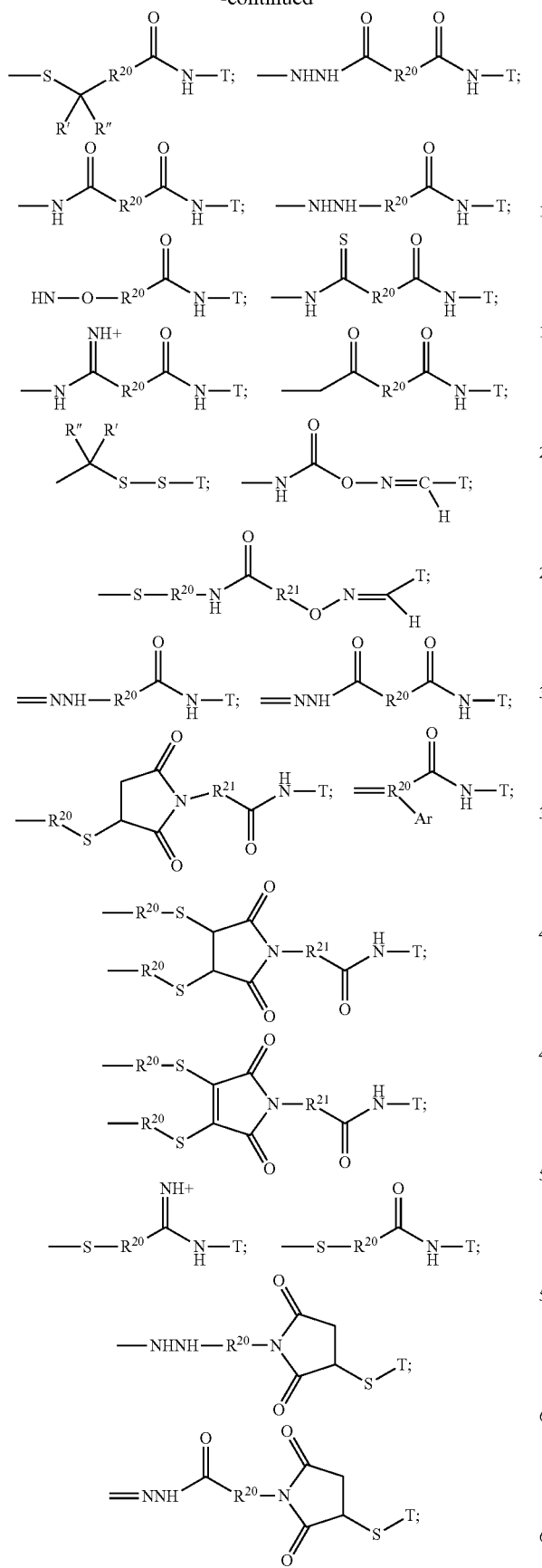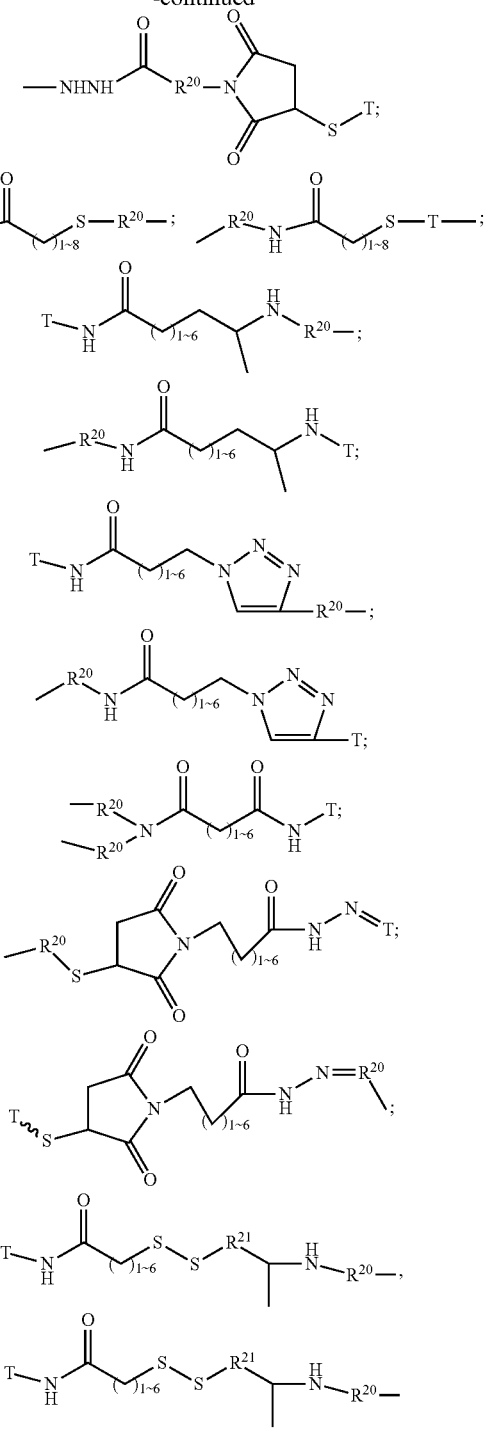

wherein $R^{20}$ and $R^{21}$ are selected from —$C_1$~$C_9$ alkylene-, —$C_1$~$C_7$ carbocyclo-, —O—($C_1$~$C_8$ alkyl)-, -arylene-, —$C_1$~$C_9$ alkylene-arylene-, -arylene, —$C_1$~$C_9$ alkylene-, —$C_1$~$C_9$ alkylene-($C_1$~$C_8$ carbocyclo)-, —($C_3$~$C_7$ carbocyclo)-$C_1$~$C_9$ alkylene-, —$C_3$~$C_8$ heterocyclo-, —$C_1$~$C_{10}$ alkylene-($C_3$~$C_8$ heterocyclo)-, —($C_3$~$C_8$ heterocyclo)-$C_1$~$C_9$ alkylene-, —($CH_2CH_2O)_k$—, —($CH(CH_3)CH_2O)_k$—, and —($CH_2CH_2O)_k$—$CH_2$—; k is an integer ranging from 1-20.; R' and R" are independently H or $CH_3$.

In another embodiment, conjugation of W to T covalently as illustrated above can be via various chemical reactions.

Examples of the formation of amide linkages:

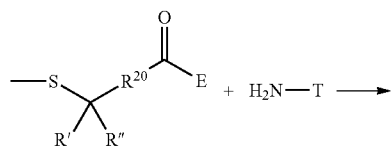

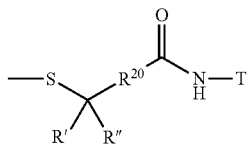

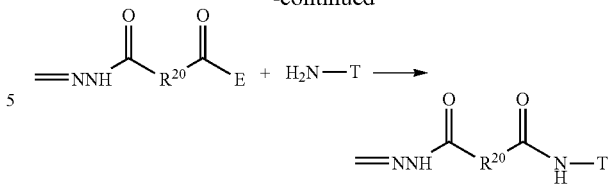

Wherein the Stretcher unit contains a reactive site of E, which can form an amide bond with a primary or secondary amino group of a binding molecule. Example of the reactive E, includes, but is not limited to, such as hydroxysuccinimidyl esters (NHS, Sulfa-NHS, etc), 4-nitrophenyl esters, pentafluorophenyl esters, tetrafluorophenyl (includes sulfo-tetrafluorophenyl) esters, anhydrides, acid chlorides, sulfonyl chlorides, isocyanates and isothiocyanates.

Examples of thiol ether or disulfide bond linkages:

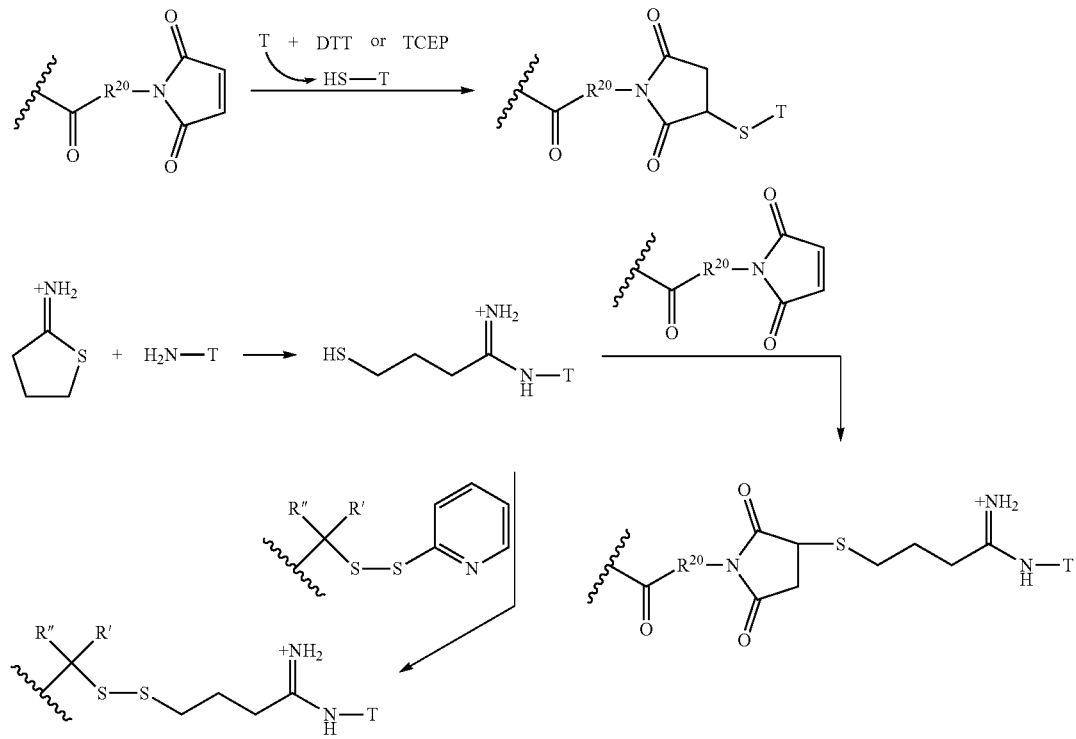

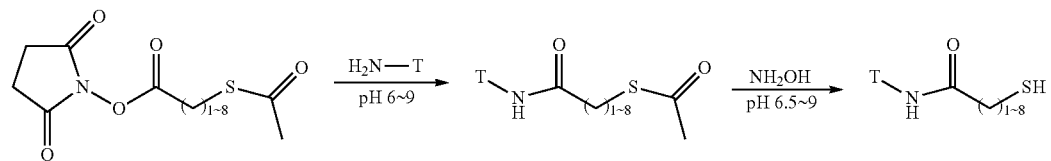

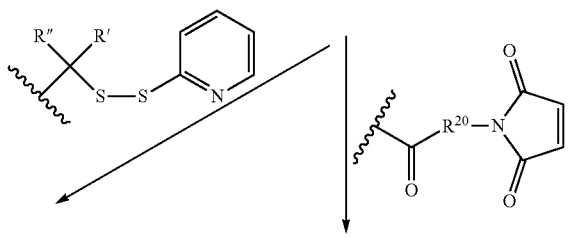

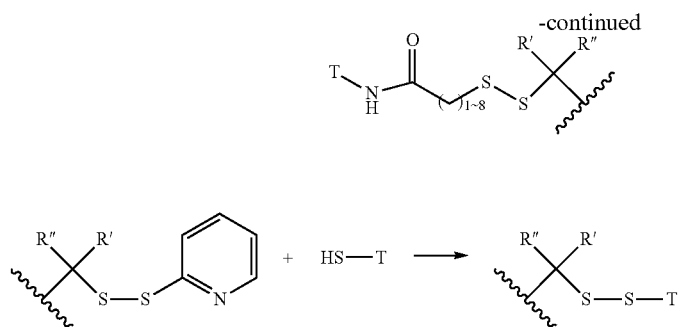

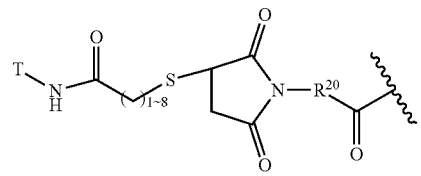

Wherein the Stretcher unit contains a sulfhydryl reactive site, which can form a thiol ether or disulfide bond with a thiol group which is generated by reduction of an intramolecular disulfide bond of the binding ligand T, or generated by a chemical modification on the binding ligand T.

In yet another aspect of the invention, the reactive group of the Stretcher contains a reactive site that is reactive to an aldehyde (—CHO) or a ketone (—C(=O)R) group that can be chemically modified on a binding molecular T. For example, a carbohydrate on a binding molecular T can be mildly oxidized using a reagent such as sodium periodate to generate an aldehyde or a ketone (—C(=O)R) group; or an amine on an amino acid at the N-termini of antibodies (or proteins or peptides) can react with pyridoxal 5′-phosphate (PLP) in a buffer solution to introduce ketone groups. The resulting (—C=O) unit can be condensed with a Stretcher that contains a functionality such as a hydrazide, an oxime, a primary or secondary amine, a hydrazine, a thiosemicarbazone, a hydrazine carboxylate, and an arylhydrazide.

Examples of the conjugation of the hydrazone, or the oxime or imine linkages:

wherein $R^{20}$ and $R^{21}$ are described above, $R^{25}$ is an organic substituent of an amino acid.

In another aspect of the invention, the Stretchers (which may contain a spacer V and/or an amino acid) can be linked to the binding molecules (T), followed by conjugation of a potent antimitotic agent to the binding molecule-stretcher moiety in an aqueous buffered solution.

Examples of these two-step conjugations (a cytotoxic drug linked to $R^{16}$ is omitted here) are:

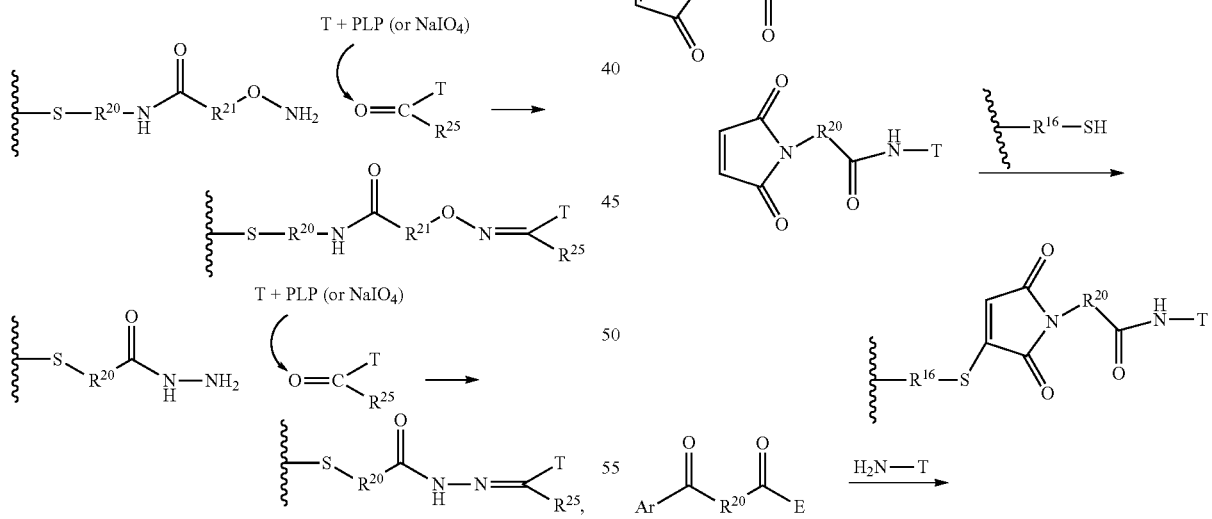

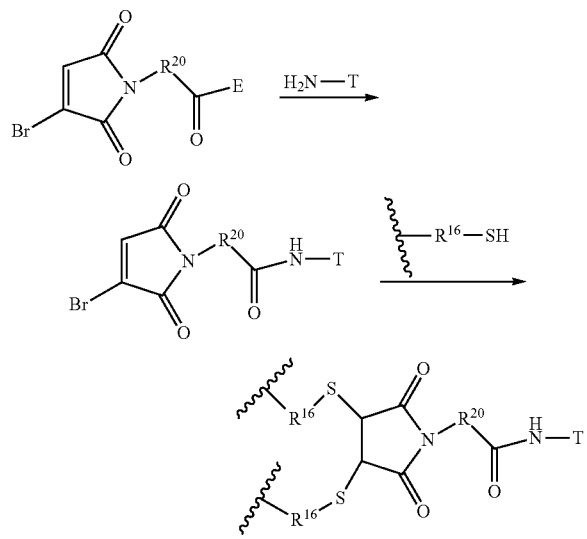
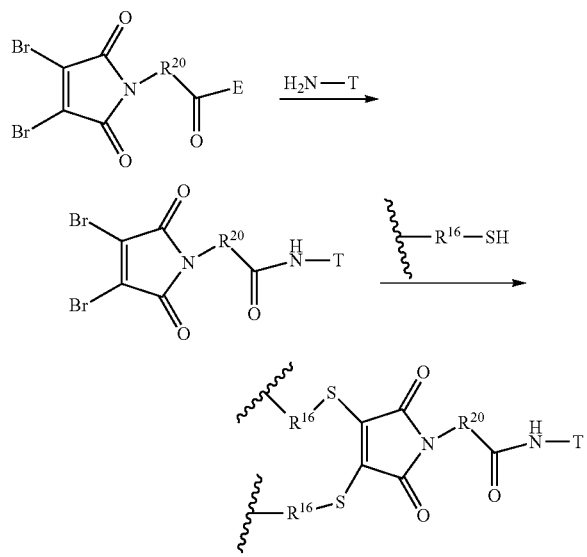
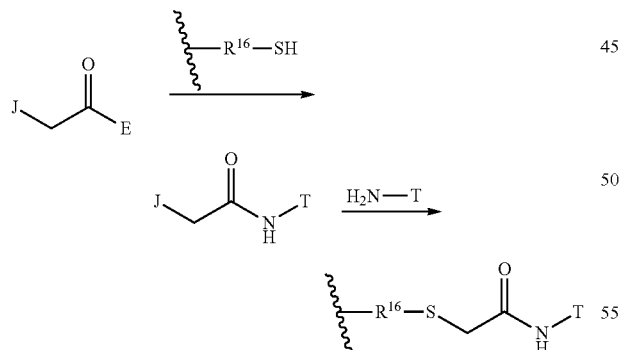
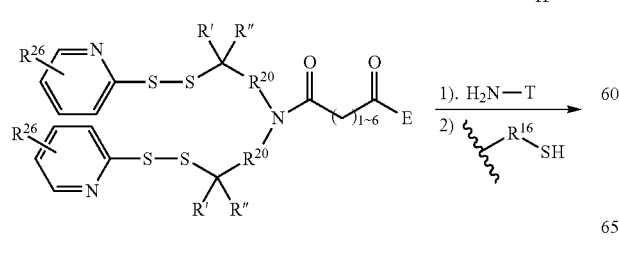
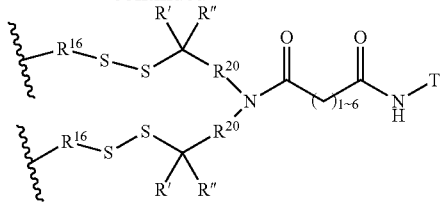

wherein E includes, but is not limited to, such as hydroxysuccinimidyl esters (NHS, SulfoNHS, etc), 4-nitrophenyl esters, pentafluorophenyl esters, tetrafluorophenyl (includes sulfo-tetrafluorophenyl) esters, anhydrides, acid chlorides, sulfonyl chlorides, isocyanates and isothiocyanates. R' and R" are independently H or $CH_3$; $R^{20}$, $R^{16}$ and Ar are defined in various embodiment throughout this inventions; $R^{26}$ is H, or F, or $NO_2$ independently; J is F, Cl, Br, I, tosylate (TsO) or mesylate (MsO) independently and wherein

bears at least one antimitotic agent/drug as

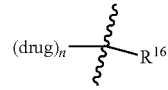

In another aspect of the invention, the Stretchers can be linked to a potent antimitotic agent first, followed by conjugation of the binding molecules (T) in an aqueous pH 3~10 (preferably pH 5~8.5) buffered solution containing up to 50% of organic cosolvents. Examples of these kinds of two-step conjugations:

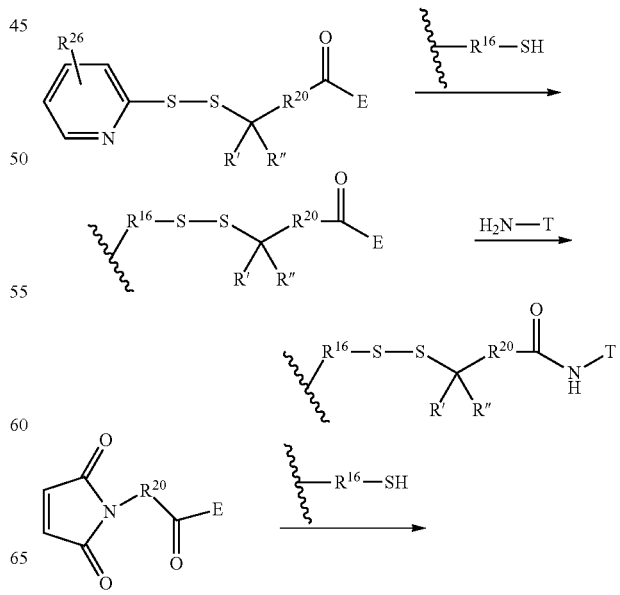

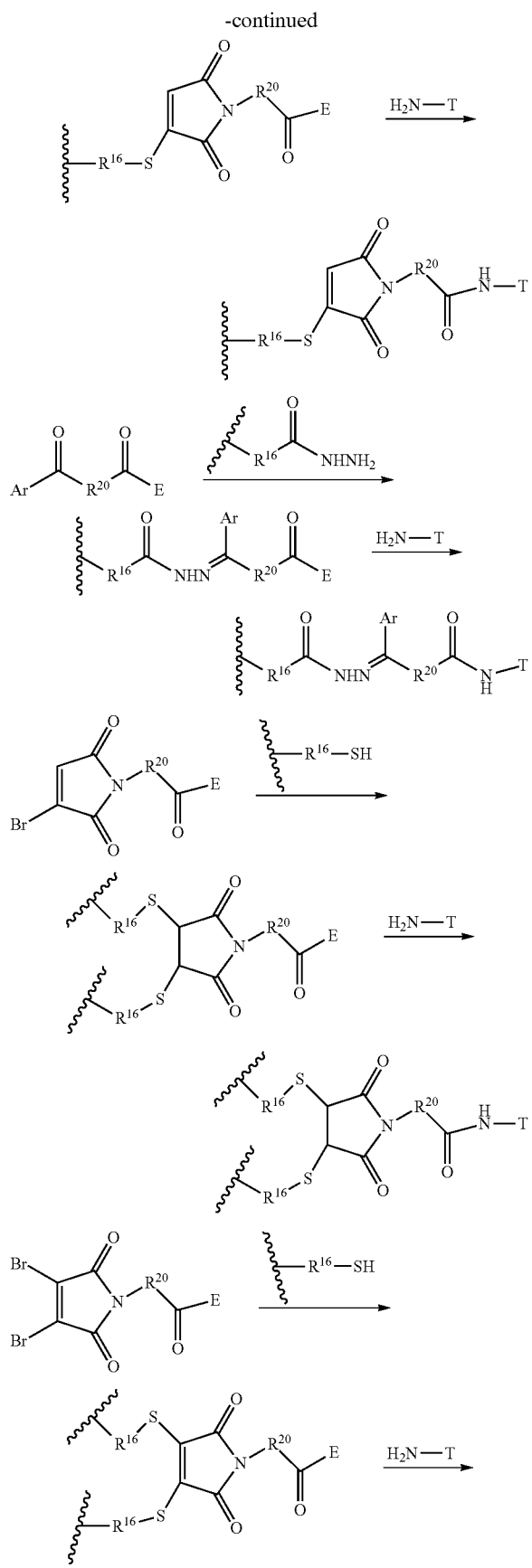

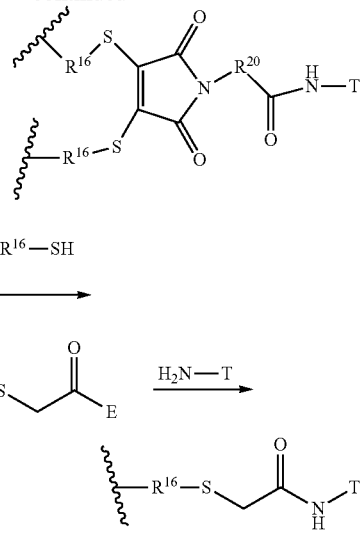

wherein E includes, but is not limited to, such as hydroxysuccinimidyl esters (NHS, SulfoNHS, etc), 4-nitrophenyl esters, pentafluorophenyl esters, tetrafluorophenyl (includes sulfo-tetrafluorophenyl) esters, anhydrides, acid chlorides, sulfonyl chlorides, isocyanates and isothiocyanates. R' and R" are independently H or $CH_3$; $R^{16}$, $R^{20}$ and Ar are defined in various embodiment throughout this inventions; $R^{26}$ is H, or F, or $NO_2$ independently; J is F, Cl, Br, I, tosylate (TsO) or mesylate (MsO) independently and wherein

bears at least one antimitotic agent/drug.

The Amino Acid unit (-Aa-), when present, links the Stretcher unit to the Spacer unit if the Spacer unit is present, links the Stretcher unit to the antimitotic agent unit if the Spacer unit is absent, and links the binding molecule (T) unit to the antimitotic agent unit if the Stretcher unit and Spacer unit are absent. -(Aa)r- is a natural or unnatural amino acid, dipeptide, tripeptide, tetrapeptide, pentapeptide, hexapeptide, heptapeptide, octapeptide, nonapeptide, decapeptide, undecapeptide or dodecapeptide unit, and r is an integer ranging from 0 to 12. The term amino acid as used herein refers generally to aminoalkylcarboxylate, where the alkyl radical is optionally substituted, such as with alkyl, acyl, hydroxy alkyl, sulfhydrylalkyl, aminoalkyl, carboxyalkyl, and the like, The structures of the natural and unnatural amino acids and peptides are described in the book: G. C. Barrett and D. T. Elmore, "Amino Acid and Peptide", Cambridge University Press, 2004. In addition, amino acid refers to beta, gamma, and longer amino acids with intra chain containing methyl, benzyl, hydroxymethyl, thiomethyl, carboxyl, carboxylmethyl, guanidinopropyl, and the like. More preferably the amino acid is selected from arginine, asparagine, aspartic acid, citrulline, cysteine, glycine, glutamic acid, leucine, lysine, glutamic acid, glutamine, serine, ornithine, phenylalanine, threonine, tyrosine, valine and the like.

The Amino Acid unit used in this invention can be enzymatically cleaved by one or more enzymes, including a tumor-associated protease, to liberate the antimitotic agent, which in one embodiment is protonated in vivo upon release to provide an antimitotic agent.

The Spacer unit (-V-), when present, links an Amino Acid unit to the antimitotic agent when an Amino Acid unit is present. Alternately, the Spacer unit links the Stretcher unit to antimitotic agent when the Amino Acid unit is absent. The Spacer unit also links antimitotic agent to the binding molecule (T) when both the Amino Acid unit and Stretcher unit are absent. The spacer linkers may contain function groups that substantially increase the water solubility, biological transport, preferential renal clearance, uptake, absorption, biodistribution, and/or bioavailability of the conjugate are described herein. Spacer units are of two general types: self-immolative and non self-immolative. A non self-immolative Spacer unit is one in which part or all of the Spacer unit remains bound to antimitotic agent after cleavage, particularly enzymatic, of an Amino Acid unit from the antimitotic agent-Linker-binding molecule conjugate or the antimitotic agent-Linker Compound.

Examples of the self-immolative spacer linkers:

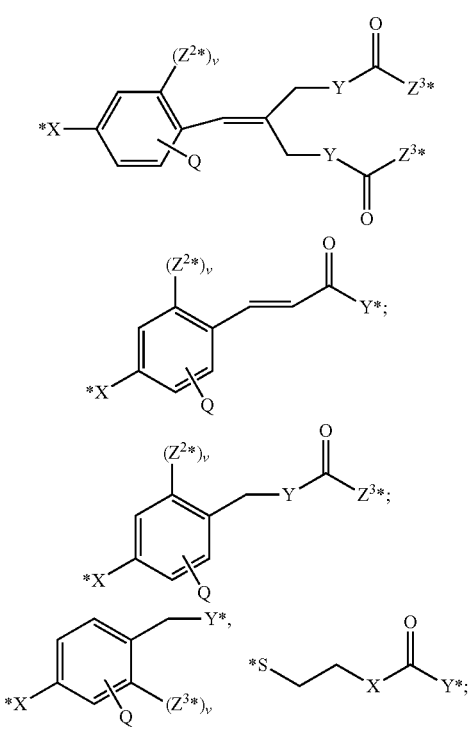

wherein the (*) atom is the point of attachment of additional spacer or releasable linker units, the antimitotic agent, and/or the binding molecule (T); X, Y and $Z^3$ are independently NH, O, or S; $Z^2$ is H, NH, O or S independently. v is 0 or 1; Q in independently H, OH, $C_1$~$C_6$ alkyl, (OCH$_2$CH$_2$)$_n$F, Cl, Br, I, OR$^{17}$, or SR$^{17}$, NR$^{17}$R$^{18}$, N=NR$^{17}$, N=R$^{17}$, NR$^{17}$R$^{18}$, NO$_2$, SOR$^{17}$R$^{18}$, SO$_2$R$^{17}$, SO$_3$R$^{17}$, OSO$_3$R$^{17}$, PR$^{17}$R$^{18}$, POR$^{17}$R$^{18}$, PO$_2$R$^{17}$R$^{18}$, OPO(OR$^{17}$)(OR$^{18}$), OC(O)PO(OR$^{17}$)(OR$^8$) or OCH$_2$PO(OR$^{17}$)(OR$^{18}$) wherein R$^{17}$, R$^{18}$ are independently H, $C_1$~$C_8$ of alkyl; $C_2$~$C_8$ of alkenyl, alkynyl, heteroalkyl; $C_3$~$C_8$ of aryl, heterocyclic, carbocyclic, cycloalkyl, heterocycloalkyl, heteroaralkyl, alkylcarbonyl; or pharmaceutical cation salts.

Examples of the non-self-immolative spacer linkers:

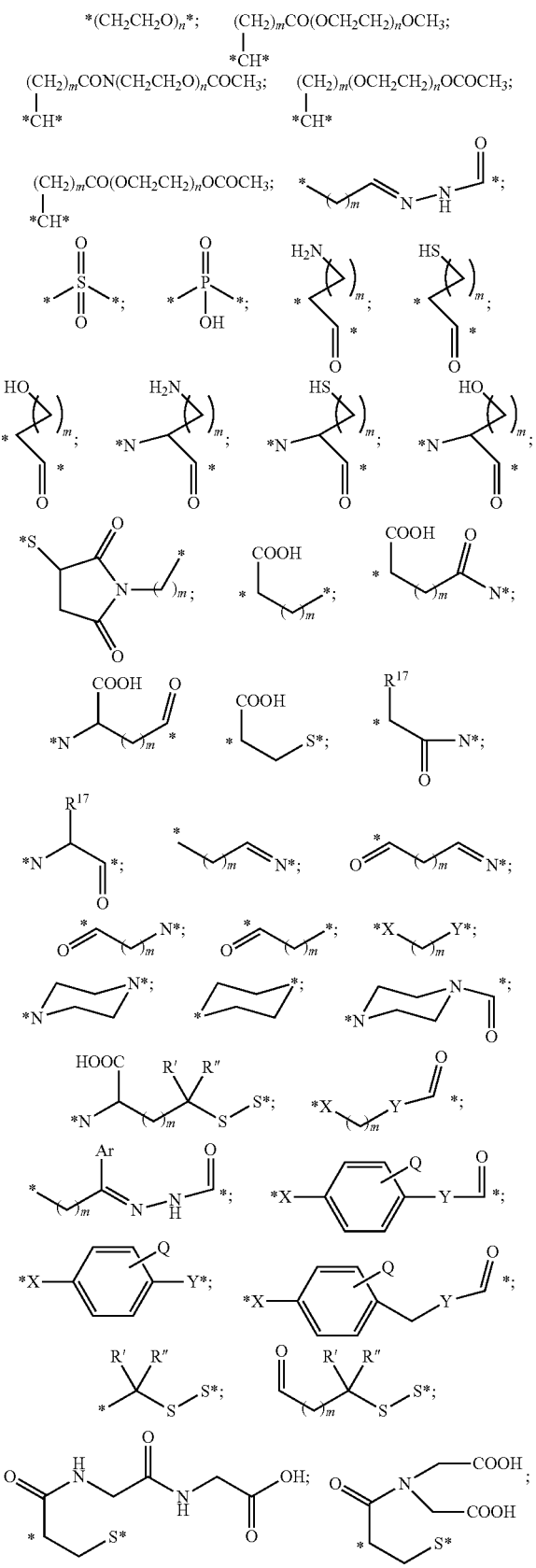

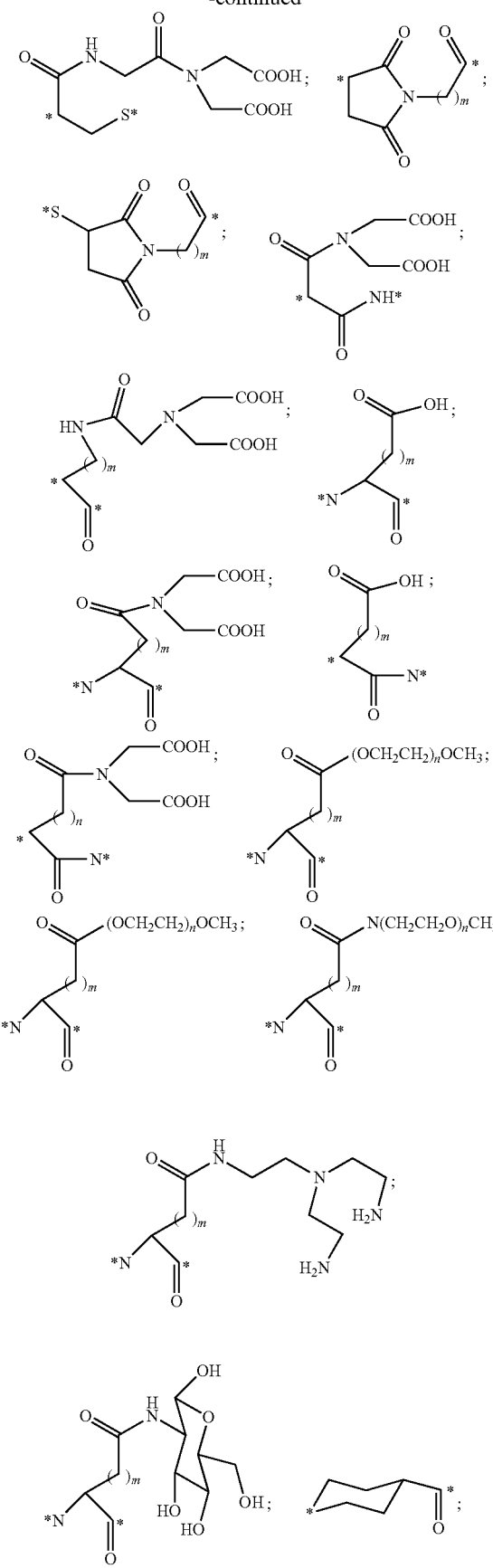
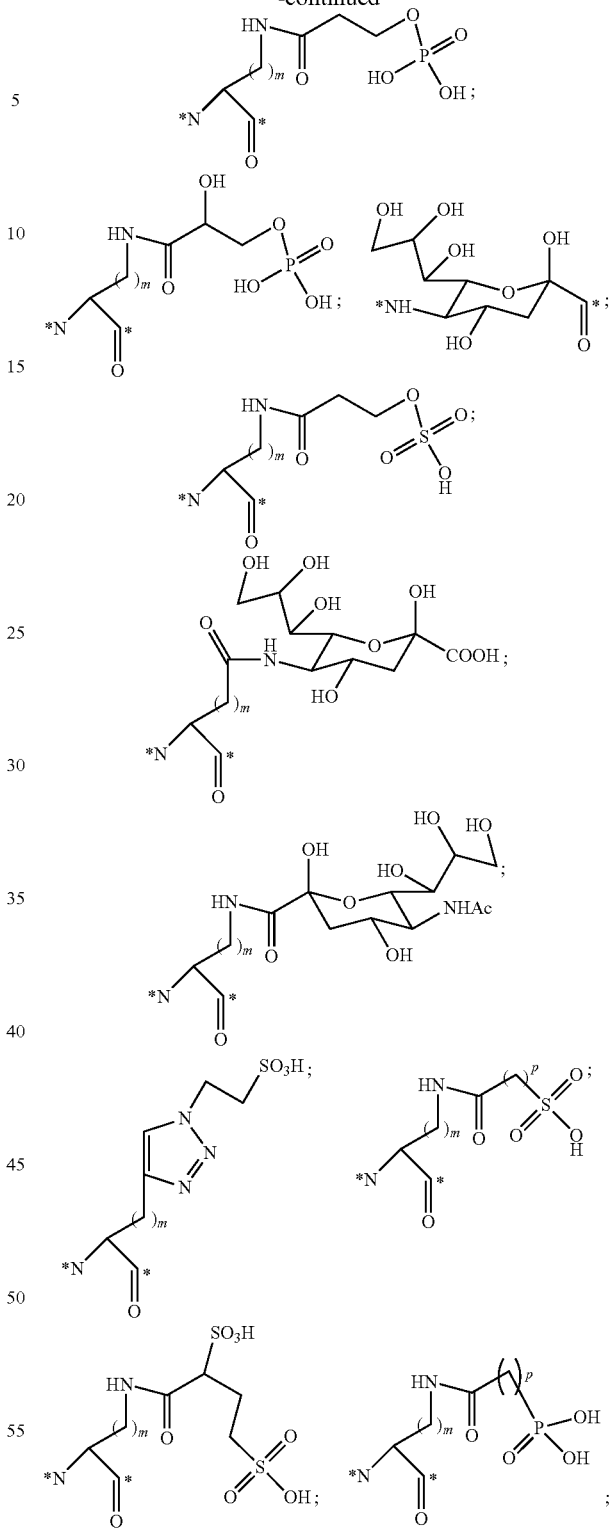

Where the (*) atom is the point of attachment of additional spacer or releasable linkers, the antimitotic agents, and/or the binding molecules; m is 1~10; n is 1~20.

The binding molecule (T) may be of any kind presently known, or that become known, molecule that binds to, complexes with or reacts with a moiety of a cell population sought to be therapeutically or otherwise biologically modified. The binding molecule unit acts to deliver the antimitotic agents to the particular target cell population with which the binding molecule (T) reacts.

The cell binding agents include, but are not limited to, large molecular weight proteins such as, for example, full-length antibodies (polyclonal and monoclonal antibodies); single chain antibodies; fragments of antibodies such as Fab, Fab', F(ab')$_2$, F$_v$, [Parham, J. Immunol. 131, 2895-2902 (1983)], fragments produced by a Fab expression library, anti-idiotypic (anti-Id) antibodies, CD R's, and epitope-binding fragments of any of the above which immunospecifically bind to cancer cell antigens, viral antigens or microbial antigens; interferons (such as type I, II, III); peptides; lymphokines such as IL-2, IL-3, IL-4, IL-6, GM-CSF, interferon-gamma (IFN-γ); hormones such as insulin, TRH (thyrotropin releasing hormones), MSH (melanocyte-stimulating hormone), steroid hormones, such as androgens and estrogens, melanocyte-stimulating hormone (MSH); growth factors and colony-stimulating factors such as epidermal growth factors (EGF), granulocyte-macrophage colony-stimulating factor (GM-CSF), transforming growth factors (TGF), such as TGFα, TGFβ, insulin and insulin like growth factors (IGF-I, IGF-II) G-CSF, M-CSF and GM-CSF [Burgess, Immunology Today, 5, 155-158 (1984)]; vaccinia growth factors (VGF); fibroblast growth factors (FGFs); smaller molecular weight proteins, poly-peptide, peptides and peptide hormones, such as bombesin, gastrin, gastrin-releasing peptide; platelet-derived growth factors; interleukin and cytokines, such as interleukin-2 (IL-2), interleukin-6 (IL-6), leukemia inhibitory factors, granulocyte-macrophage colony-stimulating factor (GM-CSF); vitamins, such as folate; apoproteins and glycoproteins, such as transferrin {O'Keefe et al, 260 J. Biol. Chem. 932-937 (1985)}; sugar-binding proteins or lipoproteins, such as lectins; cell nutrient-transport molecules; and small molecular inhibitors, such as prostate-specific membrane antigen (PSMA) inhibitors and small molecular tyrosine kinase inhibitors (TKI), non-peptides or any other cell binding molecule or substance, such as bioactive polymers (Dhar, et al, Proc. Natl. Acad. Sci. 2008, 105, 17356-61); dendrimers (Lee, et al, Nat. Biotechnol. 2005, 23, 1517-26; Almutairi, et al; Proc. Natl. Acad. Sci. 2009, 106, 685-90); nanoparticles (Liang, et al, ACS Nano, 2008, 19, 1309-12; Medarova, et al, Nat. Med. 2007, 13, 372-7; Javier, et al, Bioconjugate Chem. 2008, 19, 1309-12); liposomes (Medinai, et al, Curr. Phar. Des. 2004, 10, 2981-9); viral capsides (Flenniken, et al, Viruses Nanotechnol. 2009, 327, 71-93). In general monoclonal antibodies are preferred as a cell-surface binding agent if an appropriate one is available.

Prior to conjugating with the antimitotic agents of this invention, the binding molecules can be modified through attachment of a more specific peptide, a protein, or a drug, or the other functional molecules with a heterobifunctional cross linker such as with linkers of Amine-to-Nonselective (succinimidyl (NHS)-diazirine (SDA), NHS ester/Azide), Amine-to-Sulfhydryl (NHS ester/maleimide, NHS ester/pyridyldithiol, NHS esters/haloacetyl), Sulfhydryl-to-Carbohydrate (Maleimide/Hydrazide, Pyridyldithiol/Hydrazide), Hydroxyl-to-Sulfhydryl (Isocyanate/Maleimide), Amine-to-DNA (NHS ester/Psoralen), Amine-to-Carboxyl (Carbodiimide).

In the SDA linkage modification, the NHS ester of a SDA linker reacts with primary an amine group of a binding molecule backbone in pH 6-9 buffer to form a stable amide bond upon release of NHS. Then photoactivation of the diazirine with long-wave UV light (330-370 nm) creates a reactive carbene intermediate that can react with an amine group of a more specific peptide or a protein or the other functional molecule. The order of these two steps can be different as this: an amine group of a functional molecule reacts with a SDA linker first following by photoactive reaction of a binding molecule with long-wave UV light (330-370 nm). The SDA crosslinkers can be cleavable (with a disulfide bond inside such as SDAD linker).

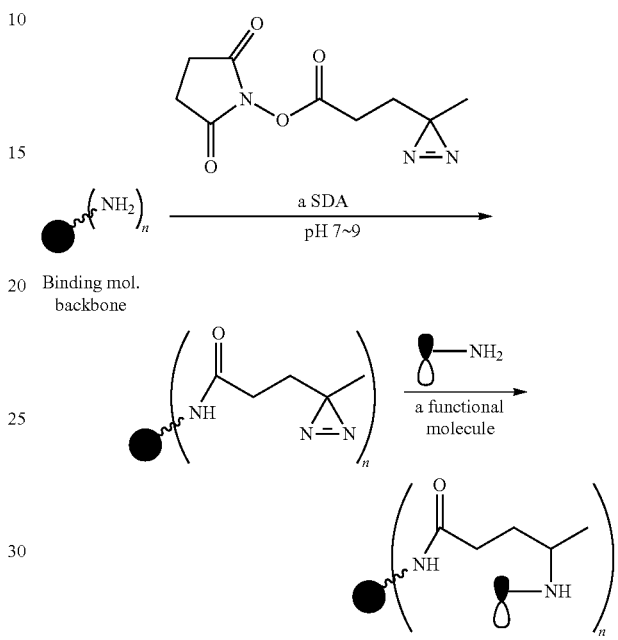

In the NHS ester/Azide linkage modification, the NHS ester of the linker reacts with primary an amine group of a binding molecule backbone in pH 6~9 buffer to form a stable amide. Then an alkynyl group on a more specific peptide or a protein or the other functional molecule reacts to the azide on the other side of the linker via Azide-Alkyne Huisgen Cycloaddition to form a 1,2,3-triazole linkage (click chemistry). Also, the NHS ester of the linker reacts with primary an amine group of a functional molecule in pH 6~9 buffer to form a stable amide. Then an alkynyl group being linked on a binding molecule reacts to the azide on the other side of the linker via Azide-Alkyne Huisgen Cycloaddition to form a 1,2,3-triazole linkage.

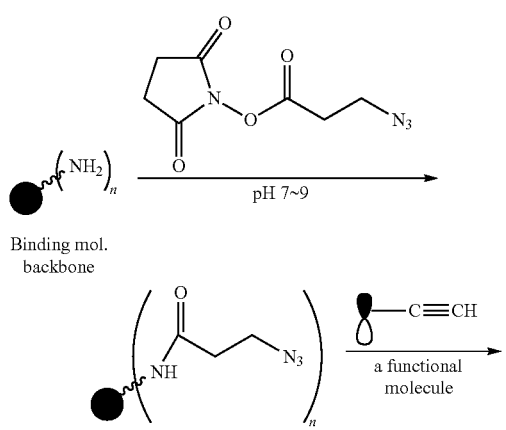

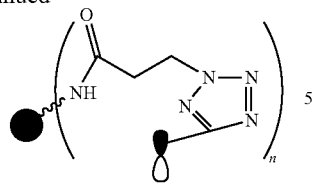

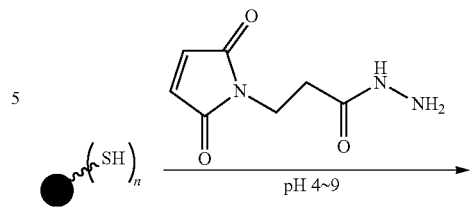

In the Amine-to-Sulfhydryl linkage modification, the NHS ester of the linker reacts with a primary amine group of a binding molecule backbone in pH 6~9 buffer to form a stable amide bond. Then a sulfhydryl on a more specific peptide or a protein or the other functional molecule reacts to the maleimide, or pyridyldithiol, or haloacetyl on the other side of the Amine-tosulfhydryl linker at pH 4.5~8.5 to form a thioether or a disulfide bond. The conjugation with the Amine-to-Sulfhydryl linker can be in different orders. For instance, an amine group of a functional molecule can be reacted with the linker to form an amide bond first, following by reaction with a sulfhydryl on a binding molecule. Also a sulfhydryl group of a functional molecule can be reacted with the linker to form a thioether or a disulfide bond at pH 4.5~7 first, following by reaction with an amine group on a binding molecule at pH 6~9 to form an amide bond.

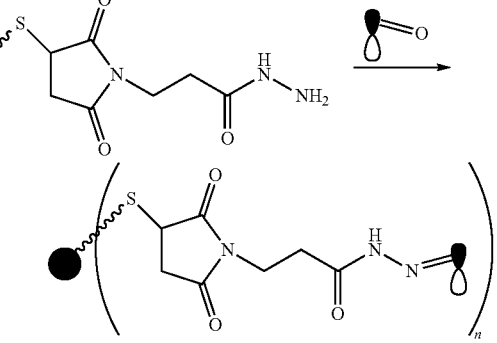

In the Hydroxyl-to-Sulfhydryl linkage modification, the sulfhydryl group of a binding molecule can be reacted with the maleimide or the pyridyldithiol on the linker to form a thioether or a disulfide bond at pH 6~8 first, Then a hydroxy group on a functional molecule reacts with the isocyanate on the linker to form a carbamate bond at pH 8~9. Also the sulfhydryl group on a functional molecule can react with the linker to form a thioether or a disulfide bond at pH 6~8 first, following by reaction with a hydroxy on a binding molecule form a carbamate bond at pH 8~9.

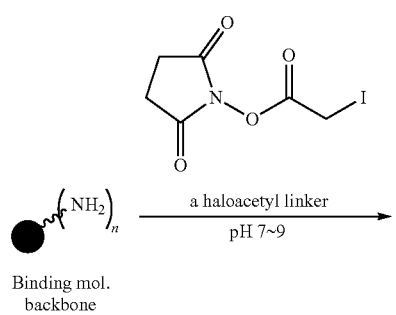

Binding mol. backbone

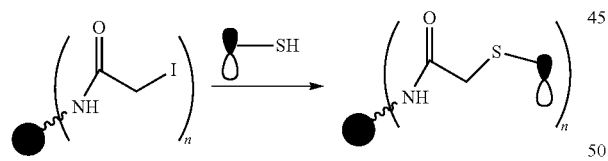

In the Sulfhydryl-to-Carbohydrate linkage modification, the sulfhydryl group of a binding molecule can be reacted with the maleimide or the pyridyldithiol on the linker to form a thioether or a disulfide bond at pH 4.5~8 first, Then a carbonyl (aldehyde/ketone) group on a functional molecule reacts with the hydrazide to form an hydrazone bond. Also the sulfhydryl group on a functional molecule can react with the linker to form a thioether or a disulfide bond at pH 4.5~8 first, following by reaction with a carbohydrate, or an oxidized carbohydrate, or an carbonyl (aldehyde/ketone) group on a binding molecule form an hydrazone bond.

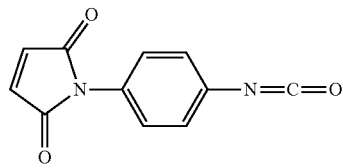

Binding mol. backbone

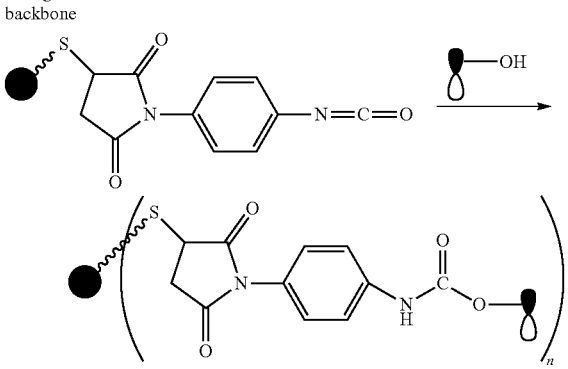

In yet another aspect of the invention, the production of antibodies used in the present invention involves in vivo or in vitro procedures or combinations thereof. Methods for producing polyclonal anti-receptor peptide antibodies are well-known in the art, such as in U.S. Pat. No. 4,493,795 (to Nestor et al). A monoclonal antibody is typically made by fusing myeloma cells with the spleen cells from a mouse that has been immunized with the desired antigen (Kohler, G.; Milstein, C. (1975). Nature 256: 495-497). The detailed procedures are described in "Antibodies—A Laboratory Manual", Harlow and Lane, eds., Cold Spring Harbor Laboratory Press, New York (1988), which is incorporated herein by reference. Particularly monoclonal antibodies are produced by immunizing mice, rats, hamsters or any other mammal with the antigen of interest such as the intact target cell, antigens isolated from the target cell, whole virus, attenuated whole virus, and viral proteins. Splenocytes are typically fused with myeloma cells using polyethylene glycol (PEG) 6000. Fused hybrids are selected by their sensitivity to HAT (hypoxanthine-aminopterin-thymine). Hybridomas producing a monoclonal antibody useful in practicing this invention are identified by their ability to immunoreact specified receptors or inhibit receptor activity on target cells.

A monoclonal antibody used in the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques, such as using protein-A affinity chromatography; anion, cation, hydrophobic, or size exclusive chromatographies (particularly by affinity for the specific antigen after Protein A, and sizing column chromatography); centrifugation, differential solubility, or by any other standard technique for the purification of proteins.

Media useful for the preparation of these compositions are both well-known in the art and commercially available and include synthetic culture media. An exemplary synthetic medium is Dulbecco's minimal essential medium (DMEM; Dulbecco et al., Viral. 8:396 (1959)) supplemented with 4.5 gm/I glucose, 20 mm glutamine, 20% fetal calf serum and with an anti-foaming agent, such as polyoxyethylene-polyoxypropylene block copolymer.

In addition, antibody-producing cell lines can also be created by techniques other than fusion, such as direct transformation of B lymphocytes with oncogenic DNA, or transfection with an oncovirus, such as Epstein-Barr virus (EBV, also called human herpesvirus 4 (HHV-4)) or Kaposi's sarcoma-associated herpesvirus (KSHV). See, U.S. Pat. Nos. 4,341,761; 4,399,121; 4,427,783; 4,444,887; 4,451,570; 4,466,917; 4,472,500; 4,491,632; 4,493,890. A monoclonal antibody may also be produced via an anti-receptor peptide or peptides containing the carboxyl terminal as described well-known in the art. See Niman et al., Proc. Natl. Acad. Sci. USA, 80: 4949-4953 (1983); Geysen et al., Proc. Natl. Acad. Sci. USA, 82: 178-182 (1985); Lei et al. Biochemistry 34(20): 6675-6688, (1995). Typically, the anti-receptor peptide or a peptide analog is used either alone or conjugated to an immunogenic carrier, as the immunogen for producing anti-receptor peptide monoclonal antibodies.

There are also a number of other well-known techniques for making monoclonal antibodies as binding molecules in this invention. Particularly useful are methods of making fully human antibodies. One method is phage display technology which can be used to select a range of human antibodies binding specifically to the antigen using methods of affinity enrichment. Phage display has been thoroughly described in the literature and the construction and screening of phage display libraries are well known in the art, see, e.g., Dente et al, Gene. 148(1):7-13 (1994); Little et al, Biotechnol Adv. 12(3):539-55 (1994); Clackson et al., Nature 352: 264-628 (1991); Huse et al., Science 246:1275-1281 (1989).

Monoclonal antibodies derived by hybridoma technique from another species than human, such as mouse, can be humanized to avoid human anti-mouse antibodies when infused into humans. Among the more common methods of humanization of antibodies are complementarity-determining region grafting and resurfacing. These methods have been extensively described, see e.g. U.S. Pat. Nos. 5,859,205 and 6,797,492; Liu et al, Immunol Rev. 222:9-27 (2008); Almagro et 35 al, Front Biosci. 1; 13:1619-33 (2008); Lazar et al, Mol Immunol. 44(8):1986-98 (2007); Li et al, Proc. Natl. Acad. Sci. USA. 103(10):3557-62 (2006) each incorporated herein by reference. Fully human antibodies can also be prepared by immunizing transgenic mice, rabbits, monkeys, or other mammals, carrying large portions of the human immunoglobulin heavy and light chains, with an immunogen. Examples of such mice are: the Xenomouse. (Abgenix, Inc.), the HuMAb-Mouse (Medarex/BMS), the VelociMouse (Regeneron), see also U.S. Pat. Nos. 6,596,541, 6,207,418, 6,150,584, 6,111,166, 6,075,181, 5,922,545, 5,661,016, 5,545,806, 5,436,149 and 5,569,825. In human therapy, murine variable regions and human constant regions can also be fused to construct called "chimeric antibodies" that are considerably less immunogenic in man than murine mAbs (Kipriyanov et al, Mol Biotechnol. 26:39-60 (2004); Houdebine, Curr Opin Biotechnol. 13:625-9 (2002) each incorporated herein by reference). In addition, site-directed mutagenesis in the variable region of an antibody can result in an antibody with higher affinity and specificity for its antigen (Brannigan et al, Nat Rev Mol Cell Biol. 3:964-70, (2002)); Adams et al, J Immunol Methods. 231:249-60 (1999)) and exchanging constant regions of a mAb can improve its ability to mediate effector functions of binding and cytotoxicity.

Antibodies immunospecific for a malignant cell antigen can also be obtained commercially or produced by any method known to one of skill in the art such as, e.g., chemical synthesis or recombinant expression techniques. The nucleotide sequence encoding antibodies immunospecific for a malignant cell antigen can be obtained commercially, e.g., from the GenBank database or a database like it, the literature publications, or by routine cloning and sequencing.

Apart from an antibody, a peptide or protein that bind/block/target or in some other way interact with the epitopes or corresponding receptors on a targeted cell can be used as a binding molecule. These peptides or proteins could be any random peptide or proteins that have an affinity for the epitopes or corresponding receptors and they don't necessarily have to be of the immunoglobulin family. These peptides can be isolated by similar techniques as for phage display antibodies (Szardenings, J Recept Signal Transduct Res. 2003; 23(4):307-49). The use of peptides from such random peptide libraries can be similar to antibodies and antibody fragments. The binding molecules of peptides or proteins may be conjugated on or linked to a large molecules or materials, such as, but is not limited, an albumin, a polymer, a liposome, a nano particle, dendrimers, as long as such attachment permits the peptide or protein to retain its antigen binding specificity.

Examples of antibodies used for conjugation of antimitotic agents in this prevention for treating cancer, autoimmune disease, and infectious disease include, but are not limited to, 3F8 (anti-OD2), Abagovomab (anti CA-125), Abciximab (anti CD41 (integrin alpha-IIb), Adalimumab (anti-TNF-α), Adecatumumab (anti-EpCAM, CD326), Afelimomab (anti-TNF-α); Afutuzumab (anti-CD20), Alacizumab pegol (anti-VEGFR2), ALD518 (anti-IL-6), Alemtuzumab (Campath, MabCampath, anti-CD52), Altumomab (anti-CEA), Anatumomab (anti-TAG-72), Anrukinzumab (IMA-638, anti-IL-13), Apolizumab (anti-HLA-DR), Arcitumomab (anti-CEA), Aselizumab (anti-L-selectin (CD62L), Atlizumab (tocilizumab, Actemra, RoActemra, anti-IL-6 receptor), Atorolimumab (anti-Rhesus factor), Bapineuzumab (anti-beta amyloid), Basiliximab (Simulect, antiCD25 (a chain of IL-2 receptor), Bavituximab (anti-phosphatidylserine), Bectumomab (LymphoScan, anti-CD22), Belimumab (Benlysta, LymphoStat-B, anti-BAFF), Benralizumab (anti-CD125), Bertilimumab (anti-CCL11 (eotaxin-1)), Besilesomab (Scintimun, anti-CEA-related antigen), Bevacizumab (Avastin, anti-VEGF-A), Biciromab (FibriScint, anti-fibrin II beta chain), Bivatuzumab (anti-CD44 v6), Blinatumomab (BiTE, anti-CD19), Brentuximab (cAC10, anti-CD30 TNFRSF8), Briakinumab (anti-IL-12, IL-23) Canakinumab (Ilaris, anti-IL-1), Cantuzumab (C242, anti-CanAg), Capromab, Catumaxomab (Removab, anti-EpCAM, anti-CD3), CC49 (anti-TAG-72), Cedelizumab (anti-CD4), Certolizumab pegol (Cimzia anti-TNF-α), Cetuximab (Erbitux, IMC-C225, anti-EGFR), Citatuzumab bogatox (anti-EpCAM), Cixutumumab (anti-IGF-1), Clenoliximab (anti-CD4), Clivatuzumab (anti-MUC1), Conatumumab (anti-TRAIL-R2), CR6261 (anti-Influenza A hemagglutinin), Dacetuzumab (anti-CD40), Daclizumab (Zenapax, anti-CD25 (a chain of IL-2 receptor)), Daratumumab (anti-CD38 (cyclic ADP ribose hydrolase), Denosumab (Prolia, anti-RANKL), Detumomab (anti-B-lymphoma cell), Dorlimomab, Dorlixizumab, Ecromeximab (anti-OD3 ganglioside), Eculizumab (Soliris, anti-CS), Edobacomab (anti-endotoxin), Edrecolomab (Panorex, Mab17-1A, anti-EpCAM), Efalizumab (Raptiva, anti-LFA-1 (CD11a), Efungumab (Mycograb, anti-Hsp90), Elotuzumab (anti-SLAMF7), Elsilimomab (anti-IL-6), Enlimomab pegol (anti-ICAM-1 (CD54)), Epitumomab (anti-episialin), Epratuzumab (anti-CD22), Erlizumab (anti-ITGB2 (CD18)), Ertumaxomab (Rexomun, anti-HER2/neu, CD3), Etaracizumab (Abegrin, anti-integrin $\alpha_v\beta_3$), Exbivirumab (anti-hepatitis B surface antigen), Fanolesomab (Neutro-Spec, anti-CD15), Faralimomab (anti-interferon receptor), Farletuzumab (anti-folate receptor 1), Felvizumab (anti-respiratory syncytial virus), Fezakinumab (anti-IL-22), Figitumumab (anti-IGF-1 receptor), Fontolizumab (anti-IFN-γ), Foravirumab (anti-rabies virus glycoprotein), Fresolimumab (anti-TGF-β), Galiximab (anti-CD80), Gantenerumab (anti-beta amyloid), Gavilimomab (anti-CD147 (basigin)), Gemtuzumab (anti-CD33), Girentuximab (anti-carbonic anhydrase 9), Glembatumumab (CR011, anti-GPNMB), Golimumab (Simponi, anti-TNF-α), Gomiliximab (anti-CD23 (IgE receptor)), Ibalizumab (anti-CD4), Ibritumomab (anti-CD20), Igovomab (Indimacis-125, anti-CA-125), Imciromab (Myoscint, anti-cardiac myosin), Infliximab (Remicade, anti-TNF-α), Intetumumab (anti-CD51), Inolimomab (anti-CD25 (a chain of IL-2 receptor)), Inotuzumab (anti-CD22), Ipilimumab (anti-CD152), Iratumumab (anti-CD30 (TNFRSF8)), Keliximab (anti-CD4), Labetuzumab (CEA-Cide, anti-CEA), Lebrikizumab (anti-IL-13), Lemalesomab (anti-NCA-90 (granulocyte antigen)), Lerdelimumab (anti-TGF beta 2), Lexatumumab (anti-TRAIL-R2), Libivirumab (anti-hepatitis B surface antigen), Lintuzumab (anti-CD33), Lucatumumab (anti-CD40), Lumiliximab (anti-CD23 (IgE receptor), Mapatumumab (anti-TRAIL-R1), Maslimomab (anti-T-cell receptor), Matuzumab (anti-EGFR), Mepolizumab (Bosatria, anti-IL-5), Metelimumab (anti-TGF beta 1), Milatuzumab (anti-CD74), Minretumomab (anti-TAG-72), Mitumomab (BEC-2, anti-OD3 ganglioside), Morolimumab (anti-Rhesus factor), Motavizumab (Numax, anti-respiratory syncytial virus), Muromonab-CD3 (Orthoclone OKT3, anti-CD3), Nacolomab (anti-C242), Naptumomab (anti-5T4), Natalizumab (Tysabri, anti-integrin $\alpha_4$), Nebacumab (anti-endotoxin), Necitumumab (anti-EGFR), Nerelimomab (anti-TNF-α), Nimotuzumab (Theracim, Theraloc, anti-EGFR), Nofetumomab, Ocrelizumab (anti-CD20), Odulimomab (Afolimomab, anti-LFA-1 (CD11a)), Ofatumumab (Arzerra, anti-CD20), Olaratumab (anti-PDGF-R α), Omalizumab (Xolair, anti-IgE Fc region), Oportuzumab (anti-EpCAM), Oregovomab (OvaRex, anti-CA-125), Otelixizumab (anti-CD3), Pagibaximab (anti-lipoteichoic acid), Palivizumab (Synagis, Abbosynagis, anti-respiratory syncytial virus), Panitumumab (Vectibix, ABX-EGF, anti-EGFR), Panobacumab (anti-*Pseudomonas aeruginosa*), Pascolizumab (anti-IL-4), Pemtumomab (Theragyn, anti-MUC1), Pertuzumab (Omnitarg, 2C4, anti-HER2/neu), Pexelizumab (anti-CS), Pintumomab (anti-adenocarcinoma antigen), Priliximab (anti-CD4), Pritumumab (anti-vimentin), PRO 140 (anti-CCR5), Racotumomab (1E10, anti-(N-glycolylneuraminic acid (NeuGc, NGNA)-gangliosides GM3)), Rafivirumab (anti-rabies virus glycoprotein), Ramucirumab (anti-VEGFR2), Ranibizumab (Lucentis, anti-VEGF-A), Raxibacumab (anti-anthrax toxin, protective antigen), Regavirumab (anti-cytomegalovirus glycoprotein B), Reslizumab (anti-IL-5), Rilotumumab (anti-HOF), Rituximab (MabThera, Rituxanmab, anti-CD20), Robatumumab (anti-IGF-1 receptor), Rontalizumab (anti-IFN-α), Rovelizumab (LeukArrest, anti-CD11, CD18), Rupluzumab Antova, anti-CD154 (CD40L)), Satumomab (anti-TAG-72), Sevirumab (anti-cytomegalovirus), Sibrotuzumab (anti-FAP), Sifalimumab (anti-IFN-α), Siltuximab (anti-IL-6), Siplizumab (anti-CO2), (Smart) MI95 (anti-CD33), Solanezumab (anti-beta amyloid), Sonepcizumab (anti-sphingosine-1-phosphate), Sontuzumab (anti-episialin), Stamulumab (anti-myostatin), Sulesomab (LeukoScan, (anti-NCA-90 (granulocyte antigen), Tacatuzumab (anti alpha-fetoprotein), Tadocizumab (anti-integrin $\alpha_{IIb}\beta_3$), Talizumab (anti-IgE), Tanezumab (anti-NGF), Taplitumomab (anti-CD19), Tefibazumab (Aurexis, (anti-clumping factor A), Telimomab, Tenatumomab (anti-tenascin C), Teneliximab (anti-CD40), Teplizumab (anti-CD3), TGN1412 (anti-CD28), Ticilimumab (Tremelimumab, (anti-CTLA-4), Tigatuzumab (anti-TRAIL-R2), TNX-650 (anti-IL-13), Tocilizumab (Atlizumab, Actemra, RoActemra, (anti-IL-6 receptor), Toralizumab (anti-CD154 (CD40L)), Tositumomab (anti-CD20), Trastuzumab (Herceptin, (anti-HER2/neu), Tremelimumab (anti-CTLA-4), Tucotuzumab celmoleukin (anti-EpCAM), Tuvirumab (anti-hepatitis B virus), Urtoxazumab (anti-*Escherichia coli*), Ustekinumab (Stelara, anti-IL-12, IL-23), Vapaliximab (anti-AOC3 (VAP-1)), Vedolizumab, (anti-integrin $\alpha_4\beta_7$), Veltuzumab (anti-CD20), Vepalimomab (anti-AOC3 (VAP-1)), Visilizumab (Nuvion, anti-CD3), Vitaxin (anti-vascular integrin avb3), Volociximab (anti-integrin $\alpha_5\beta_1$), Votumumab (HumaSPECT, anti-tumor antigen CTAA16.88), Zalutumumab (HuMax-EGFr, (anti-EGFR), Zanolimumab (HuMax-CD4, anti-CD4), Ziralimumab (anti-CD147 (basigin)), Zolimomab (anti-CD5), Etanercept (Enbrel®), Alefacept (Amevive®), Abatacept (Orencia®), Rilonacept (Arcalyst), 14F7 [anti-IRP-2 (Iron Regulatory Protein 2)], 14G2a (anti-GD2 ganglioside, from Nat. Cancer Inst. for melanoma and solid tumors), J591

(anti-PSMA, Weill Cornell Medical School for prostate cancers), 225.28S [anti-HMW-MAA (High molecular weight-melanoma-associated antigen), Sorin Radiofarmaci S.R.L. (Milan, Italy) for melanoma], COL-1 (anti-CEACAM3, CGM1, from Nat. Cancer Inst. USA for colorectal and gastric cancers), CYT-356 (Oncoltad®, for prostate cancers), HNK20 (Ora Vax Inc. for respiratory syncytial virus), ImmuRAIT (from Immunomedics for NHL), Lym-1 (anti-HLA-DR10, Peregrine Pharm. for Cancers), MAK-195F [anti-TNF (tumor necrosis factor; TNFA, TNF-alpha; TNFSF2), from Abbott/Knoll for Sepsis toxic shock], MEDI-500 [T10B9, anti-CD3, TRaP3 (T cell receptor alpha/beta), complex, from Medimmune Inc for Graft-versus-host disease], RING SCAN [anti-TAG 72 (tumour associated glycoprotein 72), from Neoprobe Corp. for Breast, Colon and Rectal cancers], Avicidin (anti-EPCAM (epithelial cell adhesion molecule), anti-TACSTD1 (Tumor-associated calcium signal transducer 1), anti-GA733-2 (gastrointestinal tumor-associated protein 2), anti-EGP-2 (epithelial glycoprotein 2); anti-KSA; KS1/4 antigen; M4S; tumor antigen 17-1A; CD326, from NeoRx Corp. for Colon, Ovarian, Prostate cancers and NHL]; LymphoCide (Immunomedics, NJ), Smart ID10 (Protein Design Labs), Oncolym (Techniclone Inc, CA), Allomune (BioTransplant, CA), anti-VEGF (Genentech, CA); CEAcide (Immunomedics, NJ), IMC-1C11 (ImClone Systems, NJ) and Cetuximab (ImClone, NJ).

Other antibodies as binding ligands include, but are not limited to, are antibodies against the following antigens: Aminopeptidase N (CD13), Annexin A1, B7-H3 (CD276, various cancers), CA125, CA15-3 (carcinomas), CA19-9 (carcinomas), L6 (carcinomas), Lewis Y (carcinomas), Lewis X (carcinomas), alpha fetoprotein (carcinomas), CA242, placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma), CD22 (leukemia, lymphoma, multiple myeloma, SLE), CD30, CD33, CD38 (multiple myeloma), CD40 (lymphoma, multiple myeloma, leukemia), CD51 (Metastatic melanoma, sarcoma), CD52, CD56 (small cell lung cancers, ovarian cancer, Merkel cell carcinoma, and the liquid tumor, multiple myeloma), CD66e (cancers), CD70 (metastatic renal cell carcinoma and non-Hodgkin lymphoma), CD74 (multiple myeloma), CD80 (lymphoma), CD98 (cancers), mucin (carcinomas), CD221 (solid tumors), CD227 (breast, ovarian cancers), CD262 (NSCLC and other cancers), CD309 (ovarian cancers), CD326 (solid tumors), CEACAM3 (colorectal, gastric cancers), CEACAM5 (carcinoembryonic antigen; CEA, CD66e) (breast, colorectal and lung cancers), DLL4 (A-like-4), EGFR (Epidermal Growth Factor Receptor, various cancers), CTLA4 (melanoma), CXCR4 (CD184, Heme-oncology, solid tumors), Endoglin (CD105, solid tumors), EPCAM (epithelial cell adhesion molecule, bladder, head, neck, colon, NHL prostate, and ovarian cancers), ERBB2 (Epidermal Growth Factor Receptor 2; lung, breast, prostate cancers), FCGR1 (autoimmune diseases), FOLR (folate receptor, ovarian cancers), GD2 ganglioside (cancers), G-28 (a cell surface antigen glyvolipid, melanoma), GD3 idiotype (cancers), Heat shock proteins (cancers), HER1 (lung, stomach cancers), HER2 (breast, lung and ovarian cancers), HLA-DR10 (NHL), HLA-DRB (NHL, B cell leukemia), human chorionic gonadotropin (carcinoma), IGF1R (insulin-like growth factor I receptor, solid tumors, blood cancers), IL-2 receptor (interleukin 2 receptor, T-cell leukemia and lymphomas), IL-6R (interleukin 6 receptor, multiple myeloma, RA, Castleman's disease, IL6 dependent tumors), Integrins ($\alpha v\beta 3$, $\alpha 5\beta 1$, $\alpha 6\beta 4$, $\alpha 11\beta 3$, $\alpha 5\beta 5$, $\alpha v\beta 5$, for various cancers), MAGE-I (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 or MUC1-KLH (breast, ovarian, cervix, bronchus and gastrointestinal cancer), MUC16 (CA125) (Ovarian cancers), CEA (colorectal), gp100 (melanoma), MARTI (melanoma), MPG (melanoma), MS4A1 (membrane-spanning 4-domains subfamily A, small cell lung cancers, NHL), Nucleolin, Neu oncogene product (carcinomas), P21 (carcinomas), Paratope of anti-(N-glycolylneuraminic acid, Breast, Melanoma cancers), PLAP-like testicular alkaline phosphatase (ovarian, testicular cancers), PSMA (prostate tumors), PSA (prostate), ROBO4, TAG 72 (tumour associated glycoprotein 72, AML, gastric, colorectal, ovarian cancers), T cell transmembrane protein (cancers), Tie (CD202b), TNFRSF10B (tumor necrosis factor receptor superfamily member 10B, cancers), TNFRSF13B (tumor necrosis factor receptor superfamily member 13B, multiple myeloma, NHL, other cancers, RA and SLE), TPBG (trophoblast glycoprotein, Renal cell carcinoma), TRAIL-R1 (Tumor necrosis apoprosis Inducing ligand Receptor 1, lymphoma, NHL, colorectal, lung cancers), VCAM-1 (CD106, Melanoma), VEGF, VEGF-A, VEGF-2 (CD309) (various cancers). Some other tumor associated antigens recognized by antibodies have been reviewed (Gerber, et al, mAbs 1:3, 247-253 (2009); Novellino et al, Cancer Immunol Immunother. 54(3), 187-207 (2005). Franke, et al, Cancer Biother Radiopharm. 2000, 15, 459-76). Many other antigens are: many other Cluster of Differentiations (CD4, CDS, CD6, CD7, CD8, CD9, CD10, CD11a, CD11 b, CD11c, CD12w, CD14, CD15, CD16, CDw17, CD18, CD21, CD23, CD24, CD25, CD26, CD27, CD28, CD29, CD31, CD32, CD34, CD35, CD36, CD37, CD41, CD42, CD43, CD44, CD45, CD46, CD47, CD48, CD49b, CD49c, CD53, CD54, CD55, CD58, CD59, CD61, CD62E, CD62L, CD62P, CD63, CD68, CD69, CD71, CD72, CD79, CD79a, CD79b, CD81, CD82, CD83, CD86, CD87, CD88, CD89, CD90, CD91, CD95, CD96, CD100, CD103, CD105, CD106, CD109, CD117, CD120, CD127, CD133, CD134, CD135, CD138, CD141, CD142, CD143, CD144, CD147, CD151, CD152, CD154, CD156, CD158, CD163, CD166, CD168, CD184, CDw186, CD195, CD202 (a, b), CD209, CD235a, CD271, CD303, CD304), Apo2, ASLG659, BMPR1B (bone morphogenetic protein receptor), CRIPTO, Annexin A1, Nucleolin, Endoglin (CD105), ROBO4, Amino-peptidase N, Δ-like-4 (DLL4), VEGFR-2 (CD309), CXCR4 9CD184), Tie2, B7-H3, WT1, MUC1, LMP2, HPV E6 E7, EGFRvIII, HER-2/neu, Idiotype, MAGE A3, p53 nonmutant, NY-ESO-1, GD2, CEA, MelanA/MART1, Napi3b (NAPI-3B, NPTIIb, SLC34A2, solute carrier family 34, member 2, type II sodium-dependent phosphate transporter 3b), Ras mutant, gp100, p53 mutant, Proteinase3 (PR1), bcr-abl, Tetratocarcinoma-derived growth factors), EphA receptors, EphB receptors, EGFr, EGFRvIII, ETBR (Endothelin), HER2/neu, HER3, HLA-DOB (MHC class II molecule Ia antigen), integrins, IRTA2, MPF (MPF, MSLN, SMR, megakaryocyte potentiating factor, mesothelin), cripto, Sema Sb (FLJ10372, KIAA1445, Mm42015, SEMA5B, 5EMAG, semaphoring 5 bHlog, sdema domain, seven thrombospondin repeats, cytoplasmic domain), PSCA, STEAP1 (six transmembrane epithelial antigen of prostate), and STEAP2 (HGNC 8639, IPCA-1, PCANP1, STAMP1, STEAP2, STMP, prostate) Tyrosinase, Survivin, hTERT, Sarcoma translocation breakpoints, EphA2, PAP, ML-IAP, AFP, EpCAM, ERG (TMPRSS2 ETS fusion gene), NA17, PAX3, ALK, Androgen receptor, Cyclin B1, Polysialic acid, MYCN, RhoC, TRP-2, GD3, Fucosyl GM1, Mesothelin, PSCA, MAGE A1, sLe(a), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-13, MAD-CT-2, Fas-related antigen 1.

In another specific embodiment, the antimitotic agent-binding molecule conjugates of the invention are used in accordance with the compositions and methods of the invention for the treatment of cancers. The cancers include, but are not limited, Adrenocortical Carcinoma, Anal Cancer, Bladder Cancer, Brain Tumor (Adult, Brain Stem Glioma, Childhood, Cerebellar Astrocytoma, Cerebral Astrocytoma, Ependymoma, Medulloblastoma, Supratentorial Primitive Neuroectodermal and Pineal Tumors, Visual Pathway and Hypothalamic Glioma), Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Eye Cancer, Intraocular Melanoma, Gallbladder Cancer, Gastric Cancer (Stomach), Germ Cell Tumor, Extragonadal, Gestational Trophoblastic Tumor, Head and Neck Cancer, Hypopharyngeal Cancer, Islet Cell Carcinoma, Kidney Cancer (renal cell cancer), Laryngeal Cancer, Leukemia (Acute Lymphoblastic, Acute Myeloid, Chronic Lymphocytic, Chronic Myelogenous, Hairy Cell), Lip and Oral Cavity Cancer, Liver Cancer, Lung Cancer (Non-Small Cell, Small Cell, Lymphoma (AIDS-Related, Central Nervous System, Cutaneous T-Cell, Hodgkin's Disease, Non-Hodgkin's Disease, Malignant Mesothelioma, Melanoma, Merkel Cell Carcinoma, Metasatic Squamous Neck Cancer with Occult Primary, Multiple Myeloma, and Other Plasma Cell Neoplasms, Mycosis Fungoides, Myelodysplastic Syndrome, Myeloproliferative Disorders, Nasopharyngeal Cancer, Neuroblastoma, Oral Cancer, Oropharyngeal Cancer, Osteosarcoma, Ovarian Cancer (Epithelial, Germ Cell Tumor, Low Malignant Potential Tumor), Pancreatic Cancer (Exocrine, Islet Cell Carcinoma), Paranasal Sinus and Nasal Cavity Cancer, Parathyroid Cancer, Penile Cancer, Pheochromocytoma Cancer, Pituitary Cancer, Plasma Cell Neoplasm, Prostate Cancer Rhabdomyosarcoma, Rectal Cancer, Renal Cell Cancer (kidney cancer), Renal Pelvis and Ureter (Transitional Cell), Salivary Gland Cancer, Sezary Syndrome, Skin Cancer, Skin Cancer (Cutaneous T-Cell Lymphoma, Kaposi's Sarcoma, Melanoma), Small Intestine Cancer, Soft Tissue Sarcoma, Stomach Cancer, Testicular Cancer, Thymoma (Malignant), Thyroid Cancer, Urethral Cancer, Uterine Cancer (Sarcoma), Unusual Cancer of Childhood, Vaginal Cancer, Vulvar Cancer, Wilms' Tumor In another specific embodiment, the antimitotic agent-binding molecule conjugates of the invention are used in accordance with the compositions and methods of the invention for the treatment or prevention of an autoimmune disease. The autoimmune diseases include, but are not limited, Achlorhydra Autoimmune Active Chronic Hepatitis, Acute Disseminated Encephalomyelitis, Acute hemorrhagic leukoencephalitis, Addison's Disease, Agammaglobulinemia, Alopecia areata, Amyotrophic Lateral Sclerosis, Ankylosing Spondylitis, Anti-GBMITBM Nephritis, Antiphospholipid syndrome, Antisynthetase syndrome, Arthritis, Atopic allergy, Atopic Dermatitis, Autoimmune Aplastic Anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome Types I, II, & III, Autoimmune progesterone dermatitis, Autoimmune thrombocytopenic purpura, Autoimmune uveitis, Balo disease/Balo concentric sclerosis, Bechets Syndrome, Berger's disease, Bickerstaffs encephalitis, Blau syndrome, Bullous Pemphigoid, Castleman's disease, Chagas disease, Chronic Fatigue Immune Dysfunction Syndrome, Chronic inflammatory demyelinating polyneuropathy, Chronic recurrent multifocal ostomyelitis, Chronic lyme disease, Chronic obstructive pulmonary disease, Churg-Strauss syndrome, Cicatricial Pemphigoid, Coeliac Disease, Cogan syndrome, Cold agglutinin disease, Complement component 2 deficiency, Cranial arteritis, CREST syndrome, Crohns Disease (a type of idiopathic inflammatory bowel diseases), Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Discoid lupus erythematosus, Eczema, Endometriosis, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressiva, Fibromyalgia, Fibromyositis, Fibrosing aveolitis, Gastritis, Gastrointestinal pemphigoid, Giant cell arteritis, Glomerulonephritis, Goodpasture's syndrome, Graves' disease, Guillain-Barre syndrome, Hashimoto's encephalitis, Hashimoto's thyroiditis, Haemolytic anaemia, Henoch-Schonlein purpura, Herpes gestationis, Hidradenitis suppurativa, Hughes syndrome (See Antiphospholipid syndrome), Hypogammaglobulinemia, Idiopathic Inflammatory Demyelinating Diseases, Idiopathic pulmonary fibrosis, Idiopathic thrombocytopenic purpura (See Autoimmune thrombocytopenic purpura), IgA nephropathy (Also Berger's disease), Inclusion body myositis, Inflammatory demyelinating polyneuopathy, Interstitial cystitis, Irritable Bowel Syndrome, Juvenile idiopathic arthritis, Juvenile rheumatoid arthritis, Kawasaki's Disease, Lambert-Eaton myasthenic syndrome, Leukocytoclastic vasculitis, Lichen planus, Lichen sclerosus, Linear IgA disease (LAD), Lou Gehrig's Disease (Also Amyotrophic lateral sclerosis), Lupoid hepatitis, Lupus erythematosus, Majeed syndrome, Meniere's disease, Microscopic polyangiitis, Miller-Fisher syndrome, Mixed Connective Tissue Disease, Morphea, Mucha-Habermann disease, Muckle-Wells syndrome, Multiple Myeloma, Multiple Sclerosis, Myasthenia gravis, Myositis, Narcolepsy, Neuromyelitis optica (Devic's Disease), Neuromyotonia, Occular cicatricial pemphigoid, Opsoclonus myoclonus syndrome, Ord thyroiditis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria, Parry Romberg syndrome, Parsonnage-Turner syndrome, Pars planitis, Pemphigus, Pemphigus vulgaris, Pernicious anaemia, Perivenous encephalomyelitis, POEMS syndrome, Polyarteritis *nodosa*, Polymyalgia rheumatica, Polymyositis, Primary biliary cirrhosis, Primary sclerosing cholangitis, Progressive inflammatory neuropathy, Psoriasis, Psoriatic Arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatoid fever, Sarcoidosis, Schizophrenia, Schmidt syndrome, Schnitzler syndrome, Scleritis, Scleroderma, Sjögren's syndrome, Spondyloarthropathy, Sticky blood syndrome, Still's Disease, Stiff person syndrome, Subacute bacterial endocarditis, Susac's syndrome, Sweet syndrome, Sydenham Chorea, Sympathetic ophthalmia, Takayasu's arteritis, Temporal arteritis (giant cell arteritis), Tolosa-Hunt syndrome, Transverse Myelitis, Ulcerative Colitis (a type of idiopathic inflammatory bowel diseases), Undifferentiated connective tissue disease, Undifferentiated spondyloarthropathy, Vasculitis, Vitiligo, Wegener's granulomatosis, Wilson's syndrome, Wiskott-Aldrich syndrome In another specific embodiment, a binding molecule used for the conjugate for the treatment or prevention of an autoimmune disease includes, but are not limited to, anti-elastin antibody; Abys against epithelial cells antibody; Anti-Basement Membrane Collagen Type IV Protein antibody; Anti-Nuclear Antibody; Anti ds DNA; Anti ss DNA, Anti Cardiolipin Antibody IgM, IgG; anti-celiac antibody; Anti Phospholipid Antibody IgK, IgG; Anti SM Antibody; Anti Mitochondrial Antibody; Thyroid Antibody; Microsomal Antibody, T-cells antibody; Thyroglobulin Antibody, Anti SCL-70; Anti-Jo; Anti-U.sub.1RNP; Anti-La/SSB; Anti SSA; Anti SSB; Anti Perital Cells Antibody; Anti Histones; Anti RNP; C-ANCA; P-ANCA; Anti centromere; Anti-Fibrillarin, and Anti GBM Antibody, Anti-ganglioside antibody; Anti-Desmogein 3 antibody; Anti-p62 antibody; Anti-sp100 antibody; Anti-Mitochondrial (M2) antibody; Rheumatoid factor antibody; Anti-MCV antibody; Anti-topoisomerase antibody; Anti-neutrophil cytoplasmic (cANCA) antibody.

In certain preferred embodiments, the binding molecule for the conjugate in the present invention, can bind to either a receptor or a receptor complex expressed on an activated lymphocyte which is associated with an autoimmune disease. The receptor or receptor complex can comprise an immunoglobulin gene superfamily member (e.g. CD2, CD3, CD4, CD8, CD19, CD22, CD28, CD79, CD90, CD152/CTLA-4, PD-1, or ICOS), a TNF receptor superfamily member (e.g. CD27, CD40, CD95/Fas, CD134/OX40, CD137/4-1BB, INF-R1, TNFR-2, RANK, TACI, BCMA, osteoprotegerin, Apo2/TRAIL-R1, TRAIL-R2, TRAIL-R3, TRAIL-R4, and APO-3), an integrin, a cytokine receptor, a chemokine receptor, a major histocompatibility protein, a lectin (C-type, S-type, or I-type), or a complement control protein.

In another specific embodiment, useful binding ligands that are immunospecific for a viral or a microbial antigen are humanized or human monoclonal antibodies. As used herein, the term "viral antigen" includes, but is not limited to, any viral peptide, polypeptide protein (e.g. HIV gp120, HIV nef, RSV F glycoprotein, influenza virus neuraminidase, influenza virus hemagglutinin, HTLV tax, herpes simplex virus glycoprotein (e.g. gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacteria, fungi, pathogenic protozoa, or yeast polypeptide including, e.g., LPS and capsular polysaccharide 5/8) that is capable of eliciting an immune response. Examples of antibodies available 1 for the viral or microbial infection include, but are not limited to, Palivizumab which is a humanized anti-respiratory syncytial virus monoclonal antibody for the treatment of RSV infection; PRO542 which is a CD4 fusion antibody for the treatment of HIV infection; Ostavir which is a human antibody for the treatment of hepatitis B virus; PROTVIR which is a human-ized IgG. sub. 1 antibody for the treatment of cytomegalovirus; and anti-LPS antibodies.

The binding molecules-antimitotic agent conjugates of this invention can be used in the treatment of infectious diseases. These infectious diseases include, but are not limited to, *Acinetobacter* infections, Actinomycosis, African sleeping sickness (African trypanosomiasis), AIDS (Acquired immune deficiency syndrome), Amebiasis, Anaplasmosis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis, *Bacteroides* infection, Balantidiasis, *Baylisascaris* infection, BK virus infection, Black piedra, *Blastocystis hominis* infection, Blastomycosis, Bolivian hemorrhagic fever, *Borrelia* infection, Botulism (and Infant botulism), Brazilian hemorrhagic fever, Brucellosis, *Burkholderia* infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, *Chlamydia, Chlamydophila pneumoniae* infection, Cholera, Chromoblastomycosis, Clonorchiasis, *Clostridium difficile* infection, Coccidioidomycosis, Colorado tick fever, Common cold (Acute viral rhinopharyngitis; Acute coryza), Creutzfeldt-Jakob disease, Crimean-Congo hemorrhagic fever, Cryptococcosis, Cryptosporidiosis, Cutaneous larva migrans, Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), Enterococcus infection, Enterovirus infection, Epidemic typhus, Erythema infectiosum (Fifth disease), Exanthem subitum, Fasciolopsiasis, Fasciolosis, Fatal familial insomnia, Filariasis, Food poisoning by *Clostridium perfringens*, Free-living amebic infection, *Fusobacterium* infection, Gas gangrene (Clostridial myonecrosis), Geotrichosis, Gerstmann-Straussler-Scheinker syndrome, Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome, *Helicobacter pylori* infection, Hemolytic-uremic syndrome, Hemorrhagic fever with renal syndrome, Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis, Human metapneumovirus infection, Human monocytic ehrlichiosis, Human papillomavirus infection, Human parainfluenza virus infection, Hymenolepiasis, Epstein-Barr Virus Infectious Mononucleosis (Mono), Influenza, Isosporiasis, Kawasaki disease, Keratitis, *Kingella kingae* infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever, Measles, Melioidosis (Whitmore's disease), Meningitis, Meningococcal disease, Metagonimiasis, Microsporidiosis, Molluscum contagiosum, Mumps, Murine typhus (Endemic typhus), *Mycoplasma* pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease, Pertussis (Whooping cough), Plague, Pneumococcal infection, *Pneumocystis* pneumonia, Pneumonia, Poliomyelitis, *Prevotella* infection, Primary amoebic meningoencephalitis, Progressive multifocal leukoencephalopathy, Psittacosis, Q fever, Rabies, Rat-bite fever, Respiratory syncytial virus infection, Rhinosporidiosis, Rhinovirus infection, Rickettsial infection, Rickettsialpox, Rift Valley fever, Rocky mountain spotted fever, Rotavirus infection, Rubella, *Salmonellosis*, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manuum, Tinea nigra, Tinea pedis (Athlete's foot), Tinea unguium (Onychomy-cosis), Tinea versicolor (*Pityriasis versicolor*), Toxocariasis (Ocular Larva Migrans), Toxocariasis (Visceral Larva Migrans), Toxoplasmosis, Trichinellosis, Trichomoniasis, Trichuriasis (Whipworm infection), Tuberculosis, Tularemia, *Ureaplasma urealyticum* infection, Venezuelan equine encephalitis, Venezuelan hemorrhagic fever, Viral pneumonia, West Nile Fever, White piedra (Tinea blanca), *Yersinia pseudotuberculosis* infection, Yersiniosis, Yellow fever, Zygomycosis.

The binding molecules, preferable antibodies described in this patent that are against pathogenic strains include, but are not limit, *Acinetobacter baumannii, Actinomyces israelii, Actinomyces gerencseriae* and *Propionibacterium propionicus, Trypanosoma brucei*, HIV (Human immunodeficiency virus), *Entamoeba histolytica, Anaplasma* genus, *Bacillus anthracis, Arcanobacterium haemolyticum, Junin* virus, *Ascaris lumbricoides, Aspergillus* genus, Astroviridae family, *Babesia* genus, *Bacillus cereus*, multiple bacteria, *Bacteroides* genus, *Balantidium coli, Baylisascaris* genus, BK virus, *Piedraia hortae, Blastocystis hominis, Blastomyces dermatitides*, Machupo virus, *Borrelia* genus, *Clostridium botulinum*, Sabia, *Brucella* genus, usually *Burkholderia cepacia* and other *Burkholderia* species, *Mycobacterium ulcerans*, Caliciviridae family, *Campylobacter* genus, usually *Candida albicans* and other *Candida* species, *Bartonella henselae*, Group A *Streptococcus* and *Staphylococcus, Trypanosoma cruzi, Haemophilus ducreyi*, Varicella zoster virus (VZV), *Chlamydia trachomatis, Chlamydophila pneumoniae, Vibrio cholerae, Fonsecaea pedrosoi, Clonorchis sinensis, Clostridium difficile, Coccidioides immitis* and *Coccidioides posadasii*, Colorado tick fever virus, rhinoviruses, coronaviruses, CJD prion, Crimean-Congo hemorrhagic fever virus, *Cryptococcus neoformans, Cryptosporidium* genus, *Ancylostoma braziliense*; multiple parasites, *Cyclospora cayetanensis, Taenia solium*, Cytomegalovirus, Dengue viruses (DEN-1, DEN-2, DEN-3 and DEN-4)— Flaviviruses, *Dientamoeba fragilis, Corynebacterium diphtheriae, Diphyllobothrium, Dracunculus medinensis*, Ebolavirus, *Echinococcus* genus, *Ehrlichia* genus, *Enterobius vermicularis, Enterococcus* genus, Enterovirus genus, *Rickettsia prowazekii*, Parvovirus B19, Human herpesvirus 6 and Human herpesvirus 7, *Fasciolopsis buski, Fasciola hepatica* and *Fasciola gigantica*, FFI prion, Filarioidea superfamily, *Clostridium perfringens, Fusobacterium* genus, *Clostridium perfringens*; other *Clostridium* species, *Geotrichum candidum*, GSS prion, *Giardia intestinalis, Burkholderia mallei, Gnathostoma spinigerum* and *Gnathostoma hispidum, Neisseria gonorrhoeae, Klebsiella granulomatis, Streptococcus pyogenes, Streptococcus agalactiae, Haemophilus influenzae*, Enteroviruses, mainly Coxsackie A virus and Enterovirus 71, Sin Nombre virus, *Helicobacter pylori, Escherichia coli* O157:H7, Bunyaviridae family, Hepatitis A Virus, Hepatitis B Virus, Hepatitis C Virus, Hepatitis D Virus, Hepatitis E Virus, Herpes simplex virus 1, Herpes simplex virus 2, *Histoplasma capsulatum, Ancylostoma duodenale* and *Necator americanus, Hemophilus influenzae*, Human bocavirus, *Ehrlichia ewingii, Anaplasma phagocytophilum*, Human metapneumovirus, *Ehrlichia chaffeensis*, Human papillomavirus, Human parainfluenza viruses, *Hymenolepis nana* and *Hymenolepis diminuta*, Epstein-Barr Virus, Orthomyxoviridae family, *Isospora belli, Kingella kingae, Klebsiella pneumoniae, Klebsiella ozaenas, Klebsiella rhinoscleromotis*, Kuru prion, Lassa virus, *Legionella pneumophila, Legionella pneumophila, Leishmania* genus, *Mycobacterium leprae* and *Mycobacterium lepromatosis, Leptospira* genus, *Listeria monocytogenes, Borrelia burgdorferi* and other *Borrelia* species, *Wuchereria bancrofti* and *Brugia malayi*, Lymphocytic choriomeningitis virus (LCMV), *Plasmodium* genus, Marburg virus, Measles virus, *Burkholderia pseudomallei, Neisseria meningitides, Metagonimus yokagawai, Microsporidia* phylum, Molluscum contagiosum virus (MCV), Mumps virus, *Rickettsia typhi, Mycoplasma pneumoniae*, numerous species of bacteria (Actinomycetoma) and fungi (Eumycetoma), parasitic dipterous fly larvae, *Chlamydia trachomatis* and *Neisseria gonorrhoeae*, vCJD prion, *Nocardia asteroides* and other *Nocardia* species, *Onchocerca volvulus, Paracoccidioides brasiliensis, Paragonimus westermani* and other *Paragonimus* species, *Pasteurella* genus, *Pediculus humanus* capitis, *Pediculus humanus corporis, Phthirus pubis, Bordetella pertussis, Yersinia pestis, Streptococcus pneumoniae, Pneumocystis jirovecii*, Poliovirus, *Prevotella* genus, *Naegleria fowleri*, JC virus, *Chlamydophila psittaci, Coxiella burnetii*, Rabies virus, *Streptobacillus moniliformis* and Spirillum minus, Respiratory syncytial virus, *Rhinosporidium seeberi*, Rhinovirus, *Rickettsia* genus, *Rickettsia akari*, Rift Valley fever virus, *Rickettsia rickettsii*, Rotavirus, Rubella virus, *Salmonella* genus, SARS coronavirus, *Sarcoptes scabiei, Schistosoma* genus, *Shigella* genus, Varicella zoster virus, Variola major or Variola minor, *Sporothrix schenckii, Staphylococcus* genus, *Staphylococcus* genus, *Staphylococcus aureus, Streptococcus pyogenes, Strongyloides stercoralis, Treponema pallidum, Taenia* genus, *Clostridium tetani, Trichophyton* genus, *Trichophyton tonsurans, Trichophyton* genus, *Epidermophyton floccosum, Trichophyton rubrum*, and *Trichophyton mentagrophytes, Trichophyton rubrum, Hortaea werneckii, Trichophyton* genus, *Malassezia* genus, *Toxocara canis* or *Toxocara cati, Toxoplasma gondii, Trichinella spiralis, Trichomonas vaginalis, Trichuris trichiura, Mycobacterium tuberculosis, Francisella tularensis, Ureaplasma urealyticum*, Venezuelan equine encephalitis virus, *Vibrio colerae*, Guanarito virus, West Nile virus, *Trichosporon beigelii, Yersinia pseudotuberculosis, Yersinia enterocolitica*, Yellow fever virus, Mucorales order (Mucormycosis) and Entomophthorales order (Entomophthoramycosis), *Pseudomonas aeruginosa, Campylobacter* (*Vibrio*) *fetus, Aeromonas hydrophila, Edwardsiella tarda, Yersinia pestis, Shigella dysenteriae, Shigella flexneri, Shigella sonnei, Salmonella typhimurium, Treponema pertenue, Treponema carateneum, Borrelia vincentii, Borrelia burgdorferi, Leptospira icterohemorrhagiae, Pneumocystis carinii, Brucella abortus, Brucella suis, Brucella melitensis, Mycoplasma* spp., *Rickettsia prowazeki, Rickettsia tsutsugumushi, Clamydia* spp.; pathogenic fungi (*Aspergillus fumigatus, Candida albicans, Histoplasma capsulatum*); protozoa (*Entomoeba histolytica, Trichomonas tenas,*

*Trichomonas hominis, Tryoanosoma gambiense, Trypanosoma rhodesiense, Leishmania donovani, Leishmania tropica, Leishmania braziliensis, Pneumocystis pneumonia, Plasmodium vivax, Plasmodium falciparum, Plasmodium malaria*); or Helminiths (*Schistosoma japonicum, Schistosoma mansoni, Schistosoma haematobium*, and hookworms).

Other antibodies as a binding ligand in this invention for treatment of viral disease include, but are not limited to, antibodies against antigens of pathogenic viruses, including as examples and not by limitation: Poxyiridae, Herpesviridae, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Non-A/Non-B Hepatitis virus, Rhinoviridae, Coronaviridae, Rotoviridae, Oncovirus [such as, HBV (Hepatocellular carcinoma), HPV (Cervical cancer, Anal cancer), Kaposi's sarcoma-associated herpesvirus (Kaposi's sarcoma), Epstein-Barr virus (Nasopharyngeal carcinoma, Burkitt's lymphoma, Primary central nervous system lymphoma), MCPyV (Merkel cell cancer), SV40 (Simian virus 40), HCV (Hepatocellular carcinoma), HTLV-I (Adult T-cell leukemia/lymphoma)], Immune disorders caused virus: [such as Human Immunodeficiency Virus (AIDS)]; Central nervous system virus: [such as, JCV (Progressive multifocal leukoencephalopathy), MeV (Subacute sclerosing panencephalitis), LCV (Lymphocytic choriomeningitis), Arbovirus encephalitis, Orthomyxoviridae (probable) (Encephalitis lethargica), RV (Rabies), Chandipura virus, Herpesviral meningitis, Ramsay Hunt syndrome type II; Poliovirus (Poliomyelitis, Post-polio syndrome), HTLV-I (Tropical spastic paraparesis)]; Cytomegalovirus (Cytomegalovirus retinitis, HSV (Herpetic keratitis)); Cardiovascular virus [such as CBV (Pericarditis, Myocarditis)]; Respiratory system/acute viral nasopharyngitis/viral pneumonia: [Epstein-Barr virus (EBV infection/Infectious mononucleosis), Cytomegalovirus; SARS coronavirus (Severe acute respiratory syndrome) Orthomyxoviridae: Influenza virus A/B/C (Influenza/Avian influenza), Paramyxovirus: Human parainfluenza viruses (Parainfluenza), RSV (Human respiratory syncytial virus), hMPV]; Digestive system virus [MuV (Mumps), Cytomegalovirus (Cytomegalovirus esophagitis); Adenovirus (Adenovirus infection); Rotavirus, Norovirus, Astrovirus, Coronavirus; HBV (Hepatitis B virus), CBV, HAV (Hepatitis A virus), HCV (Hepatitis C virus), HDV (Hepatitis D virus), HEV (Hepatitis E virus), HGV (Hepatitis G virus)]; Urogenital virus [such as, BK virus, MuV (Mumps)].

According to a further object, the present invention also concerns pharmaceutical compositions comprising the conjugate of the invention together with a pharmaceutically acceptable carrier for treatment of cancer and autoimmune disorders. The method for treatment of cancer and autoimmune disorders can be practiced in vitro, in vivo, or ex vivo. Examples of in vitro uses include treatments of cell cultures in order to kill all cells except for desired variants that do not express the target antigen; or to kill variants that express undesired antigen. Examples of ex vivo uses include treatments of hematopoietic stem cells (HSC) prior to the performance of the transplantation (HSCT) into the same patient in order to kill diseased or malignant cells. For instance, clinical ex vivo treatment to remove tumour cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent graft-versus-host disease, can be carried out as follows. Bone marrow is harvested from the patient or other individual and then incubated in medium containing serum to which is added the conjugate of the invention, concentrations range from about 1 pM to 0.1 mM, for about 30 minutes to about 48 hours at about 37° C. The exact conditions of concentration and time of incubation (=dose) are readily determined by the skilled clinicians. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the conjugate of the invention will be supplied as solutions or as a lyophilized solid that can be redisolved in sterile water for injection. Examples of suitable protocols of conjugate administration are as follows. Conjugates are given weekly for 8 weeks as an i.v. bolus. Bolus doses are given in 50 to 500 ml of normal saline to which human serum albumin (e.g. 0.5 to 1 mL of a concentrated solution of human serum albumin, 100 mg/mL) can be added. Dosages will be about 50 µg to 20 mg/kg of body weight per week, i.v. (range of 10 µg to 200 mg/kg per injection). 8 weeks after treatment, the patient may receive a second course of treatment. Specific clinical protocols with regard to route of administration, excipients, diluents, dosages, times, etc., can be determined by the skilled clinicians.

Examples of medical conditions that can be treated according to the in vivo or ex vivo methods of killing selected cell populations include malignancy of any types of cancer, autoimmune diseases, graft rejections, and infections (viral, bacterial or parasite).

The amount of a conjugate which is required to achieve the desired biological effect, will vary depending upon a number of factors, including the chemical characteristics, the potency, and the bioavailability of the conjugates, the type of disease, the species to which the patient belongs, the diseased state of the patient, the route of administration, all factors which dictate the required dose amounts, delivery and regimen to be administered.

In general terms, the conjugates of this invention may be provided in an aqueous physiological buffer solution containing 0.1 to 10% w/v conjugates for parenteral administration. Typical dose ranges are from 1 µg/kg to 0.1 g/kg of body weight per day; a preferred dose range is from 0.01 mg/kg to 20 mg/kg of body weight per day or an equivalent dose in a human child. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmaco-kinetic properties of the compound by the chosen delivery route, and the speed (bolus or continuous infusion) and schedule of administrations (number of repetitions in a given period of time).

The conjugates of the present invention are also capable of being administered in unit dose forms, wherein the term "unit dose" means a single dose which is capable of being administered to a patient, and which can be readily handled and packaged, remaining as a physically and chemically stable unit dose comprising either the active conjugate itself, or as a pharmaceutically acceptable composition, as described hereinafter. As such, typical total daily dose ranges are from 0.01 to 100 mg/kg of body weight. By way of general guidance, unit doses for humans range from 1 mg to 3000 mg per day. Preferably the unit dose range is from 1 to 500 mg administered one to four times a day, and even more preferably from 10 mg to 500 mg, once a day. Conjugates provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via transdermal patches. The compositions may conveniently be administered in unit dosage form and may be prepared by any of the methods well known in the pharmaceutical art, for example, as described in Remington: *The Science and Practice of Pharmacy*, 21$^{th}$ ed.; Lippincott Williams & Wilkins: Philadelphia, PA, 2005.

Preferred formulations include pharmaceutical compositions in which a compound of the present invention is formulated for oral or parenteral administration. For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal. Preferred tablets contain lactose, cornstarch, magnesium silicate, croscarmellose sodium, povidone, magnesium stearate, or talc in any combination.

Liquid preparations for parenteral administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

In a specific embodiment, a conjugate of the invention is administered concurrently with the other known or will be known therapeutic agents such as the chemotherapeutic agent, the radiation therapy, immunotherapy agents, autoimmune disorder agents, anti-infectious agents or the other antibody-drug conjugates, resulting in a synergistic effect. In another specific embodiment, the synergistic drugs or radiation therapy are administered prior or subsequent to administration of a conjugate, in one aspect at least an hour, 12 hours, a day, a week, a month, in further aspects several months, prior or subsequent to administration of a conjugate of the invention.

In other embodiments, the synergistic drugs include, but not limited to:

1). Chemotherapeutic agents: a). Alkylating agents: such as [Nitrogen mustards: (chlorambucil, cyclophosphamide, ifosfamide, mechlorethamine, melphalan, trofosfamide); Nitrosoureas: (carmustine, lomustine); Alkylsulphonates: (busulfan, treosulfan); Triazenes: (dacarbazine); Platinum containing compounds: (carboplatin, cisplatin, oxaliplatin)]; b). Plant Alkaloids: such as [*Vinca* alkaloids: (vincristine, vinblastine, vindesine, vinorelbine); Taxoids: (paclitaxel, docetaxol)]; c). DNA Topoisomerase Inhibitors: such as [Epipodophyllins: (9-aminocamptothecin, camptothecin, crisnatol, etoposide, etoposide phosphate, irinotecan, teniposide, topotecan); Mitomycins: (mitomycin C)]; d). Anti-metabolites: such as {[Anti-folate: DHFR inhibitors: (methotrexate, trimetrexate); IMP dehydrogenase Inhibitors: (mycophenolic acid, tiazofurin, ribavirin, EICAR); Ribonucleotide reductase Inhibitors: (hydroxyurea, deferoxamine)]; [Pyrimidine analogs: Uracil analogs: (5-Fluorouracil, doxifluridine, floxuridine, ratitrexed (Tomudex)); Cytosine analogs: (cytarabine, cytosine arabinoside, fludarabine); Purine analogs: (azathioprine, mercaptopurine, thioguanine)]}; e). Hormonal therapies: such as {Receptor antagonists: [Antiestrogen: (megestrol, raloxifene, tamoxifen); LHRH agonists: (goscrclin, leuprolide acetate); Anti-androgens: (bicalutamide, flutamide)]; Retinoids/Deltoids: [Vitamin D3 analogs: (CB 1093, EB 1089 KH 1060, cholecalciferol, ergocalciferol); Photodynamic therapies: (verteporfin, phthalocyanine, photosensitizer Pc4, dimethoxy-hypocrellin A); Cytokines: (Interferon-alpha, Interferon-gamma, tumor necrosis factor (TNFs), human proteins containing a TNF domain)]}; f). Kinase inhibitors, such as BIBW 2992 (anti-EGFR/Erb2), imatinib, gefitinib, pegaptanib, sorafenib, dasatinib, sunitinib, erlotinib, nilotinib, lapatinib, axitinib, pazopanib.

vandetanib, E7080 (anti-VEGFR2), mubritinib, ponatinib (AP24534), bafetinib (INNO-406), bosutinib (SKI-606), cabozantinib, vismodegib, iniparib, ruxolitinib, CYT387, axitinib, tivozanib, sorafenib, bevacizumab, cetuximab, Trastuzumab, Ranibizumab, Panitumumab, ispinesib; g). Others: such as gemcitabine, epoxomicins (e.g. carfilzomib), bortezomib, thalidomide, lenalidomide, pomalidomide, tosedostat, zybrestat, PLX4032, STA-9090, Stimuvax, allovectin-7, Xegeva, Provenge, Yervoy, Isoprenylation inhibitors (such as Lovastatin), Dopaminergic neurotoxins (such as 1-methyl-4-phenylpyridinium ion), Cell cycle inhibitors (such as staurosporine), Actinomycins (such as Actinomycin D, dactinomycin), Bleomycins (such as bleomycin A2, bleomycin B2, peplomycin), Anthracyclines (such as daunorubicin, doxorubicin (adriamycin), idarubicin, epirubicin, pirarubicin, zorubicin, mtoxantrone, MDR inhibitors (such as verapamil), $Ca^{2+}$ ATPase inhibitors (such as thapsigargin), Histone deacetylase inhibitors (Vorinostat, Romidepsin, Panobinostat, Valproic acid, Mocetinostat (MGCD0103), Belinostat, PCI-24781, Entinostat, SB939, Resminostat, Givinostat, AR-42, CUDC-101, sulforaphane, Trichostatin A); Thapsigargin, Celecoxib, glitazones, epigallocatechin gallate, Disulfiram, Salinosporamide A. 2). An anti-autoimmune disease agent includes, but is not limited to, cyclosporine, cyclosporine A, aminocaproic acid, azathioprine, bromocriptine, chlorambucil, chloroquine, cyclophosphamide, corticosteroids (e.g. amcinonide, betamethasone, budesonide, hydrocortisone, flunisolide, fluticasone propionate, fluocortolone danazol, dexamethasone, Triamcinolone acetonide, beclometasone dipropionate), DHEA, enanercept, hydroxyl-chloroquine, infliximab, meloxicam, methotrexate, mofetil, mycophenylate, prednisone, sirolimus, tacrolimus.

3). An anti-infectious disease agent includes, but is not limited to, a). Aminoglycosides: amikacin, astromicin, gentamicin (netilmicin, sisomicin, isepamicin), hygromycin B, kanamycin (amikacin, arbekacin, bekanamycin, dibekacin, tobramycin), neomycin (framycetin, paromomycin, ribostamycin), netilmicin, spectinomycin, streptomycin, tobramycin, verdamicin; b). Amphenicols: azidamfenicol, chloramphenicol, florfenicol, thiamphenicol; c). Ansamycins: geldanamycin, herbimycin; d). Carbapenems: biapenem, doripenem, ertapenem, imipenem/cilastatin, meropenem, panipenem; e). Cephems: carbacephem (loracarbef), cefacetrile, cefaclor, cefradine, cefadroxil, cefalonium, cefaloridine, cefalotin or cefalothin, cefalexin, cefaloglycin, cefamandole, cefapirin, cefatrizine, cefazaflur, cefazedone, cefazolin, cefbuperazone, cefcapene, cefdaloxime, cefepime, cefminox, cefoxitin, cefprozil, cefroxadine, ceftezole, cefuroxime, cefixime, cefdinir, cefditoren, cefepime, cefetamet, cefmenoxime, cefodizime, cefonicid, cefoperazone, ceforanide, cefotaxime, cefotiam, cefozopran, cephalexin, cefpimizole, cefpiramide, cefpirome, cefpodoxime, cefprozil, cefquinome, cefsulodin, ceftazidime, cefteram, ceftibuten, ceftiolene, ceftizoxime, ceftobiprole, ceftriaxone, cefuroxime, cefuzonam, cephamycin (cefoxitin, cefotetan, cefmetazole), oxacephem (flomoxef, latamoxef); f). Glycopeptides: bleomycin, vancomycin (oritavancin, telavancin), teicoplanin (dalbavancin), ramoplanin, cubicin; g). Glycylcyclines: e.g. tigecycline; h). 13-Lactamase inhibitors: penam (sulbactam, tazobactam), clavam (clavulanic acid); i). Lincosamides: clindamycin, lincomycin; j). Lipopeptides: daptomycin, A54145, calcium-dependent antibiotics (CDA); k). Macrolides: azithromycin, cethromycin, clarithromycin, dirithromycin, erythromycin, flurithromycin, josamycin, ketolide (telithromycin, cethromycin), midecamycin, miocamycin, oleandomycin, rifamycins (rifampicin, rifampin, rifabutin, rifapentine), rokitamycin, roxithromycin, spectinomycin, spiramycin, tacrolimus (FK506), troleandomycin, telithromycin; 1). Monobactams: aztreonam, tigemonam; m). Oxazolidinones: linezolid; n). Penicillins: amoxicillin, ampicillin (pivampicillin, hetacillin, bacampicillin, metampicillin, talampicillin), azidocillin, azlocillin, benzylpenicillin, benzathine benzylpenicillin, benzathine phenoxymethyl-penicillin, clometocillin, procaine benzylpenicillin, carbenicillin (carindacillin), cloxacillin, dicloxacillin, epicillin, flucloxacillin, mecillinam (pivmecillinam), mezlocillin, meticillin, nafcillin, oxacillin, penamecillin, penicillin, pheneticillin, phenoxymethylpenicillin, piperacillin, propicillin, sulbenicillin, temocillin, ticarcillin; o). Polypeptides: bacitracin, colistin, polymyxin B; p). Quinolones: alatrofloxacin, balofloxacin, ciprofloxacin, clinafloxacin, danofloxacin, difloxacin, enoxacin, enrofloxacin, floxin, garenoxacin, gatifloxacin, gemifloxacin, grepafloxacin, kano trovafloxacin, levofloxacin, lomefloxacin, marbofloxacin, moxifloxacin, nadifloxacin, norfloxacin, orbifloxacin, ofloxacin, pefloxacin, trovafloxacin, grepafloxacin, sitafloxacin, sparfloxacin, temafloxacin, tosufloxacin, trovafloxacin; q). Streptogramins: pristinamycin, quinupristin/dalfopristin); r). Sulfonamides: mafenide, prontosil, sulfacetamide, sulfamethizole, sulfanilimide, sulfasalazine, sulfisoxazole, trimethoprim, trimethoprim-sulfamethoxazole (co-trimoxazole); s). Steroid antibacterials: e.g. fusidic acid; t). Tetracyclines: doxycycline, chlortetracycline, clomocycline, demeclocycline, lymecycline, meclocycline, metacycline, minocycline, oxytetracycline, penimepicycline, rolitetracycline, tetracycline, glycylcyclines (e.g. tigecycline); u). Other types of antibiotics: annonacin, arsphenamine, bactoprenol inhibitors (Bacitracin), DADAL/AR inhibitors (cycloserine), dictyostatin, discodermolide, eleutherobin, epothilone, ethambutol, etoposide, faropenem, fusidic acid, furazolidone, isoniazid, laulimalide, metronidazole, mupirocin, mycolactone, NAM synthesis inhibitors (e.g. fosfomycin), nitrofurantoin, paclitaxel, platensimycin, pyrazinamide, quinupristin/dalfopristin, rifampicin (rifampin), tazobactam tinidazole, uvaricin;

4). Anti-viral drugs: a). Entry/fusion inhibitors: aplaviroc, maraviroc, vicriviroc, gp41 (enfuvirtide), PRO 140, CD4 (ibalizumab); b). Integrase inhibitors: raltegravir, elvitegravir, globoidnan A; c). Maturation inhibitors: bevirimat, vivecon; d). Neuraminidase inhibitors: oseltamivir, zanamivir, peramivir; e). Nucleosides &_nucleotides: abacavir, aciclovir, adefovir, amdoxovir, apricitabine, brivudine, cidofovir, clevudine, dexelvucitabine, didanosine (ddl), elvucitabine, emtricitabine (FTC), entecavir, famciclovir, fluorouracil (5-FU), 3'-fluoro-substituted 2',3'-dideoxynucleoside analogues (e.g. 3'-fluoro-2',3'-dideoxythymidine (FLT) and 3'-fluoro-2',3'-dideoxyguanosine (FLO), fomivirsen, ganciclovir, idoxuridine, lamivudine (3TC), 1-nucleosides (e.g. β-1-thymidine and β-1-2'-deoxycytidine), penciclovir, racivir, ribavirin, stampidine, stavudine (d4T), taribavirin (viramidine), telbivudine, tenofovir, trifluridine valaciclovir, valganciclovir, zalcitabine (ddC), zidovudine (AZT); f). Non-nucleosides: amantadine, ateviridine, capravirine, diarylpyrimidines (etravirine, rilpivirine), delavirdine, docosanol, emivirine, efavirenz, foscarnet (phosphonoformic acid), imiquimod, interferon alfa, loviride, lodenosine, methisazone, nevirapine, NOV-205, peginterferon alfa, podophyllotoxin, rifampicin, rimantadine, resiquimod (R-848), tromantadine; g). Protease inhibitors: amprenavir, atazanavir, boceprevir, darunavir, fosamprenavir, indinavir, lopinavir, nelfinavir, pleconaril, ritonavir, saquinavir, telaprevir (VX-950), tipranavir; h). Other types of anti-virus drugs: abzyme, arbidol, calanolide a, ceragenin, cyanovirin-n, diarylpyrimidines, epigallocatechin gallate (EGCG), foscarnet, griffithsin, taribavirin (viramidine), hydroxyurea, KP-1461, miltefosine, pleconaril, portmanteau inhibitors, ribavirin, seliciclib.

5). Other immunotheraphy drugs: e.g. imiquimod, interferons (e.g. α, β), granulocyte colony-stimulating factors, cytokines, Interleukins (IL-1-IL-35), antibodies (e.g. trastuzumab, pertuzumab, bevacizumab, cetuximab, panitumumab, infliximab, adalimumab, basiliximab, daclizumab, omalizumab), Protein-bound drugs (e.g., Abraxane), an antibody conjugated with drugs selected from calicheamicin derivative, of maytansine derivatives (DM1 and DM4), CC-1065 and duocarmycin minor groove binders, potent taxol derivatives, doxorubicin, auristatin antimitotic drugs (e.g. Trastuzumab-DM1, Inotuzumab ozogamicin, Brentuximab vedotin, Glembatumumab vedotin, lorvotuzumab mertansine, AN-152 LMB2, TP-38, VB4-845, Cantuzumab mertansine, AVE9633, SAR3419, CAT-8015 (anti-CD22), IMGN388, IMGN529, IMGN853, milatuzumab-doxorubicin, SGN-75 (anti-CD70), Anti-CD22-MCC-DM1).

According to a still further object, the present invention is also concerned with the process of preparation of the conjugate of the invention. The conjugate and process of the present invention may be prepared in a number of ways well known to those skilled in the art. The antimitotic agents used in the conjugate can be synthesized, for example, by application or adaptation of the methods described below, or variations thereon as appreciated by the skilled artisan. The appropriate modifications and substitutions will be readily apparent and well known or readily obtainable from the scientific literature to those skilled in the art. In particular, such methods can be found in R. C. Larock, Comprehensive Organic Transformations, $2^{nd}$ Edition, Wiley-VCR Publishers, 1999.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see P. G. Wuts and T. W. Greene, Greene's Protective Groups in Organic Synthesis, Wiley-Interscience; 4th edition (2006). Some reactions may be carried out in the presence of a base, or an acid or in a suitable solvent. There is no particular restriction on the nature of the base, acid and solvent to be used in this reaction, and any base, acid or solvent conventionally used in reactions of this type may equally be used here, provided that it has no adverse effect on other parts of the molecule. The reactions can take place over a wide range of temperatures. In general, we find it convenient to carry out the reaction at a temperature of from −80° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The work-up of the reaction can be carried out by conventional means. For example, the reaction products may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography. The synthesis of the antimitotic agents and their conjugates of this invention are illustrated in the FIGS. 1-28.

The conjugates of binding molecules with potent antimitotic agents are further illustrated but not restricted by the description in the following examples.

6. EXPERIMENTAL MATERIALS

Mass spectra were obtained using a Bruker Esquire 3000 system. NMR spectra were recorded on a Bruker AVANCE300 spectrometer. Chemical shifts are reported in ppm relative to TMS as an internal standard. Ultraviolet spectra were recorded on a Hitachi U1200 spectrophotometer. HPLC was performed using an Agilent 1100 HPLC system equipped with a fraction collector and a variable wavelength detector. Thin layer chromatography was performed on Analtech GF silica gel TLC plates. Aminal acids and their derivatives as well as preloaded resins were either from Merck Chemicals International Co, or Synthetech Co., or Peptides International Inc or Chembridge International Co. or Sigma-Aldrich Co. Some of the linkers, Linkers of NHS ester/Maleimide (AMAS, BMPS, GMBS, MBS, SMCC, EMCS or Sulfo-EMCS, SMPB, SMPH, LC-SMCC, Sulfo-KMUS, SM(PEG)4, SM(PEG)6, SM(PEG)8, SM(PEG)12, SM(PEG)24); NHS ester/Pyridyldithiol (SPDP, LC-SPDP or Sulfo-LC-SPDP, SMPT, Sulfo-LC-SMPT); NHS esters/Haloacetyl (SIA, SBAP, SIAB or Sulfo-SIAB); NHS ester/Diazirine (SDA or Sulfo-SDA, LC-SDA or Sulfo-LC-SDA, SDAD or Sulfo-SDAD); Maleimide/Hydrazide (BMPH, EMCH, MPBH, KMUH); Pyridyldithiol/Hydrazide (PDPH); Isocyanate/Maleimide (PMPI) were purchased from Thermo Fisher Scientific Co. SPDB, SPP linkers were made according to the references (Cumber, A. et al, *Bioconjugate Chem.*, 1992, 3, 397-401). Human anti-CD22 antibody was from Santa Cruz Biotechnology, Inc. and Trastuzumab was from Genentech. All other chemicals or anhydrous solvents were from Sigma-Aldrich International.

Example 1. Methyl 4-(bis(2-hydroxyethyl)amino)-4-oxobutanoate (3)

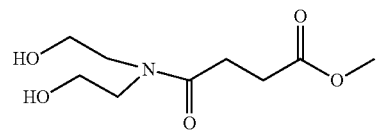

Dimethyl succinate (20.0 g, 136.9 mmol) and dihydroxyethylamine (7.20 g, 68.7 mmol) in the mixture of anhydrous toluene (500 ml) and pyridine (50 ml) were refluxed at 150° C. for 28 h. The mixture was concentrated and purified on SiO$_2$ column eluted with EtOAc/DCM (5% 25% EtOAc) to afford the title compound (12.5 g, 83% yield). ESI MS m/z+ for C$_9$H$_{17}$NaNO$_5$ (M+Na) cald 242.2, found 242.4.

Example 2. Methyl 4-(bis(2-((methylsulfonyl)oxy)ethyl)amino)-4-oxobutanoate (4)

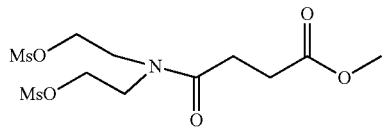 [SMILES: COC(=O)CCC(=O)N(CCOS(C)(=O)=O)CCOS(C)(=O)=O]

Methyl 4-(bis(2-hydroxyethyl)amino)-4-oxobutanoate (12.0 g, 49.56 mmol) in anhydrous pyridine (350 ml) was added methanesulfonyl chloride (20.0 g, 175.4 mmol). After stirred overnight the mixture was concentrated, diluted with EtOAc (350 ml), washed with cold 1 M NaH$_2$PO$_4$ (2×300 ml), dried over MgSO$_4$, filtered and evaporated to afford crude product (~18.8 g, 101% yield). The crude product was used for next step without further purification. ESI MS m/z+ for C$_{11}$H$_{21}$NaNO$_9$S$_2$(M+Na) cald 398.2, found 398.4.

Example 3. Methyl 4-(bis(2-(acetylthio)ethyl)amino)-4-oxobutanoate (5)

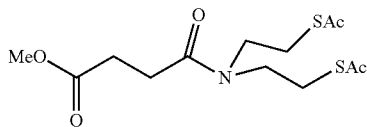

Methyl 4-(bis(2-((methylsulfonyl)oxy)ethyl)amino)-4-oxobutanoate (fresh made, 90% pure, 8.5 g, ~20 mmol) in DMA (350 ml) at 0° C. was added thioacetic acid (10 ml, 134 mmol), followed by addtion of Et$_3$N (30 ml, 215 mmol). The mixture was then stirred at room temperature overnight, concentrated, diluted with EtOAc (350 ml), washed with NaHCO$_3$ (sat, 300 ml), NaCl sat solution (300 ml) and 1 M NaH$_2$PO$_4$ (300 ml). The organic layer was dried over Na$_2$SO$_4$, filtered, evaporated and purified on SiO$_2$ column eluted with EtOAc/hexane (10%-25% EtOAc) to afford the title compound (5.1 g, 76% yield). ESI MS m/z+ for C$_{13}$H$_{21}$NaNO$_5$S$_2$(M+Na) cald 358.1, found 358.2.

Example 4. 4-(Bis(2-(pyridin-2-yldisulfanyl)ethyl)amino)-4-oxobutanoic acid (6)

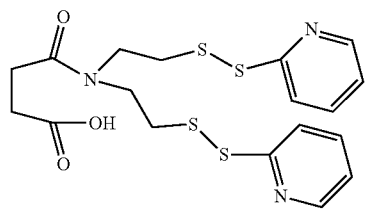 [SMILES: O=C(O)CCC(=O)N(CCSSc1ccccn1)CCSSc1ccccn1]

Methyl 4-(bis(2-(acetylthio)ethyl)amino)-4-oxobutanoate (5.0 g, 14.9 mmol) in THF (150 ml) was added NaOH (5.0 g, 125 mmol) in water (100 ml). The mixture was stirred at RT for 35 min, neutralized with H$_3$PO$_4$ to pH 7. Then 1,2-di(pyridin-2-yl)disulfane (Aldrithiol-2, 26.0 g, 118 mmol) in THF (100 ml) was added and the mixture was stirred for 4 h, concentrated and purified on SiO$_2$ column eluted with MeOH/DCM/HOAc (1:20/1%) to afford the title product (5.8 g, 85.6% yield). ESI MS m/z+ for C$_{18}$H$_{21}$NaN$_3$O$_3$S$_4$ (M+Na) cald 478.0, found 478.2.

Example 5. 2,5-dioxopyrrolidin-1-yl 4-(bis(2-(pyridin-2-yldisulfanyl)ethyl)amino)-4-oxobutanoate (7)

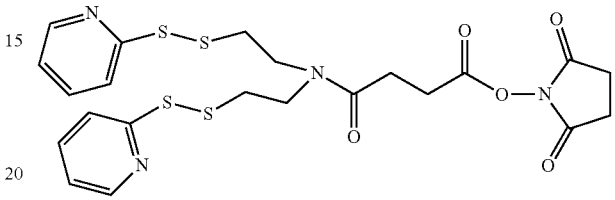

4-(Bis(2-(pyridin-2-yldisulfanyl)ethyl)amino)-4-oxobutanoic acid (5.2 g, 11.5 mmol) in DMA (100 ml) was added NHS (1.6 g, 13.9 mmol) and EDC (5.0 g, 26.1 mmol). The mixture was stirred overnight, evaporated and purified on SiO$_2$ column eluted with EtOAc/DCM (5% to 15% EtOAc) to afford the title product (5.8 g, 85.6% yield). ESI MS m/z+ for C$_{22}$H$_{24}$NaN$_4$O$_5$S$_4$ (M+Na) cald 575.1, found 575.2.

Example 6. 3,6-endoxo-Δ-tetrahydrophthalimide (12)

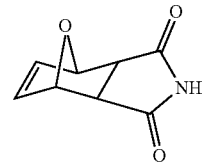 [SMILES: O=C1NC(=O)C2C3C=CC(O3)C12]

Maleimide (10.0 g, 103.0 mmol) in toluene (200 ml) was added furan (10.0 ml, 137.4 mmol). The mixture was heated inside a 1 L of autoclave bomb at 100° C. for 8 h. The bomb was cooled to room temperature, and the inside solid was rinsed with methanol, concentrated and crystallized in ethyl acetate/hexane to afford 16.7 g (99%) of the title compound. 1H NMR (CDCl$_3$): 11.12 (s, 1H) (NH), 6.68~6.64 (m, 2H), 5.18~5.13 (m, 2H), 2.97~2.92 (m, 2H). MS m/z+ for C$_8$H$_7$NaNO$_3$ (M+Na) cald 188.04, found 188.04.

Example 7. Methyl 4-((2-((3aR,4R,7S,7aS)-1,3-dioxo-3a,4,7,7a-tetrahydro-1H-4,7-epoxyisoindol-2(3H)-yl)ethyl)(2-((4R,7S,7aS)-1,3-dioxo-3a,4,7,7a-tetrahydro-1H-4,7-epoxyisoindol-2(3H)-yl)ethyl)amino)-4-oxobutanoate (13)

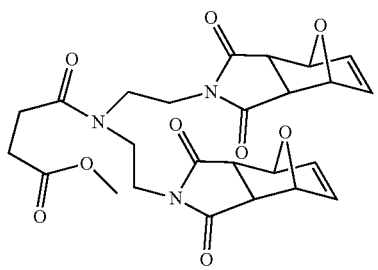 [SMILES: COC(=O)CCC(=O)N(CCN1C(=O)C2C3C=CC(O3)C2C1=O)CCN1C(=O)C2C3C=CC(O3)C2C1=O]

Methyl 4-(bis(2-((methylsulfonyl)oxy)ethyl)amino)-4-oxobutanoate (4, fresh made, 90% pure, 8.5 g, ~20 mmol) in DMA (350 ml) was added 3,6-endoxo-Δ-tetrahydrophthalimide (10.2 g, 61.8 mmol), sodium carbonate (8.0 g, 75.5 mmol) and sodium iodide (0.3 g, 2.0 mmol). The mixture was then stirred at room temperature overnight, concentrated, diluted with EtOAc (350 ml), washed with NaHCO$_3$ (sat, 300 ml), NaCl sat solution (300 ml) and 1 M NaH$_2$PO$_4$ (300 ml). The organic layer was dried over Na$_2$SO$_4$, filtered, evaporated and purified on SiO$_2$ column eluted with EtOAc/hexane (10%-30% EtOAc) to afford the title compound (7.9 g, 77% yield). ESI MS m/z+ for C$_{25}$H$_{27}$NaN$_3$O$_9$(M+Na) cald 536.2, found 536.4.

Example 8. 4-(bis(2-(2,5-dioxo-2,5-dihydro-1H-pyrrol-1-yl)ethyl)amino)-4-oxobutanoic acid (14)

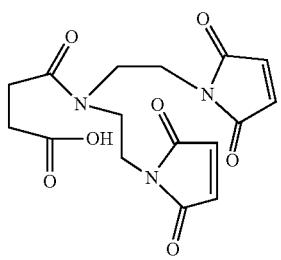 [SMILES: O=C(O)CCC(=O)N(CCN1C(=O)C=CC1=O)CCN1C(=O)C=CC1=O]

Compound 13 (3.0 g, 5.8 mmol) and trimethylstannanol (4.8 g, 26.4 mmol) in 1,2-dichloroethane (150 ml) was refluxed at 80° C. for 8 h. It was cooled to room temperature and the residue was passed a short silica gel column and eluted with dichloromethane/methanol to remove the extra trimethyltin hydroxide. Then the pooled fractions were combined, concentrated and diluted with DMA and toluene, refluxed at 120° C. overnight and purified on SiO$_2$ column eluted with MeOH/DCM (5%-10% MeOH) to afford the title compound (1.62 g, 76% yield). ESI MS m/z+ for C$_{16}$H$_{17}$NaN$_3$O$_9$(M+Na) cald 386.1, found 386.2.

Example 9. 2,5-Dioxopyrrolidin-1-yl 4-(bis(2-(2,5-dioxo-2,5-dihydro-1H-pyrrol-1-yl)ethyl)amino)-4-oxobutanoate

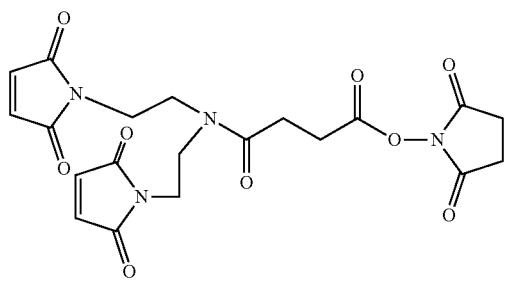 [SMILES: O=C(CCC(=O)N(CCN1C(=O)C=CC1=O)CCN1C(=O)C=CC1=O)ON1C(=O)CCC1=O]

Compound (14)) (1.60 g, 4.4 mmol) in DMA (100 ml) was added NHS (0.76 g, 6.61 mmol) and EDC (1.70 g, 8.90 mmol). The mixture was stirred overnight, evaporated and purified on SiO$_2$ column eluted with EtOAc/DCM (5% to 15% EtOAc) to afford the title product (1.72 g, 85.0% yield). ESI MS m/z+ for C$_{20}$H$_{20}$NaN$_4$O$_9$(M+Na) cald 483.1, found 483.2.

Example 10. t-Butyl 5-(3',6'-endoxo-Δ-tetrahydrophthalimido) pentanoate

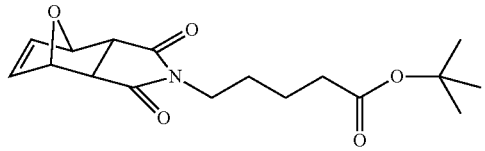 [SMILES: CC(C)(C)OC(=O)CCCCN1C(=O)C2C3C=CC(O3)C2C1=O]

t-Butyl 5-hydroxy pentanote (10.0 g, 57.4 mmol) in pyridine (60 ml) was added mesyl chloride (8.0 ml, 103.3 mmol) and the mixture was stirred for 6 h, evaporated, diluted with EtOAc, washed with cold 1M NaH$_2$PO$_4$, pH 6, dried over MgSO$_4$, filtered and evaporated to dryness. To the mixture of compound 12 (9.90 g, 60.0 mmol) and Na$_2$CO$_3$ (8.5 g, 80.1 mmol) in DMF (80 ml) was added the dryness mesylate compound. The mixture was stirred overnight, evaporated, diluted with EtOAc, washed with saline water and 1M NaH$_2$PO$_4$, pH 6, dried over MgSO$_4$, evaporated and purified on SiO$_2$ column eluted with EtOAc/CH$_2$Cl$_2$ (1:12) to afford the title compound (14.01 g, 76%). MS m/z+ for C$_{17}$H$_{23}$NaNO$_5$ (M+Na) cald 344.16, found 344.16.

Example 11. 5-maleimido-pentanoic acid (21b)

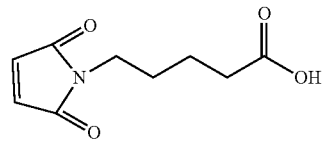 [SMILES: O=C(O)CCCCN1C(=O)C=CC1=O]

Compound 17 (5.0 g, 15.57 mmol) in 1,4-dioxane (40 ml) was added HCl (10 ml, 36%) at 4° C. and the mixture was stirred for 30 min, evaporated to dryness to form 5-(3',6'-endoxo-Δ-tetrahydrophthalimido) pentanoic acid (4.08 g, 99%). The dried compound in mixture of DMF/toluene (1:1, 40 ml) was refluxed for 6 h, evaporated and crystallized from EtOH/ether/hexane to afford the title compound (2.76 g, 90%). MS m/z+ for C$_9$H$_{12}$NO$_4$ (M+H) cald 198.07, found 198.07.

Example 12. N-succinimidyl 5-maleimido-pentanoate (23b) (DMPS Linker)

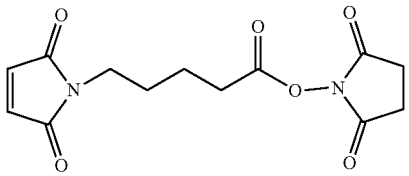 [SMILES: O=C(CCCCN1C(=O)C=CC1=O)ON1C(=O)CCC1=O]

5-maleimido-pentanoic acid 21b (2.0 g, 10.1 mmol) in CH$_2$Cl$_2$ (20 ml) was added N-hydroxysuccimide (1.50 g, 13.0 mmol) and EDC (7.0 g, 36.4 mmol) and the mixture was stirred overnight, evaporated and purified on SiO$_2$ column (EtOAc/CH$_2$Cl$_2$, 1:10) to afford the title compound 23b (2.43 g, 82%). MS m/z+ for C$_{13}$H$_{14}$NaN$_2$O$_6$(M+Na) cald 317.09, found 317.09.

Example 13. t-Butyl 5-(3',6'-endoxo-Δ-tetrahydrophthalimido)pentanoyl hydrazine-carboxylate (25a-a)

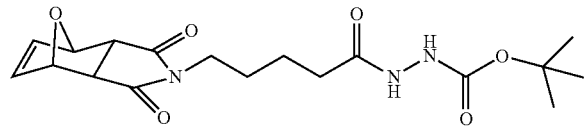 [SMILES: CC(C)(C)OC(=O)NNC(=O)CCCCN1C(=O)C2C3C=CC(O3)C2C1=O]

5-(3',6'-endoxo-Δ-tetrahydrophthalimido) pentanoic acid (1.0 g, 3.77) in DMF (30 ml) was added tert-butyl carbazate (0.60 g, 4.53 mmol) and EDC (2.0 g, 10.4 mmol). The mixture was stirred overnight, evaporated and purified on $SiO_2$ column (EtOAc/$CH_2Cl_2$, 1:10) to afford the title compound (1.18 g, 83%). MS m/z+ for $C_{18}H_{25}NaN_3O_6$(M+Na) cald 402.17, found 402.18.

Example 14. 5-maleimido-pentanoic acid hydrazide (25a-b)

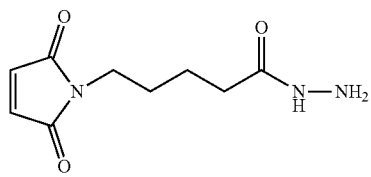 [SMILES: NNC(=O)CCCCN1C(=O)C=CC1=O]

Compound 25a-a (1.18 g, 3.11 mmol) was dissolved in the mixture of DMF/toluene (1:1, 20 ml), refluxed for 6 h and evaporated. Then the mixture dissolved in 1,4-dioxane (20 ml) was added HCl (5 ml, 36%) at 4° C. and the mixture was stirred for 30 min, evaporated to dryness and crystallized from EtOH/ether/hexane to afford the title compound (577 mg, 88%). MS m/z+ for $C_9H_{14}N_3O_3$ (M+H) cald 212.10, found 212.10.

Example 15. General Procedure for 3'-bromo-maleimdo Compounds 39 and 40, and 3',4'-dibromo-maleimdo Compounds 43 and 44

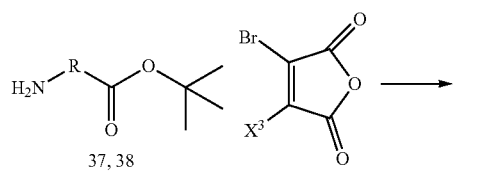

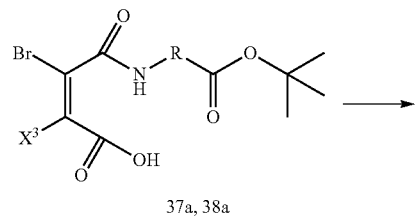

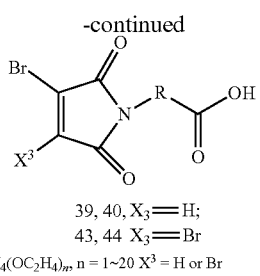

39, 40, $X_3$ = H;
43, 44 $X_3$ = Br
R = $C_1$~$C_8$ alkyl or $C_2H_4(OC_2H_4)_n$, n = 1~20 $X^3$ = H or Br Amino compound 37 or 38 (~6 g) in DMF (60 ml) was added bromomaleic anhydride (1 eq) or 2,3-dibromomaleic anhydride (1 eq) and the mixture was stirred overnight, evaporated via oil pump to dryness to afford the crude enoic acids. To the crude enoic acids were added HOAc (~50 ml) and Ac2O (2~4 g) and the reaction mixture was fluxed at 120° C. for 6~12 h, concentrated and purified on $SiO_2$ column eluted with EtOAc/$CH_2Cl_2$ (1:10~1:1) to afford (61%-87% yield) of the 3'-bromo-maleimdo compounds 39 and 40, and 3',4'-dibromomaleimdo compounds 43 and 44 respectively.

5-(3-bromo-2,5-dioxo-2,5-dihydro-1H-pyrrol-1-yl) pentanoic acid

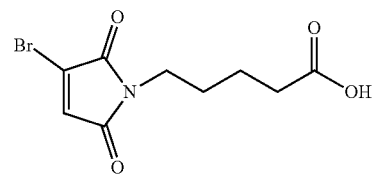 [SMILES: O=C(O)CCCCN1C(=O)C=C(Br)C1=O]

MS m/z+ for $C_9H_{11}BrNO_4$ (M+H) cald 275.98, found 275.98.

3-(2-(2-(2-(3-bromo-2,5-dioxo-2,5-dihydro-1-pyrrol-1-yl)ethoxy)ethoxy)ethoxy)-propanoic acid

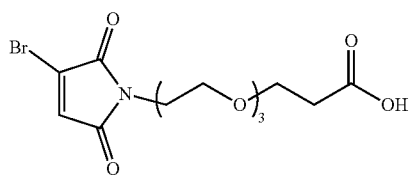

MS m/z+ for $C_{13}H_{19}BrNO_7$ (M+H) cald 380.03, found 380.03.

5-(3,4-dibromo-2,5-dioxo-2,5-dihydro-1H-pyrrol-1-yl)pentanoic acid

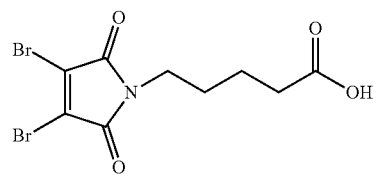 [SMILES: O=C(O)CCCCN1C(=O)C(Br)=C(Br)C1=O]

MS m/z+ for $C_9H_{10}Br_2NO_4$ (M+H) cald 353.89, found 353.89.

3-(2-(2-(2-(3,4-dibromo-2,5-dioxo-2,5-dihydro-1H-pyrrol-1-yl)ethoxy)ethoxy)ethoxy)-propanoic acid

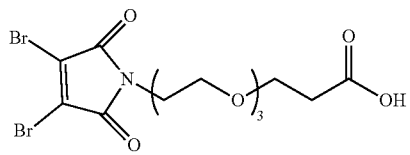

MS m/z+ for $C_{13}H_{18}Br_2NO_7$ (M+H) cald 457.94, found 457.94.

Example 16. General Procedure for NHS Ester of 3'-bromo-maleimdo Compounds 41 and 42, and NHS Ester of 3',4'-dibromo-maleimdo Compounds 45 and 46

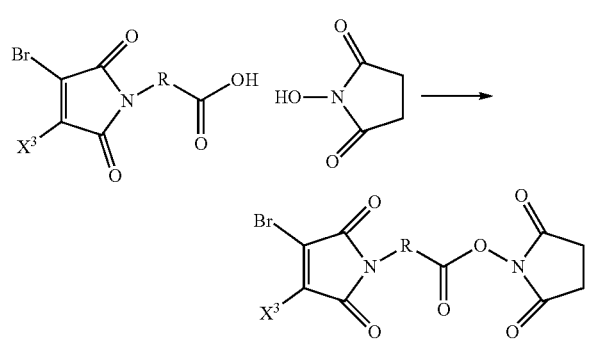

R=($C_1$~$C_8$ alkyl or $C_2H_4(OC_2H_4)_n$, n=1~20; $X^3$=H or Br
41, 42, $X_3$=H; 45, 46, $X_3$=Br To the solution of 3'-bromo-maleimdo compounds 39 and 40 (1 eq), or 3',4'-dibromo-maleimdo compounds 43 and 44 in DMA (~0.15 M) were added N-hydroxysuccinimide (1.1 eq) and EDC (2~4 eq) and the mixture was stirred overnight, concentrated and purified on $SiO_2$ column eluted with EtOAc/$CH_2Cl_2$ (1:20~1:5) to afford (70%-93% yield) of the 3'-bromo-maleimdo linkers 41 and 42, and 3',4'-dibromo-maleimdo linkers 45 and 46 respectively.

2,5-dioxopyrrolidin-1-yl 5-(3-bromo-2,5-dioxo-2,5-dihydro-1H-pyrrol-1-yl)pentanoate

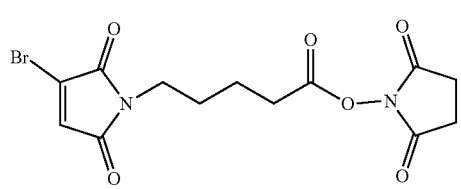 [SMILES: O=C(CCCCN1C(=O)C=C(Br)C1=O)ON1C(=O)CCC1=O]

MS m/z+ for $C_{13}H_{13}BrN_2NaO_7$ (M+Na) cald 395.00, found 395.00.

2,5-dioxopyrrolidin-1-yl 5-(3,4-dibromo-2,5-dioxo-2,5-dihydro-1H-pyrrol-1-yl)pentanoate

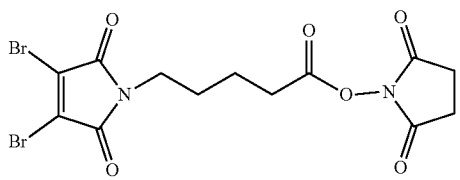 [SMILES: O=C(CCCCN1C(=O)C(Br)=C(Br)C1=O)ON1C(=O)CCC1=O]

MS m/z+ for $C_{13}H_{12}Br_2N_2NaO_6$ (M+Na) cald 472.91, found 472.91.

2,5-dioxopyrrolidin-1-yl 3-(2-(2-(2-(3-bromo-2,5-dioxo-2,5-dihydro-1H-pyrrol-1-yl)ethoxy)ethoxy)ethoxy)propanoate

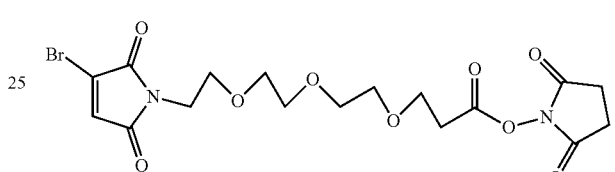

MS m/z+ for $C_{17}H_{21}BrN_2NaO_9$ (M+Na) cald 499.04, found 499.04.

2,5-dioxopyrrolidin-1-yl 3-(2-(2-(2-(3,4-dibromo-2,5-dioxo-2,5-dihydro-1H-pyrrol-1-yl)ethoxy)ethoxy)ethoxy)propanoate

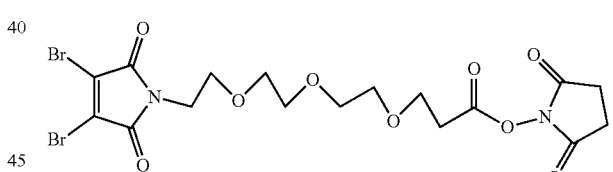

MS m/z+ for $C_{17}H_{20}Br_2N_2NaO_9$ (M+Na) cald 576.95, found 576.95.

Example 17. 4-(2-Pyridyldithio)-4-methylpentanoic acid

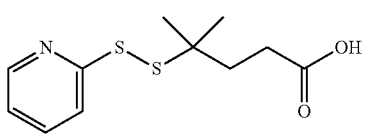 [SMILES: CC(C)(CCC(=O)O)SSc1ccccn1]

4-Mercapto-4-methylpentanoic Acid (Goff, D. et al, *Bioconjugate Chem.* 1990, 1, 381-386) (4.67 g, 31.5 mmol) in methanol (15 ml) was added the solution of 2,2'-Dithiodipyridine (30.0 g, 136.2 mmol) in the mixture of methanol (80 ml) and 100 mM sodium phosphate buffer, pH 7.5 (70 ml). After stirred for 6 h, the mixture was concentrated, extracted with EtOAc/Hexane (1:1). The aqueous solution was adjusted to pH 3 and extracted with EtOAc (3×100 ml). The organic layers were combined, dried over $Na_2SO_4$, filtered, evaporated and purified on SiO2 column (MeOH/CH2Cl2/HOAc, 1:15:0.01) to afford the title compound (7.05 g, 87%). MS m/z+ for $C_{11}H_{16}NO_2S_2$(M+H) cald 258.05, found 258.05.

Example 18. N-Succinimidyl 4-(2-pyridyldithio)-4-methylpentanoate (243) (SMDP Linker)

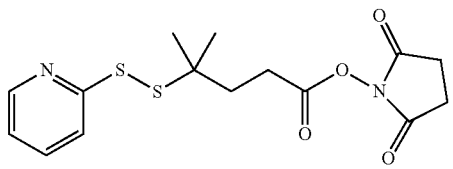 [SMILES: CC(C)(CCC(=O)ON1C(=O)CCC1=O)SSc1ccccn1]

4-(2-pyridyldithio)-4-methylpentanoic acid (2.0 g, 7.78 mmol) in $CH_2Cl_2$ (20 ml) was added N-hydroxysuccimide (1.10 g, 9.56 mmol) and EDC (4.0 g, 20.8 mmol) and the mixture was stirred overnight, evaporated and purified on $SiO_2$ column (EtOAc/$CH_2Cl_2$, 1:10) to afford the title compound (2.48 g, 90%). MS m/z+ for $C_{15}H_{18}NaN_2O_4S_2$ (M+Na) cald 377.07, found 377.08.

Example 19. (3aR,4R,6S,6aR)-6-((R)-2,2-dimethyl-1,3-dioxolan-4-yl)-2,2-dimethyltetrahydro-furo[3,4-d][1,3]dioxol-4-ol (62)

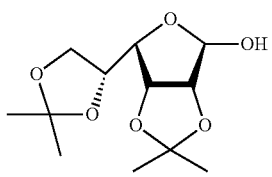

To a stirred slurry of D-gulonic-lactone (20.01 g, 112.37 mmol) and anhydrous $CuSO_4$ (25.0 g, 157.22 mmol) in dry acetone (450 mL) was added conc. $H_2SO_4$ (1.6 mL), and the mixture was stirred for 24 h at room temperature. The pH of the solution was adjusted to 7 with $Ca(OH)_2$, and the resulting slurry was filtered and evaporated in vacuo to afford a diacetonide (2,3:5,6-O-diisopropylidene-D-gulono-1,4-lactone) as a light-yellow syrup which was used in the next step without further purification. To a stirred solution of diacetonide in THF (300 mL) at −78° C. was added slowly 1 M solution of DIBAL-H (180 ml, 180 mM) in toluene. After being stirred for 1 h at −78° C., the reaction mixture was quenched with water (50 mL) and filtered through Celite. The organic layer was separated, dried ($Na_2SO_4$), and concentrated in vacuo. The residue was purified by silica gel chromatography with hexane-ethyl acetate (5:1) to give the title compound (25.27 g, 83% two steps) as colorless syrup. ESI MS m/z+ for $C_{12}H_{20}NaO_6$ (M+Na) cald 283.12, found 283.12.

Example 20. (3aR,4R,6S,6aR,Z)-6-((R)-2,2-dimethyl-1,3-dioxolan-4-yl)-2,2-dimethyl-N-(2-methylpropylidene)tetrahydrofuro[3,4-d][1,3]dioxol-4-amine oxide (64)

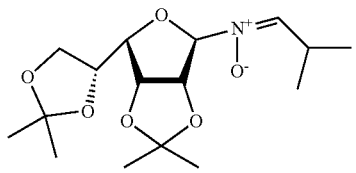

A mixture of 2,3:5,6-O-diisopropylidene-D-gulofuranose (62) (10.0 g, 38.4 mmol) and hydroxylamine hydrochloride (25.01 g, 360.87 mmol) in pyridine (150 mL) was stirred at room temperature for 1 h. The reaction mixture was concentrated in vacuo, added water (250 mL) and extracted with dichloromethane. The combined organic extracts were washed with brine, dried ($MgSO_4$), concentrated in vacuo and filtered through short silica gel column eluted with ethyl acetate to give 2,3:5,6-O-diisopropylidene-D-gulose oxime (63) (10.34 g, 98%) as a colorless vitreous substance which was used directly without further purification. A mixture of this crude oxime (63) (10.30 g, 37.43 mmol), isobutyraldehyde (3.00 g, 41.66 mmol), and $MgSO_4$ (3 g, 25 mmol) was stirred at the room temperature overnight. The mixture was filtered through a pad of Celite. The filtered was concentrated in vacuo and the residue was passed through a short $SiO_2$ column eluted with ethyl acetate to afford the title compound (11.57 g, 94% yield) as white solid. ESI MS m/z+ for $C_{16}H_{27}NO_6$ cald 329.18. found 329.18.

Example 21. (3R,SR)-2-((3aR,4R,6S,6aR)-6-((R)-2,2-dimethyl-1,3-dioxolan-4-yl)-2,2-dimethyltetrahydrofuro[3,4-d][1,3]dioxol-4-yl)-3-[(−)-10',2'-camphorsultam]-N-propylisoxazolidine-5-carboxamide (65)

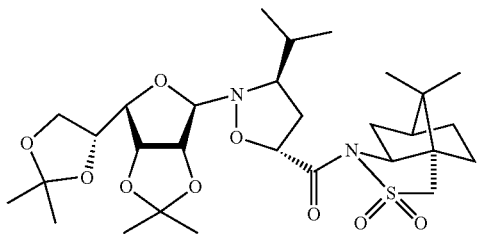

A mixture of (3 aR,4R,6S,6aR,Z)-6-((R)-2,2-dimethyl-1,3-dioxolan-4-yl)-2,2-dimethyl-N-(2-methylpropylidene)tetrahydrofuro[3,4-d][1,3]dioxol-4-amine oxide (6.00 g 18.22 mmol) and (2R)—N-(acryloyl) bornane-10,2-sultams (5.10 g, 18.95 mmol) in $CH_2Cl_2$ (50 mL) was heated under reflux for 37 h. After concentration, the residue was recrystallized from EtOH (30 mL) to give the title compound (8.72 g, 80% yield) as a colorless solid. Flash chromatography (silica gel, hexane/AcOEt 7:3) of the mother liquor gave further (0.47 g, 4%) of the title compound as a colorless solid. MS ESI: m/z: [M+Na]+, calcd for C29H46N2NaO9S 621.28. Found, 621.28.

Example 22. (3R,5R)-2-(tert-butoxycarbonyl)-3-isopropylisoxazolidine-5-carboxylic acid (67)

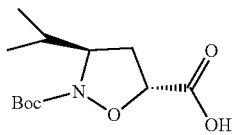 [SMILES: CC(C)[C@H]1C[C@H](C(=O)O)ON1C(=O)OC(C)(C)C]

A solution of LiOH (5.0 g, 208.7 mmol) in H₂O (60 mL) at 45° C. was added to a solution of (3R,5R)-2-((3aR,4R,6S,6aR)-6-((R)-2,2-dimethyl-1,3-dioxolan-4-yl)-2,2-dimethyltetrahydrofuro[3,4-d][1,3]dioxol-4-yl)-3-[(−)-10',2'-camphorsultam]-N-propylisoxazolidine-5-carboxamide (30.0 g, 48.2 mmol) in THF (100 mL) and MeOH (60 mL). After stirred for 1 h, the mixture was concentrated, poured into H₂O (150 mL) and the mixture was adjusted to pH 9 with 4M HCl aq. The mixture was extracted with EtOAc, then the aqueous layer was adjusted to pH 3 with 4M HCl, The mixture was extracted with EtOAc, the organic extract was washed with brine, dried over Na₂SO₄, filtered, and then concentrated in vacuo. The residue was triturated with hexane to give (3R,5R)-2-{(3aR,4R,6S,6aR)-6-[(R)-2,2-dimethyl-1,3-dioxolan-4-yl]-2,2-dimethyltetrahydrofuro[3,4-d,1,3]dioxol-4-yl}-3-isopropylisoxazolidine-5-carboxylic acid (66a) (17.1 g 88%) as a colorless solid. This material was used for the next step without further purification. MS ESI: m/z: [M+Na]+, calcd for C₁₉H₃₁NNaO₈, 424.19, Found, 424.19. To a solution of this material (8.0 g, 19.95 mmol) in MeCN (80 mL) was added 60% HCl O₄ aq. (6.0 mL, 35.77 mmol) at 45° C., and the mixture was stirred at RT for 1 h. After concentration, the residue was dissolved in 1,4-dioxane (40 mL), and then a suspension of NaHCO₃ (25 g, 297 mmol) in H₂O (32 mL) and Boc₂O (4.80 g, 22.00 mmol) was added at 4° C. The mixture was stirred at RT for 4 h, concentrated, diluted with H₂O and EtOAc/Hexane (1:1) and separated. The aqueous layer was adjusted to pH 3 with 4 M HCl aq. The mixture was extracted with EtOAc, the organic layers were washed with brine, dried over Na₂SO₄, filtered, and evaporated in vacuo. The residue was triturated with hexane to give (3R,5R)-2-(tert-butoxycarbonyl)-3-isopropylisoxazolidine-5-carboxylic acid (4.91 g, 95%) as a colorless amorphous solid. MS ESI: m/z: [M+Na]+, calcd for C₁₂H₂₁NNaO₅, 282.13, Found, 282.13.

Example 23. Methyl (R)-2-[(3R,5R)-2-[(t-butyl-yl)methoxycarbonyl]-3-isopropylisoxazolidine-5-carboxamido]-3-(triphenylmethylthio)propionate (68)

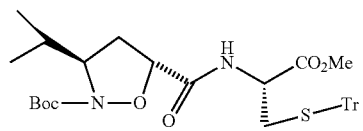

iPr2NEt (0.75 mL, 4.31 mmol) and TBTU (2.50 g, 7.78 mmol) were added to a solution of (3R,5R)-2-(tert-butoxycarbonyl)-3-isopropylisoxazolidine-5-carboxylic acid (1.01 g, 3.89 mmol) and 1-(S)-Tr-cysteine methyl ester hydrochloride (1.76 g, 4.27 mmol) in CH₂Cl₂ (15 mL) at 4° C. and the mixture was stirred at RT for overnight. The mixture was poured into NaHCO₃ (sat.) solution, extracted with CH₂Cl₂, dried over Na₂SO₄, filtered, concentrated and silica gel chromatography (hexane/AcOEt 1:2) to give the title compound (2.10 g, 87%) as colorless amorphous solid. MS ESI: m/z: [M+Na]+, calcd for C₃₅H₄₂N₂NaO₆S, 641.27, Found, 641.26.

Example 24. (3R,5R)-tert-butyl 3-isopropyl-5-(4-(methoxycarbonyl)thiazol-2-yl)isoxazolidine-2-carboxylate (69)

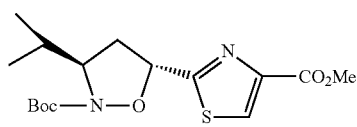 [SMILES: COC(=O)c1csc([C@H]2C[C@H](C(C)C)N(C(=O)OC(C)(C)C)O2)n1]

Tf₂O (2.0 mL, 12.0 mmol) was added to a solution of Ph₃P=O (4.10 g, 14.74 mmol) in CH₂Cl₂ (40.0 mL) and the mixture was stirred at −10° C. for 1 h. A solution of Methyl (R)-2-[(3R,5R)-2-[(t-butyl-yl)methoxycarbonyl]-3-isopropylisoxazolidine-5-carboxamido]-3-(triphenylmethylthio)propionate (68) (4.00 g, 6.47 mmol) in CH₂Cl₂ (20 mL) was added to the reaction mixture at −10° C. and the mixture was stirred at RT for 6 h, added to NaHCO₃ saturated solution at 4° C. and extracted with CH₂Cl₂. The organic extracts were washed with brine, dried over Na₂SO₄, filtered, concentrated in vacuo and SiO₂ chromatography (hexane/AcOEt 3:2) to give the corresponding thiazolidine derivative as a yellow amorphous solid. MnO₂ (5.80 g, 66.7 mmol) was added to a solution of this material in CH₂Cl₂ (60 mL) and the mixture was stirred at RT for 24 h. The mixture was filtrated via Celite, concentrated in vacuo and SiO₂ chromatography (hexane/AcOEt 3:2) to give the title compound (69) (1.75 g, 75%) as a colorless amorphous solid. ESI: m/z: [M+Na]+, calcd for C₁₆H₂₄N₂NaO₅S, 379.13, Found, 379.14.

Example 25. Methyl 2-((1R,3R)-3-(tert-butoxycarbonylamino)-1-hydroxy-4-methylpentyl)-thiazole-4-carboxylate (70)

Mo(CO)₆ (1.10 g, 3.12 mmol) was added to a solution of (3R,5R)-tert-butyl 3-isopropyl-5-(4-(methoxycarbonyl)thiazol-2-yl)isoxazolidine-2-carboxylate (69) (1.00 g, 2.81 mmol) in CH₃CN (20 ml) and H₂O (2 ml) and the mixture was stirred at 70° C. for 16 h. After concentration, the residue was diluted with EtOAc (50 mL) and a 10% aq. solution of citric acid (50 ml). NaIO₄ was added to the mixture until the aqueous layer became clear, and extracted with EtOAc. The organic extracts were washed with a 10% aq. Na₂S₂O₃ and brine, dried over Na₂SO₄, filtered, concentrated and SiO₂ chromatography (hexane/EtOAc 3:2) to give the title compound (906 mg, 90%) as a colorless solid. MS ESI: m/z: [M+Na]+, calcd for C₁₆H₂₆N₂NaO₅S, 381.14, Found, 381.14.

Example 26. Methyl 2-((1R,3R)-1-acetoxy-3-(tert-butoxycarbonyl-amino)-4-methylpentyl)-thiazole-4-carboxylate (71)

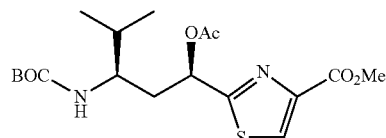

Compound 70 (900 mg, 2.51 mmol) in pyridine (15 ml) was added Ac$_2$O (0.5 ml, 5.29 mmol) and the mixture was stirred overnight, concentrated, SiO$_2$ chromatography (hexane/EtOAc 4:1) to give the title compound (950 mg, 95%) as a colorless solid. MS ESI: m/z: [M+Na]+, calcd for C$_{18}$H$_{28}$N$_2$NaO$_6$S, 423.15, Found, 423.16.

Example 27. 2-((1R,3R)-1-acetoxy-3-(tert-butoxycarbonylamino)-4-methylpentyl)thiazole-4-carboxylic acid (72)

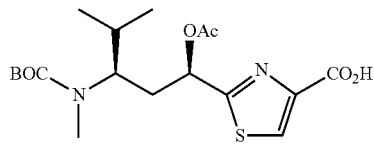 [SMILES: CC(=O)O[C@H](C[C@H](C(C)C)N(C)C(=O)OC(C)(C)C)c1nc(C(=O)O)cs1]

Compound 71 (940 mg, 2.35 mmol) in THF (15 ml) was added NaH (120 mg, 3.0 mmol, 60% in oil) at 4° C. and the mixture was stirred for 2 h, then CH$_3$I (0.155 ml, 2.49 mmol) was added. After stirred overnight, concentrated, re-dissolved in EtOAc, filtered through short SiO$_2$ column and evaporated to dryness to give a crude 2-((1R,3R)-1-acetoxy-3-(tert-butoxycarbonyl-(methyl)amino)-4-methylpentyl)thiazole-4-carboxylic acid (73a). To the dryness compound (73a) in 1,2-dichloroethane (20 ml) was added Trimethyltin hydroxide (620 mg, 3.43 mmol). The mixture was stirred at 80° C. overnight, concentrated, re-dissolved MeOH/CH$_2$Cl$_2$/HOAc (1:5:0.01, 20 ml), filtered through short SiO$_2$ column, concentrated and coevaporated with toluene to a dryness. To the dryness compound in pyridine (15 ml) was added Ac$_2$O (0.4 ml, 4.23 mmol). After stirred overnight, the mixture was concentrated, SiO$_2$ chromatography (MeOH/CH$_2$Cl$_2$/HOAc (1:10:0.01) to give the title compound (735 mg, 78%) as a colorless solid. ESI: m/z: [M+Na]+, calcd for C$_{18}$H$_{28}$N$_2$NaO$_6$S, 423.15, Found, 423.16.

Example 28. Methyl 2-((1R,3R)-3-(tert-butoxycarbonyl(methyl)amino)-1-(3-(1,3-dioxoisoindolin-2-yl)propoxy)-4-methylpentyl)thiazole-4-carboxylate (86)

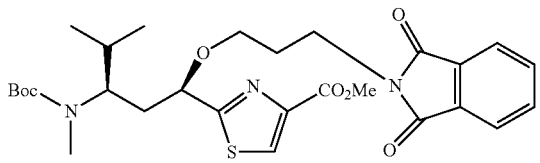 [SMILES: COC(=O)c1csc([C@@H](C[C@H](C(C)C)N(C)C(=O)OC(C)(C)C)OCCCN2C(=O)c3ccccc3C2=O)n1]

Compound 70 (850 mg, 2.37 mmol) in THF (15 ml) at −20° C. was added NaH (100 mg, 2.5 mmol, 60% in oil). After stirred for 30 min at −20° C., N-(3-Bromopropyl) phthalimide (655 mg, 2.4 mmol) was added and the mixture was stirred at −20° C. for 30 min and then warmed up to room temperature in 4 h. The reaction mixture was quenched with methanol (0.5 ml), diluted with CH$_2$Cl$_2$ (60 ml), filtered through a short silica gel column, evaporated to dryness to provide crude methyl 2-((1R,3R)-3-(tert-butoxycarbonyl-amino)-1-(3-(1,3-dioxoisoindolin-2-yl)propoxy)-4-methylpentyl)thiazole-4-carboxylate 85 which was used directly without further purification. To the crude compound 85 in THF (25 ml) at room temperature was added NaH (170 mg, 4.25 mmol, 60% in oil). After stirred for 45 min, CH$_3$I (0.20 ml, 3.21 mmol) was added. The mixture was stirred at room temperature overnight, quenched with NaH$_2$PO$_4$ (2.0 M, 2 ml). The mixture was added DMA (5 ml), evaporated in vacuo, SiO$_2$ chromatography with EtOAc/CH$_2$Cl$_2$ (1:10~1:4) to afford the title compound (921 mg, 69%). ESI: m/z: [M+Na]+, calcd for C$_{28}$H$_{37}$N$_3$NaO$_7$S, 582.22, Found, 582.22.

Example 29. 2-((1R,3R)-3-(tert-butoxycarbonyl(methyl)amino)-1-(3-(1,3-dioxoisoindolin-2-yl)propoxy)-4-methylpentyl)thiazole-4-carboxylic acid (87)

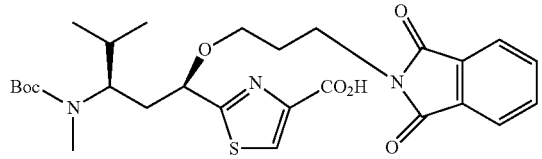 [SMILES: CC(C)[C@@H](C[C@@H](OCCCN1C(=O)c2ccccc2C1=O)c1nc(C(=O)O)cs1)N(C)C(=O)OC(C)(C)C]

To the dryness compound 86 (910 mg, 1.63 mmol) in 1,2-dichloroethane (20 ml) was added Trimethyltin hydroxide (400 mg, 2.21 mmol). The mixture was stirred at 80° C. overnight, concentrated, purified on SiO$_2$ column eluted with CH$_3$OH/CH$_2$Cl$_2$/HOAc (1:10:0.01) to afford the title compound (756 mg, 85%). ESI: m/z: [M+Na]+, calcd for C$_{27}$H$_{36}$N$_3$NaO$_7$S, 546.22. Found, 546.22.

Example 30. Methyl 2-((1R,3R)-1-acetoxy-3-(tert-butoxycarbonyl(3-(1,3-dioxoisoindolin-2-yl)propyl) amino)-4-methylpentyl)thiazole-4-carboxylate (89)

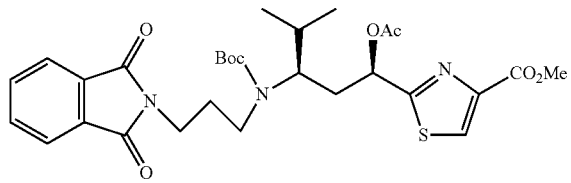 [SMILES: COC(=O)c1csc([C@@H](C[C@H](C(C)C)N(CCCN2C(=O)c3ccccc3C2=O)C(=O)OC(C)(C)C)OC(C)=O)n1]

To the compound 71 (800 mg, 2.00 mmol) in THF (30 ml) at room temperature was added NaH (150 mg, 3.75 mmol, 60% in oil). After stirred for 45 min, N-(3-Bromopropyl)-phthalimide (655 mg, 2.4 mmol) was added. The mixture was stirred at room temperature overnight, quenched with NaH$_2$PO$_4$ (2.0 M, 2 ml). The mixture was added DMA (5 ml), evaporated and purified on SiO$_2$ column eluted with EtOAc/CH$_2$Cl$_2$ (1:10~1:4) to afford the title compound (971 mg, 82%). ESI: m/z: [M+Na]+, calcd for C$_{29}$H$_{37}$N$_3$NaO$_8$S, 610.22, Found, 610.22.

Example 31. 2-((1R,3R)-1-acetoxy-3-(tert-butoxycarbonyl(3-(1,3-dioxoisoindolin-2-yl)propyl)amino)-4-methylpentyl)thiazole-4-carboxylic acid (90)

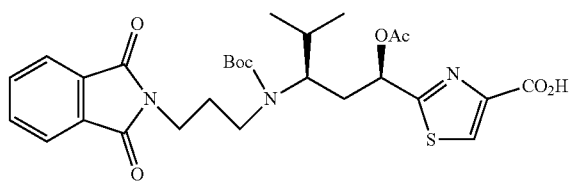 [SMILES: CC(=O)O[C@H](C[C@H](C(C)C)N(CCCN1C(=O)c2ccccc2C1=O)C(=O)OC(C)(C)C)c1nc(C(=O)O)cs1]

To the dryness compound (89) (900 mg, 1.53 mmol) in 1,2-dichloroethane (35 ml) was added trimethyltin hydroxide (400 mg, 2.21 mmol). The mixture was stirred at 80° C. overnight, concentrated. Then the mixture in pyridine (20 ml) was added Ac$_2$O (3 ml) and stirred overnight, evaporated, purified on SiO$_2$ column (MeOH/CH$_2$Cl$_2$/HOAc, 1:10:0.01) to afford the title compound (755 mg, 86%). ESI: m/z: [M+Na]+, calcd for C$_{28}$H$_{35}$N$_3$NaO$_8$S, 596.20, Found, 596.20.

Example 32. (S)-Ethyl 5-(4-(benzyloxy)phenyl)-4-(tert-butoxy-carbonylamino)-2-methylpent-2-enoate (185)

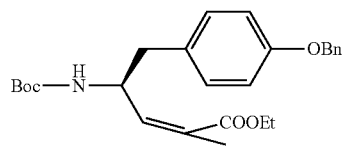

(S)-Methyl 3-(4-(benzyloxy)phenyl)-2-(tert-butoxy-carbonylamino)propanoate 184 (8.00 g, 20.76 mmol) in CH$_2$Cl$_2$ (250 ml) at −78° C. was added dropwise DIBAL (40 ml, 40 mmol, 1.0 M) in CH$_2$Cl$_2$. After stirred at −78° C. for 2 h, the reaction was quenched with addition of MeOH (5 ml). The mixture was warmed to RT, acidified with 1 M HCl to pH 4 and separated. The aqueous layer was extracted with DCM (2×150 ml). The organic layers were washed with water, dried over Na$_2$SO$_4$, filtered and evaporated to dryness to form cude aldehyde intermediate. Then the crude intermediate aldehyde was dissolved in DCM, the ylide solution prepared from 1-(1-ethoxycarbonyl ethyl)-triphenylphosphonium bromide (18.0 g, 40.64 mmol) and KOtBu (5.00 g, 44.64 mmol) in CH$_2$Cl$_2$ (80 ml) at RT was added at. After stirred at RT over night, the mixture was extracted concentrated and purified by SiO$_2$ chromatography (EtOAc/Hexane, 1:8~1:4) to afford (6.90 g, 76%) of the title compound. ESI: m/z: [M+Na]+, calcd for C$_{26}$H$_{33}$NNaO$_5$, 462.22, Found, 462.22.

Example 33. (4R)-ethyl 4-((tert-butoxycarbonyl) amino)-5-(4-hydroxyphenyl)-2-methylpentanoate (186)

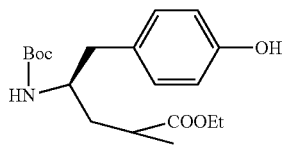 [SMILES: CCOC(=O)C(C)C[C@H](Cc1ccc(O)cc1)NC(=O)OC(C)(C)C]

(S)-Ethyl 5-(4-(benzy loxy)phenyl)-4-(tert-butoxy-carbony lamina)-2-methylpent-2-enoate (185) (6.70 g, 15.26 mmol) in a hydrogenation bottle was charged methanol (150 ml), Pd/C (0.3 g, 10% Pd). The hydrogenation reaction was conducted at 30 psi for 6 h. The mixture was filtered through Celite, evaporated and crystallized with EtOH/hexane to the title compound (186) (4.61 g, 86% yield). ESI: m/z: [M+Na]+, calcd for C$_{19}$H$_{29}$NNaO$_5$, 374.20, Found, 374.30.

Example 34. (4R)-ethyl 4-((tert-butoxycarbonyl) amino)-5-(4-hydroxy-3-nitrophenyl)-2-methylpentanoate (187)

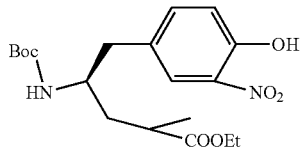 [SMILES: CCOC(=O)C(C)C[C@H](Cc1ccc(O)c([N+](=O)[O-])c1)NC(=O)OC(C)(C)C]

To a solution of compound 186 (4.50 g, 12.81 mmol) in anhydrous CH$_2$Cl$_2$ (200 ml) was added Ac$_2$O (2 ml, 21.16 mmol) and fuming HNO$_3$ (0.65 ml, 14.07 mmol). The mixture was stirred at RT for 4 h, diluted with water (150 ml), separated and the aqueous layer was extracted with EtOAc. The organic layers were combined, dried over Na$_2$SO$_4$, evaporated and purified on SiO$_2$ column (EtOAc/DCM, 1:10) to afford (4.21 g, 83%) of the title compound. ESI: m/z: [M+Na]+, calcd for C$_{19}$H$_{28}$N$_2$NaO$_7$, 419.19, Found, 419.20.

Example 35. ethyl 4-((tert-butoxycarbonyl)amino)-2-methyl-5-(3-nitro-4-(phosphonooxy)phenyl)pentanoate (188)

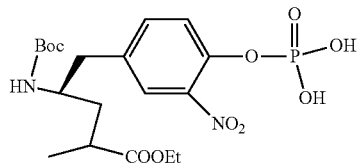 [SMILES: CCOC(=O)C(C)C[C@H](Cc1ccc(OP(=O)(O)O)c([N+](=O)[O-])c1)NC(=O)OC(C)(C)C]

Compound 187 (4.00 g, 10.09 mmol) in a mixture of CH$_3$CN (70 ml) and DMA (30 ml) was added DIPEA (4.00 ml, 23.00 mmol) at 0° C. After stirred for 2 min, POCl$_3$ (2.00 ml, 21.45 mmol) was added dropwise at 0° C. The mixture was stirred at RT for 8 h, and quenched with slowly addition of NaHCO$_3$ (3.5 g, 41.60 mmol) in water (20 ml) at 0° C. After stirred at 0° C. overnight, the mixture was concentrated and purified on C-18 cartridge (20×4 cm) eluted with gradient mixture, 25 ml/min, A: 0.5% HOAc, B: CH$_3$OH, from 100% A in 10 min, then to 75% A and 25% B in 45 min. The fractions containing the product was pooled and evaporated to afford the title compound (3.89 g, 81% yield). ESI: m/z: [M−H]−, calcd for C$_{19}$H$_{28}$N$_2$O$_{10}$P, 475.16, Found, 475.20.

Example 36. (4R)-4-((tert-butoxycarbonyl)amino)-2-methyl-5-(3-nitro-4-(phosphonooxy)phenyl)pentanoic acid (189)

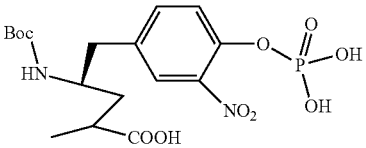 [SMILES: CC(C[C@@H](Cc1ccc(OP(=O)(O)O)c([N+](=O)[O-])c1)NC(=O)OC(C)(C)C)C(=O)O]

To a solution of LiOH (5.0 g, 208.7 mmol) in H$_2$O (60 mL) was added to a solution of compound (188) (3.75 g, 7.87 mmol) in THF (100 mL). After stirred for 4 h at 0° C., the mixture was was adjusted to pH ~6 with 4M HCl, concentrated, and purified by C-18 chromatography eluted with gradient mixture, 25 ml/min, A: 0.5% HOAc, B: CH$_3$OH, from 100% A in 10 min, then to 75% A and 25% B in 45 min. The fractions containing the product was pooled and evaporated to afford the title compound (2.82 g, 80% yield). ESI: m/z: [M–H]$^-$, calcd for C$_{17}$H$_{24}$N$_2$O$_{10}$P, 447.12, Found, 447.20.

Example 37. (4R)-5-(3-amino-4-(phosphonooxy) phenyl)-4-((tert-butoxycarbonyl)amino)-2-methylpentanoic acid (190)

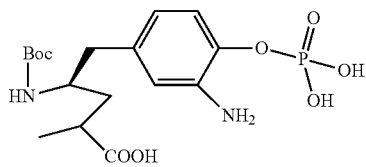 [SMILES: CC(C[C@H](Cc1ccc(OP(=O)(O)O)c(N)c1)NC(=O)OC(C)(C)C)C(=O)O]

Compound (189) (2.60 g, 5.80 mmol) in a hydrogenation bottle was charged methanol (80 ml), Pd/C (0.2 g, 10% Pd). The hydrogenation reaction was conducted at 35 psi of H$_2$ for 6 h. The mixture was filtered through Celite, evaporated to afford crude title compound (190) (2.18 g, 90% yield), which was used directly without further purification. ESI: m/z: [M+Na]+, calcd for C$_{17}$H$_{26}$N$_2$O$_8$P, 417.15, Found, 417.15.

Example 38. (S)-methyl 2-((tert-butoxycarbonyl) amino)-3-(4-hydroxy-3-nitrophenyl)propanoate (196)

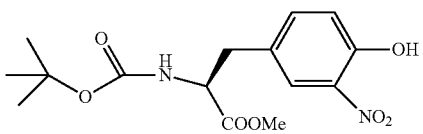 [SMILES: COC(=O)[C@H](Cc1ccc(O)c([N+](=O)[O-])c1)NC(=O)OC(C)(C)C]

To a solution of (S)-methyl 2-((tert-butoxycarbonyl) amino)-3-(4-hydroxyphenyl) propanoate (195) (4.5 g, 15.24 mmol) in anhydrous CH$_2$Cl$_2$ (240 ml) was added Ac$_2$O (4 ml, 42.32 mmol) and fuming HNO$_3$ (0.85 ml, 18.40 mmol). The mixture was stirred at RT for 4 h, diluted with water (150 ml), separated and the aqueous layer was extracted with EtOAc. The organic layers were combined, dried over Na$_2$SO$_4$, evaporated and purified on SiO$_2$ column (EtOAc/DCM, 1:10) to afford (4.30 g, 83%) of the title compound. ESI: m/z: [M+Na]+, calcd for C$_{15}$H$_{20}$N$_2$NaO$_7$, 363.13, Found, 363.20.

Example 39. (S)-methyl 2-((tert-butoxycarbonyl) amino)-3-(3-nitro-4-(phosphonooxy)phenyl)propanoate (197)

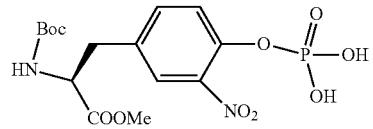 [SMILES: COC(=O)[C@H](Cc1ccc(OP(=O)(O)O)c([N+](=O)[O-])c1)NC(=O)OC(C)(C)C]

To a solution of compound 196 (4.10 g, 12.05 mmol) in a mixture of CH$_3$CN (90 ml) was added DIPEA (4.00 ml, 23.00 mmol) at 0° C. After stirred for 2 min, POCl$_3$ (2.00 ml, 21.45 mmol) was added dropwise at 0° C. The mixture was stirred at RT for 8 h, and quenched with slowly addition of NaHCO$_3$ (3.5 g, 41.60 mmol) in water (20 ml) at 0° C. After stirred at 0° C. overnight, the mixture was concentrated and purified on C-18 cartridge (20×4 cm) eluted with gradient mixture, 25 ml/min, A: 0.5% HOAc, B: CH$_3$OH, from 100% A in 10 min, then to 75% A and 25% B in 45 min. The fractions containing the product was pooled and evaporated to afford (4.20 g, 83%) the title compound. ESI: m/z: [M–H]$^-$, calcd for C$_{15}$H$_{20}$N$_2$O$_{10}$P, 419.08. Found, 419.10.

Example 40. 3-[3-amino-4-(phosphonooxy)phenyl]-(2R)-2-{[(tert-butoxy)carbonyl]amino}-propanoic acid (198)

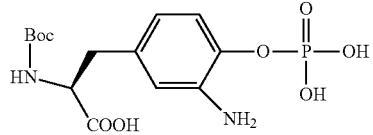 [SMILES: CC(C)(C)OC(=O)N[C@@H](Cc1ccc(OP(=O)(O)O)c(N)c1)C(=O)O]

To the dryness compound (197) (4.0 g, 9.52 mmol) in the mixture of 1,2-dichloroethane (50 ml) and DMA (60 ml) was added trimethyltin hydroxide (4.00 g, 22.1 mmol). The mixture was stirred at 80° C. for 6 h, evaporated, filtered through short SiO$_2$ column eluted with water/MeCN (1:4). The fractions containing the product were pooled, concentrated to generate (S)-2-((tert-butoxycarbonyl)amino)-3-(3-nitro-4-(phosphonooxy)phenyl)propanoic acid. In a hydrogenation bottle was charged DMA (70 ml), Pd/C (0.3 g, 10% Pd), followed by the addition of the prepared propanoic acid. The hydrogenation reaction was conducted at 30 psi of hydrogen for 6 h. The mixture was filtered through Celite, evaporated, and crystallized to afford (2.86 g, 80% yield) of the title compound (198), which was used directly without further purification. ESI: m/z: [M–H]$^-$, calcd for C$_{14}$H$_{20}$N$_2$O$_8$P, 375.10, Found, 375.10.

Example 41. Benzyl 3-[4-(benzyloxy)phenyl]-(2R)-2-{[(tert-butoxy)carbonyl]-(methyl)-amino}-propanoate (200)

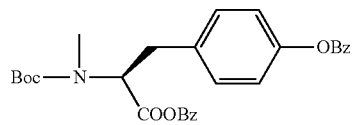

A solution of benzyl 3-[4-(benzyloxy)phenyl]-(2R)-2-{[(tert-butoxy)carbonyl]-amino}propanoate (4.0 g, 8.67 mmol) in THF (60 ml) was added NaH (430 mg, 10.75 mmol, 60% in oil). After stirred at RT for 1 h, CH₃I (1.82 g, 12.82 mmol) was added, and the mixture was stirred overnight, quenched with CH₃OH (0.5 ml), evaporated and purified on SiO2 column (EtOAc/CH₂Cl₂, 1:10) to afford the title compound (3.83 g, 93%). MS ESI: m/z: [M+Na]+, calcd for $C_{29}H_{33}NNaO_5$, 498.24, Found, 498.24.

Example 42. (2R)-2-{[(tert-butoxy)carbonyl] (methyl)amino}-3-(4-hydroxy-3-nitrophenyl)propanoic acid (201)

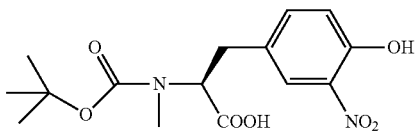 [SMILES: CN(C(=O)OC(C)(C)C)[C@@H](Cc1ccc(O)c([N+](=O)[O-])c1)C(=O)O]

Compound 200 (3.80 g, 8.00 mmol) in a hydrogenation bottle was charged methanol (80 ml), Pd/C (0.3 g, 10% Pd). The hydrogenation reaction was conducted at 30 psi of hydrogen for 6 h. The mixture was filtered through Celite, evaporated to afford crude (2R)-2-{[(tert-butoxy)carbonyl](methyl)amino}-3-(4-hydroxyphenyl)propanoic acid (201a), which was used directly without further purification. To the compound 201a in anhydrous CH₂Cl₂ (240 ml) at −25° C. was added dropwise a mixture of SnCl₄ (1.5 ml, 12.75 mmol) and fuming HNO₃ (0.60 ml, 12.98 mmol) in CH₂Cl₂ (40 ml). The mixture was stirred at −25° C. for 75 min, quenched with saturated NaHCO₃ to pH 3~4, separated and the aq. layer was extracted with EtOAc. The organic layers were combined, dried over Na₂SO₄, concentrated and purified on SiO₂ column (MeOH/DCM/HOAc 1:8:0.01) to afford (1.98 g, 73%) of the title compound. ESI: m/z: [M+Na]+, calcd for $C_{15}H_{20}N_2NaO_7$, 363.13, Found, 363.13.

Example 43. (2R)-2-{[(tert-butoxy)carbonyl] (methyl)amino}-3-[3-nitro-4-(phosphonooxy)-phenyl]propanoic acid (202)

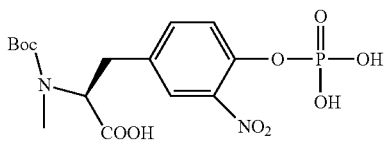 [SMILES: CN(C(=O)OC(C)(C)C)[C@@H](Cc1ccc(OP(=O)(O)O)c([N+](=O)[O-])c1)C(=O)O]

To a solution of compound 201 (1.98 g, 5.82 mmol) in a mixture of CH₃CN (30 ml) and DMA (30 ml) was added DIPEA (2.00 ml, 11.50 mmol) at 0° C. After stirred for 2 min, POCl₃ (1.10 ml, 11.79 mmol) was added dropwise at 0° C. The mixture was stirred at RT for 8 h, and quenched with slowly addition of NaHCO₃ (2.0 g, 23.80 mmol) in water (10 ml) at 0° C. After stirred at 0° C. overnight, the mixture was concentrated and purified on C-18 cartridge (20×4 cm) eluted with gradient mixture, 25 ml/min, A: 0.5% HOAc, B: CH₃OH, from 100% A in 10 min, then to 75% A and 25% B in 45 min. The fractions containing the product was pooled and evaporated to afford (1.96, 80%) the title compound. ESI: m/z: [M−H], calcd for $C_{15}H_{20}N_2O_{10}P$, 419.09, Found, 419.09.

Example 44. 3-[3-amino-4-(phosphonooxy)phenyl]-(2R)-2-[(tert-butoxycarbonyl)(methyl)-amino]-propanoic acid (203)

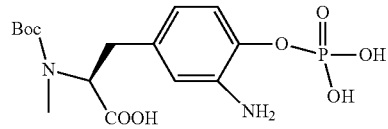 [SMILES: CN(C(=O)OC(C)(C)C)[C@@H](Cc1ccc(OP(=O)(O)O)c(N)c1)C(=O)O]

Compound 202 (1.96 g, 4.67 mmol) in a hydrogenation bottle was charged DMA (60 ml), Pd/C (0.2 g, 10% Pd). The hydrogenation reaction was conducted at 30 psi of hydrogen for 6 h. The mixture was filtered through Celite, evaporated to dryness to afford (1.74 g, 95%) of the title compound (203), which was used directly without further purification. ESI: m/z: [M−H]⁻, calcd for $C_{15}H_{22}N_2O_8P$, 389.12, Found, 389.12.

Example 45. Tert-butyl N-(1-oxo-1-phenylpropan-2-(2R)-yl)carbamate (204)

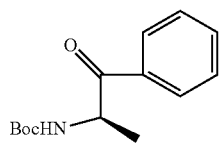 [SMILES: C[C@@H](NC(=O)OC(C)(C)C)C(=O)c1ccccc1]

(1S,2R)-(+)-Norephedrine (7.0 g, 46.29 mmol) in the mixture of THF (40 ml) and 1M NaHCO₃ (100 ml) at 4° C. was added dropwise Boc₂O (10.15 g, 46.53 mmol) in THF (60 ml) in 45 min. The mixture then stirred at RT for 6 h, concentrated, extracted with EtOAc, dried over Na₂SO₄, concentrated and filtered through short SiO₂ column eluted with EtOAc/Hexane (1:2), concentrated to afford the crude tert-butyl N-((1S)-hydroxy-1-phenylpropan-2-(2R)-yl)carbamate (204b) (10.81, 93%). MS ESI: m/z+: [M+Na]+, calcd for $C_{14}H_{21}NaNO_3$, 274.15, Found, 274.15. The crude compound was used directly without further purification. The compound (204b) in CH₂Cl₂ (50 ml) was added Dess-Martin periodinane solution in CH₂Cl₂ (180 ml, 0.3 M). After stirred for 1 h, the mixture was added ice cold NaOH (1 M, 100 ml), separated and the organic layers were washed with 1M NaH₂PO₄, pH 6 (100 ml), dried over Na₂SO₄, evaporated and purified on SiO2 column (EtOAc/hexane 1:5) to afford the title compound 204 (9.34 g, 81% in two steps). MS ESI: m/z+: [M+Na]+, calcd for $C_{14}H_{19}NaNO_3$, 272.14, Found, 272.14.

Example 46. (1R,3R)-3-((2S,3S)—N-(methyl)-3-methyl-2-((R)-1-methylpiperidine-2-carboxamido)-pentamido)-4-methyl-1-(4-((1-oxo-1-phenylpropan-2-yl)carbamoyl)thiazol-2-yl)-pentyl acetate (205)

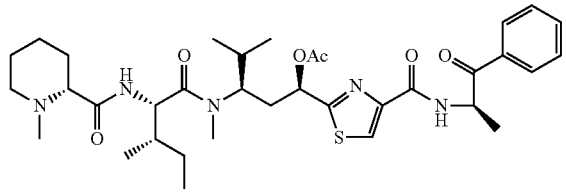 [SMILES: CC[C@H](C)[C@H](NC(=O)[C@H]1CCCCN1C)C(=O)N(C)[C@H](C[C@@H](OC(C)=O)c1nc(C(=O)N[C@H](C)C(=O)c2ccccc2)cs1)C(C)C]

Compound 204 (180 mg, 0.722 mmol) in 4 ml of dioxane was added HCl conc. (1.0 ml, 37%) at 4° C. and the mixture was stirred at RT for 30 min, evaporated and coevaporated with toluene to dryness. Then to the dryness solid in DMA (7 ml) were added compound 106 (251 mg, 0.466 mmol), EDC (305 mg, 1.56 mmol) and DIPEA (0.13 ml, 0.747 mmol) and the mixture was stirred for 8 h, evaporated and purified on SiO$_2$ column (EtOAc/CH$_2$Cl$_2$, 1:4) to afford the title compound 205 (255.3 mg, 82%). ESI: m/z+: [M+Na]+, calcd for C$_{35}$H$_{51}$NaN$_5$O$_6$S, 692.36. Found, 692.36.

Example 47. (1R,3R)-3-((2S,3S)—N,3-dimethyl-2-((R)-1-methylpiperidine-2-carboxamido)-pentanamido)-1-(4-((R)-1-(2,5-dioxo-2,5-dihydro-1H-pyrrol-1-yl)-12-oxo-15-phenyl-3,6,9-trioxa-13,14-diazaheptadec-14-en-16-ylcarbamoyl)thiazol-2-yl)-4-methylpentyl acetate (206)

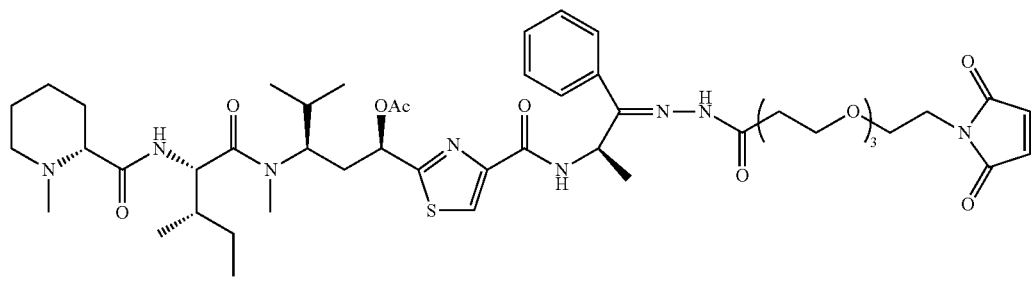

Compound 205 (75 mg, 0.112 mmol) in methanol (5 ml) was added compound 12 (50 mg in HCl salt, 0.126 mmol) and HOAc (3 ul, 0.052 mmol). The mixture was stirred overnight, neutralized with DIPEA (23 ul, 0.132 mmol), evaporated and purified on SiO$_2$ cartridge (4 g, EtOAc/CH$_2$Cl$_2$, 1:5~1:3) to afford the title compound 206 (79.3 mg, 70%). MS ESI: m/z+: [M+Na]+, calcd for C$_{50}$H$_{74}$NaN$_8$O$_{12}$S, 1033.51, Found, 1033.50.

Example 48. (1S,2R)-2-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-1-phenyl-propyl 3-(2-(2-(2-(2,5-dioxo-2,5-dihydro-1H-pyrrol-1-yl)ethoxy)ethoxy)ethoxy)-propanoate (211)

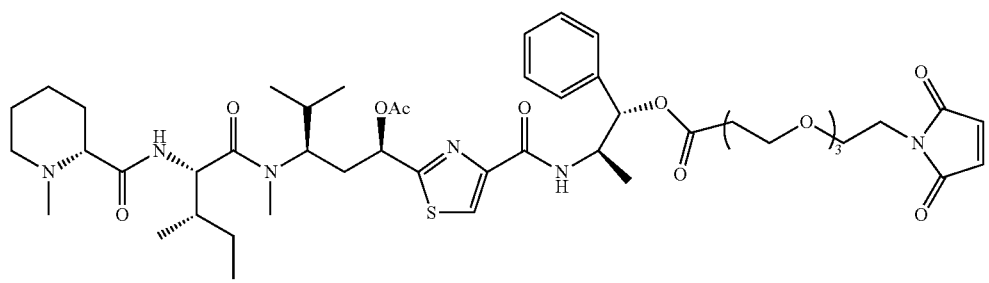

Compound 208a (95 mg, 0.141 mmol) and 3-(2-(2-(2-(2,5-dioxo-2,5-dihydro-1H-pyrrol-1-yl)ethoxy)ethoxy)ethoxy)propanoic acid (55 mg, 0.182 mmol) in CH$_2$Cl$_5$ (5 ml) were added DCC (122 mg, 0.591 mmol) and DMAP (25 mg, 0.204 mmol) and the mixture was stirred overnight, evaporated and purified with SiO$_2$ chromatography (EtOAc/CH$_2$Cl$_2$, 1:3) to afford the title compound (95.1 mg, 71%). MS ESI: m/z+: [M+Na]$^+$, calcd for C$_{48}$H$_{70}$NaN$_6$O$_{12}$S, 977.47. Found, 977.47.

Example 49. 2,5-dioxopyrrolidin-1-yl 2-((1R,3R)-1-acetoxy-3-((2S,3S)—N,3-dimethyl-2-((R)-1-methylpiperidine-2-carboxamido)pentanamido)-4-methylpentyl)thiazole-4-carboxylate (234)

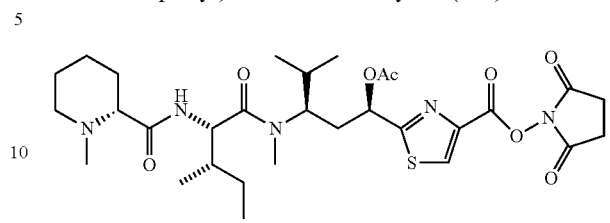

Compound 106 (788.1 mg, 1.464 mmol) in DMF (10 ml) were added NHS (202.0 mg, 1.756 mmol) and EDC (980 mg, 5.104 mmol) and the mixture was stirred overnight, evaporated and purified with SiO$_2$ chromatography (EtOAc/CH$_2$Cl$_2$, 1:3) to afford the title compound (762.8 mg, 82%). MS ESI: m/z+: [M+Na]$^+$, calcd for C$_{30}$H$_{45}$NaN$_5$O$_8$S, 658.30, Found, 658.30.

Example 50. (4R)-4-(tert-butoxycarbonylamino)-5-(3-(5-(2,5-dioxo-2,5-dihydro-1H-pyrrol-1-yl)pentanamido)-4-(phosphonooxy)phenyl)-2-methylpentanoic acid (235)

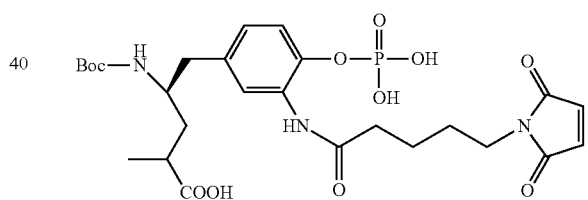

Compound 190 (825.1 mg, 1.973 mmol) in DMF (7 ml) was added 2,5-dioxopyrrolidin-1-yl 5-(2,5-dioxo-2,5-dihydro-1H-pyrrol-1-yl)pentanoate (23d) (711 mg, 2.417 mmol) and DIPEA (0.250 ml, 1.438 mmol), and the mixture was stirred overnight, evaporated and purified with C-18 chromatography (4×25 cm, v=15 ml/min, 100% of 1% HOAc to 75% of 1% HOAc/25% MeOH in 45 min) to afford the title compound 235 (895.7 mg, 76%). MS ESI: m/z−: [M−H]$^−$, calcd for C$_{26}$H$_{35}$N$_3$O$_{11}$P, 596.21, Found, 596.21.

Example 51. (4R)-4-(tert-butoxycarbonylamino)-5-(3-(3-(2-(2-(2-(2,5-dioxo-2,5-dihydro-1H-pyrrol-1-yl)ethoxy)ethoxy)ethoxy)propanamido)-4-(phosphonooxy)phenyl)-2-methylpentanoic acid (236)

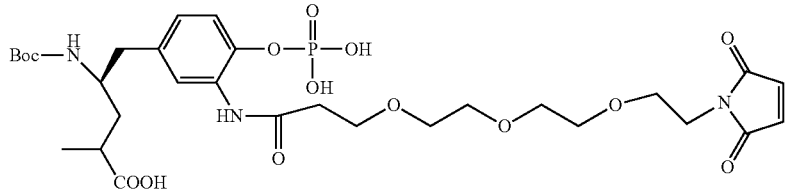 [SMILES: CC(C[C@H](Cc1ccc(OP(=O)(O)O)c(NC(=O)CCOCCOCCOCCN2C(=O)C=CC2=O)c1)NC(=O)OC(C)(C)C)C(=O)O]

Compound 190 (632.5 mg, 1.512 mmol) in DMF (7 ml) were added 2,5-dioxopyrrolidin-1-yl 3-(2-(2-(2-(2,5-dioxo-2,5-dihydro-1H-pyrrol-1-yl)ethoxy)ethoxy)ethoxy)propanoate (24c) (727 mg, 1.826 mmol) and DIPEA (0.250 ml, 1.438 mmol), and the mixture was stirred overnight, evaporated and purified with C-18 chromatography (4×25 cm, v=15 ml/min, 100% of 1% HOAc to 75% of 1% HOAc/25% MeOH in 45 min) to afford the title compound 236 (763.2 mg, 72%). MS ESI: m/z–: [M–H]$^-$, calcd for $C_{30}H_{44}N_3O_{14}P$, 700.25, Found, 700.25.

Example 52. (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-(5-(2,5-dioxo-2,5-dihydro-1H-pyrrol-1-yl)pentanamido)-4-(phosphonooxy)phenyl)-2-methylpentanoic acid (239)

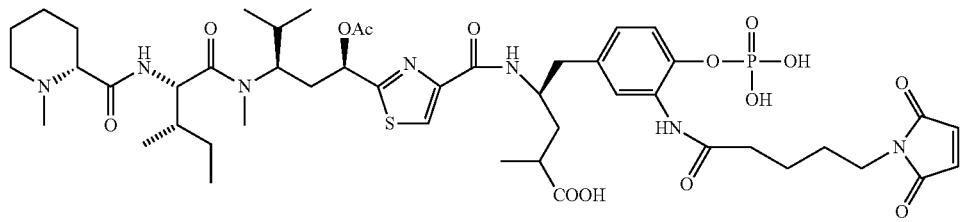

Compound 235 (102 mg, 0.171 mmol) in 1,4-dioxane (4 ml) was added conc. HCl (1 ml, 37%) and the mixture was stirred for 30 min, evaporated to dryness to afford the crude compound 237. To the crude compound in DMA (5 ml) were added compound 234 (110 mg, 0.173 mmol) and DIPEA (30 ul, 0.172 mmol), and the mixture was stirred for overnight, evaporated and purified by SiO$_2$ chromatography (1% HOAc in water/acetone, 1:9~1:4) to afford the title compound 239 (123.2 mg, 71%). MS ESI: m/z–: [M–H]$^-$, calcd for $C_{47}H_{67}N_7O_{14}PS$, 1016.42, Found, 1016.42.

Example 53. (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-(3-(2-(2-(2-(2,5-dioxo-2,5-dihydro-1H-pyrrol-1-yl)ethoxy)ethoxy)ethoxy)-propanamido)-4-(phosphonooxy)phenyl)-2-methylpentanoic acid (240)

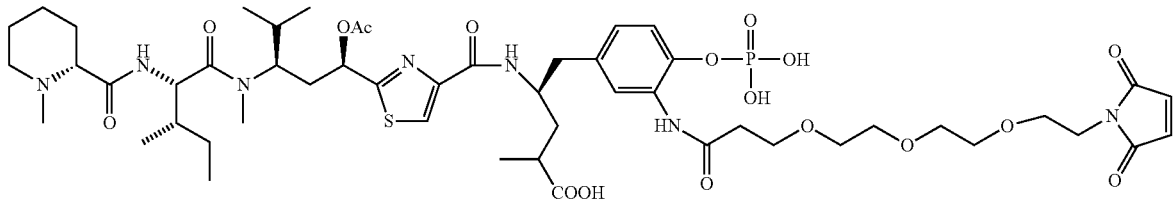

Compound 236 (108 mg, 0.154 mmol) in 1,4-dioxane (4 ml) was added conc. HCl (1 ml, 37%) and the mixture was stirred for 30 min, evaporated to dryness to afford the crude compound 238. To the crude compound in DMA (5 ml) were added compound 234 (110 mg, 0.173 mmol) and DIPEA (30 ul, 0.172 mmol), and the mixture was stirred for overnight, evaporated and purified by SiO$_2$ chromatography (1% HOAc in water/acetone, 1:9~1:4) to afford the title compound 240 (131.2 mg, 76%). MS ESI: m/z–: [M–H]$^-$, calcd for C$_{51}$H$_{75}$N$_7$O$_{17}$PS, 1120.47, Found, 1120.48.

Example 54. (4R)-4-(tert-butoxycarbonylamino)-2-methyl-5-(4-(phosphonooxy)-3-(4-(pyridin-2-yldisulfanyl)butanamido)phenyl)pentanoic acid (244)

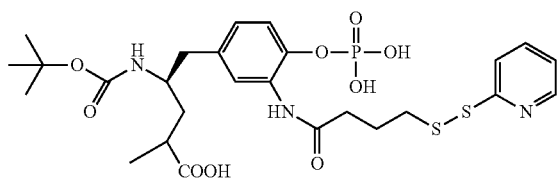 [SMILES: CC(C[C@H](Cc1ccc(OP(=O)(O)O)c(NC(=O)CCCSSc2ccccn2)c1)NC(=O)OC(C)(C)C)C(=O)O]

To a solution of compound 190 (548.3 mg, 1.311 mmol) in DMF (10 ml) were added succinimidyl 4-(pyridin-2-yl)disulfanyl)-butyrate (550.2 mg, 1.687 mmol) and DIPEA (0.18 ml, 1.03 mmol). The mixture was stirred overnight, evaporated and purified by SiO$_2$ chromatography (1% HOAc in water/acetone, 1:9~1:4) to afford the title compound 244 (660.2 mg, 80%). MS ESI: m/z–: [M–H]$^-$, calcd for C$_{26}$H$_{36}$N$_3$O$_9$PS$_2$, 628.16, Found, 628.16.

Example 55. (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-2-methyl-5-(4-(phosphonooxy)-3-(4-(pyridin-2-yldisulfanyl)butanamido)phenyl)pentanoic acid (248)

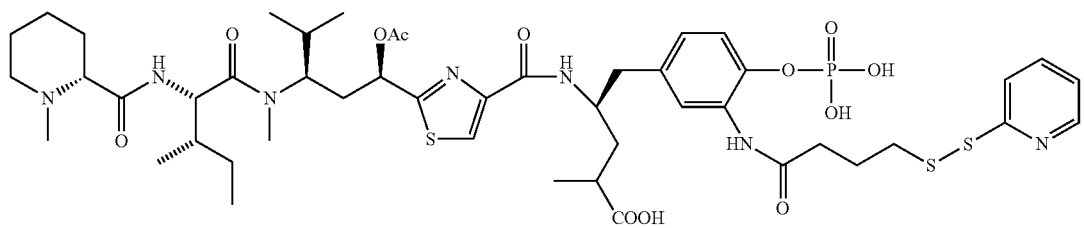

Compound 244 (110.5 mg, 0.175 mmol) in 1,4-dioxane (4 ml) was added conc. HCl (1 ml, 37%) and the mixture was stirred at 4° C. for 30 min, evaporated to dryness to afford the crude compound 246. To the crude compound in DMA (5 ml) were added compound 234 (110 mg, 0.173 mmol) and DIPEA (30 ul, 0.172 mmol). The mixture was stirred for overnight, evaporated and purified by SiO$_2$ chromatography (1% HOAc in water/acetone, 1:9~1:4) to afford the title compound 248 (129.1 mg, 71%). MS ESI: m/z–: [M–H]$^-$, calcd for C$_{47}$H$_{68}$N$_7$O$_{12}$PS$_3$, 1048.38. Found, 1048.38.

Example 56. (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-(4-mercaptobutanamido)-4-(phosphonooxy)phenyl)-2-methylpentanoic acid (248b)

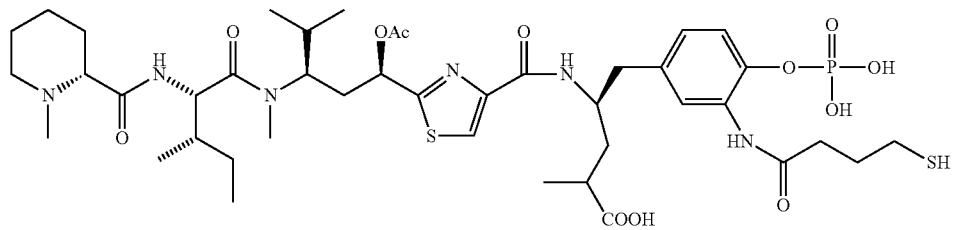

Compound 248 (30 mg, 0.0285 mmol) in a mixture of DMA (2 ml) and NaH$_2$PO$_4$ (0.1 M, pH 7) was added dithiothreitol (20 mg, 0.129 mmol). The mixture was stirred for 2 h, evaporated and purified by SiO$_2$ chromatography (1% HOAc in water/CH$_3$CN, 1:9~1:4) to afford the title compound 248b (22 mg, 85%). MS ESI: m/z−: [M−H]$^-$, calcd for C$_{42}$H$_{64}$N$_6$O$_{12}$PS$_2$, 939.38. Found, 939.38.

Example 57. 4-(4-bromobutyl)-10-oxa-4-azatricyclo[S.2.1.0^{2,6}]dec-8-ene-3,5-dione (271)

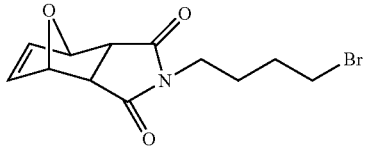 [SMILES: O=C1C2C3C=CC(O3)C2C(=O)N1CCCCBr]

10-oxa-4-azatricyclo[5.2.1.0^{2,6}]dec-8-ene-3,5-dione (6.0 g, 36.35 mmol) and NaH (1.50 g, 37.50 mmol, 60% in oil) were stirred in DMA (60 ml) for 1 h, then 1,4-dibromobutane (35.0 g, 162.10 mmol) and NaI (0.50 g, 3.33 mmol) were added. The mixture was stirred overnight, quenched with CH$_3$OH (0.5 ml), evaporated, purified on SiO$_2$ column (EtOAc/Hexane, 1:8) to afford the title compound (9.34 g, 86%). MS ESI: m/z+: [M+Na]$^+$, calcd for C$_{12}$H$_{14}$BrNaNO$_3$, 322.02, Found, 322.02.

Example 58. Methyl 2-((1R,3R)-3-(tert-butoxycarbonylamino)-1-[4'-(3",6"-endoxo-Δ-tetrahydrophthalimido)butyloxy]-4-methylpentyl)thiazole-4-carboxylate (272)

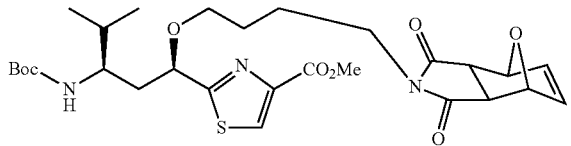 [SMILES: COC(=O)c1csc([C@@H](C[C@@H](NC(=O)OC(C)(C)C)C(C)C)OCCCCN2C(=O)C3C4C=CC(O4)C3C2=O)n1]

Methyl 2-((1R,3R)-3-(tert-butoxycarbonylamino)-1-hydroxy-4-methylpentyl)thiazole-4-carboxylate (70) (1.0 g, 2.79 mmol) and NaH (120 mg, 3.00 mmol, 60% in oil) were stirred in THF (30 ml) for 20 min and compound 271 (1.00 g, 3.34 mmol) and NaI (50 mg, 0.33 mmol) were added. The mixture was stirred overnight, quenched with MeOH (0.5 ml), evaporated and purified on SiO$_2$ column (EtOAc/CHCl$_2$, 1:10) to afford the title compound (1.36 g, 84%). MS ESI: m/z+: [M+Na]+, calcd for C$_{28}$H$_{39}$NaN$_3$O$_8$S, 600.25, Found, 600.25.

Example 59. Methyl 2-((1R,3R)-3-(N,N-tert-butoxycarbonylmethylamino)-1-4'-(3",6"-endoxo-Δ-tetrahydrophthalimido)butyloxy]-4-methylpentyl)thiazole-4-carboxylate (273)

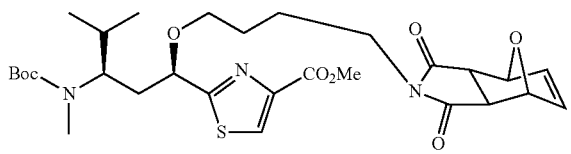 [SMILES: COC(=O)c1csc([C@@H](C[C@H](C(C)C)N(C)C(=O)OC(C)(C)C)OCCCCN2C(=O)C3C4C=CC(O4)C3C2=O)n1]

Compound 272 (1.30 g, 2.25 mmol) and NaH (108 mg, 2.70 mmol, 60% in oil) stirred in DMF (80 ml) for 1 h was added CH$_3$I (460 mg, 3.24 mmol). The mixture was stirred overnight, evaporated and purified on SiO$_2$ column (EtOAc/CH$_2$Cl$_2$, 1:12~1:8) to afford the title compound (1.01 g, 76%). MS ESI: m/z+: [M+Na]$^+$, calcd for C$_{29}$H$_{41}$NaN$_3$O$_8$S, 614.26, Found, 614.26.

Example 60. 2-((1R,3R)-3-(N,N-tert-butoxycarbonylmethyl-amino)-1-(4'-maleimido-butyloxy)-4-methylpentyl)thiazole-4-carboxylic acid (274)

To the dryness compound (273) (900 mg, 1.52 mmol) in a mixture of 1,2-dichloroethane (30 ml) and toluene was added trimethyltin hydroxide (400 mg, 2.21 mmol). The mixture was stirred at 100° C. overnight, concentrated, purified on SiO$_2$ column eluted with MeOH/CH$_2$Cl$_2$/HOAc (1:10:0.01) to afford the title compound (730 mg, 94%). ESI: m/z: [M+Na]+, calcd for C$_{24}$H$_{35}$N$_3$NaO$_7$S, 532.22, Found, 532.22.

Example 61. Methyl 2-((1R,3R)-1-acetoxy-3-(N,N-(tert-butoxycarbonyl)(4'-(3",6"-endoxo-Δ-tetrahydrophthalimido)butyl)amino)-4-methylpentyl)-thiazole-4-carboxylate (275)

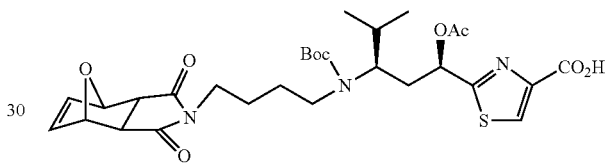

Compound 71 (1.50 g, 3.74 mmol) and NaH (180 mg, 4.50 mmol, 60% in oil) stirred in DMF (80 ml) for 1 h was added compound 271 (1.48 g, 4.94 mmol) and NaI (70 mg, 0.467 mmol). The mixture was stirred overnight, evaporated and purified on SiO$_2$ column (EtOAc/CH$_2$Cl$_2$, 1:10~1:6) to afford the title compound (1.60 g, 69%). MS ESI: m/z+: [M+Na]$^+$, calcd for C$_{30}$H$_{41}$NaN$_3$O$_9$S, 642.26, Found, 642.26.

Example 62. 2-((1R,3R)-1-acetoxy-3-(N,N-(tert-butoxycarbonyl)(4'-maleimidobutyl)amino)-4-methylpentyl)-thiazole-4-carboxylic acid (276)

To the dryness compound (275) (800 mg, 1.29 mmol) in a mixture of 1,2-dichloroethane (40 ml) and toluene was added trimethyltin hydroxide (400 mg, 2.21 mmol). The mixture was stirred at 100° C. overnight, filtered through a short SiO$_2$ column, washed the column with MeOH/CH$_2$Cl$_2$/HOAc (1:5:0.01) and evaporated to dryness. To the crude dryness mixture in pyridine (15 ml) was added Ac$_2$O (0.3 ml, 3.17 mmol) at 0° C. The mixture was stirred at RT overnight, evaporated and purified on SiO2 column eluted with MeOH/CH$_2$Cl$_2$/HOAc (1:10:0.01) to afford the title compound (578.4 mg, 74%). ESI: m/z: [M+Na]+, calcd for C$_{29}$H$_{39}$N$_3$NaO$_9$S, 628.24, Found, 628.24.

Example 63. Phenylalanine-ketoepoxide

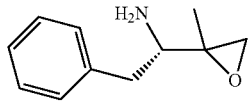

N-Boc phenylalanine-ketoepoxide (Sun, L. et al, J. Mol. Catalysis A: Chem., 2005, 234 (1-2), 29-34) (300 mg, 1.08 mmol) in 1,4-dioxane (8 mL) at 0° C. was added hydrochloric acid (37%, 2 mL). The mixture was stirred for 1 hour at which time TLC showed complete consumption of starting material. The resulting solution was diluted with toluene (10 ml), evaporated and crystallized with EtOH/Hexane to yield HCl salt of the title compound (201 mg, 87%). ESI: m/z: [M+H]+, calcd for $C_{11}H_{16}NO$, 178.12, Found, 178.12.

Example 64. (S,E)-Ethyl 5-phenyl-4-(tert-butoxycarbonylamino)-2-methylpent-2-enoate (327)

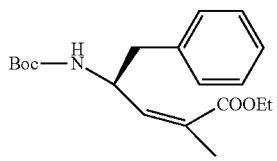 [SMILES: CCOC(=O)/C(C)=C\[C@H](Cc1ccccc1)NC(=O)OC(C)(C)C]

L-t-Boc-phenylalanine methyl ester 326 (5.60 g, 20.05 mmol) in $CH_2Cl_2$ (80 ml) at −78° C. was added dropwise DIBAL (40 ml, 40 mmol, 1.0 M) in $CH_2Cl_2$. After stirred at −78° C. for 45 min, the ylide solution prepared from 1-(1-ethoxycarbonyl ethyl)-triphenylphosphonium bromide (18.0 g, 40.64 mmol) and KOtBu (5.00 g, 44.64 mmol) in $CH_2Cl_2$ (80 ml) at RT was added at −78° C. After stirred at −78° C. for 1 h and RT over night, the mixture was poured into 1 L of $NaH_2PO_4$ (sat.) solution with vigorously stirring. Separated and the aqueous phase was extracted with $CH_2Cl_2$. The organic layers were dried over $Na_2SO_4$, concentrated and purified by $SiO_2$ chromatography (EtOAc/Hexane, 1:7~1:5) to afford 5.50 g (83% yields) of the title compound. ESI: m/z: [M+Nat]+, calcd for $C_{19}H_{27}NNaO_4$, 356.19, Found, 356.20.

Example 65. Ethyl 3-((S)-1-(tert-butoxycarbonylamino)-2-phenylethyl)-2-methyloxirane-2-carboxylate (328)

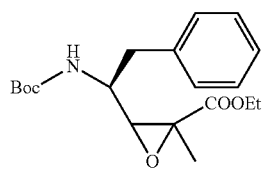

The compound 327 (5.0 g, 15.0 mmol) in $CH_2Cl_2$ (80 ml) was added 3-chloroperoxy-benzoic acid (5.5 g, 22.3 mmol) and the mixture was stirred overnight, diluted with $NaHCO_3$ (25 ml, sat.), separated and extracted the aqueous solution with $CH_2Cl_2$. The organic layers were combined, dried over $Na_2SO_4$, filtered, evaporated and purified on SiO2 column (1:4 EtOAc/Hexane) to afford 4.71 g (90% yield) of the title compound. ESI: m/z: [M+Na]+, calcd for $C_{19}H_{27}NNaO_5$, 372.19, Found, 372.20.

Example 66. 3-((S)-1-(tert-butoxycarbonylamino)-2-phenylethyl)-2-methyloxirane-2-carboxylic acid (329)

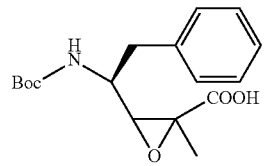 [SMILES: CCOC(=O)C1(C)OC1[C@H](Cc1ccccc1)NC(=O)OC(C)(C)C]

To a solution of LiOH (5.0 g, 208.7 mmol) in $H_2O$ (60 mL) was added to a solution of compound (328) (4.70 g, 13.45 mmol) in THF (100 mL). After stirred for 1 h, the mixture was concentrated, poured into $H_2O$ (150 mL) and the mixture was adjusted to pH~4 with 4M HCl aq. The mixture was extracted with EtOAc, dried over $Na_2SO_4$, concentrated and purified by $SiO_2$ chromatography (MeOH/DCM/HOAc 1:10:0.01) to afford (3.97 g, 92%) of the title compound. ESI: m/z: [M+Na]+, calcd for $C_{17}H_{23}NNaO_5$, 344.16, Found 344.16.

Example 67. 3-((S)-1-(((9H-fluoren-9-yl)methoxy)carbonylamino)-2-phenylethyl)-2-methyloxirane-2-carboxylic acid (331)

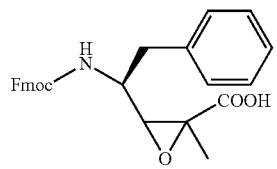

To a solution of compound (329) (3.90 g, 12.14 mmol) in $CH_2Cl_2$ (40 ml) at 0° C., was added TFA (10 ml) and the mixture was stirred at 0° C. for 30 min, diluted with toluene, evaporated to dryness to form the crude TFA salt of compound 330. In a solution of $Na_2CO_3$ (5.0 g, 47.16 mmol) in mixture of $H_2O$ (60 mL) and ethanol (30 ml) were added the crude compound 330 and Fmoc-Cl (3.70 g, 14.30 mmol). After stirred for 6 h, the mixture was concentrated, poured into $H_2O$ (150 mL) and the mixture was adjusted to pH~4 with 4M HCl aq. The mixture was extracted with EtOAc, dried over $Na_2SO_4$, concentrated and purified by $SiO_2$ chromatography (MeOH/DCM/HOAc 1:10:0.01) to afford 3.87 g (72% yields in 2 steps) of the title compound. ESI: m/z: [M+Na]+, calcd for $C_{27}H_{25}NNaO_5$, 466.17, Found 466.17.

Example 68. General Solution Peptide Coupling Procedure

The HCl salt of an amine (1 eq) was dissolved in $CH_2Cl_2$ or DMF (0.2 M) and cooled to 4° C. in an ice bath, followed by the addition of the appropriate Boc-protected amino acid (1.3 eq), EDC (2 eq), or TBTU (2 eq), or PyBrOP (2 eq), HOBt (1.5 eq) and DIPEA (3.5 eq). The reaction was allowed to slowly warm to room temperature and stirred for 15 h, after which it was diluted with EtOAc and washed successively with aqueous solutions of 1M HCl, saturated sodium bicarbonate, water and saturated sodium chloride. The organic layer was dried with Na2SO4, filtered and concentrated under reduced pressure. Purification by column chromatography (0% to 20% MeOH:$CH_2Cl_2$) yielded Boc protected peptide.

Example 69. General Boc Deprotection Procedure

The Boc protected amino acid was dissolved in 20% TFA in $CH_2Cl_2$ or 4 M HCl in dioxane and stirred 30 min, or until the reaction was deemed complete by TLC. The solution was then concentrated under reduced pressure to give the TFA or HCl salt of the peptide. The TFA salt of the peptide was coevaporated with 2% HCl in $CH_2Cl_2$/Toluene for 3~4 times to generate the HCl salt.

Example 70. General Solid Phase Peptide Synthesis (SPPS) Procedure

Boc SPPS was used Merrifield resin or modified PAM resin or MBHA resin. Fmoc SPPS was used Wang resin, or 2-chlorotrityl resin, or HMPB, MBHA resin. The pre-treatment of the resin (pre-swell) and the first loading of an amino compound were followed the manufacture's labels or notes. Resin bound Boc protected amino acids were deprotected with 20% TFA in $CH_2Cl_2$ or 3M HCl in dioxane for 30 minutes and washed with DMF, MeOH, 50% DIPEA ($iPr_2Net$) in $CH_2Cl_2$ and $CH_2Cl_2$. For steps involving the deprotection of multiple free amines, this step was repeated once before acylation to ensure completeness of reaction. Resin bound Fmoc protected amino acids were deprotected with 20% piperidine in DMF for 30 minutes and washed with DMF, MeOH and $CH_2Cl_2$. For steps involving the deprotection of multiple free amines, this step was repeated once before acylation to ensure completeness of reaction. The free amine beads were then suspended in a solution of the protected amino acid (3 eq per eq of free amine), TBTU or PyBrOP (3 eq per eq of free amine) and DIPEA (5 eq per eq of free amine) and mixed for 4 h, and then washed with DMF, MeOH and $CH_2Cl_2$. For steps involving the acylation of multiple free amines, the coupling procedure was repeated once before deprotection to ensure completeness of reaction. These steps were repeated until the desired peptide was synthesized.

Example 71. General Cleavage of Peptides from Wang Resin or 2-Chlorotrityl Resin The peptide bound with Wang resin was mixed with 50% TFA in $CH_2Cl_2$ and tri-isopropylsilane (1~5%) or the peptide bound with 2-Chlorotrityl resin was mixed with 1% TFA in $CH_2Cl_2$. Mixed for 2 h and then filtered. The resin was washed with $CH_2Cl_2$ (3×30 ml), Methanol (3×30 ml), which were combined with the filtrate and evaporated to almost dryness. Cold $Et_2O$ was then added to precipitate the desired deprotected peptide.

Example 72. General Cleavage of Peptides from Merrifield, MBHA or PAM Resin

The peptide bound with the resins was mixed with $HF/Me_2S$/anisole (10:1:1) or $CH_3SO_3H/Me_2S$/anisole (20:1:1), or HF/anisole/Me2S/p-thiocresol (10:1:1:0.2) for peptide containing Cys. Mixed for 2 h, concentrated under a stream of N2, diluted with TFA and filtered. The resin was washed with $CH_2Cl_2$ (3×30 ml), Methanol (3×30 ml), which were combined with the filtrate and condensed under reduced pressure to almost dryness. Cold $Et_2O$ was then added to precipitate the desired deprotected peptide.

Example 73. Chromatographic Purification

The crude peptide mixture was then purified through $SiO_2$ column chromatography (10% to 25% MeOH in $CH_2Cl_2$) or by a reverse phase HPLC eluted with gradient from 100% of water (optionally containing 1% HOAc) to 30% of water (containing 1% HOAc)/70% methanol in 1 h, pooled the fraction, evaporated to give the desired protected.

Example 74. Conjugate Preparation

A binding molecule, preferably an antibody can be conjugated to an antimitotic agents of this prevention through amide, or thiol ether or disulfide bond linkage. In a experiment of generating free thiols on an antibody, the antibodies (mAbs) (>5 mg/mL) in PBS containing 50 mM sodium borate, pH 8.0, were treated with dithiothreitol (10 mM final) at 35° C. for 30 min. After gel filtration (G-25, PBS containing 1 mM EDTA), thiol determination using Ellman's reagent [5,5'-dithiobis(2-nitrobenzoic acid)] indicated that there were approximately eight thiols per mAb. The free thiols were also introduced through conjugation of Traut's Reagent (2-Iminothiolane) (Jue, R., et al. Biochem. 1978, 17 (25): 5399-5405), or through conjugation of SATP (N-succinimidyl-S-acetylthiopropionate) or SAT(PEG)4 linkers at pH 7~8, followed by releasing SH group with hydroxylamine treatment (Duncan, R, et al, Anal. Biochem. 1983, 132, 68-73, Fuji, N. et al, *Chem. Pharm. Bull.* 1985, 33, 362-367). On average, 5-8 of free thiols were introduced on mAbs.

To the mAbs containing free thiols at 4° C. were added the drug bearing maleimide or bromoacetamide (0.5 M sodium borate buffer pH 9 was required to promote mAb alkylation with bromoacetamide) (1.2~1.5 equiv of drug derivatives/SH group ratio) in cold DMA (2~20% v/v). After 1~2 h, the reactions were quenched with excess cysteine; the conjugates were concentrated by centrifugal ultrafiltration, gel filtered (G-25, PBS), and sterile filtered. Protein concentration and drug loading were determined by spectral analysis at 280 and 252 nm, respectively. Size-exclusion HPLC was used to determine percent monomer of each conjugate prepared, and RP-HPLC established that there was less than 0.5% unconjugated cysteine-equenched drug. The resulting conjugate was monomeric and contained, on the average, 3.2-4.2 antimitotic agents linked per antibody molecule for these thiol ether linked conjugation.

For the conjugation through DMPS, SMDP, SMPT, SPP, SPDP, SPDB, SMCC, or SM(PEG)n linkers. A solution of mAb (>5 mg/mL) in aqueous buffer (50 mM PBS, 50 mM NaCl, 1 mM EDTA) at pH 6.5~7.5 was incubated for 2 h with a 6- to 10-fold molar excess of a linker. The reaction mixture was purified via a Sephadex G25 gel filtration column to remove low molecular weight material. (The concentration of the antibody was determined spectrophotometrically if the linkers contained a pyridylthio. The coefficients for the antibody $\varepsilon_{280nm}=2067550$ $M^{-1}$ $cm^{-1}$. An aliquot of the modified antibody was treated with an excess (>20 equiv) of dithiothreitol and the release of pyridine-2-thione determined using the known extinction coefficients of $\varepsilon_{343\ nm}=8080$ $M^{-1}$ $cm^{-1}$ and $\varepsilon_{280nm}=5100$ $M^{-1}$ $cm^{-1}$ for pyridine-2-thione). The modified antibody was treated with 1.2~1.5 equiv of an antimitotic agent bearing a thiol group. The reaction mixture was incubated for 5~18 h at RT. The reaction mixture was purified via a Sephadex G25 gel filtration column to remove the unconjugated drug and other low molecular weight species. The concentration of the conjugate was determined spectrophotometrically at 280 and 252 nm. The resulting conjugate was monomeric and contained, on the average, 3.2-4.5 antimitotic agent molecules linked per antibody molecule.

Example 75. In Vitro Cytotoxicity Assays

BJAB (Burkitt's lymphoma), BT-474 (breast carcinoma) cells, Namalwa (human Burkitt's lymphoma), Ramos (human Burkitt's lymphoma), COLO 205 (human colon adenocarcinoma), and A375 (human malignant melanoma) were from ATCC. The breast tumor line KPL-4 was from Dr. J. Kurebayashi (Kurebayashi, J. et al. Br J Cancer 1999; 79: 707-17). The cultures were maintained in RPMI 1640 supplemented with 10% heat-inactivated fetal bovine serum (FBS). All cell lines were cultured in a humidified incubator at 37° C., 6% $CO_2$. The cytotoxicity study was performed using a clonogenic assay similar to a reference described (Franken, et al, Nature Protocols 1, 2315-2319 (2006)). The test cell lines were plated into 6-well culture dishes at a constant number of 5000 cells per well. The cells were incubated with varying concentrations (1 pM to 50 nM) of the test-agent (the antimitotic agents or their conjugates) for 72 h. The medium was then aspirated from the plates and replaced with fresh medium. The cultures were allowed to grow and form colonies for a total of 7 to 10 days after plating. The cultures were then fixed and stained with 0.2% crystal violet in 10% formalin/PBS, and the colonies were counted. Plating efficiency of non-treated cells (medium alone) was determined by dividing the number of colonies counted by the number of cells plated. The surviving fraction of cells exposed to a toxic agent was determined by dividing the number of colonies in wells that were exposed to the agent by the number of colonies in the control wells.

REFERENCES

Zanda, M.; et al, Can. Pat. Appl. CA 2710693 (2011).
Chai, Y.; et al. Eur. Pat. Appl. 2174947 (2010), PCT WO 2010034724.
Leamon, C.; et al, PCT WO 2010033733, WO 2009002993.
Ellman, J.; et al, PCT WO 2009134279; PCT WO 2009012958
Matschiner, G.; et al, PCT WO 2009095447.
Vlahov, I.; et al, PCT WO 2009055562, WO 2008112873.
Low, P.; et al, PCT WO 2009026177.
Richter, W., PCT WO 2008138561.
Kjems, J.; et al, PCT WO 2008125116.
Davis, M.; et al, PCT WO 2008076333.
Diener, J.; et al, U.S. Pat. Appl. 20070041901, WO 2006096754
Matschiner, G.; et al, PCT WO 2006056464.
Vaghefi, F.; et al, PCT WO 2006033913
Doemling, A., Ger. Offen. DE 102004030227; PCT WO 2004005327; WO 2004005326; WO 2004005269.
Stanton, M.; et al, U.S. Pat. Appl. Publ. 20040249130.
Hoefle, G.; et al, Ger. Offen. DE 10254439; DE 10241152; DE 10008089.
Leung, D.; et al, PCT WO 2002077036.
Reichenbach, H.; et al, Ger. Offen. DE 19638870
Shibue, T., et al., Bioorg Med Chem Lett, 2011. 21(1): p. 431-4.
Floyd, W. C., 3rd, et al., ChemMedChem, 2011. 6(1): p. 49-53.
Shibue, T., et al., *Total Syntheses of Tubulysins*. Chemistry, 2010.
Kubicek, K., et al., Angew Chem Int Ed Engl, 2010. 49(28): p. 4809-12.
Chai, Y., et al., Chem Biol, 2010. 17(3): p. 296-309.
Chandrasekhar, S., et al, J Org Chem, 2009. 74(24): p. 9531-4.
Pando, O., et al., Org Lett, 2009. 11(24): p. 5567-9.
Reddy, J. A., Mol Pharm, 2009. 6(5): p. 1518-25.
Ullrich, A., et al., Angew Chem Int Ed Engl, 2009. 48(24): p. 4422-5.
Ullrich, A.; et al, European J. Org. Chem. 2009, 36, 6367-6378
Schluep, T., et al., Clin Cancer Res, 2009. 15(1): p. 181-9.
Balasubramanian, R., et al., J Med Chem, 2009. 52(2): p. 238-40.
Leamon, C. P., et al., Cancer Res, 2008. 68(23): p. 9839-44.
Vlahov, L R., et al., Bioorg Med Chem Lett, 2008. 18(16): p. 4558-61.
Patterson, A. W., et al, J Org Chem, 2008. 73(12): p. 4362-9.
Balasubramanian, R., et al., Bioorg Med Chem Lett, 2008. 18(9): p. 2996-9.
Raghavan, B., et al., J Med Chem, 2008. 51(6): p. 1530-3.
Richter, C. D., et al., Nat Chem Biol, 2008. 4(1): p. 75-81.
Patterson, A. W., et al., Chemistry, 2007. 13(34): p. 9534-41.
Wang, Z., et al., Chem Biol Drug Des, 2007. 70(2): p. 75-86.
Sani, M., et al., Angew Chem Int Ed Engl, 2007. 46(19): p. 3526-9.
Wipf, P. et al, Org Lett, 2007. 9(8): p. 1605-7.
Sasse, F., et al, Nat Chem Biol, 2007. 3(2): p. 87-9.
Peltier, H. M., et al., J Am Chem Soc, 2006. 128(50): p. 16018-9.
Domling, A., et al., Angew Chem Int Ed Engl, 2006. 45(43): p. 7235-9.
Khalil, M. W., et al., Chembiochem, 2006. 7(4): p. 678-83.
Kaur, G., et al., Biochem J, 2006. 396(2): p. 235-42.
Wipf, P., et al, Org Lett, 2004. 6(22): p. 4057-60.
Steinmetz, H., et al., Angew Chem Int Ed Engl, 2004. 43(37): p. 4888-92.
Friestad, G. K., et al, Org Lett, 2004. 6(19): p. 3249-52.
Sandmann, A., et al, Chem Biol, 2004. 11(8): p. 1071-9.
Sasse, F., et al., J Antibiot (Tokyo), 2000. 53(9): p. 879-85.

What is claimed is:
1. A conjugate having a structure of Formula (I'):

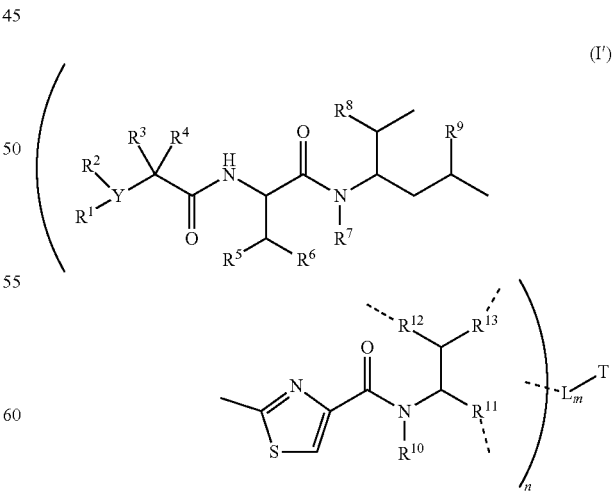

or a pharmaceutically acceptable salt or solvate thereof, wherein T is a cell-binding ligand, a dendrimer or a liposome; L is a releasable linker;

----- is a linkage bond that L connects to an atom in a moiety inside the bracket independently; n is 1~20 and m is 1~10;

wherein the cell-binding ligand is an antibody, or an antibody fragment that binds to a target cell;

wherein the releasable linker L has a formula of: $-W_w-(Aa)_r-V_v-$, wherein: -W- is a stretcher unit, which links the moiety inside the bracket to an amino acid unit (Aa) when present, or V when an Aa is not present, and W is independently a self-immolative spacer, a peptidyl unit, a hydrazone, a disulfide, a thioether, an ester, or an amide bond; w is 0 or 1; wherein Aa is independently a natural or unnatural amino acid unit; r is independently an integer ranging from 0 to 12; $(Aa)_r$ represents a natural or unnatural amino acid, dipeptide, tripeptide, tetrapeptide, pentapeptide, hexapeptide, heptapeptide, octapeptide, nonapeptide, decapeptide, undecapeptide or dodecapeptide unit; wherein V is a spacer unit and is independently absent, O, NH, S, $C_1$-$C_8$ alkyl, $C_2$-$C_8$ heteroalkyl, alkenyl, or alkynyl, $C_3$-$C_8$ aryl, heterocyclic, carbocyclic, cycloalkyl, alkylcycloalkyl, heterocycloalkyl, heteroaralkyl, heteroalkylcycloalkyl, or alkylcarbonyl, or one to four amino acid units, or $(CH_2CH_2O)_r$, r is an integer ranging from 0 to 12; and v is 0, 1 or 2;

wherein $R^1$, $R^2$, $R^3$, and $R^4$ are independently H, $C_1$~$C_8$ alkyl; $C_2$~$C_8$ heteroalkyl, or heterocyclic; $C_3$~$C_8$ aryl, Ar-alkyl, cycloalkyl, alkylcycloalkyl, heterocycloalkyl, heteroalkylcycloalkyl, carbocyclic, or alkylcarbonyl; or $R^1$ and $R^2$, $R^1$ and $R^3$, $R^2$ and $R^3$, or $R^3$ and $R^4$ form a 3~7 membered carbocyclic, cycloalkyl, heterocyclic, or heterocycloalkyl ring system;

wherein Y is N or CH;

wherein $R^5$, $R^6$, $R^8$ and $R^{10}$ are independently H, or $C_1$~$C_4$ alkyl, or heteroalkyl; or $R^5$ and $R^6$ form a 3~7 membered carbocyclic, cycloalkyl, heterocyclic, or heterocycloalkyl ring system;

wherein $R^7$ is independently H, $R^{14}$, $-R^{14}C(=O)X^1R^{15}$, or $-R^{14}XR^{15}$, wherein $X^1$ is O, S, S—S, NH, or $NR^{14}$, and wherein $R^{14}$ and $R^{15}$ are independently $C_1$~$C_8$ alkyl, heteroalkyl; $C_2$~$C_8$ alkenyl, alkynyl; heterocyclic; or $C_3$~$C_8$ aryl, carbocyclic, cycloalkyl, heterocycloalkyl, heteroaralkyl, heteroalkylcycloalkyl, alkylcarbonyl;

wherein $R^9$ is independently H, $-OH$, $-OR^{14}$, $-OC(=O)R^{14}$, $-OC(=O)NHR^{14}$, $-OP(=O)(OR^{14})_2$, or $-OR^{14}OP(=O)(OR^{15})_2$, wherein $R^{14}$ and $R^{15}$ are independently $C_1$~$C_8$ alkyl, heteroalkyl; $C_2$~$C_8$ alkenyl, alkynyl, heterocyclic; or $C_3$~$C_8$ aryl, carbocyclic, cycloalkyl, alkylcycloalkyl, heterocycloalkyl, heteroalkylcycloalkyl, heteroaralkyl, alkylcarbonyl;

wherein $R^{11}$ is independently H, $-R^{14}$, $-R^{14}C(=O)R^{16}$, $-R^{14}X_2R^{16}$, $-R^{14}-$, $-R^{14}C(=O)R^{17}-$, $-R^{14}X_2R^{17}-$, or $-R^{14}C(=O)X^2-$, wherein $X^2$ is $-O-$, $-S-$, $-NH-$, $-N(R^{14})-$, $-O-R^{14}-$, $-S-R^{14}-$, $-S(=O)-R^{14}-$, or $-NHR^{14}-$, and wherein $R^{14}$ is $C_1$~$C_8$ alkyl, heteroalkyl; $C_2$~$C_8$ alkenyl, alkynyl, heterocyclic; or $C_3$~$C_8$ aryl, carbocyclic, cycloalkyl, alkylcycloalkyl, heterocycloalkyl, heteroalkylcycloalkyl, heteroaralkyl, alkylcarbonyl; $R^{16}$ is H, OH, $R^{14}$ or one to four amino acid units; $R^{17}$ is absent, $C_1$~$C_8$ alkyl, or heteroalkyl; $C_2$~$C_8$ alkenyl, alkynyl, or heterocyclic; $C_3$~$C_8$ arylene, heterocyclic, carbocyclic, heterocycloalkyl; or an amino acid, or two amino acid units, provided that when $R^{11}$ is $-R^{14}C(=O)X^2-$ and connects to L, wherein $X^2$ is $-O-$, $R^{14}$ is not $C_1$~$C_8$ alkyl;

wherein $R^{12}$ is independently $R^{14}$, $-O-$, $-S-$, $-N-$, $=N-$, $-NNH-$, $-OH$, $-SH$, $-NH_2$, $=NH$, $=NNH_2$, $-NH(R^{14})$, $-OR^{14}$, $-N(R^{14})-$, $-OR^{14}-$, $-C(O)O-$, $-C(O)NHR^{14}-$, $-SR^{14}-$, $-S(=O)R^{14}-$, $-NHR^{14}-$, $-CH_2OP(=O)(OR^{15})-$, $-P(=O)(OR^{15})-$, $-C(O)OP(=O)(OR^{15})-$, $-OP(=O)(OR^{15})O-$, or $-SO_2R^{14}-$, $-C(O)OR^{16}-$, $-COR^{16}$, $-COOR^{14}-$, $-C(O)NH-$, $-C(O)NH_2$, $-C(O)NHR^{14}$, $-SR^{14}$, $-S(=O)R^{14}$, $-P(=O)(OR^{16})_1$, $-OP(=O)(OR^{16})_2$, $-CH_2OP(=O)(OR^{16})_2$, or $-SO_2R^{16}$, wherein $R^{14}$ and $R^{15}$ are independently H, $C_1$~$C_8$ alkyl, heteroalkyl; $C_2$~$C_8$ alkenyl, alkynyl, heterocyclic; or $C_3$~$C_8$ aryl, cycloalkyl, carbocyclic, alkylcycloalkyl, heterocycloalkyl, heteroaralkyl, heteroalkylcycloalkyl, alkylcarbonyl; $R^{16}$ is H, OH, $R^{14}$ or one to four amino acid units;

wherein $R^{13}$ is $C_1$~$C_{10}$ alkyl, heteroalkyl, alkyl acid, alkyl amide, alkyl amine, or Ar; Ar is an aromatic or hetero aromatic group, composed of one or several rings, and comprising four to ten carbon atoms; the hetero aromatic group is an aromatic group that has one or several carbon atoms replaced by hetero atoms; wherein in the aromatic group, one or several H atoms are optionally replaced independently by $R^{17}$, F, Cl, Br, I, $OR^{16}$, $SR^{16}$, $NR^{16}R^{17}$, $N=NR^{16}$, $N=R^{16}$, $NR^{16}R^{17}$, $NO_2$, $SOR^{16}R^{17}$, $SO_2R^{16}$, $SO_3R^{16}$, $OSO_3R^{16}$, $PR^{16}R^{17}$, $POR^{16}R^{17}$, $PO_2R^{16}R^{17}$, $OP(O)(OR^{17})_2$, $OCH_2OP(O)(OR^{17})_2$, $OC(O)OP(O)(OR^{17})_2$, $PO(OR^{16})(OR^{17})$, $OP(O)(OR^{17})OP(O)(OR^{17})_2$, $OC(O)R^{17}$ or $OC(O)NHR^{17}$, wherein $R^{16}$ and $R^{17}$ are independently H, OH, $C_1$~$C_8$ alkyl, or heteroalkyl; $C_2$~$C_8$ alkenyl, alkynyl, or heterocyclic; $C_3$~$C_8$ aryl, cycloalkyl, alkylcycloalkyl, carbocyclic, heterocycloalkyl, heteroalkylcycloalkyl, heteroaralkyl, alkylcarbonyl, or C4-C12 glycoside;

or $R^{12}$ and $R^{13}$ form a 3~7 membered carbocyclic, cycloalkyl, heterocyclic, aromatic or heterocycloalkyl ring system.

2. The conjugate according to claim 1, having a structure of Formula (V):

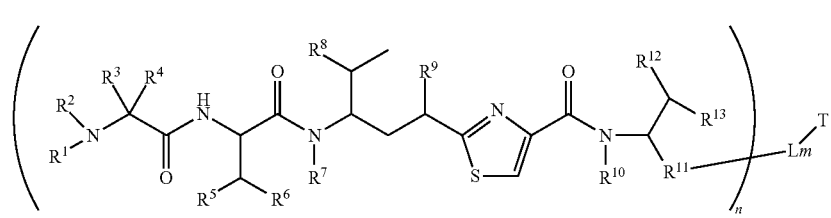

or a pharmaceutically acceptable salt or solvate thereof, wherein T, L, n, m, Y, $R^1$, $R^2$, $R^3$, $R^4$, $R^5$, $R^6$, $R^7$, $R^8$, $R^9$, $R^{10}$ and $R^{13}$ are defined the same as in claim 1;
wherein $R^{11}$ is independently —$R^{14}$—, —$R^{14}$C(=O) $R^{17}$—, —$R^{14}X_2R^{17}$—, or —$R^{14}$C(=O)$X^2$—, wherein $R^{17}$ is independently $C_1$~$C_8$ alkyl; $C_2$~$C_5$ alkenyl, alkynyl, or heteroalkyl; $C_3$~$C_8$ aryl, arylene, heterocyclic, carbocyclic, or heterocycloalkyl, or an amino acid, or two amino acid; $X^2$ is —O—, —S—, —NH—, —N($R^{14}$)—, —O—$R^{14}$—, —S—$R^{14}$—, —S(=O)—$R^{14}$—, or —NH$R^{14}$—; $R^{14}$ is $C_1$~$C_8$ alkyl, or heteroalkyl; $C_2$~$C_8$ alkenyl, alkynyl, or heterocyclic; or $C_3$~$C_8$ aryl, carbocyclic, cycloalkyl, alkylcycloalkyl, heterocycloalkyl, heteroalkylcycloalkyl, heteroaralkyl, or alkylcarbonyl;

wherein $R^{12}$ is independently $R^{14}$, —OH, —SH, —$NH_2$, =NH, =$NNH_2$, —NH($R^{14}$), —O$R^{14}$, —CO$R^{16}$, —C(O)$NH_2$, —C(O)NH$R^{14}$, —S$R^{14}$, —S(=O)$R^{14}$, —P(=O)(O$R^{16}$)$_2$, —OP(=O) (O$R^{16}$)$_2$, —$CH_2$OP(=O)(O$R^{16}$)$_2$, or —$SO_2R^{16}$; wherein $R^{14}$ is H, $C_1$~$C_8$ alkyl, heteroalkyl; $C_2$~$C_8$ alkenyl, alkynyl, heterocyclic; $C_3$~$C_8$ aryl, cycloalkyl, carbocyclic, alkylcycloalkyl, heterocycloalkyl, heteroaralkyl, heteroalkylcycloalkyl, alkylcarbonyl, and $R^{16}$ is H, OH, $R^{14}$ or one to four amino acid units.

3. The conjugate according to claim 1, having a structure of Formula (VI):

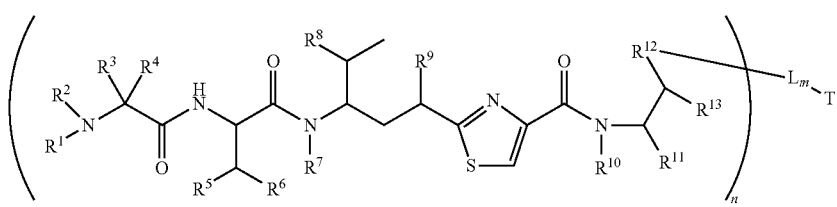

(VI)

or a pharmaceutical acceptable salt or solvate thereof,
wherein T, L, n, m, $R^1$, $R^2$, $R^3$, $R^4$, $R^5$, $R^6$, $R^7$, $R^8$, $R^9$, $R^{10}$, and $R^{13}$ are defined the same as in claim 1;
wherein $R^{11}$ is independently H, —$R^{14}$, —$R^{14}$C(=O) $R^{16}$, —$R^{14}X_2R^{16}$, wherein $X^2$ is —O—, —S—, —NH—, —N($R^{14}$)—, —O—$R^{14}$—, —S—$R^{14}$—, —S(=O)—$R^{14}$—, or —NH$R^{14}$—; $R^{14}$ is $C_1$~$C_8$ alkyl, heteroalkyl; $C_2$~$C_8$ alkenyl, alkynyl, heterocyclic; or $C_3$~$C_8$ aryl, cycloalkyl, carbocyclic, alkylcycloalkyl, heterocycloalkyl, heteroalkylcycloalkyl, heteroaralkyl, alkylcarbonyl; $R^{16}$ is H, OH, $R^{14}$ or one to four amino acid units;
wherein $R^{12}$ is independently —$R^{14}$—, —O—, —S—, —NH—, =N—, =NNH—, —N($R^{14}$)—, —O$R^{14}$—, —C(O)O—, —C(O)NH—, —C(O)NH$R^{14}$—, —S$R^{14}$—, —S(=O)$R^{14}$—, —NH$R^{14}$—, —$CH_2$OP(=O)(O$R^{15}$)—, —P(=O)(O$R^{15}$)—, —C(O)OP(=O)(O$R^{15}$)—, —OP(=O)(O$R^{15}$)O—, or —$SO_2R^{14}$—; $R^{14}$ and $R^{15}$ are independently H, $C_1$~$C_8$ alkyl, or heteroalkyl; $C_1$~$C_8$ alkenyl, alkynyl, or heterocyclic; or $C_3$~$C_8$ aryl, carbocyclic, cycloalkyl, alkylcycloalkyl, heterocycloalkyl, heteroaralkyl, heteroalkylcycloalkyl, or alkylcarbonyl; provided that $R^{12}$ is not H.

4. The conjugate according to claim 1, having a structure of Formula (VII):

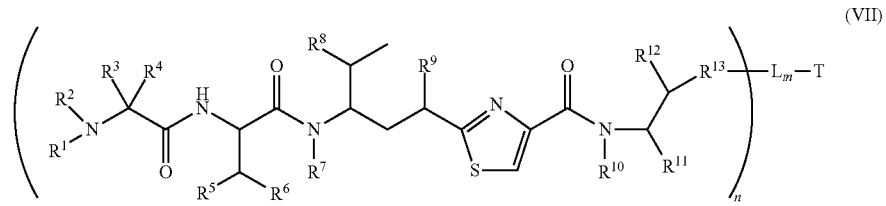

(VII)

or a pharmaceutically acceptable salt solvate thereof,
wherein T, L, n, m, Y, $R^1$, $R^2$, $R^3$, $R^4$, $R^5$, $R^6$, $R^7$, $R^8$, $R^9$, and $R^{10}$ are defined the same as in claim 1;
wherein $R^{11}$ is independently H, —$R^{14}$, —$R^{14}$C(=O) $R^{16}$, —$R^{14}X_2R^{16}$, wherein $X^2$ is —O—, —S—, —NH—, —N($R^{14}$)—, —O—$R^{14}$—, —S—$R^{14}$—, —S(=O)—$R^{14}$—, or —NH$R^{14}$—; $R^{14}$ is $C_1$~$C_8$ alkyl, heteroalkyl; $C_2$~$C_8$ alkenyl, alkynyl, heterocyclic; or $C_3$~$C_8$ aryl, cycloalkyl, carbocyclic, alkylcycloalkyl, heterocycloalkyl, heteroalkylcycloalkyl, heteroaralkyl, alkylcarbonyl; $R^{16}$ is H, OH, $R^{14}$ or one to four amino acid units;
wherein $R^{12}$ is independently $R^{14}$, —OH, —SH, —$NH_2$, =NH, =$NNH_2$, —NH($R^{14}$), —O$R^{14}$, —CO$R^{16}$, C(O)$NH_2$, C(O)NH$R^{14}$, —S$R^{14}$, —S(=O)$R^{14}$, —P(=O)(O$R^{16}$)$_2$, —OP(=O) (O$R^{16}$)$_2$, —$CH_2$OP(=O)(O$R^{16}$)$_2$, or —$SO_2R^{16}$, wherein $R^{14}$ is H, $C_1$~$C_8$ alkyl, heteroalkyl; $C_2$~$C_8$ alkenyl, alkynyl, heterocyclic; or $C_3$~$C_8$ aryl, cycloalkyl, carbocyclic, alkylcycloalkyl, heterocycloalkyl, heteroaralkyl, heteroalkylcycloalkyl, alkylcarbonyl; $R^{16}$ is H, OH, $R^{14}$ or one to four amino acid units;
wherein $R^{13}$ is $C_1$~$C_{10}$ alkyl, heteroalkyl, alkyl acid, alkyl amide, alkyl amine, or Ar; Ar is an aromatic or hetero aromatic group, composed of one or several rings, and comprising four to ten carbon atoms; the hetero aromatic group is an aromatic group that has one or several carbon atoms replaced by hetero atoms; Ar is an aromatic group, wherein one or several H atoms are optionally replaced independently by $R^{18}$, F, Cl, Br, I, $OR^{16}$, $SR^{16}$, $NR^{16}R^{17}$, $N=NR^{16}$, $N=R^{16}$, $NR^{16}R^{18}$, $NO_2$, $SOR^{16}R^{18}$, $SO_2R^{16}$, $SO_3R^{16}$, $OSO_3R^{16}$, $PR^{16}R^{18}$, $POR^{16}R^{18}$, $PO_2R^{16}R^{18}$, $OPO_3R^{16}R^{18}$, $CH_2OPO_3R^{16}R^{18}$, $OP(O)(OR^{16})OP(O)(OR^{18})_2$, $C(O)OPO_3R^{16}R^{18}$, or $PO_3R^{16}R^{18}$, wherein $R^{16}$, $R^{18}$ are independently H, $C_1$–$C_8$ alkyl; $C_2$–$C_8$ alkenyl, alkynyl, or heteroalkyl; $C_3$–$C_8$ aryl, heterocyclic, carbocyclic, cycloalkyl, alkylcycloalkyl, heterocycloalkyl, heteroaralkyl, heteroalkylcycloalkyl, or alkylcarbonyl; $C_4$–$C_{12}$ glycoside; or a pharmaceutical salt.

5. The conjugate according to claim 1, having a structure of formula Va, Vb, Vc, Vd, Ve, Vf, Vg, Vh, VIa, VIb, VIc, VIe, VIf, VIg, VIh, VIi, VIIa, VIIb, VIIc, VIId, VIIe, VIIf, VIIg, VIIh, VIIi, VIIj, VIIk, VIII, VIIm, VIIn, VIIo, VIIq, VIIr, VIIs, or VIIt, which are illustrated below:

Va

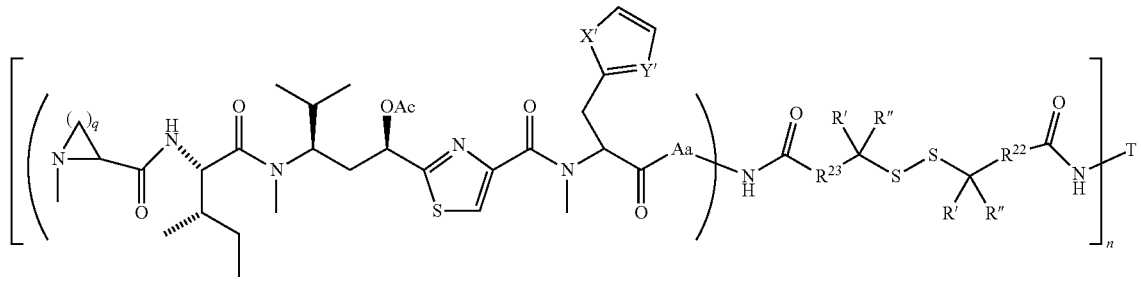

Vb

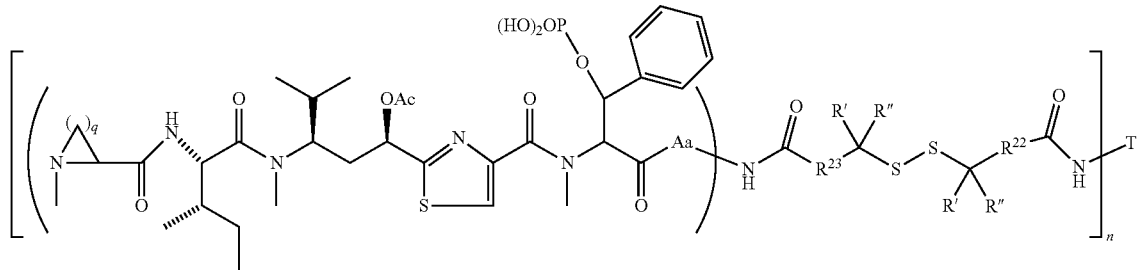

Vc

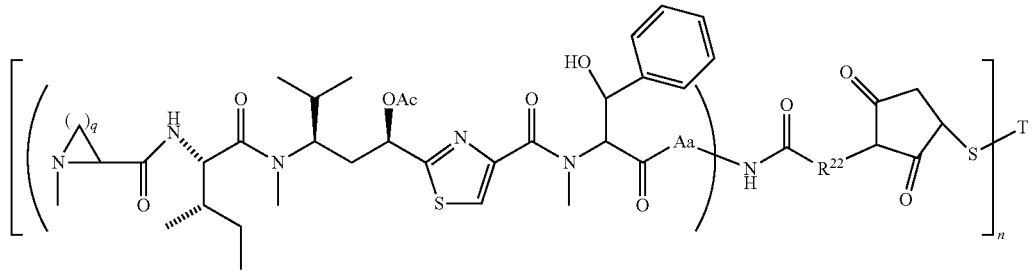

Vd

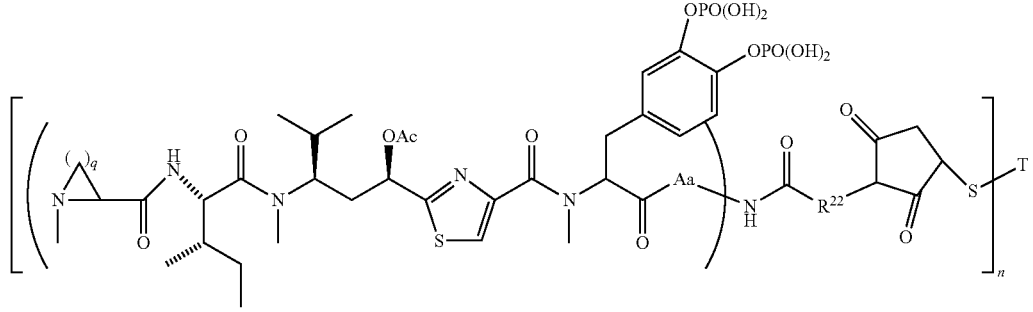

Ve
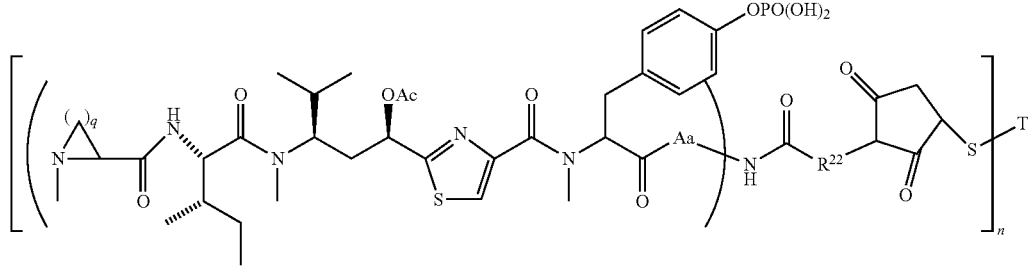
Vf
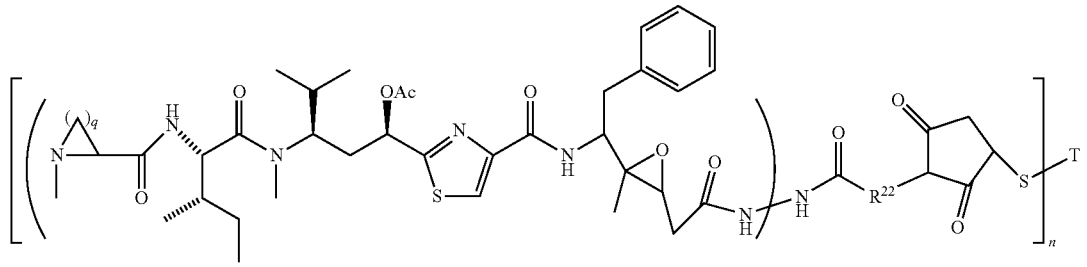
Vg
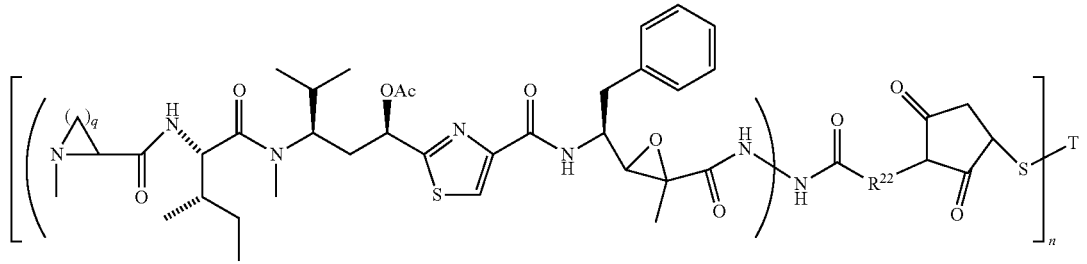
Vh
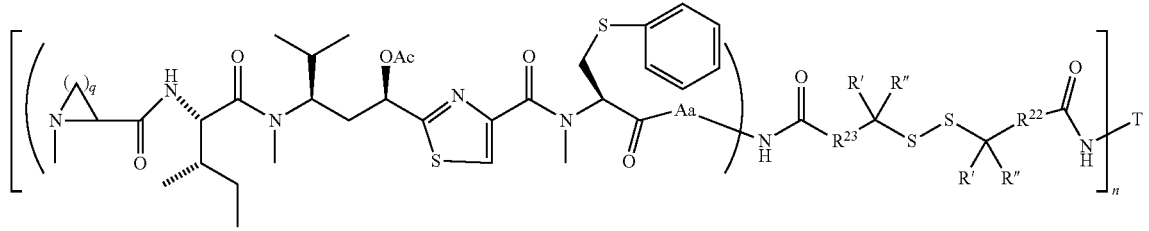
VIa
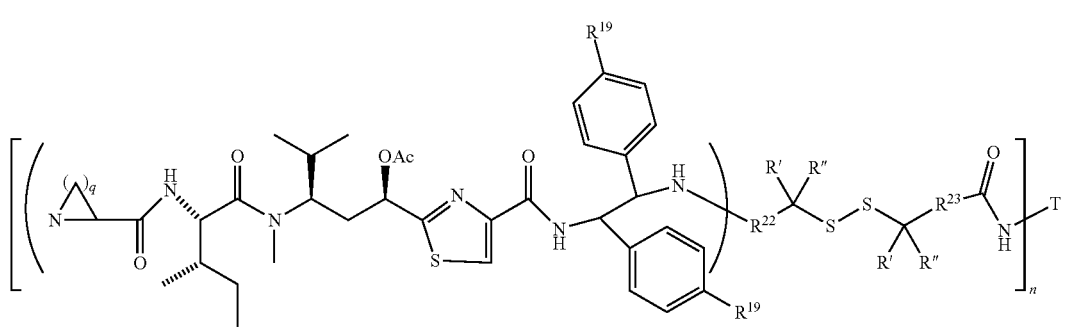

-continued
VIb
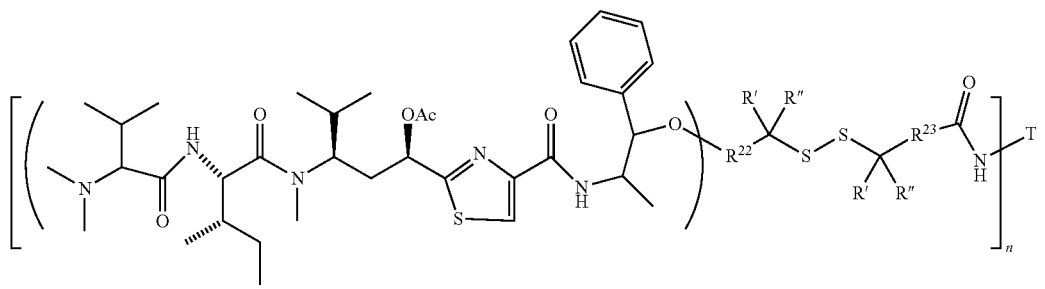
VIc
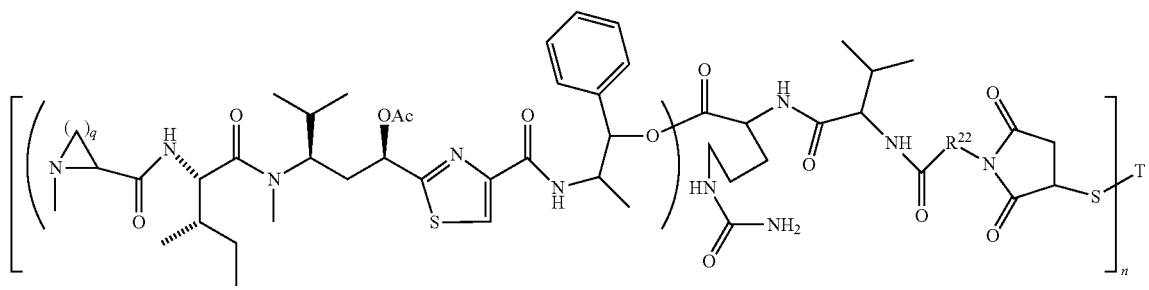
VId
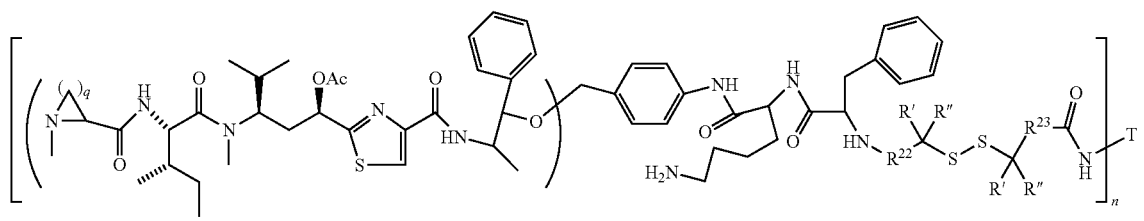
VIf
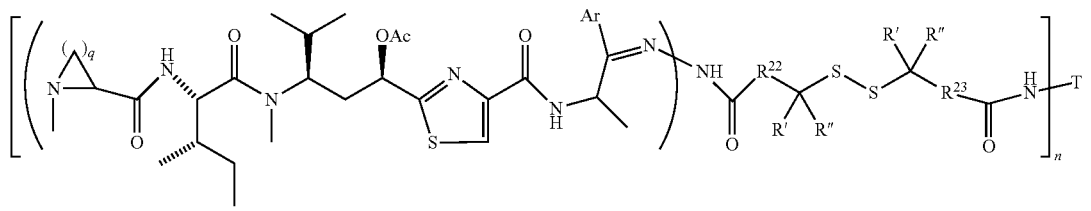
VIg
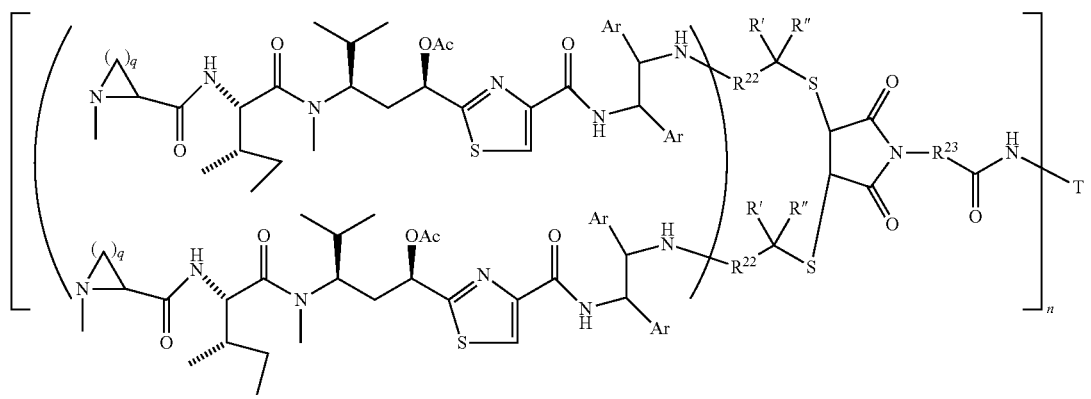

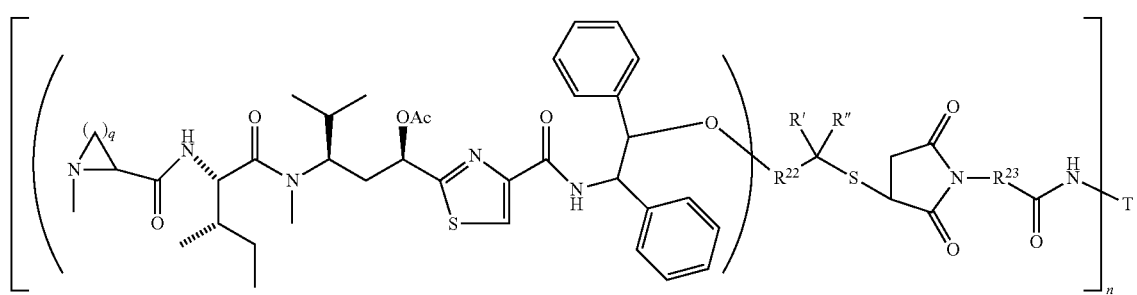
VIh
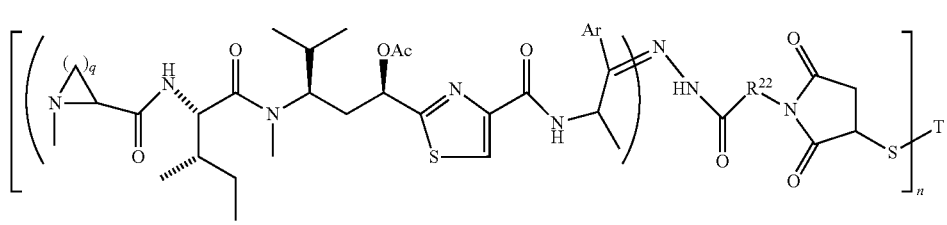
VIi
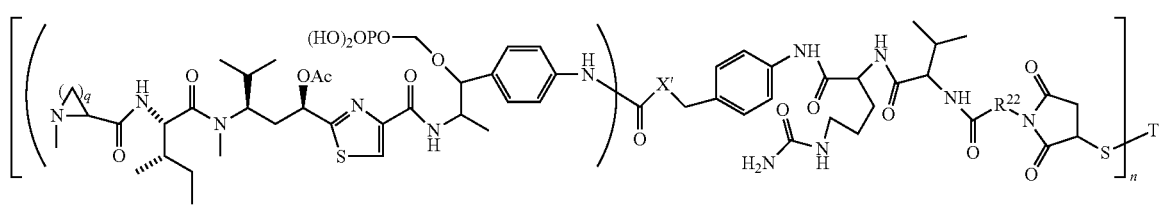
VIIa
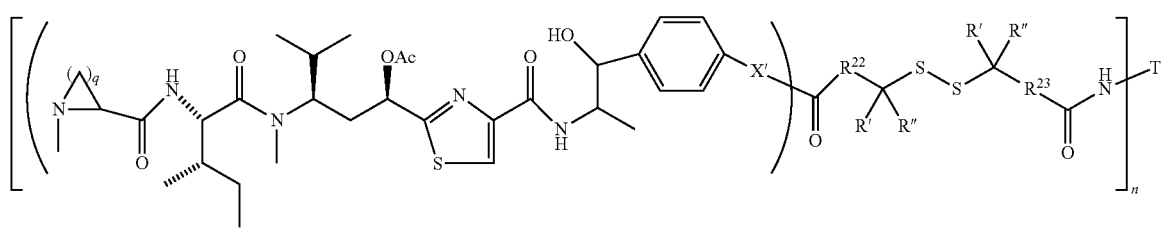
VIIb
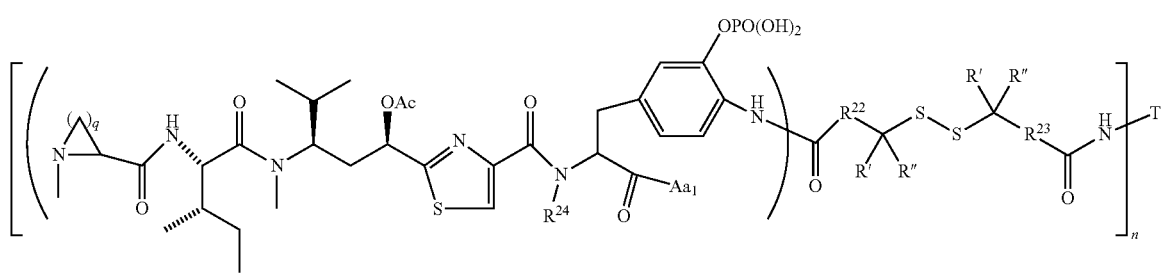
VIIc
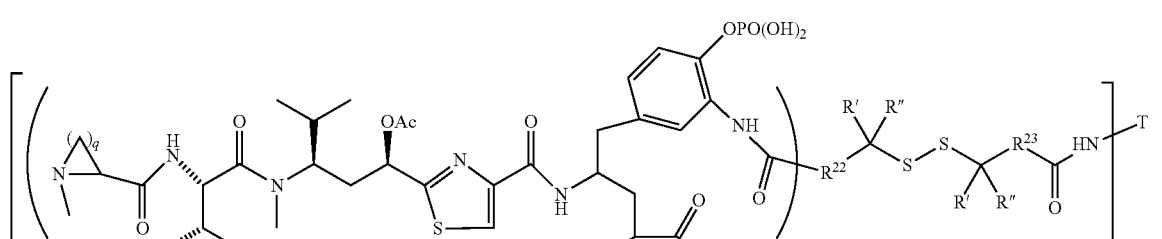
VIId -continued
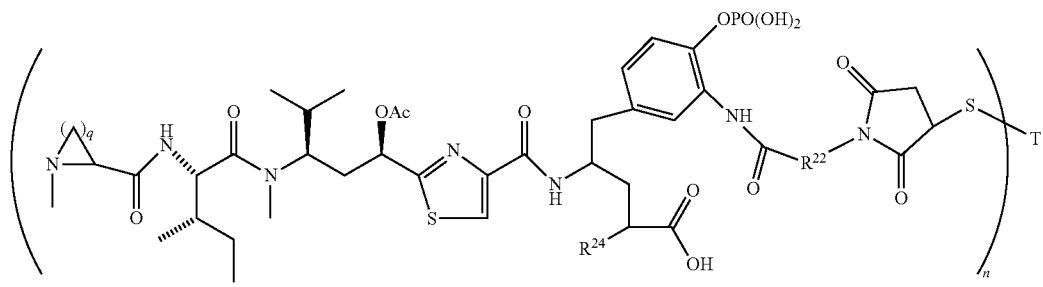
VIIe
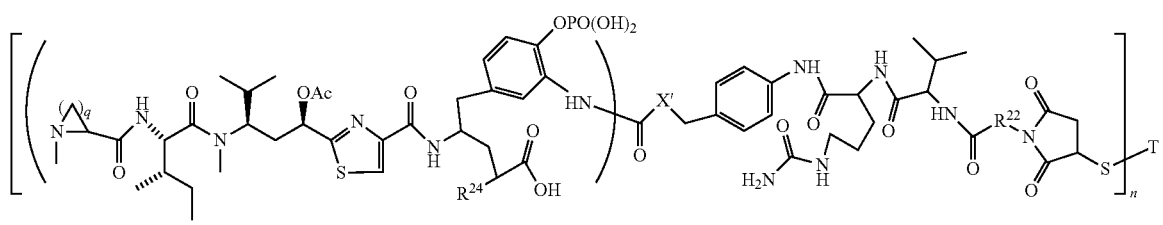
VIIf
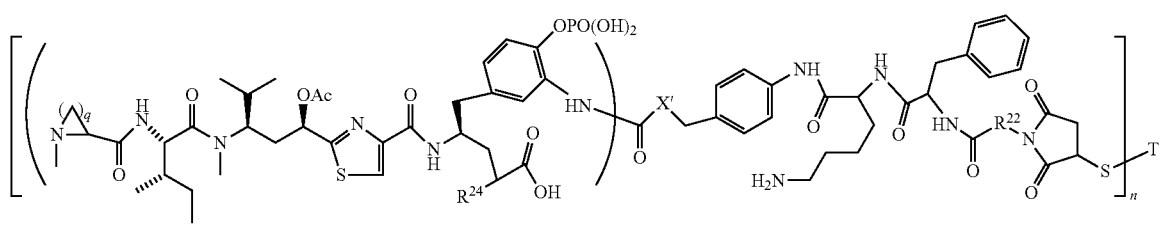
VIIg
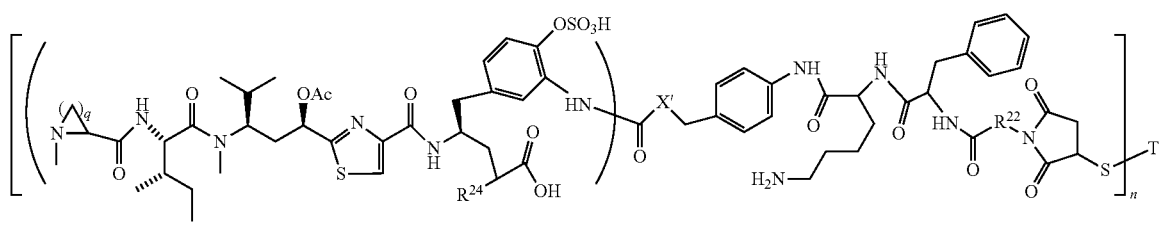
VIIh
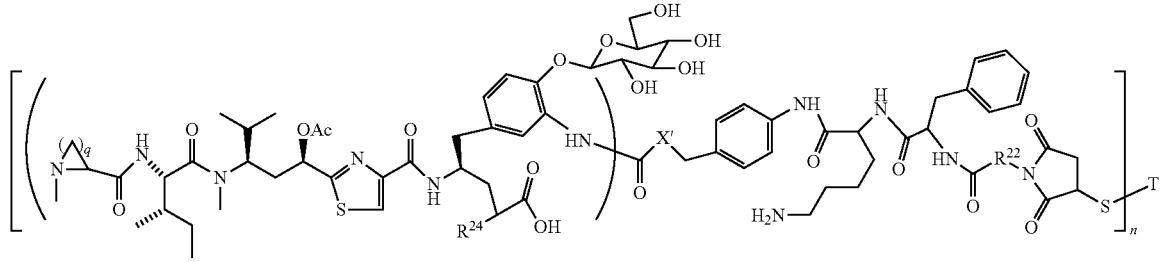
VIIi
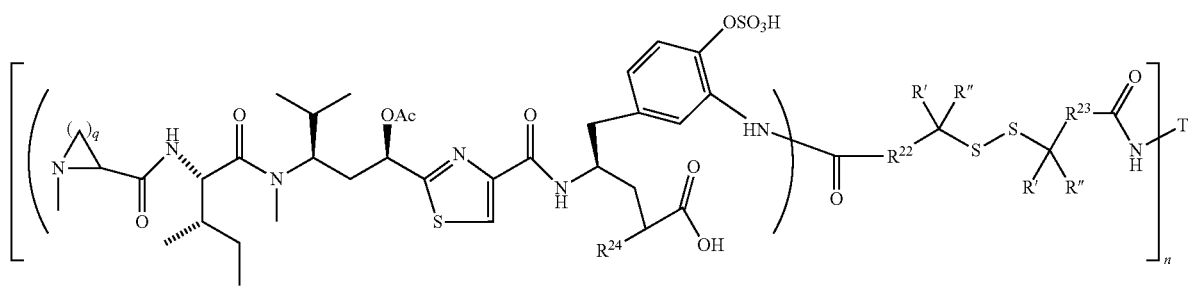
VIIj -continued
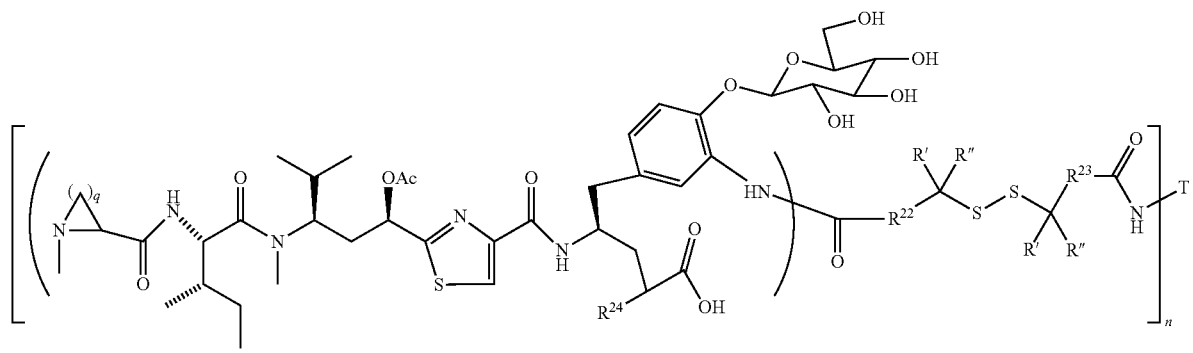
VIIk
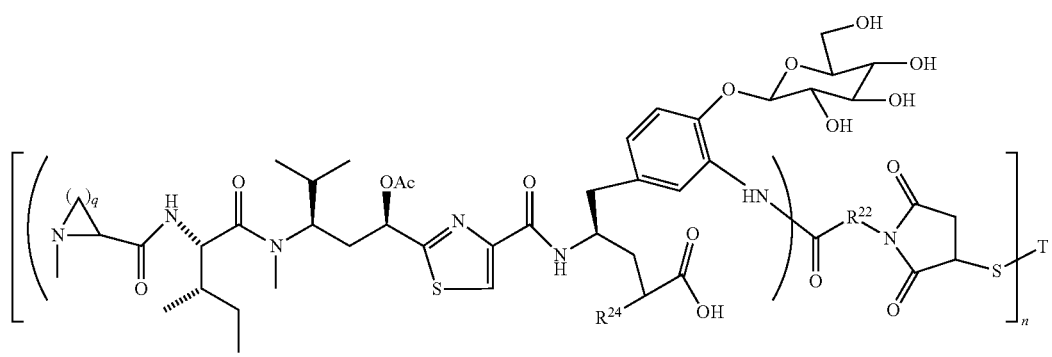
VIIl
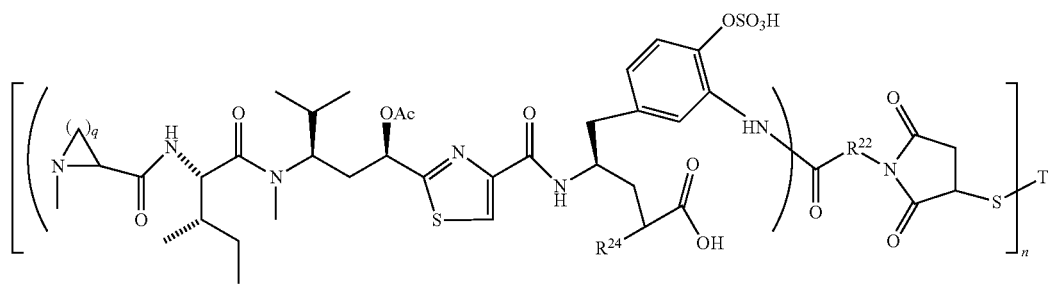
VIIm
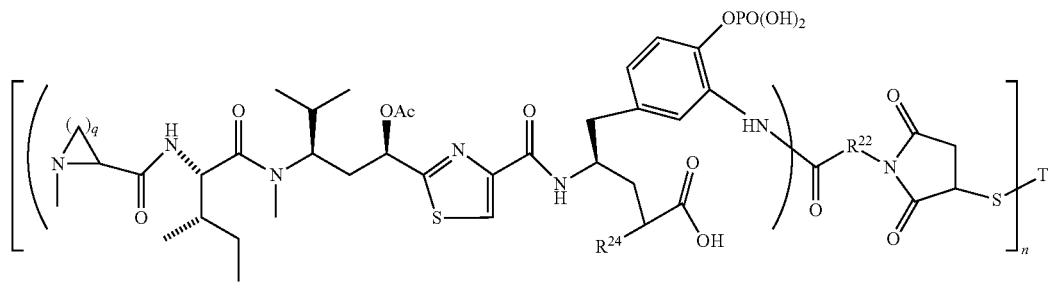
VIIn
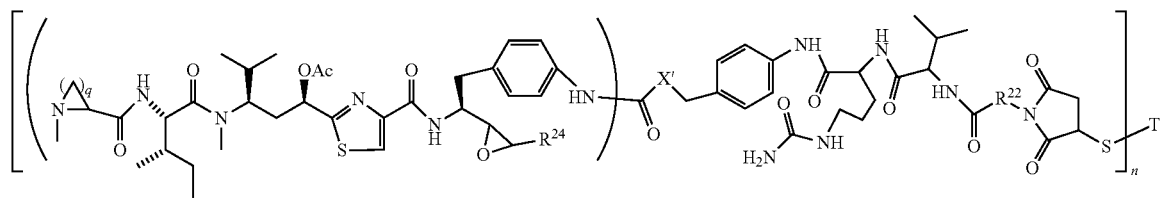
VIIo -continued VIIq
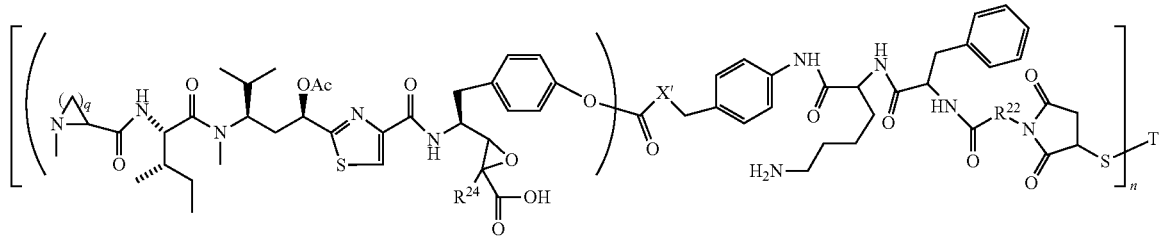

VIIr
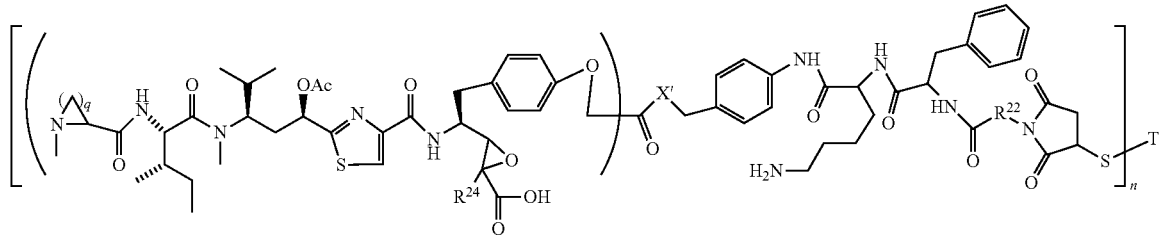

VIIs
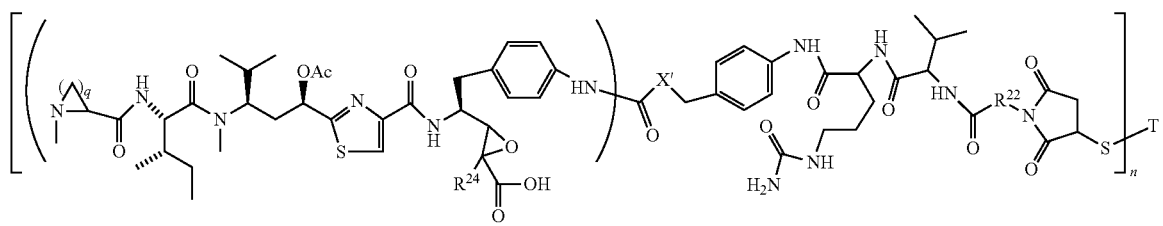

VIIt
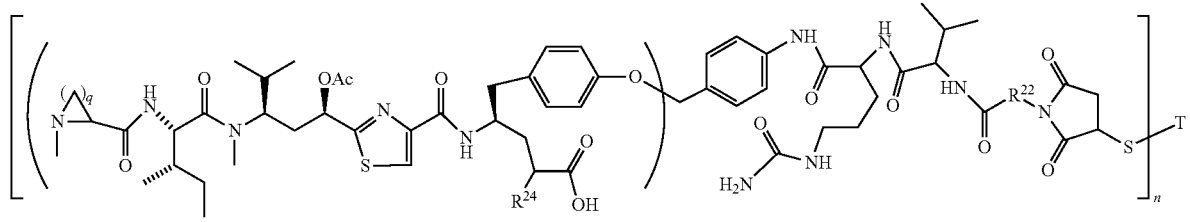

wherein Aa is a natural or unnatural amino acid; Ar is aryl; n is 1~20; q=1~5; X', Y' and are independently CH, O, S, NH, or $NR^{22}$; $R^{22}$, $R^{23}$ and $R^{24}$ are independently $C_1$~$C_8$ alkyl; $C_2$~$C_8$ alkenyl, alkynyl, or heteroalkyl; $C_3$~$C_8$ aryl, heterocyclic, carbocyclic, cycloalkyl, alkylcycloalkyl, heterocycloalkyl, Ar-alkyl, heteroalkylcycloalkyl, or heteroaralkyl, or —(OCH$_2$CH$_2$)n; R' and R" are independently H or CH$_3$.

6. The conjugate according to claim 1, having a structure of formula: mAb-TZO1, mAb-TZO4, mAb-TZO5, mAb-TZO7, mAb-TZ10a, mAb-TZ10b, mAb-TZ11, mAb-TZ12, mAb-TZ13, mAb-TZ14, mAb-TZ17, mAb-TZ19, mAb-TZ20, mAb-TZ21, mAb-TZ22, mAb-TZ23, mAb-TZ24, or mAb-TZ25, which are illustrated below:

mAb-TZ01
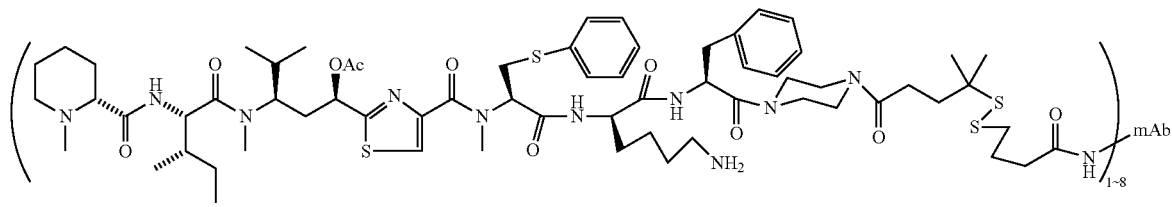

mAb-TZ04
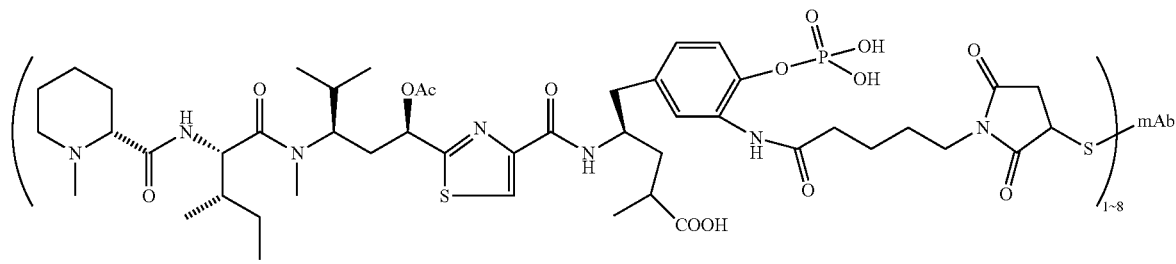
mAb-TZ05
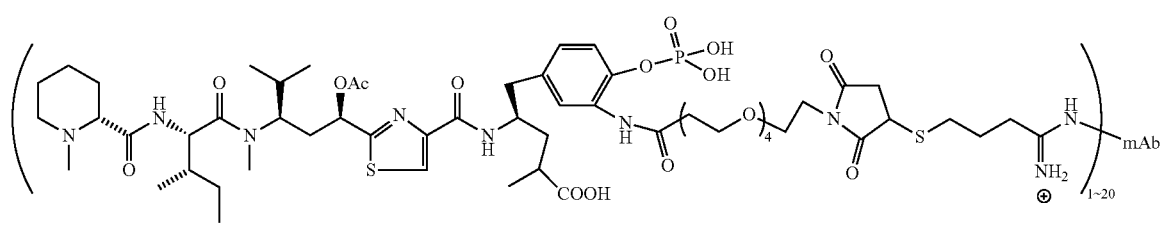
mAb-TZ07
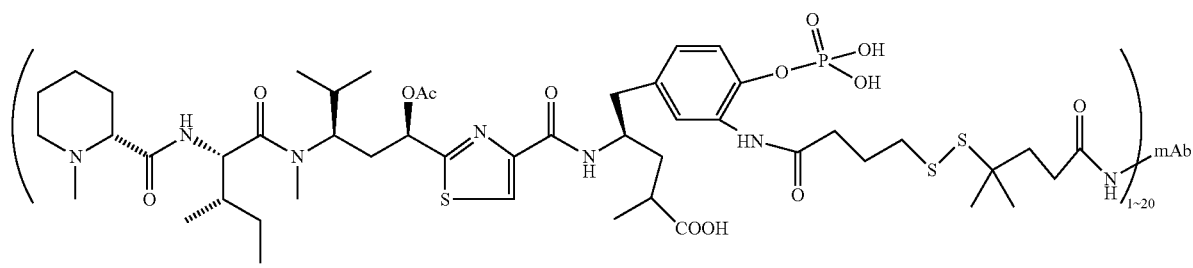
mAb-TZ10a
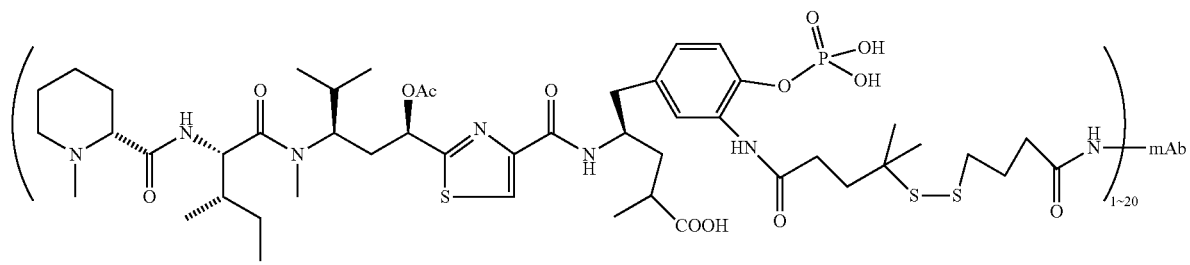
mAb-TZ10b
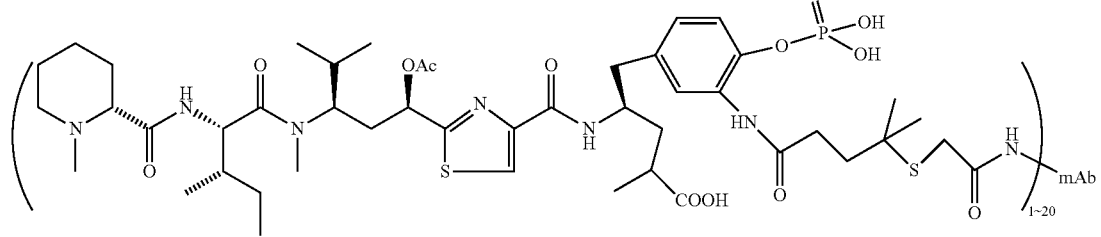

-continued
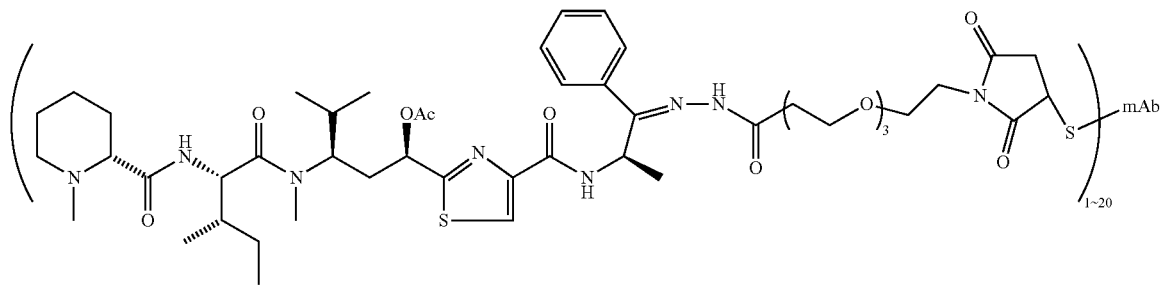
mAb-TZ11
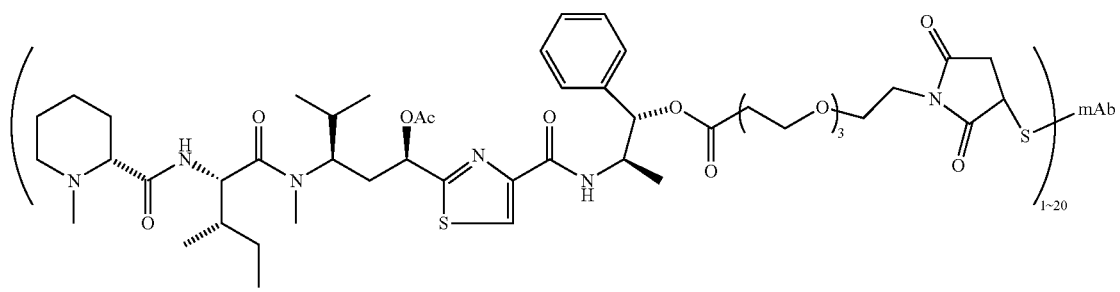
mAb-TZ12
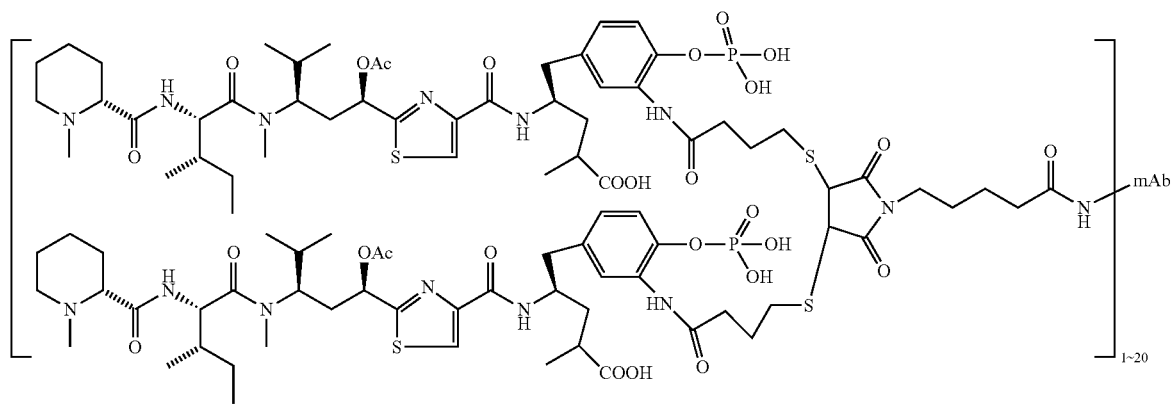
mAb-TZ13
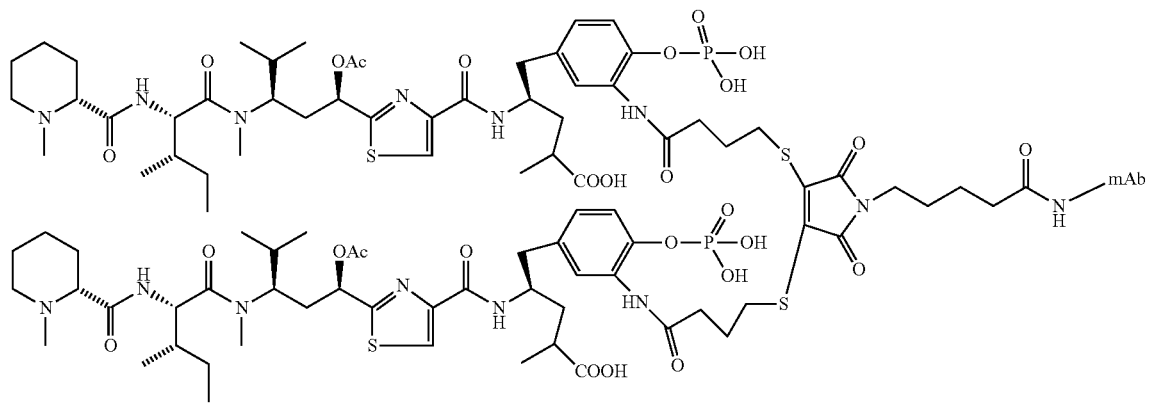
mAb-TZ14 mAb-TZ17
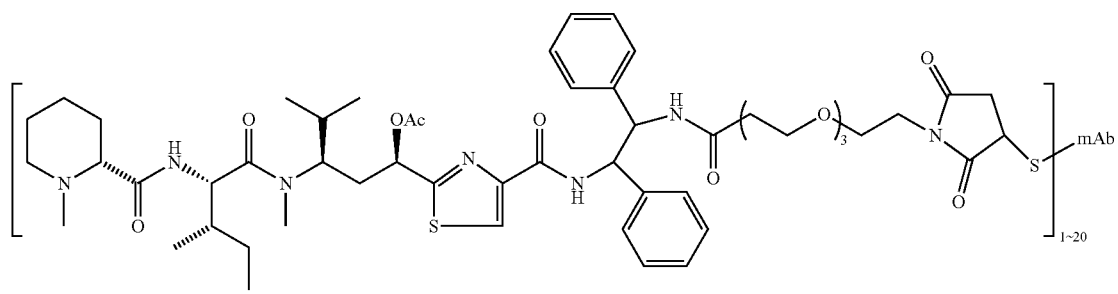
mAb-TZ19
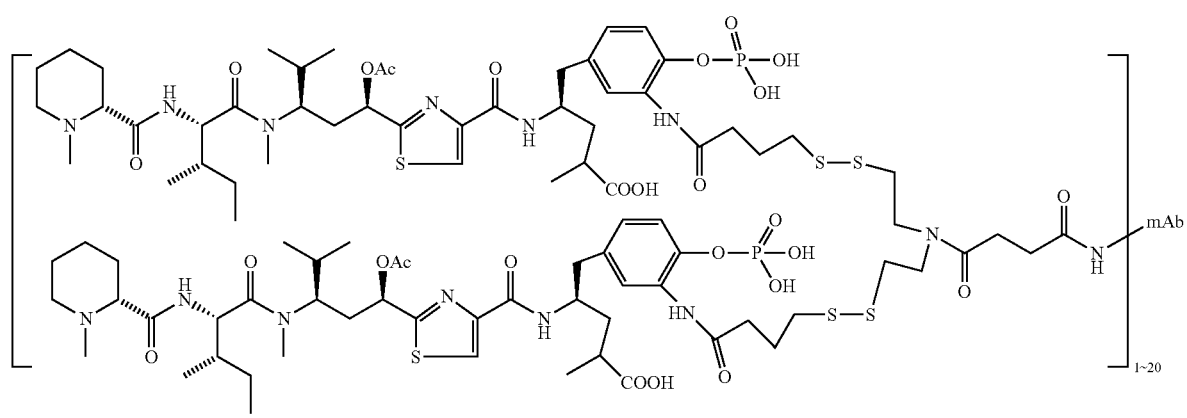
mAb-TZ20
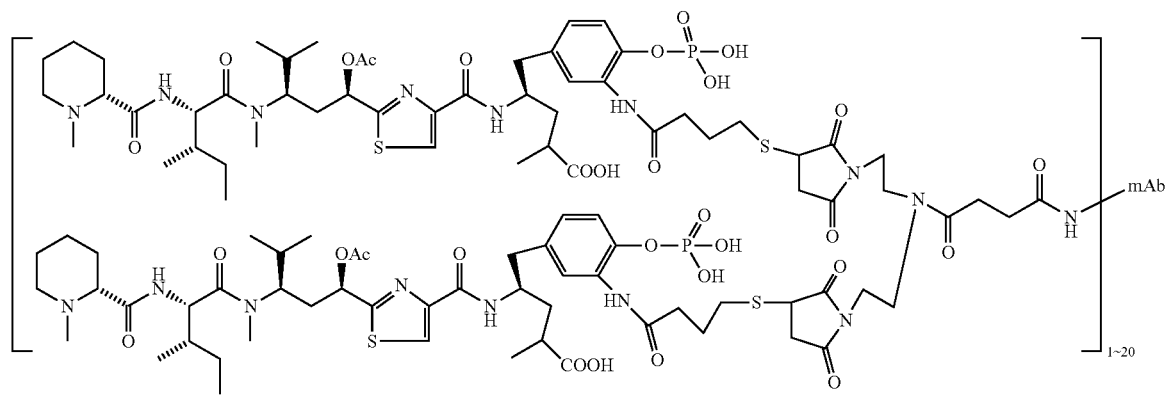
mAb-TZ21
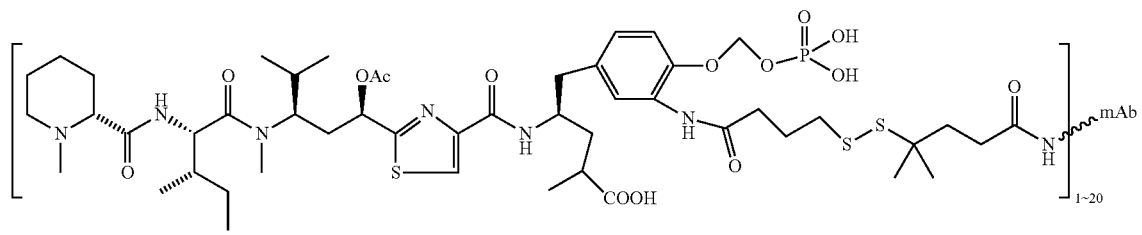

-continued mAb-TZ22

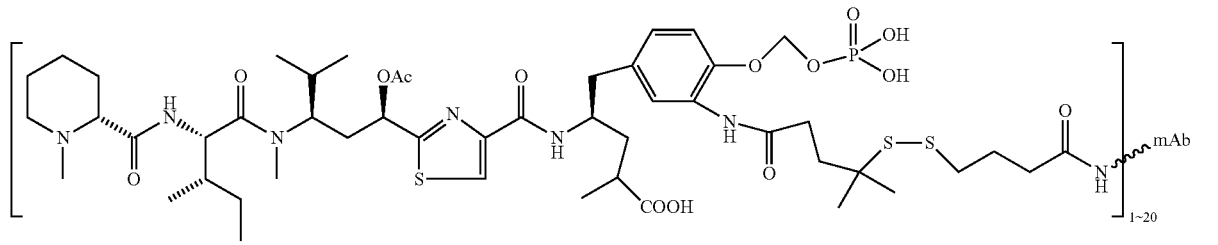

mAb-TZ23

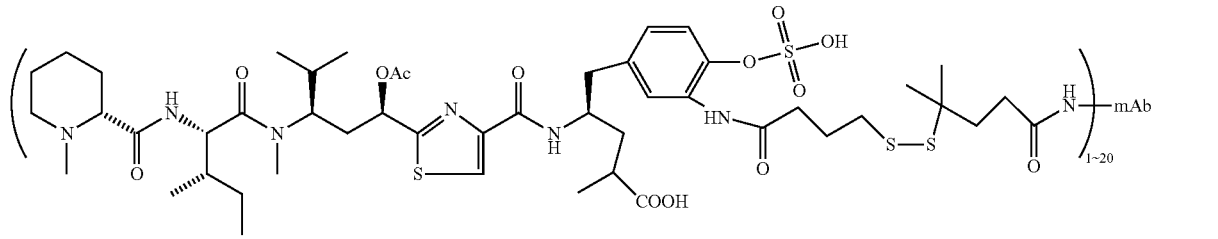

mAb-TZ24

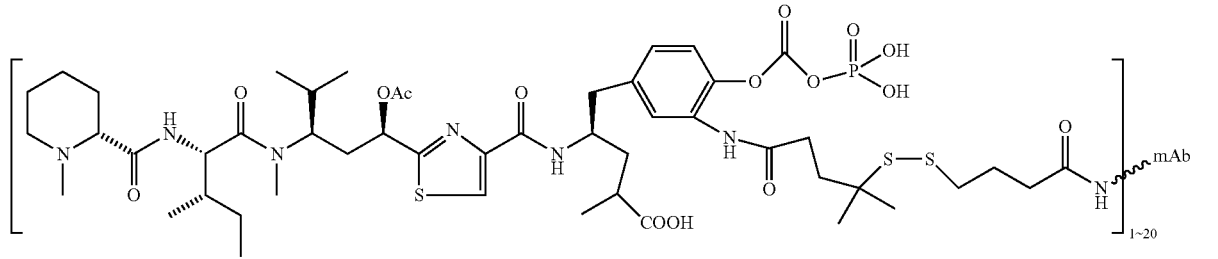

mAb-TZ25

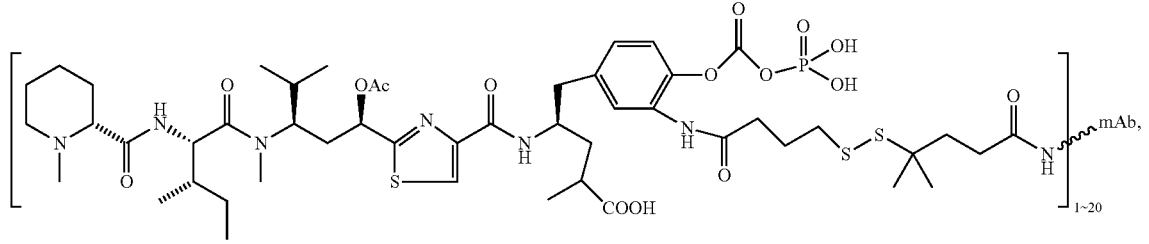

wherein mAb is an antibody.

7. The conjugate of claim 1, wherein the cell-binding ligand is capable of binding to target cells selected from the group consisting of tumor cells, autoimmune cells, myeloid cells, B cells, and melanocytes.

8. The conjugate according to claim 1, wherein when n in Formula (I') is 2, the linker L has following formula:

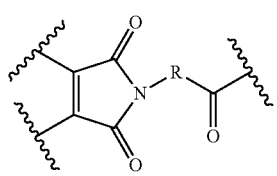

wherein R is $C_1$~$C_8$ alkyl or $C_2H_4(OC_2H_4)_n$, n is 1~20.

9. The conjugate of claim 1, wherein when n in Formula (I') is 2, the conjugate has following formula:

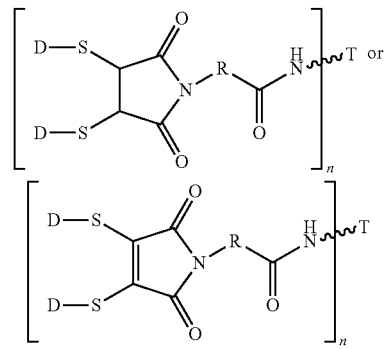

wherein R is $C_1$~$C_8$ alkyl or $C_2H_4(OC_2H_4)_n$, n is 1~20; D is a cytotoxic agent, which is a moiety inside the bracket of Formula (I), T is a cell-binding ligand.

10. The conjugate of claim 1, wherein when n in Formula (I') is 2, the conjugate has following formula:

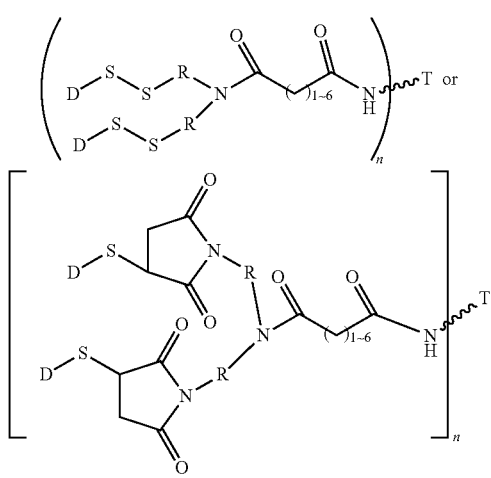

wherein R is $C_1$~$C_8$ alkyl or $C_2H_4(OC_2H_4)_n$, n is 1~20; D is a cytotoxic agent, which is a moiety inside the bracket of Formula (I'), T is a cell-binding ligand.

11. A pharmaceutical composition comprising a therapeutically effective amount of the conjugate of claim 1, or a pharmaceutically acceptable salt thereof, and a carrier, diluent, or excipient therefor.

12. A method for preparing the conjugate according to claim 1, comprising reacting a cell binding agent with a molecule having a structure of formula: 232a, 232b, 232c, 232d, 232e, 232f, 232g, 232h, 232i, 232j, 232k, 232l, 232m, 232n, 232o, 232p, 232q, 232r, 232s, 232t, 221a, 221b, 233a, 233b, 233c, 233d, 222a, 241, 242, 247, 248, 206, 211, 346, 350, 354, 357, 361, 366, 371, or 376, which are illustrated below:

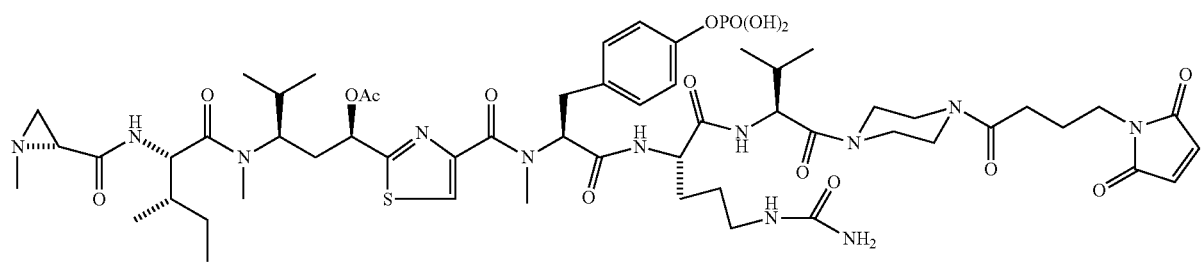

232a

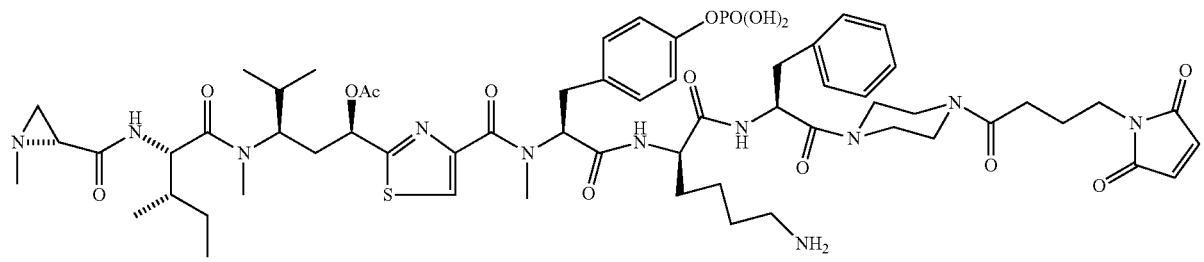

232b

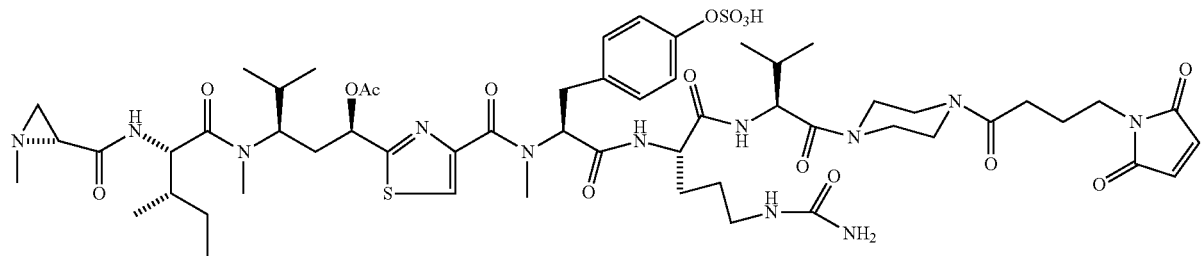

232c

232d
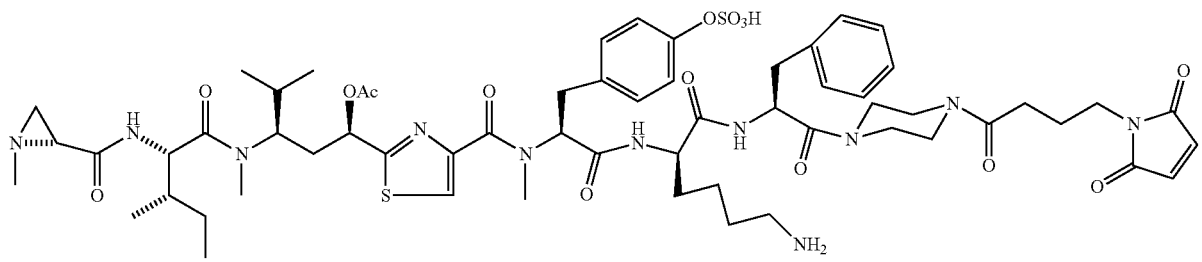
232e
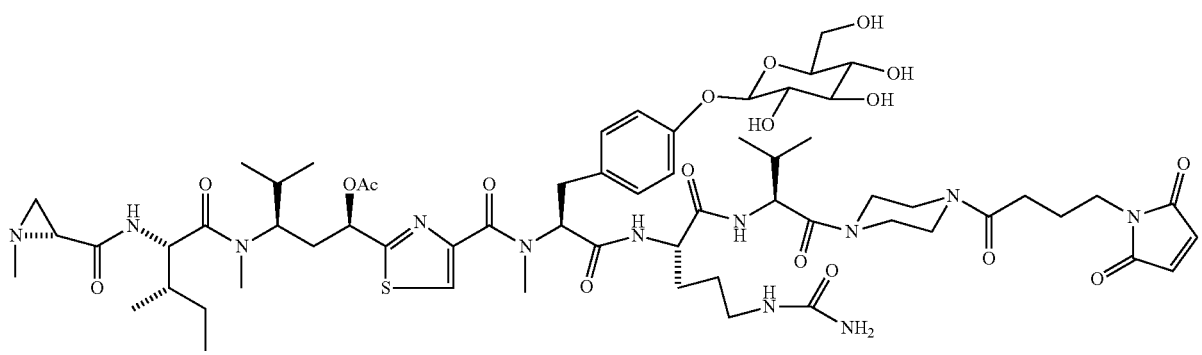
232f
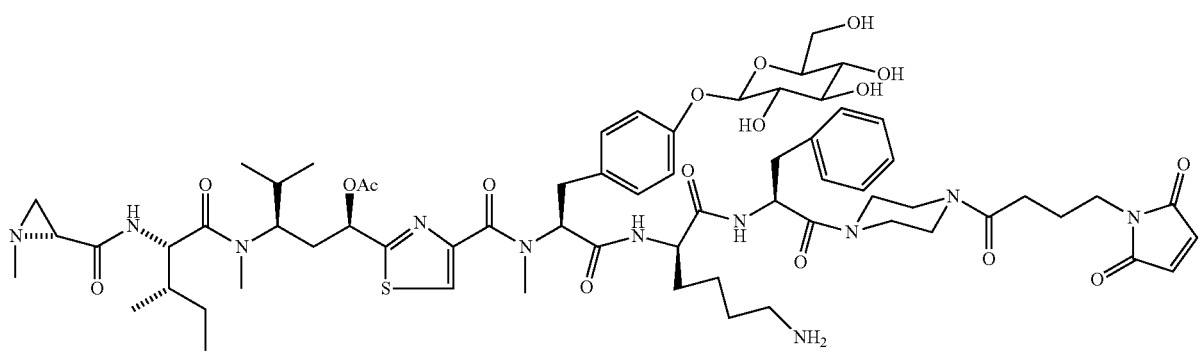
232g
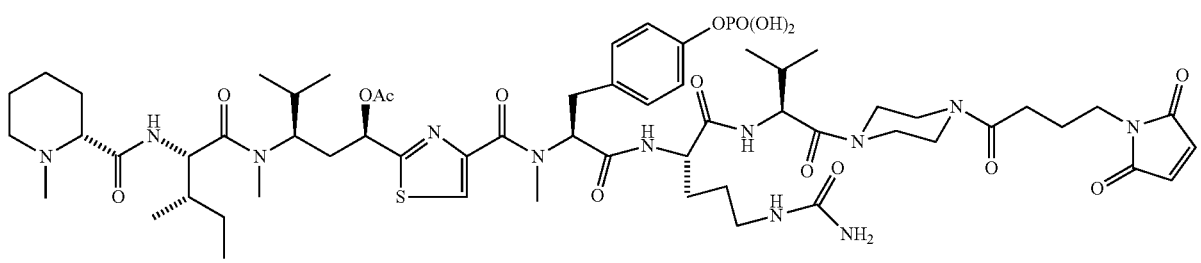
232h
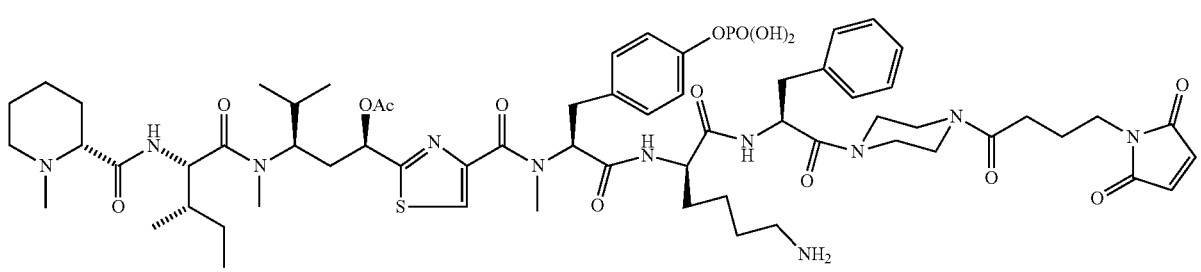

-continued
232i
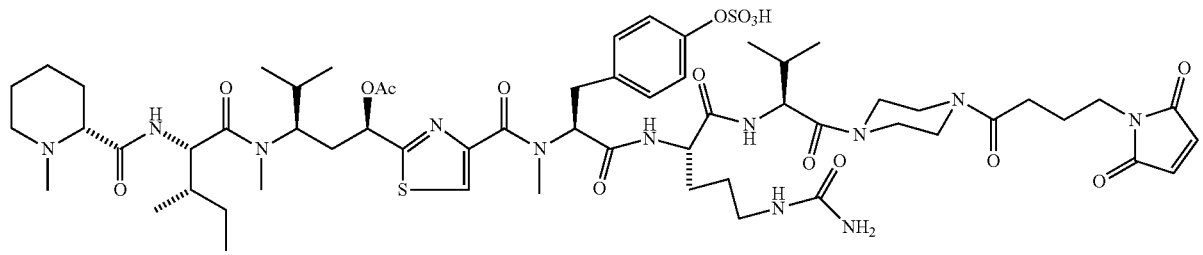
232j
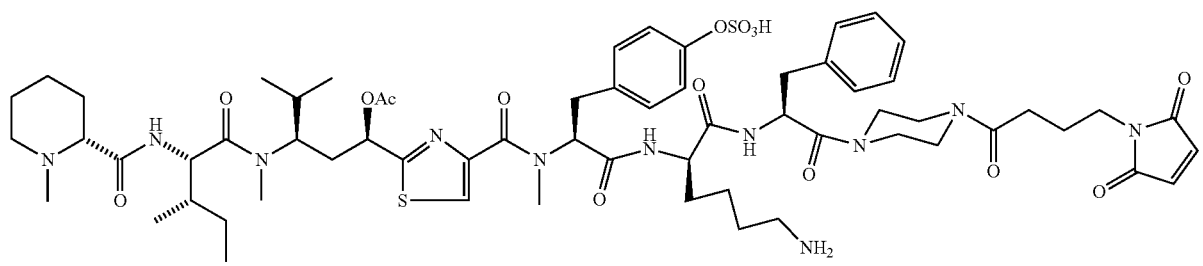
232k
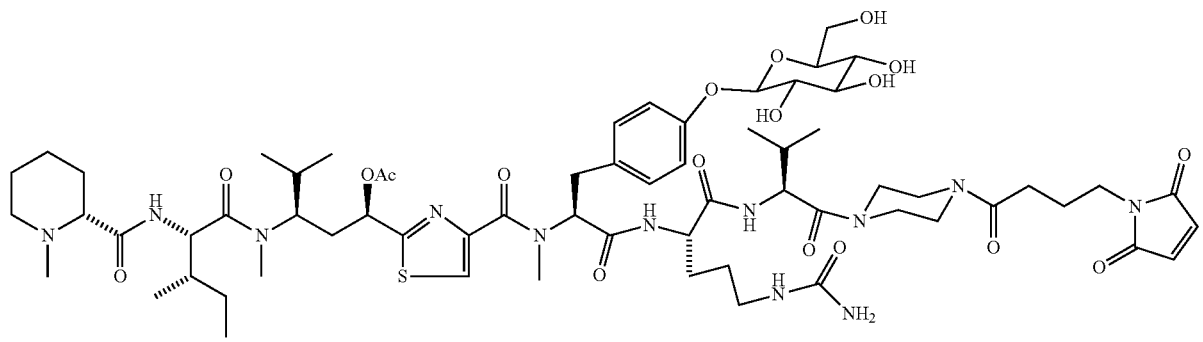
232l
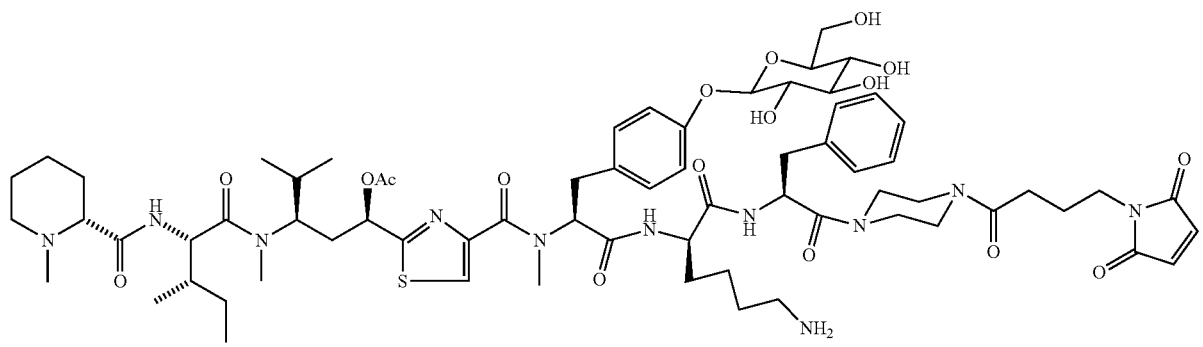
232m
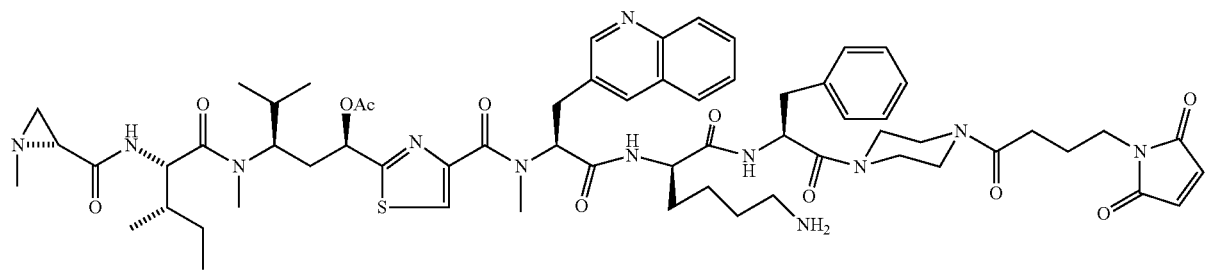

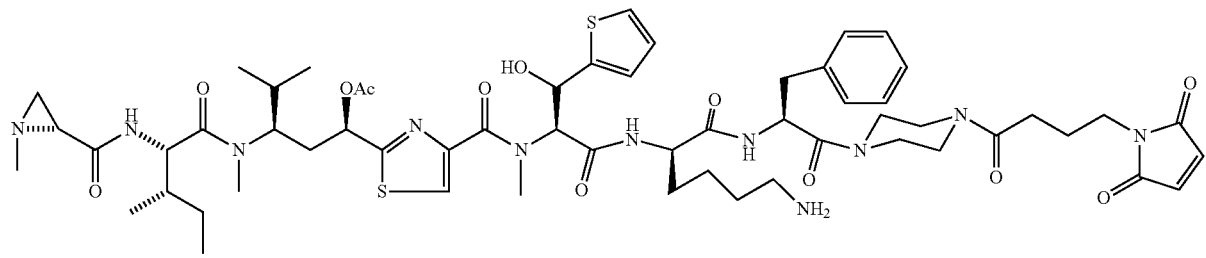
232n
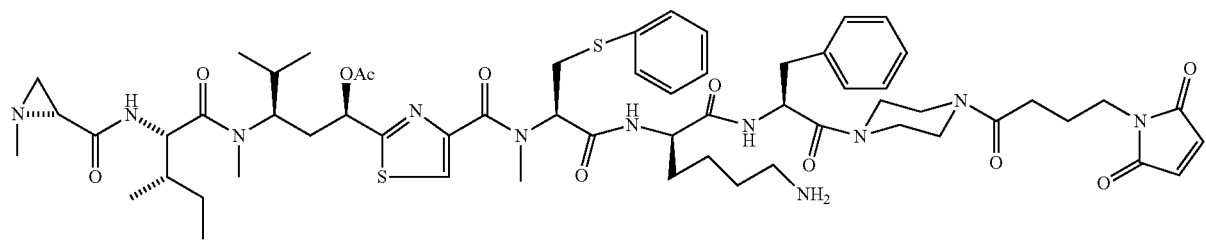
232o
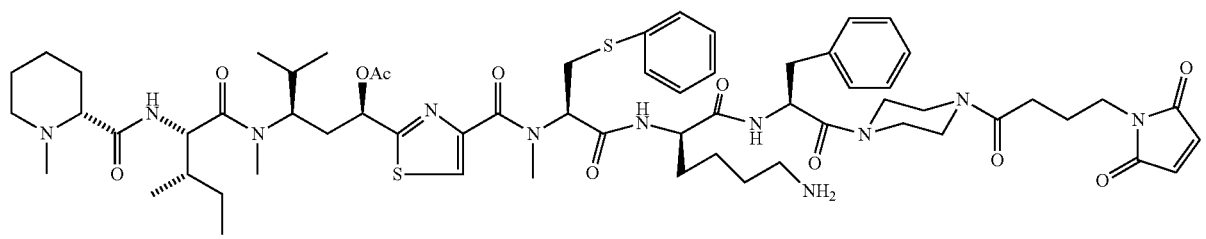
232p
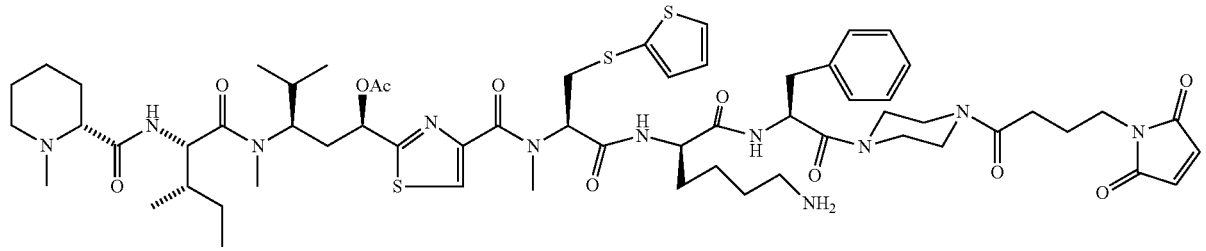
232q
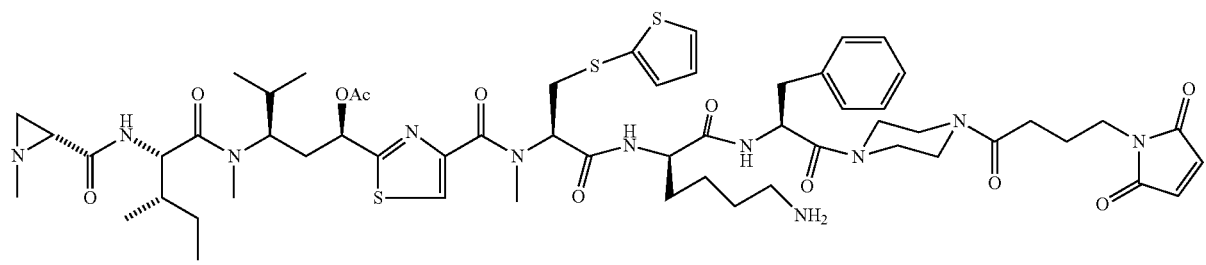
232r
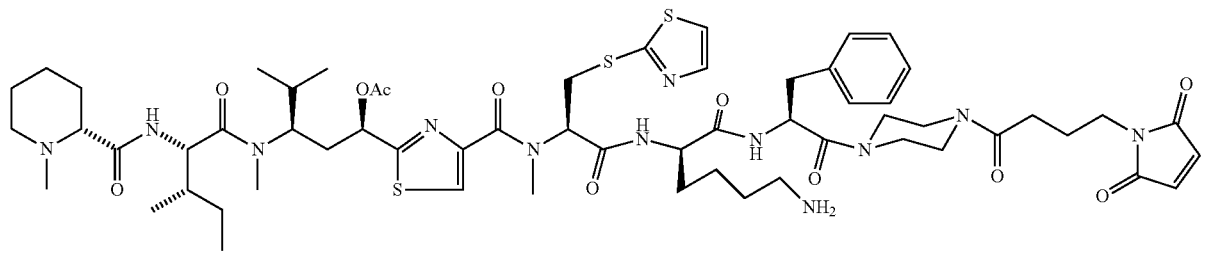
232s -continued
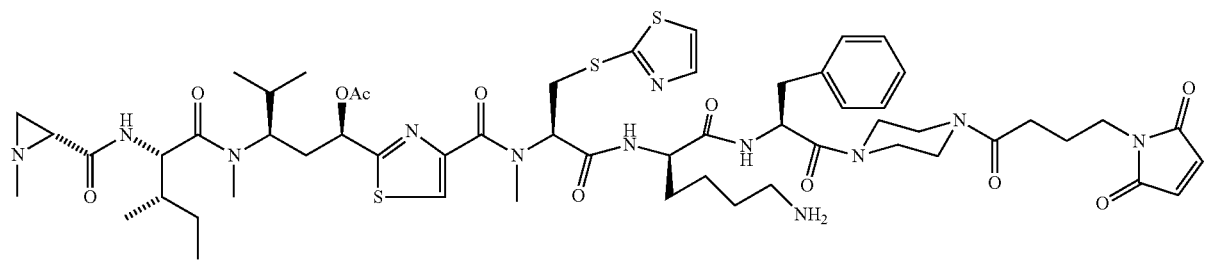
232t
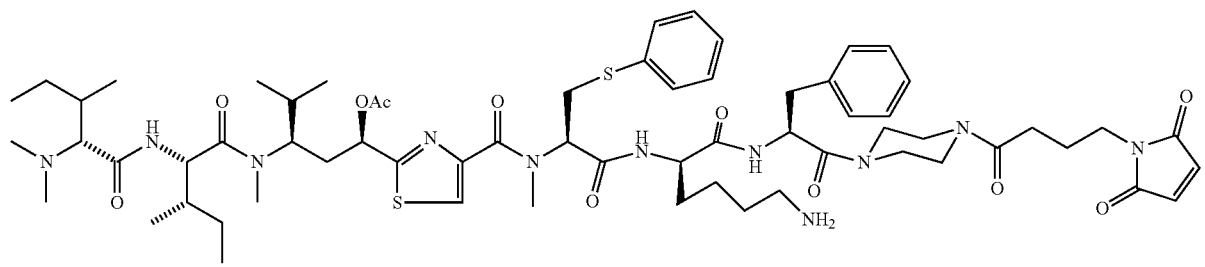
221a
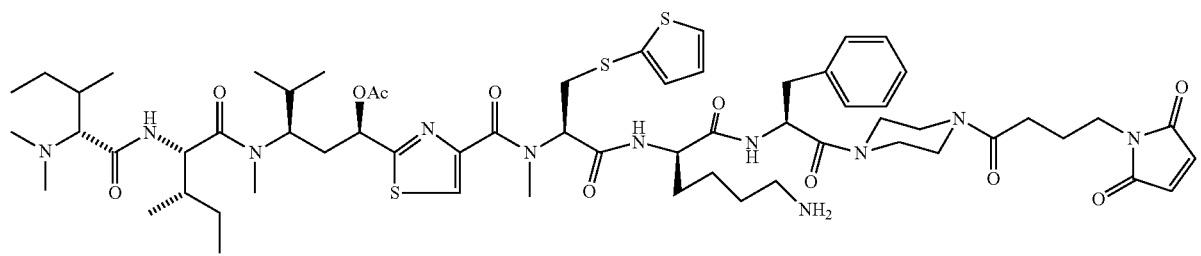
221b
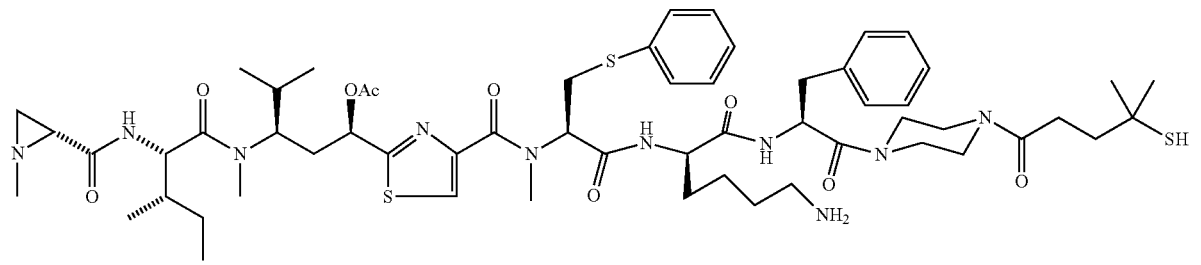
233a
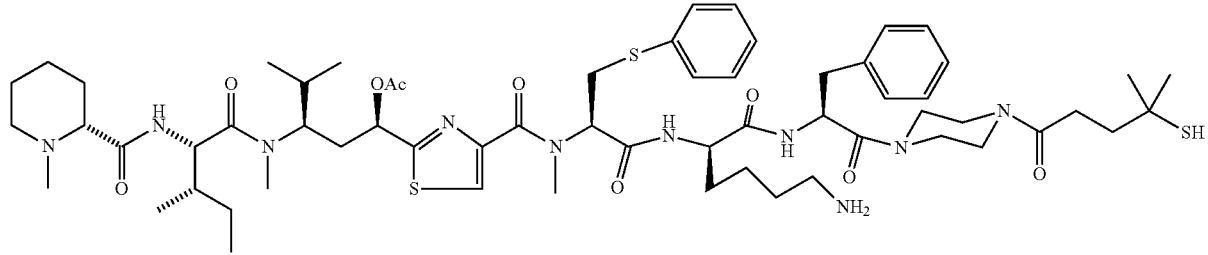
233b -continued
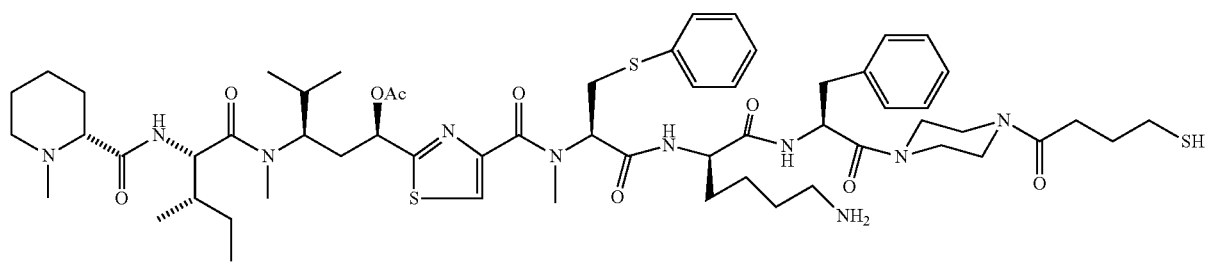
233c
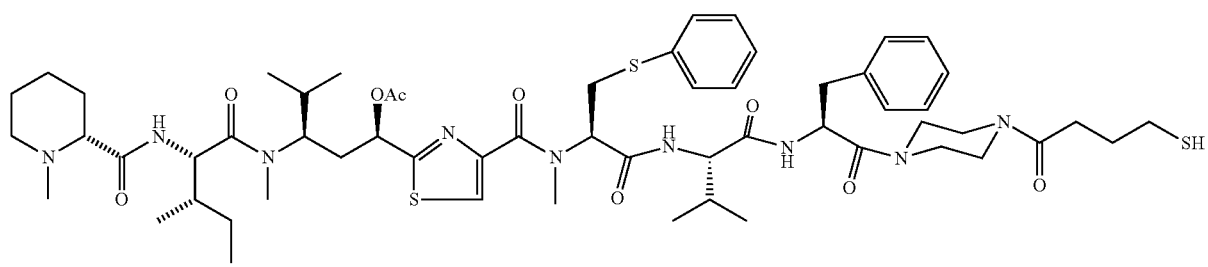
233d
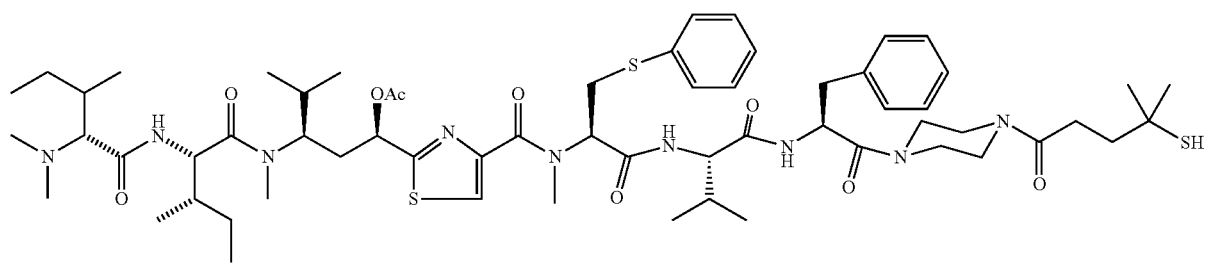
222a
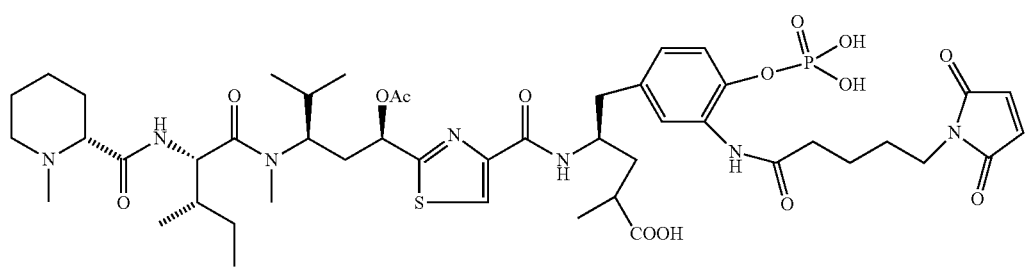
241
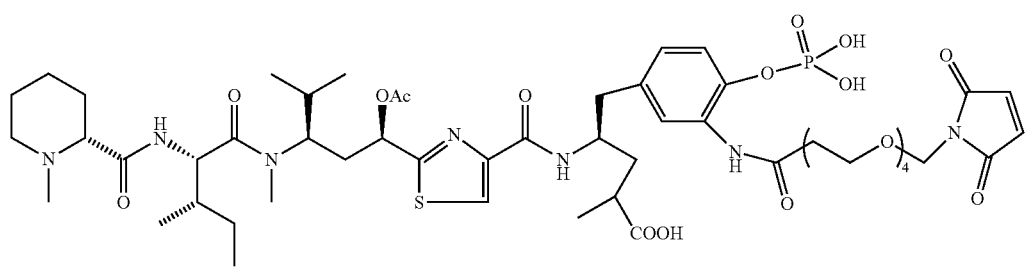
242

247
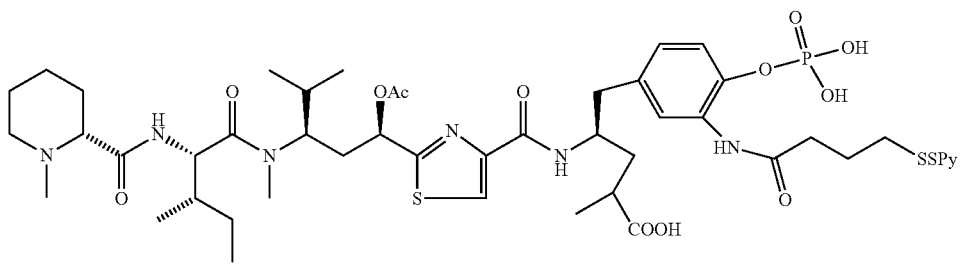
248
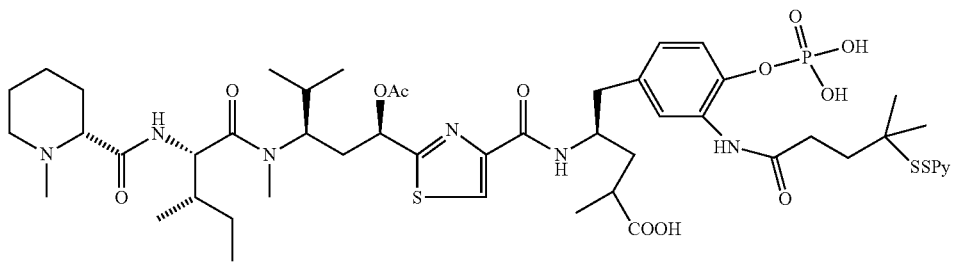
206
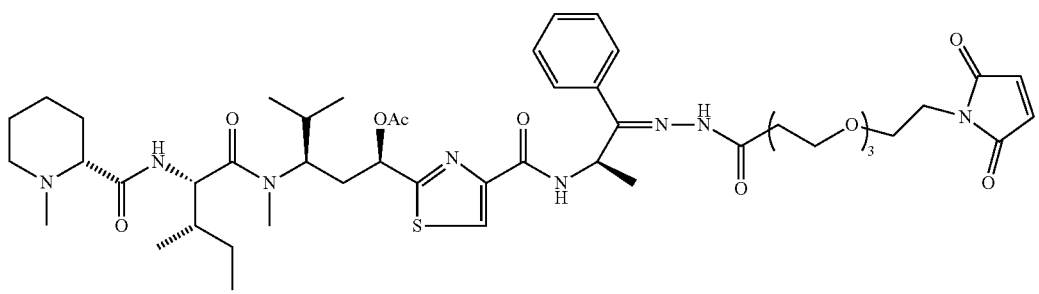
211
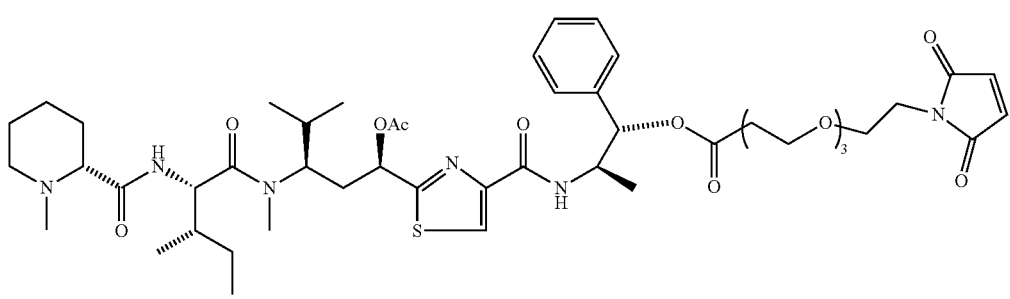
346
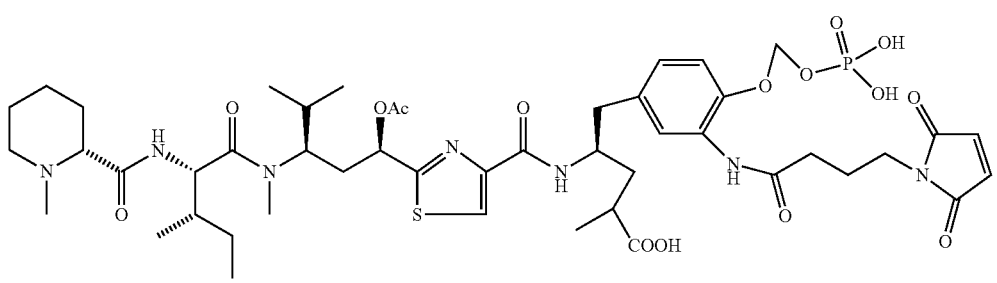

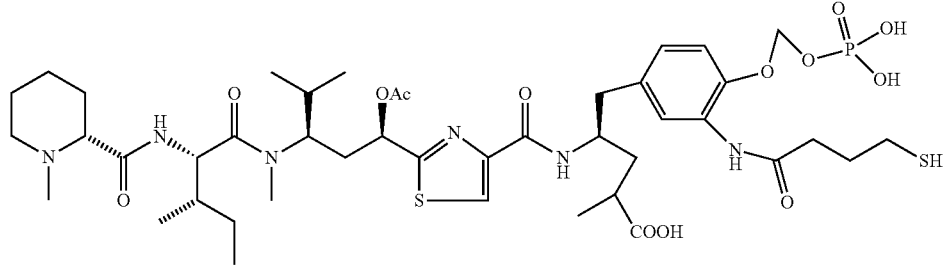
350
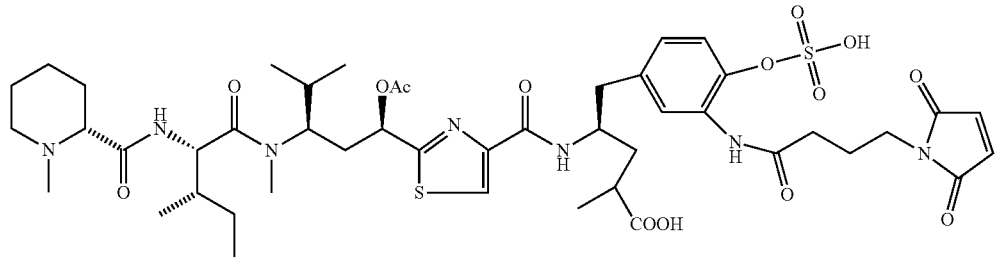
354
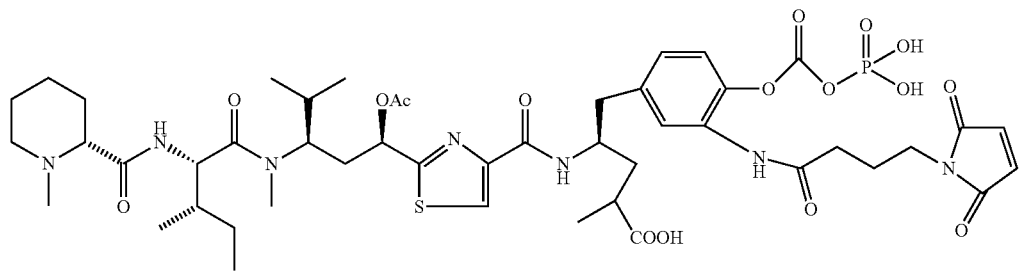
357
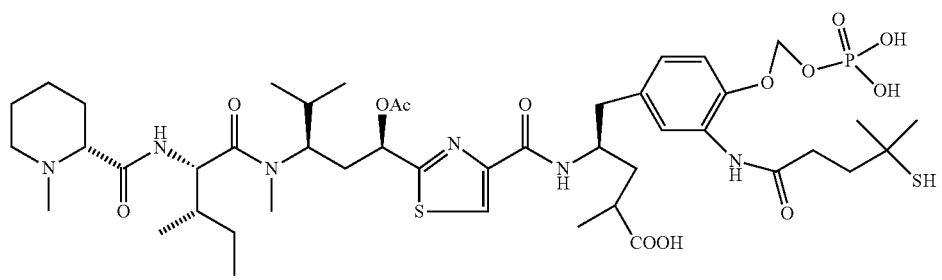
361
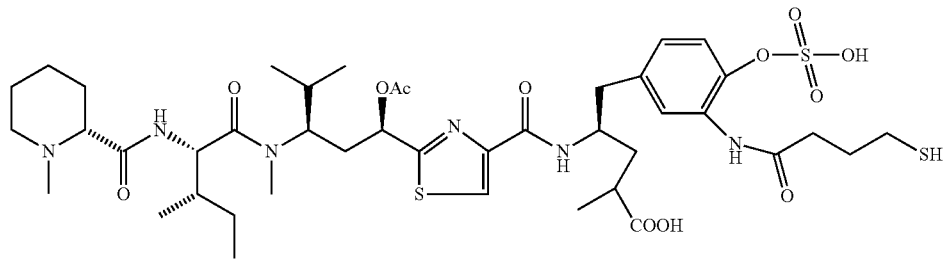
366

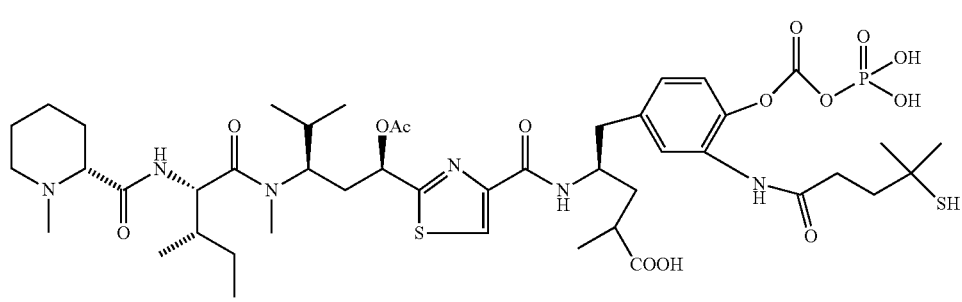

371

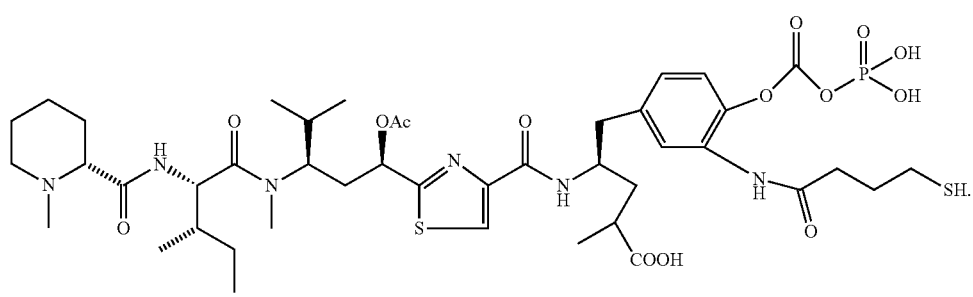

376

13. The conjugate of claim 1, wherein the cell-binding ligand is a monoclonal antibody, a single chain monoclonal antibody, a monoclonal antibody fragment that binds to the target cell, a chimeric antibody, or a chimeric antibody fragment that binds to the target cell.

14. The conjugate of claim 1, wherein the cell-binding ligand is capable of binding Apo2, BAFF-R, bone morphogenetic protein receptor, IGF-IR, CA125, CanAg, E16, ErbB2, MUC1, MUC16, Napi3b, TF, EpCAM, FcRH2, C242, CD2, CD3, CD4, CD5, CD6, CD11, CD18, CD19, CD20, CD21, CD22, CD26, CD30, CD33, CD37, CD38, CD40, CD44, CD56, CD70, CD72, CD79, CD90, CD105, CD138, CR, CR1, CRGF, CRIPTO, CXCR5, LY64, TDGF1, endothelin B receptor, EphA receptors, EphB receptors, Endothelin, FCRH1, HER2/neu, HER3, MHC class II molecule Ia antigen, integrins, IRTA2, LIV-1, MPF, Napi2b, PDL1, FLJ10372, KIAA1445, Mm42015, SEMA5B, SEMAG, six transmembrane epithelial antigen of prostate 1, IPCA-1, PCANP1, STMP, prostate antigens; insulin growth factor receptor, or folate receptor on target cells.

15. A pharmaceutical composition comprising the conjugate of claim 1, and a therapeutic agent selected from the group consisting of chemotherapeutic agents, immunotherapy agents, and anti-autoimmune disorder agents.

16. A conjugate having a structure of Formula (VIII):

or a pharmaceutically acceptable salt or solvate thereof, wherein T is a cell-binding ligand, a dendrimer or a liposome; L is a releasable linker;

----- is a linkage bond that L connects to an atom in a moiety inside the bracket independently; n is 1~20 and m is 1~10;

wherein the cell-binding ligand is an antibody, or an antibody fragment that binds to a target cell;

wherein the releasable linker L has a formula of: -$W_w$-$(Aa)_r$-$V_v$—, wherein: -W- is a stretcher unit, which links the moiety inside the bracket to an amino acid unit (Aa) when present, or V when an Aa is not present, and W is independently a self-immolative spacer, a peptidyl unit, a hydrazone, a disulfide, a thioether, an ester, or an amide bond; w is 0 or 1;

wherein Aa is independently a natural or unnatural amino acid unit; r is independently an integer ranging from 0 to 12; $(Aa)_r$ represents a natural or unnatural amino acid, dipeptide, tripeptide, tetrapeptide, pentapeptide, hexapeptide, heptapeptide, octapeptide, nonapeptide, decapeptide, undecapeptide or dodecapeptide unit; wherein V is a spacer unit and is independently H, O, NH, S, $C_1$~$C_8$ alkyl, $C_2$~$C_8$ heteroalkyl, alkenyl, or alkynyl, $C_3$~$C_8$ aryl, heterocyclic, carbocyclic, cycloalkyl, alkylcycloalkyl, heterocycloalkyl, heteroaralkyl, heteroalkylcycloalkyl, or alkylcarbonyl, or one to four (VIII)

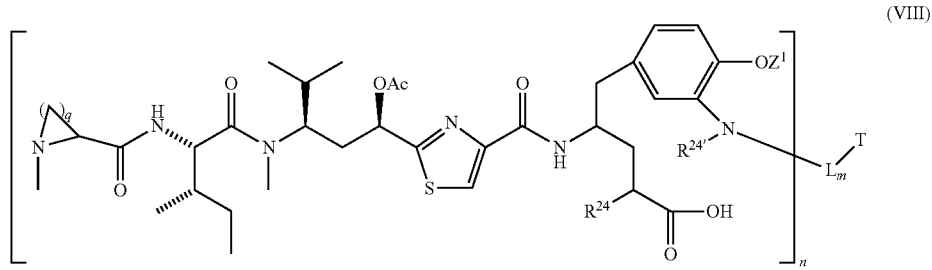

amino acid units, or $(CH_2CH_2O)_r$, r is an integer ranging from 0 to 12; and v is 0, 1 or 2;
wherein q=1~5;
wherein $Z^L$ is H, $CH_2OP(O)(OR^{18})_2$, $PO(OR^{18})_2$, $C(O)OP(O)(OR^{18})_2$, $P(O)(OR^{18})OP(O)(OR^{18})_2$, $C(O)R^{18}$, $C(O)NHR^{18}$, $SO_2(OR^{18})$, $C_4$-$C_{12}$ glycoside, or $C_1$~$C_8$ alkyl, carboxyalkyl, or heterocyclic; $R^{18}$ is H, $C_1$~$C_5$ alkyl, or heteroalkyl; $C_2$~$C_8$ alkenyl, alkynyl, carboxyalkyl, or heterocyclic; $C_3$~$C_8$ aryl, or alkylcarbonyl; and
wherein $R^{24}$ and $R^{24'}$ are independently H or $CH_3$.

17. The conjugate according to claim 2, wherein:
(i) $R^{12}$ is H when $R^{10}$ is not H, or
(ii) $R^{12}$ is H when $R^{13}$ is:

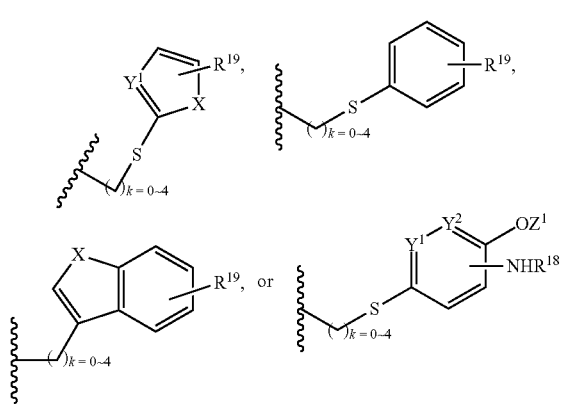

wherein $Z^1$ is H, $CH_2OP(O)(OR^{18})_2$, $C(O)OP(O)(OR^{18})_2$, $PO(OR^{18})_2$, $P(O)(OR^{18})OP(O)(OR^{18})_2$, $C(O)R^{18}$, $C(O)NHR^{18}$, $SO_2(OR^{18})$, $C_4$-$C_{12}$ glycoside, $C_1$-$C_8$ alkyl, or $C_3$-$C_8$ carboxyalkyl, or heterocyclic;

$R^{19}$ is H, OH, $NH_2$, $OSO_2(OR^{18})$, $XCH_2OP(O)(OR^{18})_2$, $XPO(OR^{18})_2$, $XC(O)OP(O)(OR^{18})_2$, $XC(O)R^{18}$, $XC(O)NHR^{18}$, $C_1$~$C_8$ alkyl, carboxylic acid derivative; $C_2$~$C_8$ alkenyl, alkynyl, heterocyclic, or carboxyalkyl; $C_3$~$C_8$ aryl, or alkylcarbonyl; or a pharmaceutical salt;
X is O, S, or NH;
$Y^1$ and $Y^2$ are N or CH independently; and
$R^{18}$ is H, $C_1$~$C_8$ alkyl, or heteroalkyl; $C_2$~$C_8$ carboxyalkyl, alkenyl, alkynyl, or heterocyclic; or $C_3$~$C_8$ aryl, or alkylcarbonyl.

18. The conjugate according to claim 4, wherein:
(i) $R^{12}$ is H when $R^{10}$ is not H, or
(ii) $R^{12}$ is H when $R^{11}$ is:

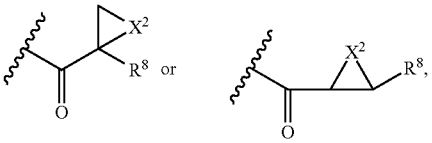

wherein $X^2$ is O, S, or N—$R^8$; $R^8$ is H, $C_1$~$C_6$ alkyl or heteroalkyl.

19. A method for treatment of a cancer, an autoimmune disease, or an infectious disease comprising administering to a patient in need thereof a pharmaceutical composition comprising a therapeutically effective amount of the conjugate according to claim 1.

20. The method according to claim 19, further comprising administering concurrently an effective amount of a therapeutic agent selected from the group consisting of chemotherapeutic agents, radiation therapy agents, immunotherapy agents, anti-autoimmune disorder agents, and anti-infectious agents.

* * * * *